(12) United States Patent
Bayburt et al.

(10) Patent No.: US 8,772,500 B2
(45) Date of Patent: Jul. 8, 2014

(54) TRPV3 MODULATORS

(71) Applicant: AbbVie Inc., North Chicago, IL (US)

(72) Inventors: Erol K. Bayburt, Gurnee, IL (US);
Bruce Clapham, Lindenhurst, IL (US);
Phil B. Cox, Grayslake, IL (US);
Jerome F. Daanen, Racine, WI (US);
Michael J. Dart, Highland Park, IL (US); Gregory A. Gfesser, Lindenhurst, IL (US); Arthur Gomtsyan, Vernon Hills, IL (US); Michael E. Kort, Lake Bluff, IL (US); Philip R. Kym, Libertyville, IL (US); Robert G. Schmidt, Antioch, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/658,374

(22) Filed: Oct. 23, 2012

(65) Prior Publication Data

US 2013/0131036 A1    May 23, 2013

(30) Foreign Application Priority Data

Oct. 24, 2011    (WO) ................ PCT/CN2011/001761

(51) Int. Cl.
| | | |
|---|---|---|
| *C07D 213/00* | (2006.01) | |
| *C07D 213/28* | (2006.01) | |
| *C07D 211/74* | (2006.01) | |
| *C07D 421/00* | (2006.01) | |
| *C07D 401/00* | (2006.01) | |

(52) U.S. Cl.
USPC .................... 546/344; 546/278.1; 546/268.1; 514/277; 514/252.03

(58) Field of Classification Search
USPC ...................................... 546/278.1; 514/277
See application file for complete search history.

(56) References Cited

U.S. PATENT DOCUMENTS

| | | | |
|---|---|---|---|
| 5,112,828 A | 5/1992 | Zipperer et al. | |
| 6,114,532 A | 9/2000 | Ries et al. | |
| 7,396,910 B2 | 7/2008 | Bevan et al. | |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 2009/0082471 A1 | 3/2009 | Czarnik | |
| 2009/0088416 A1 | 4/2009 | Czarnik | |
| 2009/0093422 A1 | 4/2009 | Tung et al. | |
| 2009/0093516 A1 | 4/2009 | Li et al. | |
| 2009/0105147 A1 | 4/2009 | Masse | |
| 2009/0105307 A1 | 4/2009 | Galley et al. | |
| 2009/0105338 A1 | 4/2009 | Czarnik | |
| 2009/0111840 A1 | 4/2009 | Herold et al. | |
| 2009/0118238 A1 | 5/2009 | Czarnik | |
| 2009/0131363 A1 | 5/2009 | Harbeson | |
| 2009/0131485 A1 | 5/2009 | Liu et al. | |
| 2009/0137457 A1 | 5/2009 | Harbeson | |
| 2012/0010190 A1 | 1/2012 | Bissantz et al. | |

FOREIGN PATENT DOCUMENTS

| | | |
|---|---|---|
| CN | 101883772 A | 11/2010 |
| EP | 0400344 A1 | 12/1990 |
| IN | 200900517 A2 | 11/2010 |
| WO | 9429281 A1 | 12/1994 |
| WO | 9504042 A1 | 2/1995 |
| WO | 9507271 A1 | 3/1995 |
| WO | 9710223 A1 | 3/1997 |
| WO | 9940072 A1 | 8/1999 |
| WO | 0222572 A2 | 3/2002 |
| WO | 03086294 A2 | 10/2003 |
| WO | 03086294 A3 | 10/2003 |
| WO | 2004043958 A1 | 5/2004 |
| WO | 2005099353 A2 | 10/2005 |
| WO | 2006008754 A1 | 1/2006 |
| WO | 2006122156 A2 | 11/2006 |
| WO | 2006122156 A3 | 11/2006 |
| WO | 2007056124 A2 | 5/2007 |
| WO | 2010004379 A2 | 1/2010 |
| WO | 2010070452 A1 | 6/2010 |
| WO | 2012019315 A1 | 2/2012 |
| WO | 2013062964 A2 | 5/2013 |

OTHER PUBLICATIONS

Donato Ivan Coppi, Antonio Salomone, Filippo Maria Perna and Vito Capriati, Chem. Commun., 2011, 47, 9918-9920.*
Dorwald; Side Reactions in Organic Synthesis, 2005, Wiley-VCH, Weinheim.*
Hailes, in Comprehensive Heterocyclic Chemistry III, Elsevier, Oxford, 2008, chapter 2.05—Oxetanes and Oxetenes: Monocyclic, chapter summary.*
Wermuth; Practice of Medicinal Chemistry, Third edition, 2008, Elsevier.*
Alexander et al., "The Photochemical Synthesis of a Tricyclo[2.2.0. 02,5]hexane," J. American Chem. Soc., 1976, 98(14): 4324-4325.
Aley et al., "Nitric oxide signaling in pain and nociceptor sensitization in the rat," J Neurosci., 1998, 18(17): 7008-7014.
Berge et al., "Pharmaceutical salts," J. Pharm Sci., 1977, 66(1): 1-19.
Beylot et al., "In vivo studies of intrahepatic metabolic pathways," Diabetes Metab., 1997, 23(3): 251-257.

(Continued)

*Primary Examiner* — John Mabry
*Assistant Examiner* — Daniel Carcanague

(57) ABSTRACT

Disclosed herein are modulators of TRPV3 of formula (II):

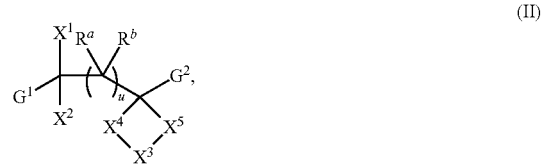

(II)

wherein $G^1$, $X^1$, $X^2$, $X^3$, $X^4$, $X^5$, $G^2$, $R^a$, $R^b$, and u are as defined in the specification. Compositions comprising such compounds and methods for treating conditions and disorders using such compounds and compositions are also presented.

33 Claims, No Drawings

(56) References Cited

OTHER PUBLICATIONS

Blagojevic et al., "Role of Heavy Water in Boron Neutron Capture Therapy," Topics in Dosimetry & Treatment Planning for Neutron Capture Therapy, R. Zamenhoff, G. Solares, O. Harling, Editors, 1994, Advanced Medical Publishing, Madison Wisconsin pp. 125-134.
Blake et al., "Studies with deuterated drugs," J Pharm Sci., 1975, 64(3): 367-391.
Brickner et al., "Synthesis and antibacterial activity of U-100592 and U-100766, two oxazolidinone antibacterial agents for the potential treatment of multidrug-resistant gram-positive bacterial infections," J Med Chem., 1996, 39(3): 673-679.
Caterina, MJ, "Transient receptor potential ion channels as participants in thermosensation and thermoregulation," Am J Physiol Regul Integr Comp Physiol., 2007, 292(1): R64-R76.
Caterina et al., "A capsaicin-receptor homologue with a high threshold for noxious heat," Nature, 1999, 398(6726): 436-441.
Chung et al., "2-aminoethoxydiphenyl borate activates and sensitizes the heat-gated ion channel TRPV3," J Neurosci. 2004, 24(22):5177-5182.
Chung et al., "Biphasic currents evoked by chemical or thermal activation of the heat-gated ion channel, TRPV3," J Biol Chem., 2005, 280(16): 15928-15941.
Chung et al., "Warm temperatures activate TRPV4 in mouse 308 keratinocytes," J Biol Chem., 2003, 278(34): 32037-32046.
Chung et al., "TRPV3 and TRPV4 mediate warmth-evoked currents in primary mouse keratinocytes," J Biol Chem., 2004, 279(20): 21569-21575.
Coppi et al., "2-Lithiated-2-phenyloxetane: a new attractive synthon for the preparation of oxetane derivatives," Chem. Commun (Camb)., 2011, 47(35): 9918-9920.
Czajka et al., "Effect of deuterium oxide on the reproductive potential of mice," Ann N Y Acad Sci., 1960, 84: 770-779.
Czajka et al., "Physiological effects of deuterium on dogs," Am J Physiol. 1961, 201(2): 357-362.
Dörwald, FZ, "1.3 Hard and Soft Acids and Bases," Side Reactions in Organic Synthesis, 2005, Wiley-VCH, Weinheim (390 pages).
Drug labeling information for Tylenol® with codeine, Revised Aug. 2010, taken from PDR® 3D™ (Digital Drug Database) available at www.pdrnetwork.com, printed Mar. 22,2013 (9 pages)
Facer et al., "Differential expression of the capsaicin receptor TRPV1 and related novel receptors TRPV3, TRPV4 and TRPM8 in normal human tissues and changes in traumatic and diabetic neuropathy," BMC Neurol., 2007, 7: 11-22.
Foster et al., "Deuterium Isotope Effects in the Metabolism of Drugs and Xenobiotics: Implications for Drug Design," Advances in Drug Research, 1985, vol. 14 Academic press, London, pp. 2-36.
Green et al. Editors, Protecting Groups in Organic Synthesis, 3rd Ed., John Wiley & Sons, NY, 1999, 20 pages.
Güler et al., "Heat-evoked activation of the ion channel, TRPV4," J Neurosci., 2002, 22(15): 6408-6414.
Hailes et al., "2.05—Oxetanes and Oxetenes: Monocyclic" Comprehensive Heterocyclic Chemistry III, Elsevier, Oxford, 2008, pp. 321-364.
Harper et al., "1-3,4-Dichlorobenzamidomethyl)cyclohexyldimethylamine and Related Compounds as Potential Analgesics," Journal of Medicinal Chemistry, 1974, 17(11): 1188-1193.
Hattersley et al., "Some Reactions with 4-Cyano-4-phenyltetrahydropyran" Journal of Medicinal Chemistry, 1967, 10(1): 128-129.
Hu et al., "2-aminoethoxydiphenyl borate is a common activator of TRPV1, TRPV2, and TRPV3," J Biol Chem., 2004, 279(34): 35741-35748.
Hu et al., "Potentiation of TRPV3 channel function by unsaturated fatty acids," J Cell Physiol. 2006, 208(1): 201-212.
International Search Report and Written Opinion for PCT/CN2010/001213, mailed May 19, 2011 (11 pages).
International Search Report and Written Opinion for PCT/CN2011/001761, mailed Aug. 2, 2012 (17 pages).
International Search Report for PCT/US2012/061476, mailed Jun. 17, 2013 (6 pages).
International Search Report for PCT/US2012/061478, mailed Jun. 17, 2013 (7 pages).
IUPAC 1974 Recommendations for Section E, Fundamental Stereochemistry, Pure Appl. Chem., 1976, 45: 13-30.
Kato et al., "Synthesis of Deuterated Mosapride Citrate," J Labelled Compd Rad., 1995, 36(10): 927-932.
Kushner et al., "Pharmacological uses and perspectives of heavy water and deuterated compounds," Can J Physiol Pharmacol., 1999, 77(2): 79-88.
Lee et al., "TRPV channels as thermosensory receptors in epithelial cells," Pflugers Arch.—Eur J Physiol. 2005, 451(1): 160-167.
Lee-Ruff et al., "Enantiomerically pure cyclobutane derivatives and their use in organic synthesis," Chem Rev., 2003, 103(4): 1449-1483.
Lizondo et al., "Linezolid. Oxazolidinone Antibacterial," Drugs Fut., 1996, 21(11): 1116-1123.
MacPherson et al., "More than cool: promiscuous relationships of menthol and other sensory compounds" Mol Cell Neurosci. 2006, 32(4): 335-343.
Mallesham et al., "Highly efficient CuI-catalyzed coupling of aryl bromides with oxazolidinones using Buchwald's protocol: a short route to linezolid and toloxatone," Org Lett., 2003, 5(7): 963-965.
Montell, C. "Preventing a Perm with TRPV3," Cell, 2010, 141(2): 218-220.
Moqrich et al., "Impaired thermosensation in mice lacking TRPV3, a heat and camphor sensor in the skin," Science, 2005, 307(5714): 1468-1472.
Moussaieff et al., "Incensole acetate, an incense component, elicits psychoactivity by activating TRPV3 channels in the brain," FASEB J., 2008, 22(8): 3024-3034.
Nilius et al., "Transient receptor potential cation channels in disease," Physiol Rev., 2007, 87(1): 165-217.
Okuhara et al., "Transient receptor potential channels as drug targets," Expert Opin Ther Targets, 2007, 11(3): 391-401.
Ong et al., "Novel Tetracyclic Spiropiperidines. II. Synthesis of 2-Aryl-2,3-dihydrospiro[benzofuran-3,4'-piperidines] (1,2)," Journal of Heterocyclic Chemistry, 1981, 18(4): 815-820.
Peier et al., "A heat-sensitive TRP channel expressed in keratinocytes," Science, 2002, 296(5575): 2046-2049.
Prescott, D.M., Editor, "Methods in Cell Biology," vol. XIV, Academic Press, New York, N.Y. 1976, 12 pages.
Smith et al., "TRPV3 is a temperature-sensitive vanilloid receptor-like protein," Nature 2002, 418(6894): 186-190.
Steinhoff et al., "A TR(I)P to pruritus research: role of TRPV3 in inflammation and itch," J. Invest. Dermatology, 2009, 129(3): 531-535.
Thomson JF, "Physiological effects of D20 in mammals," Ann NY Acad Sci., 1960, 84: 736-744.
Vogt-Eisele et al., "Monoterpenoid agonists of TRPV3," Br J Pharmacol. 2007, 151(4): 530-540.
Wermuth Editor, The Practice of Medicinal Chemistry, 3rd Edition, Elsevier, 2008, pp. 126, 276, 294, 328, 343, 350, 431, 432, 440, 452, 533, 535, 536, 724 and 725.
Wissenbach et al., "TRP channels as potential drug targets," Biology of the Cell., (2004), 96(1): 47-54.
Xu et al., "Camphor activates and strongly desensitizes the transient receptor potential vanilloid subtype 1 channel in a vanilloid-independent mechanism," J Neurosci. 2005, 25(39): 8924-8937.
Xu et al., "Oregano, thyme and clove-derived flavors and skin sensitizers activate specific TRP channels," Nat Neurosci. 2006, 9(5): 628-635.
Xu et al., "TRPV3 is a calcium-permeable temperature-sensitive cation channel," Nature, 2002, 418(6894): 181-186.
Yoshida et al., Editors, "Nitric oxide activates TRP channels by cysteine S-nitrosylation," Nat Chem Biol., 2006, 2(11): 596-607.
Zhang et al., "Cyclization reactions of 3,3-dimethyl-1-(1H-1,2,4-triazolo-1-yl)-2-butanone or substituted 1-(1H-1,2,4-triazolo-1-yl)acetophenone with dibromide compounds and its biological activities," Gaodeng Xuexiao Huaxue Xuebao, 24(3): 431-435 (retrieved from STN Database accession No. 2003:247751 abstract).
U.S. Appl. No. 13/761,862, filed Feb. 7, 2013, File History.
U.S. Appl. No. 13/658,355, filed Oct. 23, 2012, File History.

(56) References Cited

OTHER PUBLICATIONS

Hardouin et al, "BF3•OEt2—Mediated Rearrangement of Cyclopropyl Carbinols: A Concise Route to Polycyclic Cyclobutanes," J. Org. Chem., 66(12): 4450-4452 (2001).

Kanemoto et al., "Novel Synthesis of Monofluorocyclobutanes by the Ring Expansion Fluorination of Cyclopropylmethanols With an Amine-Metal, Fluoride-Pyridinium Poly(Hydrogen Fluoride)-Complex," Tetrahedron Letters, 28(5): 6313-6316 (1987).

McCarty et al., "Central Stimulants. α,α-Disubstituted 2-Piperidinemethanols and 1,1-Disubstitued Heptahydrooxazolo[3,4-a]pyridines," J. Am. Chem. Soc., 179(2): 472-480 (1957).

Yus et al., "Intramolecular carbolithiation promoted by a DTBB-catalysed chlorine-lithium exchange," Tetrahedron, 59(43):8525-8542 (2003).

Extended European Search Report for Application No. 10855736.4 dated Dec. 4, 2013.

\* cited by examiner

TRPV3 MODULATORS

CROSS-REFERENCE TO RELATED PATENT APPLICATIONS

This patent application claims the benefit of International Patent Application No. PCT/CN2011/001761 (filed Oct. 24, 2011). The entire text of that International Patent Application is incorporated by reference into this application.

TECHNICAL FIELD

Compounds that are Transient Receptor Potential Vanilloid 3 (TRPV3) modulators, compositions comprising such compounds, and methods for treating conditions and disorders using such compounds and compositions, are disclosed herein.

BACKGROUND OF THE INVENTION

A subset of the vanilloid channels (TRPV1-4) are referred to as thermoTRPs to reflect the observation that heat elicits channel opening across a continuum of temperatures with thresholds ranging from 25° C. to 52° C. (Caterina, M. J.; Rosen, T. A.; Tominaga, M.; Brake, A. J.; Julius, D., *Nature* 1999, 398, 436-441). TRPV3 characteristically responds to innocuous heat >31° C., exhibits exquisite sensitivity around the physiological temperature of humans, 37° C., and sensitizes dramatically following repetitive heating (Smith, G. D.; Gunthorpe, M. J.; Kelsell, R. E.; Hayes, P. D.; Reilly, P.; Facer, P.; Wright, J. E.; Jerman, J. C.; Walhin, J. P.; Ooi, L.; Egerton, J.; Charles, K. J.; Smart, D.; Randall, A. D.; Anand, P.; Davis, J. B., *Nature* 2002, 418, 186-190; Xu, H.; Ramsey, I. S.; Kotecha, S. A.; Moran, M. M.; Chong, J. A.; Lawson, D.; Ge, P.; Lilly, J.; Silos-Santiago, I.; Xie, Y.; DiStefano, P. S.; Curtis, R.; Clapham, D. E., *Nature* 2002, 418, 181-186; Peier, A. M.; Reeve, A. J.; Andersson, D. A.; Moqrich, A.; Earley, T. J.; Hergarden, A. C.; Story, G. M.; Colley, S.; Hogenesch, J. B.; McIntyre, P.; Bevan, S.; Patapoutian, A., *Science* 2002, 296, 2046-2049).

TRPV3 is a nonselective cation channel with permeability for calcium, but also to other cations, for example sodium. Multiple compounds that have been shown to activate TRPV3, include: monoterpenes, camphor (Peier, A. M. et al., 2002; Moqrich, A.; Hwang, S. W.; Earley, T. J.; Petrus, M. J.; Murray, A. N.; Spencer, K. S.; Andahazy, M.; Story, G. M.; Patapoutian, A., *Science* 2005, 307, 1468-1472; Xu, H.; Blair, N. T.; Clapham, D. E., *J. Neurosci.* 2005, 25, 8924-8937), carvacrol, and thymol (Xu, H.; Delling, M.; Jun, J. C.; Clapham, D. E. *Nat. Neurosci.* 2006, 9, 628-635; Vogt-Eisele, A. K.; Weber, K.; Sherkheli, M. A.; Vielhaber, G.; Panten, J.; Gisselmann, G.; Hatt, H., *Br J. Pharmacol.* 2007, 151, 530-540; Story, G. M., *Mol Cell Neurosci.* 2006, 32, 335-343; Vogt-Eisele, A. K. et al., 2007); cinnamaldehyde (Macpherson, L. J. et al., 2006); incensole acetate (Moussaieff, A.; Rimmerman, N.; Bregman, T.; Straiker, A.; Felder, C. C.; Shoham, S.; Kashman, Y.; Huang, S. M.; Lee, H.; Shohami, E.; Mackie, K.; Caterina, M. J.; Walker, J. M.; Fride, E.; Mechoulam, R., *FASEB J.* 2008, 22, 3024-3034); and vanilloid analogs, eugenol and ethyl vanillin (Hu, H. Z.; Gu, Q.; Wang, C.; Colton, C. K.; Tang, J.; Kinoshita-Kawada, M.; Lee, L. Y.; Wood, J. D.; Zhu, M. X., *J Biol. Chem.* 2004, 279, 35741-35748; Vogt-Eisele, A. K. et al., 2007; Xu, H. et al., 2006). Though relatively weak ($EC_{50}$, ~40 µM) and nonspecific across TRPs, 2-aminoethoxydiphenylborate (2-APB) and diphenylboronic anhydride (DPBA) have been widely and productively used to characterize key attributes of TRPV3 in cellular assays and electrophysiology (Hu, H. Z. et al., 2004; Chung, M. K.; Lee, H.; Mizuno, A.; Suzuki, M.; Caterina, M. J. *J Neurosci.* 2004, 24, 5177-5182; Chung, M. K.; Güler, A. D.; Caterina, M. J., *J Biol. Chem.* 2005, 280, 15928-15941). While heat and direct ligand binding are clearly central to TRPV3 pharmacology, accumulating evidence of potentiation by arachidonic acid, other unsaturated fatty acid derivatives (Hu, H. Z.; Xiao, R.; Wang, C.; Gao, N.; Colton, C. K.; Wood, J. D.; Zhu, M. X., *J Cell Physiol.* 2006, 208, 201-212), and nitric oxide (Aley, K. O.; McCarter, G.; Levine, J. D., *J Neurosci.* 1998, 18, 7008-7014; Yoshida, T.; Inoue, R.; Morii, T.; Takahashi, N.; Yamamoto, S.; Hara, Y.; Tominaga, M.; Shimizu, S.; Sato, Y.; Mori, Y., *Nat Chem Biol.* 2006, 2, 596-607) suggests that authentic activation involves stimulation of G protein-coupled receptors and downstream second messenger signal cascades (e.g., phospholipase C, protein kinase C) that mediate local inflammatory responses and nociceptor sensitization that could enhance TRPV3 function (Xu, H. et al., 2006) in a pathophysiological, as compared to basal state.

Evidence suggests that transcriptional regulation of the TRPV3 gene restricts its basal expression and is responsible for enhanced expression following nerve injury. Levels of TRPV3 mRNA recovered from rat L4 and L5 DRG neurons is elevated in the spinal nerve ligation model of neuropathic pain, as compared to uninjured rats (U.S. Pat. No. 7,396,910). Similar upregulation of TRPV3 has been observed in sensory neurons following peripheral nerve injury in humans (Facer, P.; Casula, M. A.; Smith, G. D.; Benham, C. D.; Chessell, I. P.; Bountra, C.; Sinisi, M.; Birch, R.; Anand, P., *BMC Neurol.* 2007, 7, 11-22; Smith G. D. et al., 2002).

One feature that distinguishes TRPV3 from the other thermoTRPs is its relatively prominent localization in skin (Peier, A. M. et al., 2002; Xu, H. et al., 2002). TRPV3 is also expressed in dorsal root ganglion, trigeminal ganglion, spinal cord and brain (Xu, H. et al., 2002; Smith G. D. et al., 2002). Its distinctive tissue profile, with significant expression in keratinocytes proximal to nociceptive neurons (Chung, M. K.; Lee, H.; Caterina, M. J., *J Biol. Chem.* 2003, 278, 32037-32046; Chung, M. K.; Lee, H.; Mizuno, A.; Suzuki, M.; Caterina, M. J. *J Biol. Chem.* 2004, 279, 21569-21575; Peier, A. M. et al., 2002; Xu, H. et al., 2002) as well as upregulation of TRPV3 in disease states is consistent with a likely role of TRPV3 in pain (Caterina M J., *Am J Physiol Regul Integr Comp Physiol.* 2007, 292, R64-R76; Lee, H.; Caterina, M. J., *Pflugers Arch.* 2005, 451, 160-167; Güler, A. D.; Lee, H.; Iida, T.; Shimizu, I.; Tominaga, M.; Caterina, M., *J. Neurosci.* 2002, 22, 6408-6414; Chung, M. K. et al., 2003; Chung, M. K.; Lee, H.; Mizuno, A.; Suzuki, M.; Caterina, M. J. *J Biol Chem.* 2004, 279, 21569-21575). In a keratinocyte cell line, stimulation of TRPV3 leads to release of inflammatory mediators including interleukin-1. Thus TRPV3 may also play an important role in regulating inflammation, itch (Steinhoff, M. and Biro, T. *J. Invest. Dermatology,* 2009, 129, 531-535) and pain that results from the release of inflammatory stimuli. In addition, localization of TRPV3 in non-neuronal tissues, especially skin, suggests also that pharmacological modulation of the channel may provide a therapy to treat diseases that impair the skin barrier (Montell, C. *Cell,* 2010, April 16, 218-220) and have additional, as yet unidentified, benefit for disease states beyond pain. Accordingly, compounds that can modulate one or more functions of TRPV3 can have various therapeutic utilities.

SUMMARY

Disclosed herein are compounds of Formula (I):

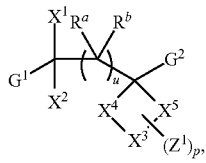

(I)

and pharmaceutically acceptable salts, solvates, salts of solvates, or solvates of salts thereof, wherein:

each occurrence of $R^a$ and $R^b$, are each independently hydrogen, alkyl, haloalkyl, halogen, OH, O(alkyl), or a phenyl group which is optionally substituted with 1, 2, 3, 4, or 5 substituents independently selected from the group consisting of alkyl, haloalkyl, and halogen;

u is 0, 1, or 2;

$X^3$ is $CH_2$, O, S, $S(O)_2$, or $N(R^{1x})$ wherein $R^{1x}$ is hydrogen, alkyl, —C(O)alkyl, or —C(O)O(alkyl);

$X^4$ is a bond or $(CH_2)_m$, and $X^5$ is $(CH_2)_n$, with the proviso that when $X^4$ is a bond and n is 1, then $X^3$ is $CH_2$;

m and n are integers that can be the same or different, and are each independently 1, 2, 3, 4, or 5;

each $Z^1$ group is an optional substituent on any substitutable carbon atom of the ring containing $X^3$, $X^4$, and $X^5$, and is independently alkyl, $C(O)R^{cz}$, $S(O)_2R^{cz}$, $N(R^{1d})(R^{2d})$, $OR^c$, oxo, $=NOR^{z1}$, $=NNR^{z1}R^{z2}$, $=NR^{z3}$, halogen, haloalkyl, —($C_1$-$C_6$ alkylenyl)-$OR^c$, —($C_1$-$C_6$ alkylenyl)-$C(O)R^{cz}$, —($C_1$-$C_6$ alkylenyl)-$S(O)_2R^{cz}$, or —($C_1$-$C_6$ alkylenyl)-$N(R^{1d})(R^{2d})$; two $Z^1$ groups that are resided on the same carbon atom, together with the carbon atom to which they are attached optionally form a 4-6 membered monocyclic cycloalkyl or monocyclic heterocycle ring; wherein said ring is optionally substituted with 1, 2, 3, or 4 substituents independently selected from the group consisting of alkyl, haloalkyl, and halogen;

$R^{z1}$, $R^{z2}$, $R^{z3}$ are each independently hydrogen, alkyl, —C(O)(alkyl), —C(O)-$G^d$, or haloalkyl;

$R^{cz}$, at each occurrence, is independently alkyl, haloalkyl, $NH_2$, N(H)(alkyl), or $N(alkyl)_2$;

$R^{1d}$, at each occurrence, is independently hydrogen, alkyl, haloalkyl, C(O)alkyl, or C(O)O(alkyl);

$R^{2d}$ and $R^c$, at each occurrence, are each independently hydrogen, alkyl, or haloalkyl;

p is 0, 1, 2, 3, or 4;

—$X^1$ is —OH and $X^2$ is hydrogen; or —$X^1$ is =O or =$NOR^{10}$ and $X^2$ is absent;

$R^{10}$ is hydrogen, alkyl, or —C(O)alkyl;

$G^1$ is aryl, heteroaryl, cycloalkyl, heterocycle, or cyclaoalkenyl; each of which is optionally substituted with 1, 2, 3, 4, or 5 substituents independently selected from the group consisting of alkyl, alkenyl, alkynyl, halogen, haloalkyl, $OR^{gc}$, $N(R^{gc})_2$, $N(R^{gc})C(O)alkyl$, heteroaryl, and heterocycle; wherein the heteroaryl and the heterocycle moieties are each independently unsubstituted or substituted with 1, 2, 3, 4, or 5 substituents selected from the group consisting of alkyl, O(alkyl), halogen, and haloalkyl; and wherein each $R^{gc}$ is independently hydrogen, alkyl, or haloalkyl;

$G^2$ is $G^{2d}$ or —$(CR^{1g}R^{2g})_r$-$G^{2d}$ wherein:

r is 1, 2, or 3;

$R^{1g}$ and $R^{2g}$ are the same or different, and are each independently hydrogen, alkyl, halogen, $OR^{1gc}$, $N(R^{1gc})_2$, C(O) alkyl, or haloalkyl; wherein each $R^{1gc}$ is independently hydrogen, alkyl, or haloalkyl;

$G^{2d}$ is aryl, heteroaryl, cycloalkyl, heterocycle, or cyclaoalkenyl, each of which is optionally substituted with 1, 2, 3, 4, or 5 substituents independently selected from the group consisting of $G^d$, alkyl, alkenyl, alkynyl, halogen, haloalkyl, —CN, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$, —$(CR^{1a}R^{1b})_q$-$G^d$, —$(CR^{1a}R^{1b})_q$—$OR^f$, —$(CR^{1a}R^{1b})_q$—$OC(O)R^f$, —$(CR^{1a}R^{1b})_q$—$OC(O)N(R^f)_2$, —$(CR^{1a}R^{1b})_q$—$S(O)_2R^e$, —$(CR^{1a}R^{1b})_q$—$S(O)_2N(R^f)_2$, —$(CR^{1a}R^{1b})_q$—$C(O)R^f$, —$(CR^{1a}R^{1b})_q$—$C(O)OR^f$, —$(CR^{1a}R^{1b})_q$—$C(O)N(R^f)_2$, —$(CR^{1a}R^{1b})_q$—$N(R^f)_2$, —$(CR^{1a}R^{1b})_q$—$N(R^f)C(O)R^f$, —$(CR^{1a}R^{1b})_q$—$N(R^f)S(O)_2R^e$, —$(CR^{1a}R^{1b})_q$—$N(R^f)C(O)O(R^e)$, —$(CR^{1a}R^{1b})_q$—$N(R^f)C(O)N(R^f)_2$, and —$(CR^{1a}R^{1b})_q$—CN;

$R^{1a}$ and $R^{1b}$, are the same or different, and at each occurrence are each independently hydrogen, halogen, alkyl, or haloalkyl;

each occurrence of $R^f$ is independently hydrogen, alkyl, halolalkyl, $G^d$, or —$(CR^{1a}R^{1b})_q$-$G^d$;

each occurrence of $R^e$ is independently alkyl, halolalkyl, $G^d$, or —$(CR^{1a}R^{1b})_q$-$G^d$;

q, at each occurrence, is independently 1, 2, or 3;

each occurrence of $G^d$ is independently aryl, heteroaryl, cycloalkyl, heterocycle, or cycloalkenyl; and is each optionally substituted with 1, 2, 3, 4, or 5 substituents independently selected from the group consisting of alkyl, alkenyl, alkynyl, halogen, haloalkyl, —CN, —$OR^j$, —$OC(O)R^j$, —$OC(O)N(R^j)_2$, —$S(O)_2R^k$, —$S(O)_2N(R^j)_2$, —$C(O)R^j$, —$C(O)OR^j$, —$C(O)N(R^j)_2$, —$N(R^j)_2$, —$N(R^j)C(O)R^j$, —$N(R^j)S(O)_2R^k$, —$N(R^j)C(O)O(R^k)$, —$N(R^j)C(O)N(R^j)_2$, —$(CR^{1a}R^{1b})_q$—$OR^j$, —$(CR^{1a}R^{1b})_q$—$OC(O)R^j$, —$(CR^{1a}R^{1b})_q$—$OC(O)N(R^j)_2$, —$(CR^{1a}R^{1b})_q$—$S(O)_2R^k$, —$(CR^{1a}R^{1b})_q$—$S(O)_2N(R^j)_2$, —$(CR^{1a}R^{1b})_q$—$C(O)R^j$, —$(CR^{1a}R^{1b})_q$—$C(O)OR^j$, —$(CR^{1a}R^{1b})_q$—$C(O)N(R^j)_2$, —$(CR^{1a}R^{1b})_q$—$N(R^j)_2$, —$(CR^{1a}R^{1b})_q$—$N(R^j)C(O)R^j$, —$(CR^{1a}R^{1b})_q$—$N(R^j)S(O)_2R^k$, —$(CR^{1a}R^{1b})_q$—$N(R^j)C(O)O(R^k)$, —$(CR^{1a}R^{1b})_q$—$N(R^j)C(O)N(R^j)_2$, and —$(CR^{1a}R^{1b})_q$—CN;

each occurrence of $R^j$ is independently hydrogen, alkyl, or halolalkyl; and each occurrence of $R^k$ is independently alkyl or halolalkyl.

Another aspect relates to pharmaceutical compositions comprising therapeutically effective amount of a compound described herein or pharmaceutically acceptable salt, solvate, salt of a solvate, or solvate of a salt thereof, in combination with a pharmaceutically acceptable carrier. Such compositions can be administered in accordance with methods described herein, typically as part of a therapeutic regimen for treatment or prevention of conditions and disorders related to TRPV3 activity. More particularly, the methods are useful for treating itch and conditions related to pain such as, but not limited to, chronic pain, acute pain, neuropathic pain, nociceptive pain, osteoarthritic pain, inflammatory pain, fibromyalgia, post herpetic neuralgia, cancer pain (e.g., bone cancer pain), lower back pain, post operative pain, migraine, diabetic neuropathy, and eye pain, or combinations thereof.

Further, provided herein are uses of present compounds or pharmaceutically acceptable salts, solvates, or salts of solvates thereof, in the manufacture of medicaments for the treatment of the disease or conditions described above, alone or in combination with a pharmaceutically acceptable carrier, particularly for the treatment of itch or pain such as, but not limited to, chronic pain, acute pain, neuropathic pain, nociceptive pain, osteoarthritic pain, inflammatory pain, fibromyalgia, post herpetic neuralgia, cancer pain (e.g., bone cancer pain), lower back pain, post operative pain, migraine, diabetic neuropathy, and eye pain, or combinations thereof.

The compounds, compositions comprising the compounds, pharmaceutically acceptable salts, solvates, salts of the solvates, or solvates of the salts thereof, and methods for treating or preventing conditions and disorders by administering the compounds or compositions thereof, are further described herein.

These and other objectives are described further in the following paragraphs. These objectives should not be deemed to narrow the scope of the invention.

DETAILED DESCRIPTION OF THE INVENTION

Compounds of Formula (I):

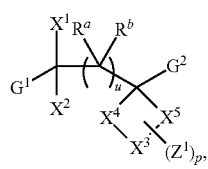

(I)

wherein $G^1$, $X^1$, $X^2$, $X^3$, $X^4$, $X^5$, $G^2$, $Z^1$, $R^a$, $R^b$, u, and p are as defined above in the Summary and below in the Detailed Description, are disclosed. Compositions comprising such compounds and methods for treating conditions and disorders using such compounds and compositions are also disclosed.

In various embodiments, compounds described herein may contain variables that occur more than one time in any substituent or in the compound described or any other formulae herein. Definition of a variable on each occurrence is independent of its definition at another occurrence. Further, combinations of variables are permissible only if such combinations result in stable compounds. Stable compounds are compounds that can be isolated from a reaction mixture.

a. Definitions

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optional a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_4$ alkenyl" means an alkenyl group containing 2-4 carbon atoms. Non-limiting examples of alkenyl include buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of 2 to 4 carbon atoms and contains at least one carbon-carbon double. Representative examples of alkenylene include, but are not limited to, —CH═CH— and —CH$_2$CH═CH—.

The term "alkyl" as used herein, means a straight or branched, saturated hydrocarbon chain containing from 1 to 10 carbon atoms. The term "$C_x$-$C_y$ alkyl" means a straight or branched chain, saturated hydrocarbon containing x to y carbon atoms. For example "$C_1$-$C_6$ alkyl" means a straight or branched chain, saturated hydrocarbon containing 1 to 6 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" means a divalent group derived from a straight or branched, saturated hydrocarbon chain of 1 to 10 carbon atoms, for example, of 1 to 6 carbon atoms. The term "$C_1$-$C_6$ alkylenyl" means a divalent group derived from a straight or branched, saturated hydrocarbon chain of 1 to 6 carbon atoms. Examples of alkylene include, but are not limited to, —CH$_2$—, —C(H)(CH$_3$)—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. The term "$C_2$-$C_4$ alkynyl" means an alkynyl group containing from 2 to 4 carbon atoms. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Non-limiting examples of the aryl groups include dihydroindenyl (e.g., 2,3-dihydro-1H-inden-1-yl), indenyl, naphthyl, dihydronaphthalenyl, and tetrahydronaphthalenyl (e.g., 1,2,3,4-tetrahydronaphthalen-1-yl). The aryl groups can be unsubstituted or substituted, and the bicyclic aryl is attached to the parent molecular moiety through any substitutable carbon atom contained within the bicyclic ring system.

The term "cycloalkyl" or "cycloalkane" as used herein, means a monocyclic or a bicyclic. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. The monocyclic or bicyclic cycloalkyl ring may contain one or two alkylene bridges, each consisting of one, two, three, or four carbon atoms, each linking two non-adjacent carbon atoms of the ring system. Non-limiting examples of such bridged cycloalkyl ring systems include bicyclo[3.1.1]heptane, bicyclo[2.2.1]heptane, bicyclo[2.2.2]octane, bicyclo[3.2.2]nonane, bicyclo[3.3.1]nonane, bicyclo[4.2.1]nonane, tricyclo[3.3.1.0$^{3,7}$]nonane (octahydro-2,5-methanopentalene or noradamantane), and tricyclo[3.3.1.1$^{3,7}$]decane (adamantane). The monocyclic and the bicyclic cycloalkyls can be unsubstituted or substituted, and are attached to the parent molecular moiety through any substitutable atom contained within the ring system.

The term "cycloalkenyl" or "cycloalkene" as used herein, means a monocyclic or a bicyclic hydrocarbon ring system. The monocyclic cycloalkenyl has four-, five-, six-, seven-, or eight-carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, three, or four carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be attached to the parent molecular moiety through any substitutable atom contained within the ring systems, and can be unsubstituted or substituted.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. The term "$C_1$-$C_4$ haloalkyl" means a $C_1$-$C_4$ alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, trifluorobutyl (such as, but not limited to, 4,4,4-trifluorobutyl), and trifluoropropyl (such as, but not limited thereto, 3,3,3-trifluoropropyl).

The term "heterocycle" or "heterocyclic" as used herein, means a monocyclic heterocycle or a bicyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Non-limiting examples of monocyclic heterocycles include azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Non-limiting examples of bicyclic heterocycles include e.g., dihydrochromenyl (e.g., 3,4-dihydro-2H-chromen-4-yl), benzopyranyl, benzothiopyranyl, 2,3-dihydrobenzofuranyl, 2,3-dihydrobenzothienyl, and 2,3-dihydro-1H-indolyl. The monocyclic and the bicyclic heterocycles may contain an alkenylene bridge of two, three, or four carbon atoms, or one or two alkylene bridges of 1, 2, 3, or 4 carbon atoms, or combinations thereof, wherein each bridge links two non-adjacent atoms of the ring system. Non-limiting examples of such bridged heterocycles include octahydro-2,5-epoxypentalene, azabicyclo[2.2.1]heptyl (including 2-azabicyclo[2.2.1]hept-2-yl), hexahydro-2H-2,5-methanocyclopenta[b]furan, hexahydro-1H-1,4-methanocyclopenta[c]furan, aza-admantane (1-azatricyclo[3.3.1.1$^{3,7}$]-decane), and oxa-adamantane (2-oxatricyclo[3.3.1.1$^{3,7}$]decane). The monocyclic and the bicyclic heterocycles can be unsubstituted or substituted, and are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quarternized.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Non-limiting examples of bicyclic heteroaryl groups include benzofuranyl, benzothienyl, benzoxazolyl, benzimidazolyl, benzoxadiazolyl, 6,7-dihydro-5H-cyclopenta[b]pyridinyl (e.g., 6,7-dihydro-5H-cyclopenta[b]pyridin-7-yl), 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolinyl (e.g., 5,6,7,8-tetrahydroquinolin-5-yl, 5,6,7,8-tetrahydroquinolin-8-yl). The monocyclic and bicyclic heteroaryl groups can be substituted or unsubstituted and are connected to the parent molecular moiety through any substitutable carbon atom or any substitutable nitrogen atom contained within the ring systems.

The term "heteroatom" as used herein, means a nitrogen, oxygen, or sulfur atom.

The term "oxo" as used herein, means a =O group.

"Treatment," "treat," or "treating" pain includes acute or chronic pain and refers to: (1) preventing pain, i.e. causing pain not to develop or occur with less intensity in a subject that may be exposed or predisposed to pain but does not yet experience or display pain, (2) inhibiting pain, i.e., arresting the development or reversing pain, or (3) relieving pain, i.e., decreasing the amount of pain experienced by the subject.

The term "subject" includes animals such as mammals, including, but not limited to, primates (e.g., humans), cows, sheep, goats, horses, dogs, cats, rabbits, rats, mice and the like. In preferred embodiments, the subject is a human.

b. Compounds

Compounds of Formula (I) are as described above.

Particular values of variable groups in compounds of Formula (I) are as follows. Such values may be used where appropriate with any of the other values, definitions, claims, or embodiments defined hereinbefore or hereinafter.

$R^a$, $R^b$, and u have values as described in the Summary. For example, in certain embodiments, u is 0 or 1. In certain embodiments, u is 0. In yet other embodiments, u is 1. In conjunction with any of the embodiments described herein above or below, $R^a$ and $R^b$, for example, are hydrogen or alkyl (e.g., methyl), or for example, $R^a$ and $R^b$ are hydrogen.

Examples of compounds of Formula (I) wherein u is 0 can be exemplified by compounds of Formula (I-a):

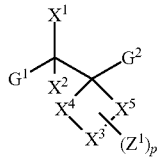
(I-a)

wherein $G^1$, $G^2$, $X^1$, $X^2$, $X^3$, $X^4$, $X^5$, $Z^1$, and p are as disclosed in the Summary and embodiments herein below.

$X^1$ and $X^2$ for Formula (I) and (I-a) have values as described in the Summary and embodiments herein below.

For example, in certain embodiments, —$X^1$ is —OH and $X^2$ is hydrogen, as exemplified by Formula (I-i):

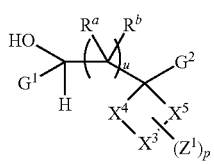
(I-i)

Compounds of Formula (I-i) can exist as stereoisomers wherein asymmetric or chiral centers are present. Thus, contemplated are compounds of Formula (I-i-a), (I-i-b), and mixtures (including racemic mixtures) of various ratios thereof:

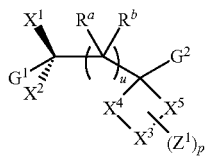
(I-i-a)

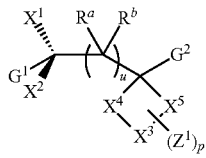
(I-i-b)

In certain embodiments, $X^2$ is absent, and —$X^1$ is =O or =$NOR^{10}$ wherein $R^{10}$ is hydrogen, alkyl, or —C(O)alkyl. Thus, included, but not limited to, are compounds of Formula (I-ii):

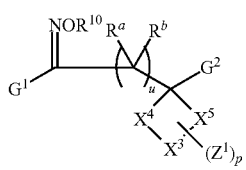
(I-ii)

$G^1$, $G^2$, $X^3$, $X^4$, $X^5$, $Z^1$, $R^{10}$, $R^a$, $R^b$, u, and p for Formula (I-a), (I-i), (I-i-a), (I-i-b), and (I-ii) have values as described in the Summary for Formula (I) and embodiments herein.

In conjunction with any of the embodiments disclosed above and below, $R^{10}$ has values as described in the Summary and herein. For example, in certain embodiments $R^{10}$ is hydrogen.

$X^3$, $X^4$, and $X^5$ for compounds of Formula (I), (I-a), (I-i), (I-i-a), (I-i-b), and (I-ii) are as described in the Summary. $X^3$, for example, is $CH_2$, O, or $N(R^{1x})$. In certain embodiments, $X^3$, for example, is O or $N(R^{1x})$. In certain embodiments, $X^3$, for example, is $CH_2$ or O. In certain embodiments, $X^3$ is O. In certain embodiments, $X^3$ is $CH_2$. In certain embodiments, $X^3$, for example, is $N(R^{1x})$.

In certain embodiments, $X^3$ is O or $N(R^{1x})$, $X^4$ is $(CH_2)_m$, and $X^5$ is $(CH_2)_n$ wherein m is 1, 2, or 3, and n is 1 or 2.

In certain embodiments, $X^3$ is $N(R^{1x})$, $X^4$ is $(CH_2)_m$, and $X^5$ is $(CH_2)_n$ wherein m is 1, 2, or 3, and n is 1 or 2.

In certain embodiments, $X^3$ is $N(R^{1x})$, $X^4$ is a bond, $X^5$ is $(CH_2)_n$, and n is 2, 3, or 4.

In certain embodiments, $X^3$ is O, $X^4$ is $(CH_2)_m$, and $X^5$ is $(CH_2)_n$ wherein m is 1, 2, or 3, and n is 1 or 2.

In certain embodiments, $X^3$ is O, $X^4$ is a bond, $X^5$ is $(CH_2)_n$, and n is 2, 3, or 4.

In certain embodiments, $X^3$ is $CH_2$, $X^4$ is a bond or $(CH_2)_m$, and $X^5$ is $(CH_2)_n$; wherein m and n are each independently 1 or 2.

In conjunction with embodiments herein above and below, $R^{1x}$ has values as described in the Summary. For example, $R^{1x}$ is hydrogen, alkyl (e.g., methyl), or —C(O)O(alkyl) (e.g., —C(O)O(tert-butyl)).

In certain embodiments, $X^3$, $X^4$, and $X^5$ together is:

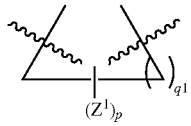
(a)

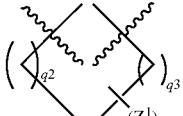
(b)

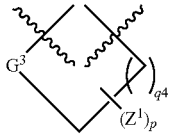
(c)

wherein $G^3$ is O or $N(R^{1x})$, q1 is 1, 2, 3, or 4, q2 and q4, are each independently 1, 2, or 3; q3 is 1 or 2; and the curvy lines represent the points of attachment. In certain embodiments, $X^3$, $X^4$, and $X^5$ together is Formula (a). In still other embodiments, $X^3$, $X^4$, and $X^5$ together is Formula (a), and q1 is 1, 2, or 4. In still other embodiments, $X^3$, $X^4$, and $X^5$ together is Formula (a), and q1 is 2. In yet other embodiments, $X^3$, $X^4$, and $X^5$ together is Formula (b) or Formula (c), wherein $G^3$ is O, and q2, q3, and q4 are each independently 1 or 2.

p is 0, 1, 2, 3, or 4. In certain embodiments, p is 0, 1, or 2. In other embodiments, p is 0 or 1. In yet other embodiments, p is 0. In still other embodiments, p is 1. In still other embodiments, p is 2. In still other embodiments, both p and us are 0.

In conjunction with embodiments herein above and below, each $Z^1$ represents optional substituent on any substitutable carbon atom of the ring containing $X^3$, $X^4$, and $X^5$, and has values as disclosed in the Summary. For example, each $Z^1$, when present, is independently alkyl (e.g., methyl), $OR^c$, oxo, or halogen (e.g., F).

In certain embodiments of compounds of Formula (I), (I-a), (I-i), (I-i-a), (I-i-b), and (I-ii), $X^3$ is $CH_2$, p is 1 or 2, and each $Z^1$ is independently alkyl (e.g., methyl) or $OR^c$.

In the embodiments wherein $X^3$, $X^4$, and $X^5$ together is Formula (a), examples of the compounds of Formula (I) include those as depicted in Formula (I-iii):

(I-iii)

wherein q1 is 1, 2, 3, or 4. In certain embodiments, q1 is 2.

In the embodiments wherein q1 is 2 in Formula (I-iii), such compounds can be represented by Formula (I-iv):

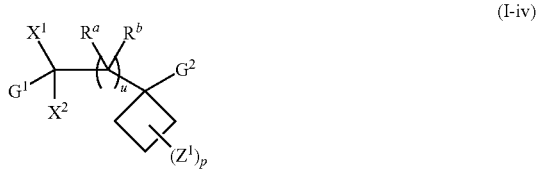

(I-iv)

The variables $G^1$, $G^2$, $X^1$, $X^2$, $R^a$, $R^b$, u, $Z^1$, and p of Formula (I-iii) and (I-iv) are as described in the Summary and the embodiments herein above and below.

In the embodiments wherein the variable, p, in Formula (I-iv) is 2, and that two different $Z^1$ groups are situated on the third carbon atom of the cyclobutyl moiety; or when p is 1 and the $Z^1$ group is situated on the third carbon atom of the cyclobutyl moiety; various geometric isomers resulting from the disposal of these substituents ($Z^1$) around such symmetrical cyclobutyl moiety are contemplated and are within the scope of this invention. For example, Formula (I-iv-a) and (I-iv-b) wherein p is 1 and the $Z^1$ group is $OR^c$, or p is 2, and one of the $Z^1$ groups is alkyl and the other is $OR^c$ represent some of the geometric forms that compounds of Formula (I-iv) possess:

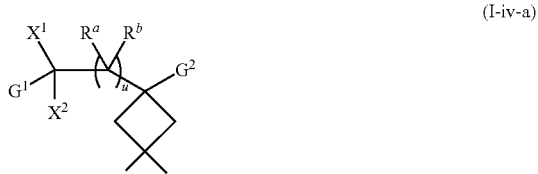

(I-iv-a)

(I-iv-b)

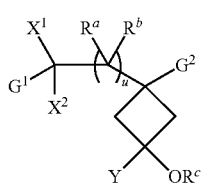

Y is H or alkyl wherein the variables $G^1$, $G^2$, $X^1$, $X^2$, $R^a$, $R^b$, $R^c$, and u of Formula (I-iv-a) and (I-iv-b) are as described in the Summary and the embodiments herein above and below.

In Formula (I-iv-a) the $OR^c$ group is on the same face of the cyclobutane ring as the substituent containing $X^1$ and is assigned the "cis" configuration while Formula (I-iv-b) is assigned the "trans" configuration with the $OR^c$ group on the opposite face of the cyclobutane ring as the substituent containing $X^1$. It is understood that both geometric isomers and mixtures thereof of various ratios are within the scope of the present invention.

$G^1$ for Formula (I), (I-a), (I-i), (I-i-a), (I-i-b), (I-ii), (I-iii), (I-iv), (I-iv-a), and (I-iv-b) are as described in the Summary. In certain embodiments, $G^1$ is heteroaryl or cycloalkyl. In certain embodiments, $G^1$ is heteroaryl. In certain embodiments, $G^1$ is cycloalkyl. Each ring as represented by $G^1$ is optionally substituted as described in the Summary and embodiments herein.

In the embodiments wherein $G^1$ is optionally substituted heteroaryl, $G^1$, for example, is an optionally substituted monocyclic heteroaryl (e.g., pyridinyl, pyrimidinyl, thiazolyl, oxazolyl, or pyrazolyl, each of which is optionally substituted). In yet other embodiments, $G^1$ is an optionally substituted bicyclic heteroaryl (e.g., 6,7-dihydro-5H-cyclopenta[b]pyridinyl, and 5,6,7,8-tetrahydroquinolinyl, each of which is optionally substituted). In the embodiments wherein $G^1$ is an optionally substituted heteroaryl, examples of the heteroaryl group include, but not limited thereto, pyridinyl, pyrimidinyl, thiazolyl, oxazolyl, pyrazolyl, 6,7-dihydro-5H-cyclopenta[b]pyridinyl, and 5,6,7,8-tetrahydroquinolinyl, each of which is optionally substituted as described in the Summary and embodiments herein. In certain embodiments, $G^1$ is optionally substituted pyridinyl. In yet other embodiments, G1 is optionally substituted pyridin-2-yl.

In certain embodiments, $G^1$ is an optionally substituted cycloalkyl. In certain embodiments, $G^1$ is a substituted cycloalkyl. Examples of the cycloalkyl group include, but are not limited to, cyclobutyl, cyclopentyl, and cyclohexyl.

In conjunction with embodiments described herein above and below, examples of the substituents of $G^1$, if present, include, but not limited to, alkyl (e.g., methyl, ethyl), halogen, haloalkyl, and $N(R^{gc})_2$. In the embodiments wherein $G^1$ is a substituted cycloalkyl, the cycloalkyl group, for example, can be substituted with one $N(R^{gc})_2$ group, and is optionally further substituted with one or two substituents selected from alkyl (e.g., methyl, ethyl), halogen, or haloalkyl. In certain embodiments, the $N(R^{gc})_2$ on the cycloalkyl moiety is situated on the carbon atom adjacent to the point of connection. In conjunction with the embodiments herein above and below, $R^{gc}$, for example, is hydrogen or alkyl (e.g., methyl).

$G^2$ for Formula (I), (I-a), (I-i), (I-i-a), (I-i-b), (I-ii), (I-iii), (I-iv), (I-iv-a), and (I-iv-b) are as described in the Summary. In certain embodiments, $G^2$ is $G^{2d}$ wherein $G^{2d}$ is aryl, heteroaryl, heterocycle, or cycloalkyl; each of which is optionally substituted. In other embodiments, $G^2$ is $G^{2d}$ wherein $G^{2d}$ is optionally substituted aryl or optionally substituted cycloalkyl. In the embodiments wherein $G^2$ is $G^{2d}$ and $G^{2d}$ is optionally substituted aryl, examples of the aryl group include, but are not limited to, phenyl, 2,3-dihydroindenyl, and 1,2,3,4-tetrahydronaphthalenyl, each of which is optionally substituted as described in the Summary and herein. In certain embodiments, $G^2$ is $G^{2d}$ wherein $G^{2d}$ is optionally substituted phenyl. In the embodiments wherein $G^2$ is $G^{2d}$ and $G^{2d}$ is optionally substituted heteroaryl, an example of the optionally substituted heteroaryl includes, but not limited to, optionally substituted pyridinyl. In the embodiments wherein $G^2$ is $G^{2d}$ and $G^{2d}$ is optionally substituted heterocycle, an example of the optionally substituted heterocycle includes, but not limited to, optionally substituted dihydrochromenyl. In the embodiments wherein $G^2$ is $G^{2d}$ and $G^{2d}$ is optionally substituted cycloalkyl, examples of the optionally substituted cycloalkyl include, but not limited to, optionally substituted cyclopentyl and optionally substituted cyclohexyl. The optional substituents of the above mentioned $G^{2d}$ groups (including the exemplary rings) are as described in the Summary and embodiments herein.

In yet other embodiments, $G^2$ is —$(CR^{1g}R^{2g})_r$-$G^{2d}$ wherein $R^{1g}$, $R^{2g}$, r, and $G^{2d}$ are as described in the Summary and embodiments herein. In certain embodiments, $G^2$ is —$(CR^{1g}R^{2g})_r$-$G^{2d}$ wherein $G^{2d}$ is aryl (e.g., phenyl) or heteroaryl (e.g., pyridinyl), each of the $G^{2d}$ rings (including the exemplary rings) is optionally substituted as described in the Summary and embodiments herein. In still other embodiments, $G^2$ is —$(CR^{1g}R^{2g})_r$-$G^{2d}$ wherein $G^{2d}$ is optionally substituted aryl (e.g., optionally substituted phenyl). In yet other embodiments, $G^2$ is —$(CR^{1g}R^{2g})_r$-$G^{2d}$ wherein $G^{2d}$ is optionally substituted heteroaryl (e.g., optionally substituted monocyclic heteroaryl such as, but not limited to, optionally substituted pyridinyl). In conjunction with the embodiments described herein above and below, $R^{1g}$, $R^{2g}$, and r, and the optional substituents of $G^{2d}$, are as described in the Summary and herein. In certain embodiments, $R^{1g}$ and $R^{2g}$ are, for example, hydrogen. In certain embodiments, one of $R^{1g}$ and $R^{2g}$ is hydrogen, and the other is alkyl (e.g., methyl) or haloalkyl (e.g., trifluoromethyl). In yet other embodiments, one of $R^{1g}$ and $R^{2g}$ is hydrogen, and the other is alkyl (e.g., methyl). In yet other embodiments, one of $R^{1g}$ and $R^{2g}$ is hydrogen, and the other is methyl. r, for example, is 1 or 2. In certain embodiments, r is 1.

In conjunction with the above and below embodiments, examples of the optional substituents of $G^{2d}$ include, but are not limited to, alkyl (e.g., methyl), halogen (e.g., F, Cl), haloalkyl (e.g., trifluoromethyl), CN, —$OR^f$ ($R^f$ is as described in the Summary, for example, $R^f$ is alkyl such as, but not limited to, methyl; haloalkyl such as, but not limited to, trifluoromethyl; or optionally substituted phenyl), —$S(O)_2 R^e$ ($R^e$, for example, is $C_1$-$C_4$ alkyl such as, but not limited to, methyl), $G^d$ (e.g., optionally substituted phenyl), $N(R^f)_2$ (each $R^f$, for example, is independently hydrogen, $C_1$-$C_6$ alkyl such as, but not limited to, methyl, ethyl), and —$(CR^{1a}R^{1b})_q$-$G^d$ (e.g., $CH_2$-phenyl). In certain embodiments, the optional substituents of $G^{2d}$ include, but not limited to, alkyl (e.g., methyl), halogen (e.g., fluorine, chlorine), haloalkyl (e.g., trifluoromethyl), —O(alkyl), or —O(haloalkyl).

It is appreciated that the present invention contemplates compounds of Formula (I), (I-a), (I-i), (I-i-a), (I-i-b), (I-ii), (I-iii), (I-iv), (I-iv-a), and (I-iv-b) with combinations of the above embodiments, including particular, more particular and preferred embodiments.

Accordingly, one aspect is directed to a group of compounds of Formula (I), (I-a), (I-i), (I-i-a), (I-i-b), (I-ii), (I-iii), (I-iv), (I-iv-a), and (I-iv-b) wherein $G^1$ is heteroaryl or cycloalkyl, each of which is optionally substituted; and $G^2$ is $G^{2d}$. In certain embodiments, $G^{2d}$ is aryl, heteroaryl, heterocycle, or cycloalkyl, each of which is optionally substituted. In certain embodiments, $G^{2d}$ is optionally substituted aryl or optionally substituted cycloalkyl. In certain embodiments, $G^{2d}$ is optionally substituted aryl. In certain embodiments, $G^{2d}$ is optionally substituted phenyl. In certain embodiments, $G^{2d}$ is optionally substituted cycloalkyl. In certain embodiments, $G^{2d}$ is optionally substituted heteroaryl. In still other embodiments, $G^{2d}$ is optionally substituted heterocycle. The optional substituents and exemplary rings of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), and (I-iv-b) wherein $G^1$ is optionally substituted heteroaryl; and $G^2$ is $G^{2d}$. In certain embodiments, $G^{2d}$ is aryl, heteroaryl, heterocycle, or cycloalkyl, each of which is optionally substituted. In certain embodiments, $G^{2d}$ is optionally substituted aryl or optionally substituted cycloalkyl. In certain embodiments, $G^{2d}$ is optionally substituted aryl. In certain embodiments, $G^{2d}$ is optionally substituted phenyl. In certain embodiments, $G^{2d}$ is optionally substituted cycloalkyl. In certain embodiments, $G^{2d}$ is optionally substituted heteroaryl. In still other embodiments, $G^{2d}$ is optionally substituted heterocycle. The optional substituents and exemplary rings of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), and (I-iv-b) wherein $G^1$ is optionally substituted monocyclic heteroaryl; and $G^2$ is $G^{2d}$. In certain embodiments, $G^{2d}$ is aryl, heteroaryl, heterocycle, or cycloalkyl, each of which is optionally substituted. In certain embodiments, $G^{2d}$ is optionally substituted aryl or optionally substituted cycloalkyl. In certain embodiments, $G^{2d}$ is optionally substituted aryl. In certain embodiments, $G^{2d}$ is optionally substituted phenyl. In certain embodiments, $G^{2d}$ is optionally substituted cycloalkyl. In certain embodiments, $G^{2d}$ is optionally substituted heteroaryl. In still other embodiments, $G^{2d}$ is optionally substituted heterocycle. The optional substituents and exemplary rings of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), and (I-iv-b) wherein $G^1$ is optionally substituted pyridinyl (e.g., pyridin-2-yl); and $G^2$ is $G^{2d}$. In certain embodiments, $G^{2d}$ is aryl, heteroaryl, heterocycle, or cycloalkyl, each of which is optionally substituted. In certain embodiments, $G^{2d}$ is optionally substituted aryl or optionally substituted cycloalkyl. In certain embodiments, $G^{2d}$ is optionally substituted aryl. In certain embodiments, $G^{2d}$ is optionally substituted phenyl. In certain embodiments, $G^{2d}$ is optionally substituted cycloalkyl. In certain embodiments, $G^{2d}$ is optionally substituted heteroaryl. In still other embodiments, $G^{2d}$ is optionally substituted heterocycle. The optional substituents and exemplary rings of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), and (I-iv-b) wherein $G^1$ is optionally substituted pyridinyl (e.g., pyridin-2-yl); and $G^2$ is $G^{2d}$ wherein $G^{2d}$ is optionally substituted aryl (e.g., optionally substituted phenyl, optionally substituted dihydroindenyl, or optionally substituted tetrahydronaphthalenyl). The optional substituents of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), and (I-iv-b) wherein $G^1$ is optionally substituted pyridinyl (e.g., pyridin-2-yl); and $G^2$ is $G^{2d}$ wherein $G^{2d}$ is optionally substituted phenyl. The optional substituents of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), and (I-iv-b) wherein $G^1$ is optionally substituted pyridinyl (e.g., pyridin-2-yl); and $G^2$ is $G^{2d}$ wherein $G^{2d}$ is optionally substituted heteroaryl (e.g., optionally substituted pyridinyl). The optional substituents of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), and (I-iv-b) wherein $G^1$ is optionally substituted pyridinyl (e.g., pyridin-2-yl); and $G^2$ is $G^{2d}$ wherein $G^{2d}$ is optionally substituted cycloalkyl (e.g., optionally substituted cyclopentyl, optionally substituted cyclohexyl). The optional substituents of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), and (I-iv-b) wherein $G^1$ is optionally substituted cycloalkyl; and $G^2$ is $G^{2d}$. In certain embodiments, $G^{2d}$ is optionally substituted aryl. In certain embodiments, $G^{2d}$ is optionally substituted phenyl. The optional substituents and the exemplary rings of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), and (I-iv-b) wherein $G^1$ is substituted cycloalkyl; and $G^2$ is $G^{2d}$. In certain embodiments, $G^{2d}$ is optionally substituted aryl. In certain embodiments, $G^{2d}$ is optionally substituted phenyl. The optional substituents and the exemplary rings of $G^1$ and $G^{2d}$ are as described in the Summary and embodiments herein above.

Yet another aspect is directed to a group of compounds of Formula (I), (I-a), (I-i), (I-i-a), (I-i-b), (I-ii), (I-iii), (I-iv), (I-iv-a), and (I-iv-b) wherein $G^1$ is optionally substituted heteroaryl; and $G^2$ is $-(CR^{1g}R^{2g})_r-G^{2d}$. In one embodiment, $G^{2d}$ is aryl or heteroaryl, each of which is optionally substituted. In certain embodiments, $G^{2d}$ is optionally substituted aryl. In yet other embodiments, $G^{2d}$ is optionally substituted phenyl. $R^{1g}$, $R^{2g}$, r, the optional substituents of $G^1$ and $G^{2d}$, and the exemplary rings of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), and (I-iv-b) wherein $G^1$ is optionally substituted monocyclic heteroaryl; and $G^2$ is $-(CR^{1g}R^{2g})_r-G^{2d}$. In one embodiment, $G^{2d}$ is aryl or heteroaryl, each of which is optionally substituted. In certain embodiments, $G^{2d}$ is optionally substituted aryl. In yet other embodiments, $G^{2d}$ is optionally substituted phenyl. $R^{1g}$, $R^{2g}$, r, the optional substituents of $G^1$ and $G^{2d}$, and the exemplary rings of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), and (I-iv-b) wherein $G^1$ is optionally substituted pyridinyl (e.g., pyridin-2-yl); and $G^2$ is $-(CR^{1g}R^{2g})_r-G^{2d}$. In one embodiment, $G^{2d}$ is aryl or heteroaryl, each of which is optionally substituted. In certain embodiments, $G^{2d}$ is optionally substituted aryl. In yet other embodiments, $G^{2d}$ is optionally substituted phenyl. $R^{1g}$, $R^{2g}$, r, and the optional substituents of $G^1$ and $G^{2d}$ are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), and (I-iv-b) wherein $G^1$ is optionally substituted pyridinyl (e.g., pyridin-2-yl); and $G^2$ is $-(CR^{1g}R^{2g})_r-G^{2d}$ wherein $G^{2d}$ is optionally substituted aryl (e.g., optionally substituted phenyl). The optional substituents of $G^1$ and $G^{2d}$, $R^{1g}$, $R^{2g}$, and r, are as described in the Summary and embodiments herein above.

Another aspect is directed to a group of compounds of Formula (I), (I-a), (I-i), (I-i-a), (I-i-b), (I-ii), (I-iii), (I-iv), (I-iv-a), and (I-iv-b) wherein $G^1$ is optionally substituted pyridinyl (e.g., pyridin-2-yl); and $G^2$ is $-(CR^{1g}R^{2g})_r-G^{2d}$ wherein $G^{2d}$ optionally substituted phenyl. The optional substituents of $G^1$ and $G^{2d}$, $R^{1g}$, $R^{2g}$, and r are as described in the Summary and embodiments herein above.

Yet another aspect is directed to a group of compounds of Formula (I), (I-iii), (I-iv), (I-iv-a), and (I-iv-b) wherein $G^1$ is an optionally substituted heteroaryl (e.g., monocyclic heteroaryl such as, but not limited to, pyridinyl, pyrimidinyl, each of which is optionally substituted as described in the Summary and embodiments herein above), $-X^1$ is $-OH$, $X^2$ is hydrogen, u is 0 or 1, $G^2$ is $G^{2d}$, and $G^{2d}$ is optionally substituted aryl. In certain embodiments, $G^1$ is optionally substituted pyridinyl (e.g., pyridin-2-yl). In yet other embodiments, $G^1$ is optionally substituted pyridinyl (e.g., pyridin-2-yl) and u is 0.

Yet another aspect is directed to a group of compounds of Formula (I), (I-iii), (I-iv), (I-iv-a), and (I-iv-b) wherein $G^1$ is an optionally substituted heteroaryl (e.g., monocyclic heteroaryl such as, but not limited to, pyridinyl, pyrimidinyl, each of which is optionally substituted as described in the Summary and embodiments herein above), $-X^1$ is $-OH$, $X^2$ is hydrogen, u is 0 or 1, $G^2$ is $G^{2d}$, and $G^{2d}$ is optionally substituted cycloalkyl (e.g., cyclopentyl, cyclohexyl, each of which is optionally substituted). In certain embodiments, $G^1$ is optionally substituted pyridinyl (e.g., pyridin-2-yl). In yet other embodiments, $G^1$ is optionally substituted pyridinyl (e.g., pyridin-2-yl), and u is 0.

Yet another aspect is directed to a group of compounds of Formula (I), (I-iii), (I-iv), (I-iv-a), and (I-iv-b) wherein $G^1$ is an optionally substituted heteroaryl (e.g., monocyclic heteroaryl such as, but not limited to, pyridinyl, pyrimidinyl, each of which is optionally substituted as described in the Summary and embodiments herein above), $-X^1$ is $-OH$, $X^2$ is hydrogen, u is 0 or 1, $G^2$ is $-(CR^{1g}R^{2g})_r-G^{2d}$, and $G^{2d}$ is optionally substituted aryl. In certain embodiments, $G^1$ is optionally substituted pyridinyl (e.g., pyridin-2-yl). In yet other embodiments, $G^1$ is optionally substituted pyridinyl (e.g., pyridin-2-yl), and u is 0. $R^{1g}$, $R^{2g}$, and r are as described in the Summary and embodiments herein.

Yet another aspect is directed to a group of compounds of Formula (I), (I-iii), (I-iv), (I-iv-a), and (I-iv-b) wherein $G^1$ is an optionally substituted cycloalkyl (e.g., cyclobutyl, cyclopentyl, cyclohexyl, each of which is optionally substituted), $-X^1$ is $-OH$, $X^2$ is hydrogen, u is 0 or 1, $G^2$ is $G^{2d}$, and $G^{2d}$ is optionally substituted phenyl. In certain embodiments, $G^1$ is a substituted cycloalkyl (e.g., cyclobutyl, cyclopentyl, cyclohexyl, each of which is substituted as described in the Summary and embodiments herein above) and u is 0.

Yet another aspect is directed to a group of compounds of Formula (I), (I-iii), (I-iv), (I-iv-a), and (I-iv-b) wherein $G^1$ is an optionally substituted heteroaryl (e.g., monocyclic heteroaryl such as, but not limited to, pyridinyl, pyrimidinyl, each of which is optionally substituted as described in the Summary and embodiments herein above), $-X^1$ is $=NOR^{10}$, $X^2$ is absent, u is 0 or 1, $G^2$ is $G^{2d}$, and $G^{2d}$ is optionally substituted aryl. In certain embodiments, $G^1$ is optionally substituted pyridinyl (e.g., pyridin-2-yl). In yet other embodiments, $G^1$ is optionally substituted pyridinyl (e.g., pyridin-2-yl) and u is 0. $R^{10}$ is as described in the summary and embodiments herein above.

Within each group of the compounds described above, $X^3$, $X^4$, $X^5$, u. $R^a$, $R^b$, $Z^1$, p, $X^1$, and $X^2$ are as described in the Summary and embodiments herein above. Thus, within each group of the compounds described above, examples of a subgroup of compounds of Formula (I), (I-a), (I-i), (I-i-a), (I-i-b), (I-ii), (I-iii), (I-iv), (I-iv-a), and (I-iv-b) include, but not limited to, those wherein $X^3$ is $CH_2$, O, or $N(R^{1x})$.

Examples of another subgroup of compounds of Formula (I), (I-a), (I-i), (I-i-a), (I-i-b), (I-ii), (I-iii), (I-iv), (I-iv-a), and (I-iv-b) include, but not limited to, those wherein $X^3$ is $CH_2$ or O.

Examples of another subgroup of compounds of Formula (I), (I-a), (I-i), (I-i-a), (I-i-b), (I-ii), (I-iii), (I-iv), (I-iv-a), and (I-iv-b) include, but not limited to, those wherein $X^3$ is O.

Other examples of a subgroup of compounds of Formula (I), (I-a), (I-i), (I-i-a), (I-i-b), (I-ii), (I-iii), (I-iv), (I-iv-a), and (I-iv-b) include, but not limited to, those wherein $X^3$ is $CH_2$.

Other examples of a subgroup of compounds of Formula (I), (I-a), (I-i), (I-i-a), (I-i-b), (I-ii), (I-iii), (I-iv), (I-iv-a), and (I-iv-b) include, but not limited to, those wherein $X^3$ is $N(R^{1x})$.

Yet other examples of a subgroup of compounds of Formula (I), (I-a), (I-i), (I-i-a), (I-i-b), (I-ii), (I-iii), (I-iv), (I-iv-a), and (I-iv-b) include, but not limited to, those wherein $X^3$ is O or $N(R^{1x})$, $X^4$ is $(CH_2)_m$, $X^5$ is $(CH_2)_n$, m is 1, 2, or 3, and n is 1 or 2.

Yet other examples of a subgroup of compounds of Formula (I), (I-a), (I-i), (I-i-a), (I-i-b), (I-ii), (I-iii), (I-iv), (I-iv-a), and (I-iv-b) include, but not limited to, those wherein $X^3$ is O, $X^4$ is $(CH_2)_m$, $X^5$ is $(CH_2)_n$, m is 1, 2, or 3, and n is 1 or 2.

Yet other examples of a subgroup of compounds of Formula (I), (I-a), (I-i), (I-i-a), (I-i-b), (I-ii), (I-iii), (I-iv), (I-iv-a), and (I-iv-b) include, but not limited to, those wherein $X^3$ is O, $X^4$ is a bond, $X^5$ is $(CH_2)_n$, and n is 2, 3, or 4.

Yet other examples of a subgroup of compounds of Formula (I), (I-a), (I-i), (I-i-a), (I-i-b), (I-ii), (I-iii), (I-iv), (I-iv-a), and (I-iv-b) include, but not limited to, those wherein $X^3$ is $CH_2$, $X^4$ is a bond or $(CH_2)_m$, $X^5$ is $(CH_2)_n$, and m and n are each independently 1 or 2.

Yet other examples of a subgroup of compounds of Formula (I), (I-a), (I-i), (I-i-a), (I-i-b), (I-ii), (I-iii), (I-iv), (I-iv-a), and (I-iv-b) include, but not limited to, those wherein $X^3$, $X^4$, and $X^5$ together are Formula (a), (b), or (c). In certain embodiments, $X^3$, $X^4$, and $X^5$ together are Formula (a). $X^3$, $X^4$, and $X^5$ together are Formula (b) or Formula (c). In certain embodiments, q1 is 1, 2, or 4. In certain embodiments, q1 is 2. In certain embodiments, $G^3$ is O and q2, q3, and q4 are each independently 1 or 2.

Yet other examples of a subgroup of compounds of Formula (I), (I-i), (I-i-a), (I-i-b), (I-ii), (I-iii), (I-iv), (I-iv-a), and (I-iv-b) include, but not limited to, those wherein u is 0 or 1.

Yet other examples of a subgroup of compounds of Formula (I), (I-a), (I-iii), (I-iv), (I-iv-a), and (I-iv-b) include, but not limited to, those wherein —$X^1$ is —OH and $X^2$ is hydrogen.

Yet other examples of a subgroup of compounds of Formula (I), (I-a), (I-iii), (I-iv), (I-iv-a), and (I-iv-b) include, but not limited to, those wherein —$X^1$ is =$NOR^{10}$ and $X^2$ is absent.

Further representative embodiments are set forth below:
(i) Oxetanyl or Tetrahydrofuranyl Ring In one embodiment, the invention is directed to compounds of Formula (II) (i.e., compounds of Formula (I) wherein p is 0):

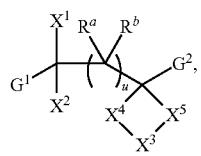

(II)

wherein:
each occurrence of $R^a$ and $R^b$, are each independently hydrogen, alkyl, haloalkyl, halogen, OH, O(alkyl), or a phenyl group which is optionally substituted with 1, 2, 3, 4, or 5 substituents independently selected from the group consisting of alkyl, haloalkyl, and halogen;

u is 0, 1, or 2;

$X^3$ is O; $X^4$ is a bond, $X^5$ is $(CH_2)_n$, and n is 2; or
$X^3$ is O; $X^4$ is $(CH_2)_m$, $X^5$ is $(CH_2)_n$, m and n are each 1; or
$X^3$ is O; $X^4$ is $(CH_2)_m$, $X^5$ is $(CH_2)_n$, m is 1, and n is 2; or
$X^3$ is O; $X^4$ is a bond, $X^5$ is $(CH_2)_n$, and n is 3; and
$X^1$ is —OH and $X^2$ is hydrogen;

$G^1$ is aryl, heteroaryl, cycloalkyl, heterocycle, or cycloalkenyl; each of which is optionally substituted with 1, 2, 3, 4, or 5 substituents independently selected from the group consisting of alkyl, alkenyl, alkynyl, halogen, haloalkyl, $OR^{gc}$, $N(R^{gc})_2$, $N(R^{gc})C(O)$alkyl, heteroaryl, and heterocycle; wherein the heteroaryl and the heterocycle moieties are each independently unsubstituted or substituted with 1, 2, 3, 4, or 5 substituents selected from the group consisting of alkyl, O(alkyl), halogen, and haloalkyl; and wherein each $R^{gc}$ is independently hydrogen, alkyl, or haloalkyl;

$G^2$ is $G^{2d}$ or —$(CR^{1g}R^{2g})_r$-$G^{2d}$ wherein:
r is 1, 2, or 3;
$R^{1g}$ and $R^{2g}$ are the same or different, and are each independently hydrogen, alkyl, halogen, $OR^{1gc}$, $N(R^{1gc})_2$, $C(O)$alkyl, or haloalkyl; wherein each $R^{1gc}$ is independently hydrogen, alkyl, or haloalkyl;

$G^{2d}$ is aryl, heteroaryl, cycloalkyl, heterocycle, or cycloalkenyl, each of which is optionally substituted with 1, 2, 3, 4, or 5 substituents independently selected from the group consisting of $G^d$, alkyl, alkenyl, alkynyl, halogen, haloalkyl, —CN, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$, —$(CR^{1a}R^{1b})_q$-$G^d$, —$(CR^{1a}R^{1b})_q$—$OR^f$, —$(CR^{1a}R^{1b})_q$—$OC(O)R^f$, —$(CR^{1a}R^{1b})_q$—$OC(O)N(R^f)_2$, —$(CR^{1a}R^{1b})_q$—$S(O)_2R^e$, —$(CR^{1a}R^{1b})_q$—$S(O)_2N(R^f)_2$, —$(CR^{1a}R^{1b})_q$—$C(O)R^f$, —$(CR^{1a}R^{1b})_q$—$C(O)OR^f$, —$(CR^{1a}R^{1b})_q$—$C(O)N(R^f)_2$, —$(CR^{1a}R^{1b})_q$—$N(R^f)_2$, —$(CR^{1a}R^{1b})_q$—$N(R^f)C(O)R^f$, —$(CR^{1a}R^{1b})_q$—$N(R^f)S(O)_2R^e$, —$(CR^{1a}R^{1b})_q$—$N(R^f)C(O)O(R^e)$, —$(CR^{1a}R^{1b})_q$—$N(R^f)C(O)N(R^f)_2$, and —$(CR^{1a}R^{1b})_q$—CN;

$R^{1a}$ and $R^{1b}$, are the same or different, and at each occurrence are each independently hydrogen, halogen, alkyl, or haloalkyl;

each occurrence of $R^f$ is independently hydrogen, alkyl, halolalkyl, $G^d$, or —$(CR^{1a}R^{1b})_q$-$G^d$;

each occurrence of $R^e$ is independently alkyl, halolalkyl, $G^d$, or —$(CR^{1a}R^{1b})_q$-$G^d$;

q, at each occurrence, is independently 1, 2, or 3;

each occurrence of $G^d$ is independently aryl, heteroaryl, cycloalkyl, heterocycle, or cycloalkenyl; and is each optionally substituted with 1, 2, 3, 4, or 5 substituents independently selected from the group consisting of alkyl, alkenyl, alkynyl, halogen, haloalkyl, —CN, —$OR^j$, —$OC(O)R^j$, —$OC(O)N(R^j)_2$, —$S(O)_2R^k$, —$S(O)_2N(R^j)_2$, —$C(O)R^j$, —$C(O)OR^j$, —$C(O)N(R^j)_2$, —$N(R^j)_2$, —$N(R^j)C(O)R^j$, —$N(R^j)S(O)_2R^k$, —$N(R^j)C(O)O(R^k)$, —$N(R^j)C(O)N(R^j)_2$, —$(CR^{1a}R^{1b})_q$—$OR^j$, —$(CR^{1a}R^{1b})_q$—$OC(O)R^j$, —$(CR^{1a}R^{1b})_q$—$OC(O)N(R^j)_2$, —$(CR^{1a}R^{1b})_q$—$S(O)_2R^k$, —$(CR^{1a}R^{1b})_q$—$S(O)_2N(R^j)_2$, —$(CR^{1a}R^{1b})_q$—$C(O)R^j$, —$(CR^{1a}R^{1b})_q$—$C(O)OR^j$, —$(CR^{1a}R^{1b})_q$—$C(O)N(R^j)_2$, —$(CR^{1a}R^{1b})_q$—$N(R^j)_2$, —$(CR^{1a}R^{1b})_q$—$N(R^j)C(O)R^j$, —$(CR^{1a}R^{1b})_q$—$N(R^j)S(O)_2R^k$, —$(CR^{1a}R^{1b})_q$—$N(R^j)C(O)O(R^k)$, —$(CR^{1a}R^{1b})_q$—$N(R^j)C(O)N(R^j)_2$, and —$(CR^{1a}R^{1b})_q$—CN;

each occurrence of $R^j$ is independently hydrogen, alkyl, or halolalkyl; and each occurrence of $R^k$ is independently alkyl or halolalkyl.

In a preferred embodiment, u is 0. In further embodiments, the compound has the configuration of Formula (II-i-a):

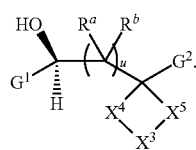

(II-i-a)

In one embodiment, the invention is directed to compounds of Formula (II) wherein:

u is 0;

$X^3$ is O; $X^4$ is a bond, $X^5$ is $(CH_2)_n$, and n is 2; or
$X^3$ is O; $X^4$ is $(CH_2)_m$, $X^5$ is $(CH_2)_n$, m and n are each 1; or
$X^3$ is O; $X^4$ is $(CH_2)_m$, $X^5$ is $(CH_2)_n$, m is 1, and n is 2; or
$X^3$ is O; $X^4$ is a bond, $X^5$ is $(CH_2)_n$, and n is 3; and
$X^1$ is —OH and $X^2$ is hydrogen;

$G^1$ is optionally substituted heteroaryl or optionally substituted cycloalkyl;

$G^2$ is $G^{2d}$; and $G^{2d}$ is optionally substituted aryl or optionally substituted heteroaryl.

In a further embodiment, the compound has the configuration of Formula (II-i-a).

In one embodiment, the invention is directed to compounds of Formula (II) wherein:

u is 0;

$X^3$ is O; $X^4$ is a bond, $X^5$ is $(CH_2)_n$, and n is 2; or
$X^3$ is O; $X^4$ is $(CH_2)_m$, $X^5$ is $(CH_2)_n$, m and n are each 1; or
$X^3$ is O; $X^4$ is $(CH_2)_m$, $X^5$ is $(CH_2)_n$, m is 1, and n is 2; or
$X^3$ is O; $X^4$ is a bond, $X^5$ is $(CH_2)_n$, and n is 3; and
$X^1$ is —OH and $X^2$ is hydrogen;

$G^1$ is optionally substituted pyridinyl, pyrimidinyl, thiazolyl, oxazolyl, or pyrazolyl;

$G^2$ is $G^{2d}$; and $G^{2d}$ is optionally substituted phenyl or optionally substituted pyridinyl.

In a further embodiment, the compound has the configuration of Formula (II-i-a).

In one embodiment, the invention is directed to compounds of Formula (II) wherein:

u is 0;

$X^3$ is O; $X^4$ is a bond, $X^5$ is $(CH_2)_n$, and n is 2; or
$X^3$ is O; $X^4$ is $(CH_2)_m$, $X^5$ is $(CH_2)_n$, m and n are each 1; or
$X^3$ is O; $X^4$ is $(CH_2)_m$, $X^5$ is $(CH_2)_n$, m is 1, and n is 2; or
$X^3$ is O; $X^4$ is a bond, $X^5$ is $(CH_2)_n$, and n is 3; and
$X^1$ is —OH and $X^2$ is hydrogen;

$G^1$ is pyridinyl or pyrimidinyl; each of which is optionally substituted with 1, 2, or 3 substituents independently selected from the group consisting of halogen, $C_1$-$C_6$-alkyl, $C_1$-$C_6$-haloalkyl, and $N(R^{gc})_2$;

$R^{gc}$ is hydrogen or $C_1$-$C_6$-alkyl;

$G^2$ is $G^{2d}$;

$G^{2d}$ is phenyl, pyridinyl, or pyrimidinyl; each of which is optionally substituted with 1, 2, or 3 substituents independently selected from the group consisting of halogen, —CN, $C_1$-$C_6$-alkyl, $C_1$-$C_6$-haloalkyl, and —$OR^f$; and $R^f$ is $C_1$-$C_6$-alkyl or $C_1$-$C_6$-haloalkyl.

In a further embodiment, the compound has the configuration of Formula (II-i-a).

In one embodiment, the invention is directed to compounds of Formula (II) wherein:

u is 0;

$X^3$ is O; $X^4$ is a bond, $X^5$ is $(CH_2)_n$, and n is 2; or
$X^3$ is O; $X^4$ is $(CH_2)_m$, $X^5$ is $(CH_2)_n$, m and n are each 1; or
$X^3$ is O; $X^4$ is $(CH_2)_m$, $X^5$ is $(CH_2)_n$, m is 1, and n is 2; or
$X^3$ is O; $X^4$ is a bond, $X^5$ is $(CH_2)_n$, and n is 3; and
$X^1$ is —OH and $X^2$ is hydrogen;

$G^1$ is pyridinyl which is optionally substituted with 1 or 2 substituents independently selected from the group consisting of halogen, $C_1$-$C_4$-alkyl, $C_1$-$C_4$-haloalkyl, and $N(R^{gc})_2$;

$R^{gc}$ is hydrogen or $C_1$-$C_4$-alkyl;

$G^2$ is $G^{2d}$;

$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —$OR^f$; and $R^f$ is $C_1$-$C_4$-alkyl or $C_1$-$C_4$-haloalkyl.

In a further embodiment, the compound has the configuration of Formula (II-i-a).

In one embodiment, the invention is directed to compounds of Formula (II) wherein:

u is 0;

$X^3$ is O; $X^4$ is a bond, $X^5$ is $(CH_2)_n$, and n is 2; or
$X^3$ is O; $X^4$ is $(CH_2)_m$, $X^5$ is $(CH_2)_n$, m and n are each 1; or
$X^3$ is O; $X^4$ is $(CH_2)_m$, $X^5$ is $(CH_2)_n$, m is 1, and n is 2; or
$X^3$ is O; $X^4$ is a bond, $X^5$ is $(CH_2)_n$, and n is 3; and
$X^1$ is —OH and $X^2$ is hydrogen;

$G^1$ is unsubstituted pyridinyl;

$G^2$ is $G^{2d}$;

$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —$OR^f$; and $R^f$ is $C_1$-$C_4$-alkyl or $C_1$-$C_4$-haloalkyl.

In a further embodiment, the compound has the configuration of Formula (II-i-a).

In one embodiment, the invention is directed to compounds of Formula (II) wherein:

u is 0;

$X^3$ is O; $X^4$ is a bond, $X^5$ is $(CH_2)_n$, and n is 2; or
$X^3$ is O; $X^4$ is $(CH_2)_m$, $X^5$ is $(CH_2)_n$, m and n are each 1; or
$X^3$ is O; $X^4$ is $(CH_2)_m$, $X^5$ is $(CH_2)_n$, m is 1, and n is 2; or
$X^3$ is O; $X^4$ is a bond, $X^5$ is $(CH_2)_n$, and n is 3; and
$X^1$ is —OH and $X^2$ is hydrogen;

$G^1$ is unsubstituted pyridin-2-yl;

$G^2$ is $G^{2d}$;

$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:

u is 0;

$X^3$ is O; $X^4$ is a bond, $X^5$ is $(CH_2)_n$, and n is 2; or
$X^3$ is O; $X^4$ is $(CH_2)_m$, $X^5$ is $(CH_2)_n$, m and n are each 1; or
$X^3$ is O; $X^4$ is $(CH_2)_m$, $X^5$ is $(CH_2)_n$, m is 1, and n is 2; or
$X^3$ is O; $X^4$ is a bond, $X^5$ is $(CH_2)_n$, and n is 3; and
$X^1$ is —OH and $X^2$ is hydrogen;

$G^1$ is unsubstituted pyridin-2-yl;

$G^2$ is $G^{2d}$;

$G^{2d}$ is phenyl which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:
u is 0;
$X^3$ is O; $X^4$ is a bond, $X^5$ is $(CH_2)_n$, and n is 2; or
$X^3$ is O; $X^4$ is $(CH_2)_m$, $X^5$ is $(CH_2)_n$, m and n are each 1; or
$X^3$ is O; $X^4$ is $(CH_2)_m$, $X^5$ is $(CH_2)_n$, m is 1, and n is 2; or
$X^3$ is O; $X^4$ is a bond, $X^5$ is $(CH_2)_n$, and n is 3; and
$X^1$ is —OH and $X^2$ is hydrogen;
$G^1$ is unsubstituted pyridin-2-yl;
$G^2$ is $G^{2d}$;
$G^{2d}$ is phenyl which is substituted with 1, 2, or 3 substituents independently selected from the group consisting of halogen, $C_1$-$C_3$-alkyl, and $C_1$-$C_3$-haloalkyl.

In a further embodiment, the compound has the configuration of Formula (II-i-a).

In one embodiment, the invention is directed to compounds of Formula (II) wherein:
u is 0;
$X^3$ is O; $X^4$ is a bond, $X^5$ is $(CH_2)_n$, and n is 2; or
$X^3$ is O; $X^4$ is $(CH_2)_m$, $X^5$ is $(CH_2)_n$, m and n are each 1; or
$X^3$ is O; $X^4$ is $(CH_2)_m$, $X^5$ is $(CH_2)_n$, m is 1, and n is 2; or
$X^3$ is O; $X^4$ is a bond, $X^5$ is $(CH_2)_n$, and n is 3; and
$X^1$ is —OH and $X^2$ is hydrogen;
$G^1$ is unsubstituted pyridin-2-yl;
$G^2$ is $G^{2d}$;
$G^{2d}$ is phenyl which is substituted with 1, 2, or 3 substituents independently selected from halogen.

In a further embodiment, the compound has the configuration of Formula (II-i-a).

In one embodiment, the invention is directed to compounds of Formula (II) wherein:
u is 0;
$X^3$ is O; $X^4$ is a bond, $X^5$ is $(CH_2)_n$, and n is 2; or
$X^3$ is O; $X^4$ is $(CH_2)_m$, $X^5$ is $(CH_2)_n$, m and n are each 1; or
$X^3$ is O; $X^4$ is $(CH_2)_m$, $X^5$ is $(CH_2)_n$, m is 1, and n is 2; or
$X^3$ is O; $X^4$ is a bond, $X^5$ is $(CH_2)_n$, and n is 3; and
$X^1$ is —OH and $X^2$ is hydrogen;
$G^1$ is unsubstituted pyridin-2-yl;
$G^2$ is $G^{2d}$;
$G^{2d}$ is pyridinyl which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:
u is 0;
$X^3$ is O; $X^4$ is a bond, $X^5$ is $(CH_2)_n$, and n is 2;
$X^1$ is —OH and $X^2$ is hydrogen;
$G^1$ is unsubstituted pyridin-2-yl or unsubstituted pyrimidin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:
u is 0;
$X^3$ is O; $X^4$ is a bond, $X^5$ is $(CH_2)_n$, and n is 2;
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:
u is 0;
$X^3$ is O; $X^4$ is a bond, $X^5$ is $(CH_2)_n$, and n is 2;
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of chloro, fluoro, trifluoromethyl, and —$OR^f$; and $R^f$ is trifluoromethyl.

In a further embodiment, the compound has the configuration of Formula (II-i-a).

In one embodiment, the invention is directed to compounds of Formula (II) wherein:
u is 0;
$X^3$ is O; $X^4$ is $(CH_2)_m$, $X^5$ is $(CH_2)_n$, m and n are each 1;
$X^1$ is —OH and $X^2$ is hydrogen;
$G^1$ is unsubstituted pyridin-2-yl or unsubstituted pyrimidin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:
u is 0;
$X^3$ is O; $X^4$ is $(CH_2)_m$, $X^5$ is $(CH_2)_n$, m and n are each 1;
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:
u is 0;
$X^3$ is O; $X^4$ is $(CH_2)_m$, $X^5$ is $(CH_2)_n$, m and n are each 1;
$X^1$ is —OH and $X^2$ is hydrogen;
$G^1$ is unsubstituted pyridin-2-yl;
$G^2$ is $G^{2d}$;

$G^{2d}$ is phenyl or pyridinyl; each of which is optionally substituted with 1, 2, or 3 substituents independently selected from the group consisting of chloro, fluoro, trifluoromethyl, and —OR$^f$; and $R^f$ is trifluoromethyl.

In a further embodiment, the compound has the configuration of Formula (II-i-a).

In one embodiment, the invention is directed to compounds of Formula (II) wherein:

u is 0;
$X^3$ is O; $X^4$ is $(CH_2)_m$, $X^5$ is $(CH_2)_n$, m is 1, and n is 2;
$X^1$ is —OH and $X^2$ is hydrogen;
$G^1$ is unsubstituted pyridin-2-yl or unsubstituted pyrimidin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —OR$^f$; and
$R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:

u is 0;
$X^3$ is O; $X^4$ is $(CH_2)_m$, $X^5$ is $(CH_2)_n$, m is 1, and n is 2;
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —OR$^f$; and
$R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:

u is 0;
$X^3$ is O; $X^4$ is $(CH_2)_m$, $X^5$ is $(CH_2)_n$, m is 1, and n is 2;
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of chloro, fluoro, trifluoromethyl, and —OR$^f$; and
$R^f$ is trifluoromethyl.

In a further embodiment, the compound has the configuration of Formula (II-i-a).

In one embodiment, the invention is directed to compounds of Formula (II) wherein:

u is 0;
$X^3$ is O; $X^4$ is a bond, $X^5$ is $(CH_2)_n$, and n is 3; and
$X^1$ is —OH and $X^2$ is hydrogen;
$G^1$ is unsubstituted pyridin-2-yl or unsubstituted pyrimidin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —OR$^f$; and
$R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:

u is 0;
$X^3$ is O; $X^4$ is a bond, $X^5$ is $(CH_2)_n$, and n is 3; and
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —OR$^f$; and
$R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:

u is 0;
$X^3$ is O; $X^4$ is a bond, $X^5$ is $(CH_2)_n$, and n is 3; and
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of chloro, fluoro, trifluoromethyl, and —OR$^f$; and
$R^f$ is trifluoromethyl.

In a further embodiment, the compound has the configuration of Formula (II-i-a).

In one embodiment, the compound of Formula (I) is selected from the group consisting of:

pyridin-2-yl{3-[4-(trifluoromethyl)phenyl]tetrahydrofuran-3-yl}methanol;
4-{3-[hydroxy(pyridin-2-yl)methyl]tetrahydrofuran-3-yl}benzonitrile;
pyridin-2-yl{3-[3-(trifluoromethoxy)phenyl]tetrahydrofuran-3-yl}methanol;
3-{3-[hydroxy(pyridin-2-yl)methyl]tetrahydrofuran-3-yl}benzonitrile;
[3-(4-methoxyphenyl)tetrahydrofuran-3-yl](pyridin-2-yl)methanol;
[3-(3,4-dimethoxyphenyl)tetrahydrofuran-3-yl](pyridin-2-yl)methanol;
[3-(3-chlorophenyl)oxetan-3-yl](pyridin-2-yl)methanol;
[3-(3,4-dichlorophenyl)oxetan-3-yl](pyridin-2-yl)methanol;
(anti)-pyridin-2-yl{2-[4-(trifluoromethyl)phenyl]tetrahydrofuran-2-yl}-methanol;
(syn)-pyridin-2-yl{2-[4-(trifluoromethyl)phenyl]tetrahydrofuran-2-yl}-methanol;
[2-(2-methylphenyl)tetrahydrofuran-2-yl](pyridin-2-yl)methanol;
[2-(3-methylphenyl)tetrahydrofuran-2-yl](pyridin-2-yl)methanol;
(anti)-pyridin-2-yl{2-[3-(trifluoromethoxy)phenyl]tetrahydrofuran-2-yl}-methanol;
(syn)-pyridin-2-yl{2-[3-(trifluoromethoxy)phenyl]tetrahydrofuran-2-yl}-methanol;
(anti)-pyridin-2-yl{2-[4-(trifluoromethoxy)phenyl]tetrahydrofuran-2-yl}-methanol;
(syn)-pyridin-2-yl{2-[4-(trifluoromethoxy)phenyl]tetrahydrofuran-2-yl}-methanol;
(anti)-pyridin-2-yl{2-[2-(trifluoromethoxy)phenyl]tetrahydrofuran-2-yl}-methanol;
(syn)-pyridin-2-yl{2-[2-(trifluoromethoxy)phenyl]tetrahydrofuran-2-yl}-methanol;
(anti)-[2-(3,4-dichlorophenyl)tetrahydrofuran-2-yl](pyridin-2-yl)methanol;
(syn)-[2-(3,4-dichlorophenyl)tetrahydrofuran-2-yl](pyridin-2-yl)methanol;

(anti)-[2-(3-fluorophenyl)tetrahydrofuran-2-yl](pyridin-2-yl)methanol;
(syn)-[2-(3-fluorophenyl)tetrahydrofuran-2-yl](pyridin-2-yl)methanol;
(anti)-[2-(2-fluorophenyl)tetrahydrofuran-2-yl](pyridin-2-yl)methanol;
(syn)-[2-(2-fluorophenyl)tetrahydrofuran-2-yl](pyridin-2-yl)methanol;
(anti)-[2-(3-chlorophenyl)tetrahydrofuran-2-yl](pyridin-2-yl)methanol;
(syn)-[2-(3-chlorophenyl)tetrahydrofuran-2-yl](pyridin-2-yl)methanol;
(anti)-pyridin-2-yl{2-[3-(trifluoromethyl)phenyl]tetrahydrofuran-2-yl}-methanol;
(syn)-pyridin-2-yl{2-[3-(trifluoromethyl)phenyl]tetrahydrofuran-2-yl}-methanol;
(anti)-[2-(3,4-difluorophenyl)tetrahydrofuran-2-yl](pyridin-2-yl)methanol;
(syn)-[2-(3,4-difluorophenyl)tetrahydrofuran-2-yl](pyridin-2-yl)methanol;
(R)-[(2S)-2-(3,4-dichlorophenyl)oxetan-2-yl](pyridin-2-yl)methanol; and
(R)-[(2R)-2-(3,4-dichlorophenyl)oxetan-2-yl](pyridin-2-yl)methanol.

(ii) Cyclopentyl, Azetidinyl, Pyrrolidinyl, or Piperidinyl Ring

In one embodiment, the invention is directed to compounds of Formula (II):

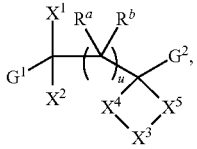

(II)

wherein:

each occurrence of $R^a$ and $R^b$, are each independently hydrogen, alkyl, haloalkyl, halogen, OH, O(alkyl), or a phenyl group which is optionally substituted with 1, 2, 3, 4, or 5 substituents independently selected from the group consisting of alkyl, haloalkyl, and halogen;

u is 0, 1, or 2;

$X^3$ is $CH_2$, $X^4$ is $(CH_2)_m$, $X^5$ is $(CH_2)_n$, m is 1, and n is 2; or $X^3$ is NH, $X^4$ is $(CH_2)_m$ and $X^5$ is $(CH_2)_n$, and m and n are each 1; or $X^3$ is NH, $X^4$ is $(CH_2)_m$ and $X^5$ is $(CH_2)_n$, m is 1, and n is 2; or $X^3$ is NH, $X^4$ is $(CH_2)_m$ and $X^5$ is $(CH_2)_n$, and m and n are each 2; and $X^1$ is —OH and $X^2$ is hydrogen;

$G^1$ is aryl, heteroaryl, cycloalkyl, heterocycle, or cycloalkenyl; each of which is optionally substituted with 1, 2, 3, 4, or 5 substituents independently selected from the group consisting of alkyl, alkenyl, alkynyl, halogen, haloalkyl, $OR^{gc}$, $N(R^{gc})_2$, $N(R^{gc})C(O)$alkyl, heteroaryl, and heterocycle; wherein the heteroaryl and the heterocycle moieties are each independently unsubstituted or substituted with 1, 2, 3, 4, or 5 substituents selected from the group consisting of alkyl, O(alkyl), halogen, and haloalkyl; and wherein each $R^{gc}$ is independently hydrogen, alkyl, or haloalkyl;

$G^2$ is $G^{2d}$ or —$(CR^{1g}R^{2g})_r$-$G^{2d}$ wherein:

r is 1, 2, or 3;

$R^{1g}$ and $R^{2g}$ are the same or different, and are each independently hydrogen, alkyl, halogen, $OR^{1gc}$, $N(R^{1gc})_2$, $C(O)$alkyl, or haloalkyl; wherein each $R^{1gc}$ is independently hydrogen, alkyl, or haloalkyl;

$G^{2d}$ is aryl, heteroaryl, cycloalkyl, heterocycle, or cycloalkenyl, each of which is optionally substituted with 1, 2, 3, 4, or 5 substituents independently selected from the group consisting of $G^d$, alkyl, alkenyl, alkynyl, halogen, haloalkyl, —CN, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$, —$(CR^{1a}R^{1b})_q$-$G^d$, —$(CR^{1a}R^{1b})_q$—$OR^f$, —$(CR^{1a}R^{1b})_q$—$OC(O)R^f$, —$(CR^{1a}R^{1b})_q$—$OC(O)N(R^f)_2$, —$(CR^{1a}R^{1b})_q$—$S(O)_2R^e$, —$(CR^{1a}R^{1b})_q$—$S(O)_2N(R^f)_2$, —$(CR^{1a}R^{1b})_q$—$C(O)R^f$, —$(CR^{1a}R^{1b})_q$—$C(O)OR^f$, —$(CR^{1a}R^{1b})_q$—$C(O)N(R^f)_2$, —$(CR^{1a}R^{1b})_q$—$N(R^f)_2$, —$(CR^{1a}R^{1b})_q$—$N(R^f)C(O)R^f$, —$(CR^{1a}R^{1b})_q$—$N(R^f)S(O)_2R^e$, —$(CR^{1a}R^{1b})_q$—$N(R^f)C(O)O(R^e)$, —$(CR^{1a}R^{1b})_q$—$N(R^f)C(O)N(R^f)_2$, and —$(CR^{1a}R^{1b})_q$—CN;

$R^{1a}$ and $R^{1b}$, are the same or different, and at each occurrence are each independently hydrogen, halogen, alkyl, or haloalkyl;

each occurrence of $R^f$ is independently hydrogen, alkyl, haloalkyl, $G^d$, or —$(CR^{1a}R^{1b})_q$-$G^d$;

each occurrence of $R^e$ is independently alkyl, haloalkyl, $G^d$, or —$(CR^{1a}R^{1b})_q$-$G^d$;

q, at each occurrence, is independently 1, 2, or 3;

each occurrence of $G^d$ is independently aryl, heteroaryl, cycloalkyl, heterocycle, or cycloalkenyl; and is each optionally substituted with 1, 2, 3, 4, or 5 substituents independently selected from the group consisting of alkyl, alkenyl, alkynyl, halogen, haloalkyl, —CN, —$OR^j$, —$OC(O)R^j$, —$OC(O)N(R^j)_2$, —$S(O)_2R^k$, —$S(O)_2N(R^j)_2$, —$C(O)R^j$, —$C(O)OR^j$, —$C(O)N(R^j)_2$, —$N(R^j)_2$, —$N(R^j)C(O)R^j$, —$N(R^j)S(O)_2R^k$, —$N(R^j)C(O)O(R^k)$, —$N(R^j)C(O)N(R^j)_2$, —$(CR^{1a}R^{1b})_q$—$OR^j$, —$(CR^{1a}R^{1b})_q$—$OC(O)R^j$, —$(CR^{1a}R^{1b})_q$—$OC(O)N(R^j)_2$, —$(CR^{1a}R^{1b})_q$—$S(O)_2R^k$, —$(CR^{1a}R^{1b})_q$—$S(O)_2N(R^j)_2$, —$(CR^{1a}R^{1b})_q$—$C(O)R^j$, —$(CR^{1a}R^{1b})_q$—$C(O)OR^j$, —$(CR^{1a}R^{1b})_q$—$C(O)N(R^j)_2$, —$(CR^{1a}R^{1b})_q$—$N(R^j)_2$, —$(CR^{1a}R^{1b})_q$—$N(R^j)C(O)R^j$, —$(CR^{1a}R^{1b})_q$—$N(R^j)S(O)_2R^k$, —$(CR^{1a}R^{1b})_q$—$N(R^j)C(O)O(R^k)$, —$(CR^{1a}R^{1b})_q$—$N(R^j)C(O)N(R^j)_2$, and —$(CR^{1a}R^{1b})_q$—CN;

each occurrence of $R^j$ is independently hydrogen, alkyl, or halolalkyl; and each occurrence of $R^k$ is independently alkyl or haloalkyl.

In a preferred embodiment, u is 0. In further embodiments, the compound has the configuration of Formula (II-i-a):

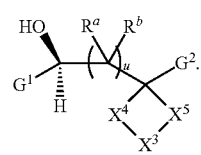

(II-i-a)

In one embodiment, the invention is directed to compounds of Formula (II) wherein:

u is 0;

$X^3$ is $CH_2$, $X^4$ is $(CH_2)_m$, $X^5$ is $(CH_2)_n$, m is 1, and n is 2; or $X^3$ is NH, $X^4$ is $(CH_2)_m$ and $X^5$ is $(CH_2)_n$, and m and n are each 1; or $X^3$ is NH, $X^4$ is $(CH_2)_m$ and $X^5$ is $(CH_2)_n$, m is 1, and n is 2; or $X^3$ is NH, $X^4$ is $(CH_2)_m$ and $X^5$ is $(CH_2)_n$, and m and n are each 2; and $X^1$ is —OH and $X^2$ is hydrogen;

$G^1$ is optionally substituted heteroaryl or optionally substituted cycloalkyl;

$G^2$ is $G^{2d}$; and $G^{2d}$ is optionally substituted aryl or optionally substituted heteroaryl.

In a further embodiment, the compound has the configuration of Formula (II-i-a).

In one embodiment, the invention is directed to compounds of Formula (II) wherein:

u is 0;

$X^3$ is $CH_2$, $X^4$ is $(CH_2)_m$, $X^5$ is $(CH_2)_n$, m is 1, and n is 2; or
$X^3$ is NH, $X^4$ is $(CH_2)_m$ and $X^5$ is $(CH_2)_n$, and m and n are each 1; or
$X^3$ is NH, $X^4$ is $(CH_2)_m$ and $X^5$ is $(CH_2)_n$, m is 1, and n is 2; or
$X^3$ is NH, $X^4$ is $(CH_2)_m$ and $X^5$ is $(CH_2)_n$, and m and n are each 2; and $X^1$ is —OH and $X^2$ is hydrogen;

$G^1$ is optionally substituted pyridinyl, pyrimidinyl, thiazolyl, oxazolyl, or pyrazolyl;

$G^2$ is $G^{2d}$; and $G^{2d}$ is optionally substituted phenyl or optionally substituted pyridinyl.

In a further embodiment, the compound has the configuration of Formula (II-i-a).

In one embodiment, the invention is directed to compounds of Formula (II) wherein:

u is 0;

$X^3$ is $CH_2$, $X^4$ is $(CH_2)_m$, $X^5$ is $(CH_2)_n$, m is 1, and n is 2; or
$X^3$ is NH, $X^4$ is $(CH_2)_m$ and $X^5$ is $(CH_2)_n$, and m and n are each 1; or
$X^3$ is NH, $X^4$ is $(CH_2)_m$ and $X^5$ is $(CH_2)_n$, m is 1, and n is 2; or
$X^3$ is NH, $X^4$ is $(CH_2)_m$ and $X^5$ is $(CH_2)_n$, and m and n are each 2; and $X^1$ is —OH and $X^2$ is hydrogen;

$G^1$ is pyridinyl or pyrimidinyl; each of which is optionally substituted with 1, 2, or 3 substituents independently selected from the group consisting of halogen, $C_1$-$C_6$-alkyl, $C_1$-$C_6$-haloalkyl, and $N(R^{gc})_2$;

$R^{gc}$ is hydrogen or $C_1$-$C_6$-alkyl;

$G^2$ is $G^{2d}$;

$G^{2d}$ is phenyl, pyridinyl, or pyrimidinyl; each of which is optionally substituted with 1, 2, or 3 substituents independently selected from the group consisting of halogen, —CN, $C_1$-$C_6$-alkyl, $C_1$-$C_6$-haloalkyl, and —$OR^f$; and $R^f$ is $C_1$-$C_6$-alkyl or $C_1$-$C_6$-haloalkyl.

In a further embodiment, the compound has the configuration of Formula (II-i-a).

In one embodiment, the invention is directed to compounds of Formula (II) wherein:

u is 0;

$X^3$ is $CH_2$, $X^4$ is $(CH_2)_m$, $X^5$ is $(CH_2)_n$, m is 1, and n is 2; or
$X^3$ is NH, $X^4$ is $(CH_2)_m$ and $X^5$ is $(CH_2)_n$, and m and n are each 1; or
$X^3$ is NH, $X^4$ is $(CH_2)_m$ and $X^5$ is $(CH_2)_n$, m is 1, and n is 2; or
$X^3$ is NH, $X^4$ is $(CH_2)_m$ and $X^5$ is $(CH_2)_n$, and m and n are each 2; and $X^1$ is —OH and $X^2$ is hydrogen;

$G^1$ is pyridinyl which is optionally substituted with 1 or 2 substituents independently selected from the group consisting of halogen, $C_1$-$C_4$-alkyl, $C_1$-$C_4$-haloalkyl, and $N(R^{gc})_2$;

$R^{gc}$ is hydrogen or $C_1$-$C_4$-alkyl;

$G^2$ is $G^{2d}$;

$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —$OR^f$; and $R^f$ is $C_1$-$C_4$-alkyl or $C_1$-$C_4$-haloalkyl.

In a further embodiment, the compound has the configuration of Formula (II-i-a).

In one embodiment, the invention is directed to compounds of Formula (II) wherein:

u is 0;

$X^3$ is $CH_2$, $X^4$ is $(CH_2)_m$, $X^5$ is $(CH_2)_n$, m is 1, and n is 2; or
$X^3$ is NH, $X^4$ is $(CH_2)_m$ and $X^5$ is $(CH_2)_n$, and m and n are each 1; or
$X^3$ is NH, $X^4$ is $(CH_2)_m$ and $X^5$ is $(CH_2)_n$, m is 1, and n is 2; or
$X^3$ is NH, $X^4$ is $(CH_2)_m$ and $X^5$ is $(CH_2)_n$, and m and n are each 2; and $X^1$ is —OH and $X^2$ is hydrogen;

$G^1$ is unsubstituted pyridinyl;

$G^2$ is $G^{2d}$;

$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —$OR^f$; and $R^f$ is $C_1$-$C_4$-alkyl or $C_1$-$C_4$-haloalkyl.

In a further embodiment, the compound has the configuration of Formula (II-i-a).

In one embodiment, the invention is directed to compounds of Formula (II) wherein:

u is 0;

$X^3$ is $CH_2$, $X^4$ is $(CH_2)_m$, $X^5$ is $(CH_2)_n$, m is 1, and n is 2; or
$X^3$ is NH, $X^4$ is $(CH_2)_m$ and $X^5$ is $(CH_2)_n$, and m and n are each 1; or
$X^3$ is NH, $X^4$ is $(CH_2)_m$ and $X^5$ is $(CH_2)_n$, m is 1, and n is 2; or
$X^3$ is NH, $X^4$ is $(CH_2)_m$ and $X^5$ is $(CH_2)_n$, and m and n are each 2; and $X^1$ is —OH and $X^2$ is hydrogen;

$G^1$ is unsubstituted pyridin-2-yl;

$G^2$ is $G^{2d}$;

$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:

u is 0;

$X^3$ is $CH_2$, $X^4$ is $(CH_2)_m$, $X^5$ is $(CH_2)_n$, m is 1, and n is 2; or
$X^3$ is NH, $X^4$ is $(CH_2)_m$ and $X^5$ is $(CH_2)_n$, and m and n are each 1; or
$X^3$ is NH, $X^4$ is $(CH_2)_m$ and $X^5$ is $(CH_2)_n$, m is 1, and n is 2; or
$X^3$ is NH, $X^4$ is $(CH_2)_m$ and $X^5$ is $(CH_2)_n$, and m and n are each 2; and $X^1$ is —OH and $X^2$ is hydrogen;

$G^1$ is unsubstituted pyridin-2-yl;

$G^2$ is $G^{2d}$;

$G^{2d}$ is phenyl which is optionally substituted with 1, 2, or 3 substituents independently selected from the group consisting of halogen, $C_1$-$C_3$-alkyl, $C_1$-$C_3$-haloalkyl, and —$OR^f$; and $R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:
u is 0;
$X^3$ is $CH_2$, $X^4$ is $(CH_2)_m$, $X^5$ is $(CH_2)_n$, m is 1, and n is 2; or
$X^3$ is NH, $X^4$ is $(CH_2)_m$ and $X^5$ is $(CH_2)_n$, and m and n are each 1; or
$X^3$ is NH, $X^4$ is $(CH_2)_m$ and $X^5$ is $(CH_2)_n$, m is 1, and n is 2; or
$X^3$ is NH, $X^4$ is $(CH_2)_m$ and $X^5$ is $(CH_2)_n$, and m and n are each 2; and
$X^1$ is —OH and $X^2$ is hydrogen;
$G^1$ is unsubstituted pyridin-2-yl;
$G^2$ is $G^{2d}$;
$G^{2d}$ is pyridinyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:
u is 0;
$X^3$ is $CH_2$, $X^4$ is $(CH_2)_m$, $X^5$ is $(CH_2)_n$, m is 1, and n is 2;
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:
u is 0;
$X^3$ is NH, $X^4$ is $(CH_2)_m$ and $X^5$ is $(CH_2)_n$, and m and n are each 1;
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:
u is 0;
$X^3$ is NH, $X^4$ is $(CH_2)_m$ and $X^5$ is $(CH_2)_n$, m is 1, and n is 2;
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

In a further embodiment, the compound has the configuration of Formula (II-i-a).

In one embodiment, the invention is directed to compounds of Formula (II) wherein:
u is 0;
$X^3$ is NH, $X^4$ is $(CH_2)_m$ and $X^5$ is $(CH_2)_n$, and m and n are each 2;
$X^1$ is —OH and $X^2$ is hydrogen;
$G^1$ is unsubstituted pyridin-2-yl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

In a further embodiment, the compound has the configuration of Formula (II-i-a).

In one embodiment, the compound of Formula (I) is selected from the group consisting of:
[4-(3,4-dichlorophenyl)piperidin-4-yl](pyridin-2-yl)methanol;
pyridin-2-yl{4-[2-(trifluoromethoxy)phenyl]piperidin-4-yl}methanol;
pyridin-2-yl{4-[4-(trifluoromethoxy)phenyl]piperidin-4-yl}methanol;
pyridin-2-yl{4-[4-(trifluoromethyl)phenyl]piperidin-4-yl}methanol;
pyridin-2-yl{4-[3-(trifluoromethoxy)phenyl]piperidin-4-yl}methanol; and
pyridin-2-yl{3-[4-(trifluoromethyl)phenyl]azetidin-3-yl}methanol.

(iii) Cyclobutyl Ring and Substituted $G^{2d}$ Aryl/Heteroaryl

In one embodiment, the invention is directed to compounds of Formula (II-a):

(II-a)

wherein:
$X^3$ is $CH_2$, $X^4$ is $(CH_2)_m$, $X^5$ is $(CH_2)_n$, m and n are each 1;
$X^1$ is —OH and $X^2$ is hydrogen;
$G^1$ is aryl, heteroaryl, cycloalkyl, heterocycle, or cycloalkenyl; each of which is optionally substituted with 1, 2, 3, 4, or 5 substituents independently selected from the group consisting of alkyl, alkenyl, alkynyl, halogen, haloalkyl, $OR^{gc}$, $N(R^{gc})_2$, $N(R^{gc})C(O)$alkyl, heteroaryl, and heterocycle; wherein the heteroaryl and the heterocycle moieties are each independently unsubstituted or substituted with 1, 2, 3, 4, or 5 substituents selected from the group consisting of alkyl, O(alkyl), halogen, and haloalkyl; and wherein each $R^{gc}$ is independently hydrogen, alkyl, or haloalkyl;
$G^2$ is $G^{2d}$ or —$(CR^{1g}R^{2g})_r$-$G^{2d}$ wherein:
r is 1, 2, or 3;
$R^{1g}$ and $R^{2g}$ are the same or different, and are each independently hydrogen, alkyl, halogen, $OR^{1gc}$, $N(R^{1gc})_2$, $C(O)$alkyl, or haloalkyl; wherein each $R^{1gc}$ is independently hydrogen, alkyl, or haloalkyl;
$G^{2d}$ is aryl, heteroaryl, cycloalkyl, heterocycle, or cycloalkenyl;
wherein the $G^{2d}$ aryl is substituted with 1, 2, 3, 4, or 5 substituents independently selected from the group consisting of alkenyl, alkynyl, —CN, —$OC(O)R^f$, —$OC(O)N(R^f)_2$, —$S(O)_2N(R^f)_2$, —$C(O)R^f$, —$C(O)OR^f$, —$C(O)N(R^f)_2$, —$N(R^f)C(O)R^f$, —$N(R^f)S(O)_2R^e$, —$N(R^f)C(O)O(R^e)$, —$N(R^f)C(O)N(R^f)_2$, —$(CR^{1a}R^{1b})_q$—$OR^f$, —$(CR^{1a}R^{1b})_q$—

OC(O)R$^f$, —(CR$^{1a}$R$^{1b}$)$_q$—OC(O)N(R$^f$)$_2$, —(CR$^{1a}$R$^{1b}$)$_q$—S(O)$_2$R$^e$, —(CR$^{1a}$R$^{1b}$)$_q$—S(O)$_2$N(R$^f$)$_2$, —(CR$^{1a}$R$^{1b}$)$_q$—C(O)R$^f$, —(CR$^{1a}$R$^{1b}$)$_q$—C(O)OR$^f$, —(CR$^{1a}$R$^{1b}$)$_q$—C(O)N(R$^f$)$_2$, —(CR$^{1a}$R$^{1b}$)$_q$—N(R$^f$)$_2$, —(CR$^{1a}$R$^{1b}$)$_q$—N(R$^f$)C(O)R$^f$, —(CR$^{1a}$R$^{1b}$)$_q$—N(R$^f$)S(O)$_2$R$^e$, —(CR$^{1a}$R$^{1b}$)$_q$—N(R$^f$)C(O)O(R$^e$), —(CR$^{1a}$R$^{1b}$)$_q$—N(R$^f$)C(O)N(R$^f$)$_2$, and —(CR$^{1a}$R$^{1b}$)$_q$—CN;

wherein the G$^{2d}$ heteroaryl and heterocyclyl are substituted with 1, 2, 3, 4, or substituents independently selected from the group consisting of G$^d$, alkyl, alkenyl, alkynyl, halogen, haloalkyl, —CN, —OR$^f$, —OC(O)R$^f$, —OC(O)N(R$^f$)$_2$, —S(O)$_2$R$^e$, —S(O)$_2$N(R$^f$)$_2$, —C(O)R$^f$, —C(O)OR$^f$, —C(O)N(R$^f$)$_2$, —N(R$^f$)$_2$, —N(R$^f$)C(O)R$^f$, —N(R$^f$)S(O)$_2$R$^e$, —N(R$^f$)C(O)O(R$^e$), —N(R$^f$)C(O)N(R$^f$)$_2$, —(CR$^{1a}$R$^{1b}$)$_q$-G$^d$, —(CR$^{1a}$R$^{1b}$)$_q$—OR$^f$, —(CR$^{1a}$R$^{1b}$)$_q$—OC(O)R$^f$, —(CR$^{1a}$R$^{1b}$)$_q$—OC(O)N(R$^f$)$_2$, —(CR$^{1a}$R$^{1b}$)$_q$—S(O)$_2$R$^e$, —(CR$^{1a}$R$^{1b}$)$_q$—S(O)$_2$N(R$^f$)$_2$, —(CR$^{1a}$R$^{1b}$)$_q$—C(O)R$^f$, —(CR$^{1a}$R$^{1b}$)$_q$—C(O)OR$^f$, —(CR$^{1a}$R$^{1b}$)$_q$—C(O)N(R$^f$)$_2$, —(CR$^{1a}$R$^{1b}$)$_q$—N(R$^f$)$_2$, —(CR$^{1a}$R$^{1b}$)$_q$—N(R$^f$)C(O)R$^f$, —(CR$^{1a}$R$^{1b}$)$_q$—N(R$^f$)S(O)$_2$R$^e$, —(CR$^{1a}$R$^{1b}$)$_q$—N(R$^f$)C(O)O(R$^e$), —(CR$^{1a}$R$^{1b}$)$_q$—N(R$^f$)C(O)N(R$^f$)$_2$, and —(CR$^{1a}$R$^{1b}$)$_q$—CN; and wherein the G$^{2d}$ cycloalkyl and cycloalkenyl are optionally substituted with 1, 2, 3, 4, or 5 substituents independently selected from the group consisting of G$^d$, alkyl, alkenyl, alkynyl, halogen, haloalkyl, —CN, —OR$^f$, —OC(O)R$^f$, —OC(O)N(R$^f$)$_2$, —S(O)$_2$R$^e$, S(O)$_2$N(R$^f$)$_2$, —C(O)R$^f$, —C(O)OR$^f$, —C(O)N(R$^f$)$_2$, —N(R$^f$)$_2$, —N(R$^f$)C(O)R$^f$, —N(R$^f$)S(O)$_2$R$^e$, —N(R$^f$)C(O)O(R$^e$), —N(R$^f$)C(O)N(R$^f$)$_2$, —(CR$^{1a}$R$^{1b}$)$_q$-G$^d$, —(CR$^{1a}$R$^{1b}$)$_q$—OR$^f$, —(CR$^{1a}$R$^{1b}$)$_q$—OC(O)R$^f$, —(CR$^{1a}$R$^{1b}$)$_q$—OC(O)N(R$^f$)$_2$, —(CR$^{1a}$R$^{1b}$)$_q$—S(O)$_2$R$^e$, —(CR$^{1a}$R$^{1b}$)$_q$—S(O)$_2$N(R$^f$)$_2$, —(CR$^{1a}$R$^{1b}$)$_q$—C(O)R$^f$, —(CR$^{1a}$R$^{1b}$)$_q$—C(O)OR$^f$, —(CR$^{1a}$R$^{1b}$)$_q$—C(O)N(R$^f$)$_2$, —(CR$^{1a}$R$^{1b}$)$_q$—N(R$^f$)$_2$, —(CR$^{1a}$R$^{1b}$)$_q$—N(R$^f$)C(O)R$^f$, —(CR$^{1a}$R$^{1b}$)$_q$—N(R$^f$)S(O)$_2$R$^e$, —(CR$^{1a}$R$^{1b}$)$_q$—N(R$^f$)C(O)O(R$^e$), —(CR$^{1a}$R$^{1b}$)$_q$—N(R$^f$)C(O)N(R$^f$)$_2$, and —(CR$^{1a}$R$^{1b}$)$_q$—CN;

R$^{1a}$ and R$^{1b}$, are the same or different, and at each occurrence are each independently hydrogen, halogen, alkyl, or haloalkyl;

each occurrence of R$^f$ is independently hydrogen, alkyl, halolalkyl, G$^d$, or —(CR$^{1a}$R$^{1b}$)$_q$-G$^d$;

each occurrence of R$^e$ is independently alkyl, halolalkyl, G$^d$, or —(CR$^{1a}$R$^{1b}$)$_q$-G$^d$;

q, at each occurrence, is independently 1, 2, or 3;

each occurrence of G$^d$ is independently aryl, heteroaryl, cycloalkyl, heterocycle, or cycloalkenyl; and is each optionally substituted with 1, 2, 3, 4, or 5 substituents independently selected from the group consisting of alkyl, alkenyl, alkynyl, halogen, haloalkyl, —CN, —OR$^j$, —OC(O)R$^j$, —OC(O)N(R$^j$)$_2$, —S(O)$_2$R$^k$, —S(O)$_2$N(R$^j$)$_2$, —C(O)R$^j$, —C(O)OR$^j$, —C(O)N(R$^j$)$_2$, —N(R$^j$)$_2$, —N(R$^j$)C(O)R$^j$, —N(R$^j$)S(O)$_2$R$^k$, —N(R$^j$)C(O)O(R$^k$), —N(R$^j$)C(O)N(R$^j$)$_2$, —(CR$^{1a}$R$^{1b}$)$_q$—OR$^j$, —(CR$^{1a}$R$^{1b}$)$_q$—OC(O)R$^j$, —(CR$^{1a}$R$^{1b}$)$_q$—OC(O)N(R$^j$)$_2$, —(CR$^{1a}$R$^{1b}$)$_q$—S(O)$_2$R$^k$, —(CR$^{1a}$R$^{1b}$)$_q$—S(O)$_2$N(R$^j$)$_2$, —(CR$^{1a}$R$^{1b}$)$_q$—C(O)R$^j$, —(CR$^{1a}$R$^{1b}$)$_q$—C(O)OR$^j$, —(CR$^{1a}$R$^{1b}$)$_q$—C(O)N(R$^j$)$_2$, —(CR$^{1a}$R$^{1b}$)$_q$—N(R$^j$)$_2$, —(CR$^{1a}$R$^{1b}$)$_q$—N(R$^j$)C(O)R$^j$, —(CR$^{1a}$R$^{1b}$)$_q$—N(R$^j$)S(O)$_2$R$^k$, —(CR$^{1a}$R$^{1b}$)$_q$—N(R$^j$)C(O)O(R$^k$), —(CR$^{1a}$R$^{1b}$)$_q$—N(R$^j$)C(O)N(R$^j$)$_2$, and —(CR$^{1a}$R$^{1b}$)$_q$—CN;

each occurrence of R$^j$ is independently hydrogen, alkyl, or halolalkyl; and each occurrence of R$^k$ is independently alkyl or halolalkyl.

In a further embodiment, the compound has the configuration of Formula (II-i-b):

(II-i-b)

In one embodiment, the invention is directed to compounds of Formula (II-a) wherein:

X$^3$ is CH$_2$, X$^4$ is (CH$_2$)$_m$, X$^5$ is (CH$_2$)$_n$, m and n are each 1;

X$^1$ is —OH and X$^2$ is hydrogen;

G$^1$ is optionally substituted heteroaryl or optionally substituted cycloalkyl;

G$^2$ is G$^{2d}$; and

G$^{2d}$ is substituted aryl or substituted heteroaryl.

In a further embodiment, the compound has the configuration of Formula (II-i-b).

In one embodiment, the invention is directed to compounds of Formula (II-a) wherein:

X$^3$ is CH$_2$, X$^4$ is (CH$_2$)$_m$, X$^5$ is (CH$_2$)$_n$, m and n are each 1;

X$^1$ is —OH and X$^2$ is hydrogen;

G$^1$ is optionally substituted pyridinyl, pyrimidinyl, thiazolyl, oxazolyl, or pyrazolyl;

G$^2$ is G$^{2d}$; and

G$^{2d}$ is substituted phenyl or substituted pyridinyl.

In a further embodiment, the compound has the configuration of Formula (II-i-b).

In one embodiment, the invention is directed to compounds of Formula (II-a) wherein:

X$^3$ is CH$_2$, X$^4$ is (CH$_2$)$_m$, X$^5$ is (CH$_2$)$_n$, m and n are each 1;

X$^1$ is —OH and X$^2$ is hydrogen;

G$^1$ is pyridinyl or pyrimidinyl; each of which is optionally substituted with 1, 2, or 3 substituents independently selected from the group consisting of halogen, C$_1$-C$_6$-alkyl, C$_1$-C$_6$-haloalkyl, and N(R$^{gc}$)$_2$;

R$^{gc}$ is hydrogen or C$_1$-C$_6$-alkyl;

G$^2$ is G$^{2d}$;

G$^{2d}$ is phenyl, pyridinyl, or pyrimidinyl; wherein the G$^{2d}$ phenyl is substituted with —CN; the G$^{2d}$ pyridinyl and pyrimidinyl are substituted with 1, 2, or 3 substituents independently selected from the group consisting of halogen, —CN, C$_1$-C$_6$-alkyl, C$_1$-C$_6$-haloalkyl, and —OR$^f$; and R$^f$ is C$_1$-C$_4$-alkyl or C$_1$-C$_4$-haloalkyl.

In a further embodiment, the compound has the configuration of Formula (II-i-b).

In one embodiment, the invention is directed to compounds of Formula (II-a) wherein:

X$^3$ is CH$_2$, X$^4$ is (CH$_2$)$_m$, X$^5$ is (CH$_2$)$_n$, m and n are each 1;

X$^1$ is —OH and X$^2$ is hydrogen;

G$^1$ is pyridinyl which is optionally substituted with 1 or 2 substituents independently selected from the group consisting of halogen, C$_1$-C$_4$-alkyl, C$_1$-C$_4$-haloalkyl, and N(R$^{gc}$)$_2$;

R$^{gc}$ is hydrogen or C$_1$-C$_4$-alkyl;

G$^2$ is G$^{2d}$;

G$^{2d}$ is phenyl or pyridinyl; wherein the G$^{2d}$ phenyl is substituted with —CN; and the G$^{2d}$ pyridinyl is substituted with 1, 2, or 3 substituents independently selected from the group consisting of halogen, C$_1$-C$_4$-alkyl, C$_1$-C$_4$-haloalkyl, and —OR$^f$; and R$^f$ is C$_1$-C$_4$-alkyl or C$_1$-C$_4$-haloalkyl.

In a further embodiment, the compound has the configuration of Formula (II-i-b).

In one embodiment, the invention is directed to compounds of Formula (II-a) wherein:

X$^3$ is CH$_2$, X$^4$ is (CH$_2$)$_m$, X$^5$ is (CH$_2$)$_n$, m and n are each 1;

X$^1$ is —OH and X$^2$ is hydrogen;
G$^1$ is unsubstituted pyridinyl;
G$^2$ is G$^{2d}$;
G$^{2d}$ is phenyl or pyridinyl; wherein the G$^{2d}$ phenyl is substituted with —CN; and the G$^{2d}$ pyridinyl is substituted with 1, 2, or 3 substituents independently selected from the group consisting of halogen, C$_1$-C$_4$-alkyl, C$_1$-C$_4$-haloalkyl, and —OR$^f$; and
R$^f$ is C$_1$-C$_4$-alkyl or C$_1$-C$_4$-haloalkyl.
In a further embodiment, the compound has the configuration of Formula (II-i-b).
In one embodiment, the invention is directed to compounds of Formula (II-a) wherein:
X$^3$ is CH$_2$, X$^4$ is (CH$_2$)$_m$, X$^5$ is (CH$_2$)$_n$, m and n are each 1;
X$^1$ is —OH and X$^2$ is hydrogen;
G$^1$ is unsubstituted pyridin-2-yl;
G$^2$ is G$^{2d}$;
G$^{2d}$ is phenyl or pyridinyl; wherein the G$^{2d}$ phenyl is substituted with —CN; and the G$^{2d}$ pyridinyl is substituted with 1, 2, or 3 substituents independently selected from the group consisting of halogen, C$_1$-C$_3$-alkyl, C$_1$-C$_3$-haloalkyl, and —OR$^f$; and
R$^f$ is C$_1$-C$_3$-alkyl or C$_1$-C$_3$-haloalkyl.
In a further embodiment, the compound has the configuration of Formula (II-i-b).
In one embodiment, the invention is directed to compounds of Formula (II-a) wherein:
X$^3$ is CH$_2$, X$^4$ is (CH$_2$)$_m$, X$^5$ is (CH$_2$)$_n$, m and n are each 1;
X$^1$ is —OH and X$^2$ is hydrogen;
G$^1$ is unsubstituted pyridin-2-yl;
G$^2$ is G$^{2d}$; and
G$^{2d}$ is phenyl which is substituted with —CN.
In a further embodiment, the compound has the configuration of Formula (II-i-b).
In one embodiment, the invention is directed to compounds of Formula (II-a) wherein:
X$^3$ is CH$_2$, X$^4$ is (CH$_2$)$_m$, X$^5$ is (CH$_2$)$_n$, m and n are each 1;
X$^1$ is —OH and X$^2$ is hydrogen;
G$^1$ is unsubstituted pyridin-2-yl;
G$^2$ is G$^{2d}$;
G$^{2d}$ is pyridinyl which is substituted with 1, 2, or 3 substituents independently selected from the group consisting of halogen, C$_1$-C$_3$-alkyl, C$_1$-C$_3$-haloalkyl, and —OR$^f$; and
R$^f$ is C$_1$-C$_3$-alkyl or C$_1$-C$_3$-haloalkyl.
In a further embodiment, the compound has the configuration of Formula (II-i-b).
In one embodiment, the invention is directed to compounds of Formula (II-a) wherein:
X$^3$ is CH$_2$, X$^4$ is (CH$_2$)$_m$, X$^5$ is (CH$_2$)$_n$, m and n are each 1;
X$^1$ is —OH and X$^2$ is hydrogen;
G$^1$ is unsubstituted pyridin-2-yl;
G$^2$ is G$^{2d}$;
G$^{2d}$ is phenyl or pyridinyl; each of which is optionally substituted with 1, 2, or 3 substituents independently selected from the group consisting of chloro, fluoro, trifluoromethyl, and —OR$^f$; and
R$^f$ is trifluoromethyl.
In a further embodiment, the compound has the configuration of Formula (II-i-b).
In one embodiment, the compound of Formula (I) is selected from the group consisting of:
pyridin-2-yl{1-[6-(trifluoromethyl)pyridin-3-yl]cyclobutyl}methanol;
pyridin-2-yl{1-[5-(trifluoromethyl)pyridin-3-yl]cyclobutyl}methanol;
pyridin-2-yl{1-[5-(trifluoromethyl)pyridin-2-yl]cyclobutyl}methanol;
pyridin-2-yl{1-[4-(trifluoromethyl)pyridin-2-yl]cyclobutyl}methanol;
(R)-pyridin-2-yl{1-[4-(trifluoromethyl)pyridin-2-yl]cyclobutyl}methanol;
(S)-pyridin-2-yl{1-[4-(trifluoromethyl)pyridin-2-yl]cyclobutyl}methanol;
pyridin-2-yl{1-[6-(trifluoromethyl)pyridin-2-yl]cyclobutyl}methanol;
(S)-pyridin-2-yl{1-[6-(trifluoromethyl)pyridin-2-yl]cyclobutyl}methanol; and
(S)-pyridin-2-yl{1-[2-(trifluoromethyl)pyridin-4-yl]cyclobutyl}methanol.

(iv) Cyclobutyl Ring and Substituted G$^1$ Heteroaryl

In one embodiment, the invention is directed to compounds of Formula (II-a):

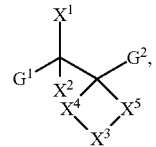

(II-a)

wherein:
X$^3$ is CH$_2$;
X$^4$ is (CH$_2$)$_m$;
X$^5$ is (CH$_2$)$_n$;
m and n are each 1;
X$^1$ is —OH and X$^2$ is hydrogen;
G$^1$ is aryl, heteroaryl, cycloalkyl, heterocycle, or cycloalkenyl;
wherein the G$^1$ aryl, cycloalkyl, heterocycle, and cycloalkenyl are optionally substituted with 1, 2, 3, 4, or 5 substituents independently selected from the group consisting of alkyl, alkenyl, alkynyl, halogen, haloalkyl, OR$^{gc}$, N(R$^{gc}$)$_2$, N(R$^{gc}$)C(O)alkyl, heteroaryl, and heterocycle; wherein the heteroaryl and the heterocycle moieties are each independently unsubstituted or substituted with 1, 2, 3, 4, or 5 substituents selected from the group consisting of alkyl, O(alkyl), halogen, and haloalkyl; and wherein each R$^{gc}$ is independently hydrogen, alkyl, or haloalkyl; and
wherein the G$^1$ heteroaryl is substituted with 1, 2, 3, 4, or 5 substituents independently selected from the group consisting of alkenyl, alkynyl, halogen, haloalkyl, OR$^{gc}$, N(R$^{gc}$)$_2$, N(R$^{gc}$)C(O)alkyl, heteroaryl, and heterocycle; wherein the heteroaryl and the heterocycle moieties are each independently unsubstituted or substituted with 1, 2, 3, 4, or 5 substituents selected from the group consisting of alkyl, O(alkyl), halogen, and haloalkyl; and wherein each R$^{gc}$ is independently hydrogen, alkyl, or haloalkyl;
G$^2$ is G$^{2d}$ or —(CR$^{1g}$R$^{2g}$)$_r$-G$^{2d}$ wherein:
r is 1, 2, or 3;
R$^{1g}$ and R$^{2g}$ are the same or different, and are each independently hydrogen, alkyl, halogen, OR$^{1gc}$, N(R$^{1gc}$)$_2$, C(O)alkyl, or haloalkyl; wherein each R$^{1gc}$ is independently hydrogen, alkyl, or haloalkyl;
G$^{2d}$ is aryl, heteroaryl, cycloalkyl, heterocycle, or cycloalkenyl, each of which is optionally substituted with 1, 2, 3, 4, or 5 substituents independently selected from the group consisting of G$^d$, alkyl, alkenyl, alkynyl, halogen, haloalkyl, —CN, —OR$^f$, —OC(O)R$^j$, —OC(O)N(R$^f$)$_2$, —S(O)$_2$R$^e$, —S(O)$_2$N(R$^f$)$_2$, —C(O)R$^j$, —C(O)OR$^f$, —C(O)N(R$^f$)$_2$, —N(R$^f$)$_2$, —N(R$^f$)C(O)R$^f$, —N(R$^f$)S(O)$_2$R$^e$, —N(R$^f$)C(O)O(R$^e$), —N(R$^f$)C(O)N(R$^f$)$_2$, —(CR$^{1a}$R$^{1b}$)$_q$-G$^d$, —(CR$^{1a}$R$^{1b}$)$_q$—OR$^f$, —(CR$^{1a}$R$^{1b}$)$_q$—OC(O)R$^f$, —$(CR^{1a}R^{1b})_q$—OC(O)N$(R^j)_2$, —$(CR^{1a}R^{1b})_q$—S(O)$_2R^e$, —$(CR^{1a}R^{1b})_q$—S(O)$_2$N$(R^j)_2$, —$(CR^{1a}R^{1b})_q$—C(O)$R^f$, —$(CR^{1a}R^{1b})_q$—C(O)O$R^f$, —$(CR^{1a}R^{1b})_q$—C(O)N$(R^j)_2$, —$(CR^{1a}R^{1b})_q$—N$(R^j)_2$, —$(CR^{1a}R^{1b})_q$—N$(R^j)$C(O)$R^f$, —$(CR^{1a}R^{1b})_q$—N$(R^j)$S(O)$_2R^e$, $(CR^{1a}R^{1b})_q$—N$(R^j)$C(O)O$(R^e)$, —$(CR^{1a}R^{1b})_q$—N$(R^j)$C(O)N$(R^j)_2$, and —$(CR^{1a}R^{1b})_q$—CN;

$R^{1a}$ and $R^{1b}$, are the same or different, and at each occurrence are each independently hydrogen, halogen, alkyl, or halolalkyl;

each occurrence of $R^f$ is independently hydrogen, alkyl, halolalkyl, $G^d$, or —$(CR^{1a}R^{1b})_q$-$G^d$;

each occurrence of $R^e$ is independently alkyl, halolalkyl, $G^d$, or —$(CR^{1a}R^{1b})_q$-$G^d$;

q, at each occurrence, is independently 1, 2, or 3;

each occurrence of $G^d$ is independently aryl, heteroaryl, cycloalkyl, heterocycle, or cycloalkenyl; and is each optionally substituted with 1, 2, 3, 4, or 5 substituents independently selected from the group consisting of alkyl, alkenyl, alkynyl, halogen, haloalkyl, —CN, —O$R^j$, —OC(O)$R^j$, —OC(O)N$(R^j)_2$, —S(O)$_2R^k$, —S(O)$_2$N$(R^j)_2$, —C(O)$R^j$, —C(O)O$R^j$, —C(O)N$(R^j)_2$, —N$(R^j)_2$, —N$(R^j)$C(O)$R^j$, —N$(R^j)$S(O)$_2R^k$, —N$(R^j)$C(O)O$(R^k)$, —N$(R^j)$C(O)N$(R^j)_2$, —$(CR^{1a}R^{1b})_q$—O$R^j$, —$(CR^{1a}R^{1b})_q$—OC(O)$R^j$, —$(CR^{1a}R^{1b})_q$—OC(O)N$(R^j)_2$, —$(CR^{1a}R^{1b})_q$—S(O)$_2R^k$, —$(CR^{1a}R^{1b})_q$—S(O)$_2$N$(R^j)_2$, —$(CR^{1a}R^{1b})_q$—C(O)$R^j$, —$(CR^{1a}R^{1b})_q$—C(O)O$R^j$, —$(CR^{1a}R^{1b})_q$—C(O)N$(R^j)_2$, —$(CR^{1a}R^{1b})_q$—N$(R^j)_2$, —$(CR^{1a}R^{1b})_q$—N$(R^j)$C(O)$R^j$, —$(CR^{1a}R^{1b})_q$—N$(R^j)$S(O)$_2R^k$, —$(CR^{1a}R^{1b})_q$—N$(R^j)$C(O)O$(R^k)$, —$(CR^{1a}R^{1b})_q$—N$(R^j)$C(O)N$(R^j)_2$, and —$(CR^{1a}R^{1b})_q$—CN;

each occurrence of $R^j$ is independently hydrogen, alkyl, or halolalkyl; and each occurrence of $R^k$ is independently alkyl or halolalkyl.

In a further embodiment, the compound has the configuration of Formula (II-i-b):

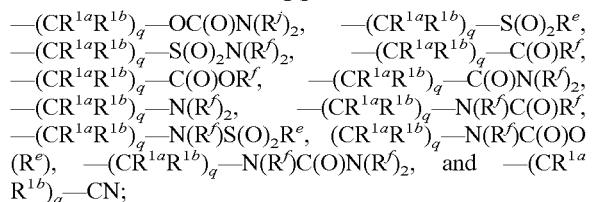

(II-i-b)

In one embodiment, the invention is directed to compounds of Formula (II-a) wherein:
$X^3$ is $CH_2$;
$X^4$ is $(CH_2)_m$;
$X^5$ is $(CH_2)_n$;
m and n are each 1;
$X^1$ is —OH and $X^2$ is hydrogen;
$G^1$ is substituted heteroaryl or optionally substituted cycloalkyl;
$G^2$ is $G^{2d}$; and
$G^{2d}$ is optionally substituted aryl or optionally substituted heteroaryl.

In a further embodiment, the compound has the configuration of Formula (II-i-b).

In one embodiment, the invention is directed to compounds of Formula (II-a) wherein:
$X^3$ is $CH_2$;
$X^4$ is $(CH_2)_m$;
$X^5$ is $(CH_2)_n$;
m and n are each 1;
$X^1$ is —OH and $X^2$ is hydrogen;
$G^1$ is substituted pyridinyl, pyrimidinyl, thiazolyl, oxazolyl, or pyrazolyl;
$G^2$ is $G^{2d}$; and
$G^{2d}$ is optionally substituted phenyl or optionally substituted pyridinyl.

In a further embodiment, the compound has the configuration of Formula (II-i-b).

In one embodiment, the invention is directed to compounds of Formula (II-a) wherein:
$X^3$ is $CH_2$;
$X^4$ is $(CH_2)_m$;
$X^5$ is $(CH_2)_n$;
m and n are each 1;
$X^1$ is —OH and $X^2$ is hydrogen;
$G^1$ is pyridinyl or pyrimidinyl; each of which is substituted with 1, 2, or 3 substituents independently selected from the group consisting of halogen, $C_1$-$C_6$-alkyl, $C_1$-$C_6$-haloalkyl, and N$(R^{gc})_2$;
$R^{gc}$ is hydrogen or $C_1$-$C_6$-alkyl;
$G^2$ is $G^{2d}$;
$G^{2d}$ is phenyl, pyridinyl, or pyrimidinyl; each of which is optionally substituted with 1, 2, or 3 substituents independently selected from the group consisting of halogen, —CN, $C_1$-$C_6$-alkyl, $C_1$-$C_6$-haloalkyl, and —O$R^f$; and
$R^f$ is $C_1$-$C_6$-alkyl or $C_1$-$C_6$-haloalkyl.

In a further embodiment, the compound has the configuration of Formula (II-i-b).

In one embodiment, the invention is directed to compounds of Formula (II-a) wherein:
$X^3$ is $CH_2$;
$X^4$ is $(CH_2)_m$;
$X^5$ is $(CH_2)_n$;
m and n are each 1;
$X^1$ is —OH and $X^2$ is hydrogen;
$G^1$ is pyridinyl which is substituted with 1 or 2 substituents independently selected from the group consisting of halogen, $C_1$-$C_4$-alkyl, $C_1$-$C_4$-haloalkyl, and N$(R^{gc})_2$;
$R^{gc}$ is hydrogen or $C_1$-$C_4$-alkyl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —O$R^f$; and
$R^f$ is $C_1$-$C_4$-alkyl or $C_1$-$C_4$-haloalkyl.

In a further embodiment, the compound has the configuration of Formula (II-i-b).

In one embodiment, the invention is directed to compounds of Formula (II-a) wherein:
$X^3$ is $CH_2$;
$X^4$ is $(CH_2)_m$;
$X^5$ is $(CH_2)_n$;
m and n are each 1;
$X^1$ is —OH and $X^2$ is hydrogen;
$G^1$ is pyridin-2-yl which is substituted with 1 or 2 substituents independently selected from the group consisting of halogen, $C_1$-$C_3$-alkyl, $C_1$-$C_3$-haloalkyl, and N$(R^{gc})_2$;
$R^{gc}$ is hydrogen or $C_1$-$C_3$-alkyl;
$G^2$ is $G^{2d}$
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —O$R^f$; and
$R^f$ is $C_1$-$C_3$-alkyl or $C_1$-$C_3$-haloalkyl.

In a further embodiment, the compound has the configuration of Formula (II-i-b).

In one embodiment, the invention is directed to compounds of Formula (II-a) wherein:

X³ is CH₂;
X⁴ is (CH₂)$_m$;
X⁵ is (CH₂)$_n$;
m and n are each 1;
X¹ is —OH and X² is hydrogen;
G¹ is pyridin-2-yl which is substituted with 1 or 2 substituents independently selected from the group consisting of halogen, $C_{1-2}$-alkyl, $C_{1-2}$-haloalkyl, and N(R$^{gc}$)₂;
R$^{gc}$ is hydrogen or $C_{1-2}$-alkyl;
G² is G$^{2d}$;
G$^{2d}$ is phenyl which is optionally substituted with 1, 2, or 3 substituents independently selected from the group consisting of halogen, $C_1$-$C_3$-alkyl, $C_1$-$C_3$-haloalkyl, and —OR$^f$; and
R$^f$ is $C_1$-$C_3$-alkyl or $C_1$-$C_3$-haloalkyl.

In a further embodiment, the compound has the configuration of Formula (II-i-b).

In one embodiment, the invention is directed to compounds of Formula (II-a) wherein:
X³ is CH₂;
X⁴ is (CH₂)$_m$;
X⁵ is (CH₂)$_n$;
m and n are each 1;
X¹ is —OH and X² is hydrogen;
G¹ is pyridin-2-yl which is substituted with 1 or 2 substituents independently selected from the group consisting of halogen, $C_{1-2}$-alkyl, $C_{1-2}$-haloalkyl, and N(R$^{gc}$)₂;
R$^{gc}$ is hydrogen or $C_{1-2}$-alkyl;
G² is G$^{2d}$
G$^{2d}$ is pyridinyl which is optionally substituted with 1, 2, or 3 substituents independently selected from the group consisting of halogen, $C_1$-$C_3$-alkyl, $C_1$-$C_3$-haloalkyl, and —OR$^f$; and
R$^f$ is $C_1$-$C_3$-alkyl or $C_1$-$C_3$-haloalkyl.

In a further embodiment, the compound has the configuration of Formula (II-i-b).

In one embodiment, the compound of Formula (I) is selected from the group consisting of:
(3-aminopyridin-2-yl){1-[3-(trifluoromethyl)phenyl] cyclobutyl}methanol;
(3-aminopyridin-2-yl){1-[4-(trifluoromethoxy)phenyl] cyclobutyl}methanol;
(3-aminopyridin-2-yl){1-[3-(trifluoromethoxy)phenyl] cyclobutyl}methanol;
(3-aminopyridin-2-yl){1-[4-(trifluoromethyl)phenyl] cyclobutyl}methanol;
(3-aminopyridin-2-yl) [1-(3,4-dichlorophenyl)cyclobutyl] methanol;
[1-(3,4-dichlorophenyl)cyclobutyl](5-methoxypyridin-2-yl) methanol; and
[1-(3,4-dichlorophenyl)cyclobutyl](4-methoxypyridin-2-yl) methanol.

(v) Cyclopropyl/Cyclohexyl Ring and G$^{2d}$ Aryl Substituents

In one embodiment, the invention is directed to compounds of Formula (II-a):

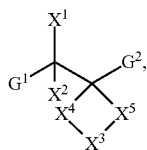

(II-a)

wherein:
X³ is CH₂; X⁴ is a bond, X⁵ is (CH₂)$_n$, and n is 1; or
X³ is CH₂; X⁴ is (CH₂)$_m$, X⁵ is (CH₂)$_n$, and m and n are both 2; and
X¹ is —OH and X² is hydrogen;
G¹ is aryl, heteroaryl, cycloalkyl, heterocycle, or cycloalkenyl; each of which is optionally substituted with 1, 2, 3, 4, or 5 substituents independently selected from the group consisting of alkyl, alkenyl, alkynyl, halogen, haloalkyl, OR$^{gc}$, N(R$^{gc}$)₂, N(R$^{gc}$)C(O)alkyl, heteroaryl, and heterocycle; wherein the heteroaryl and the heterocycle moieties are each independently unsubstituted or substituted with 1, 2, 3, 4, or 5 substituents selected from the group consisting of alkyl, O(alkyl), halogen, and haloalkyl; and wherein each R$^{gc}$ is independently hydrogen, alkyl, or haloalkyl;
G² is G$^{2d}$ or —(CR$^{1g}$R$^{2g}$)$_r$-G$^{2d}$ wherein:
r is 1, 2, or 3;
R$^{1g}$ and R$^{2g}$ are the same or different, and are each independently hydrogen, alkyl, halogen, OR$^{1gc}$, N(R$^{1gc}$)₂, C(O) alkyl, or haloalkyl; wherein each R$^{1gc}$ is independently hydrogen, alkyl, or haloalkyl;
G$^{2d}$ is aryl, heteroaryl, cycloalkyl, heterocycle, or cycloalkenyl;
wherein the G$^{2d}$ aryl is substituted with 1, 2, 3, 4, or 5 substituents independently selected from the group consisting of G$^d$, alkyl, alkenyl, alkynyl, haloalkyl, —CN, —OR$^f$, —OC(O)R$^f$, —OC(O)N(R$^f$)₂, —S(O)₂R$^e$, —S(O)₂N(R$^f$)₂, —C(O)R$^f$, —C(O)OR$^f$, —C(O)N(R$^f$)₂, —N(R$^f$)₂, —N(R$^f$)C(O)R$^f$, —N(R$^f$)S(O)₂R$^e$, —N(R$^f$)C(O)O(R$^e$), —N(R$^f$)C(O)N (R$^f$)₂, —(CR$^{1a}$R$^{1b}$)$_q$-G$^d$, —(CR$^{1a}$R$^{1b}$)$_q$—OR$^f$, —(CR$^{1a}$R$^{1b}$)$_q$—OC(O)R$^f$, —(CR$^{1a}$R$^{1b}$)$_q$—OC(O)N(R$^f$)₂, —(CR$^{1a}$R$^{1b}$)$_q$—S(O)₂R$^e$, —(CR$^{1a}$R$^{1b}$)$_q$—S(O)₂N(R$^f$)₂, —(CR$^{1a}$R$^{1b}$)$_q$—C(O)R$^f$, —(CR$^{1a}$R$^{1b}$)$_q$—C(O)OR$^f$, —(CR$^{1a}$R$^{1b}$)$_q$—C(O)N(R$^f$)₂, —(CR$^{1a}$R$^{1b}$)$_q$—N(R$^f$)₂, —(CR$^{1a}$R$^{1b}$)$_q$—N(R$^f$)C(O)R$^f$, —(CR$^{1a}$R$^{1b}$)$_q$—N(R$^f$)S(O)₂ R$^e$, —(CR$^{1a}$R$^{1b}$)$_q$—N(R$^f$)C(O)O(R$^e$), —(CR$^{1a}$R$^{1b}$)$_q$—N(R$^f$)C(O)N(R$^f$)₂, and —(CR$^{1a}$R$^{1b}$)$_q$—CN; and
wherein the G$^{2d}$ heteroaryl, cycloalkyl, heterocycle, and cycloalkenyl are optionally substituted with 1, 2, 3, 4, or 5 substituents independently selected from the group consisting of G$^d$, alkyl, alkenyl, alkynyl, halogen, haloalkyl, —CN, —OR$^f$, —OC(O)R$^f$, —OC(O)N(R$^f$)₂, —S(O)₂R$^e$, —S(O)₂N (R$^f$)₂, —C(O)R$^f$, —C(O)OR$^f$, —C(O)N(R$^f$)₂, —N(R$^f$)₂, —N(R$^f$)C(O)R$^f$, —N(R$^f$)S(O)₂R$^e$, —N(R$^f$)C(O)O(R$^e$), —N(R$^f$)C(O)N(R$^f$)₂, —(CR$^{1a}$R$^{1b}$)$_q$-G$^d$, —(CR$^{1a}$R$^{1b}$)$_q$—OR$^f$, —(CR$^{1a}$R$^{1b}$)$_q$—OC(O)R$^f$, —(CR$^{1a}$R$^{1b}$)$_q$—OC(O)N (R$^f$)₂, —(CR$^{1a}$R$^{1b}$)$_q$—S(O)₂R$^e$, —(CR$^{1a}$R$^{1b}$)$_q$—S(O)₂N (R$^f$)₂, —(CR$^{1a}$R$^{1b}$)$_q$—C(O)R$^f$, —(CR$^{1a}$R$^{1b}$)$_q$—C(O)OR$^f$, —(CR$^{1a}$R$^{1b}$)$_q$—C(O)N(R$^f$)₂, —(CR$^{1a}$R$^{1b}$)$_q$—N(R$^f$)₂, —(CR$^{1a}$R$^{1b}$)$_q$—N(R$^f$)C(O)R$^f$, —(CR$^{1a}$R$^{1b}$)$_q$—N(R$^f$)S(O)₂ R$^e$, (CR$^{1a}$R$^{1b}$)$_q$—N(R$^f$)C(O)O(R$^e$), —(CR$^{1a}$R$^{1b}$)$_q$—N(R$^f$)C (O)N(R$^f$)₂, and —(CR$^{1a}$R$^{1b}$)$_q$—CN;
R$^{1a}$ and R$^{1b}$, are the same or different, and at each occurrence are each independently hydrogen, halogen, alkyl, or haloalkyl;
each occurrence of R$^f$ is independently hydrogen, alkyl, halolalkyl, G$^d$, or —(CR$^{1a}$R$^{1b}$)$_q$-G$^d$;
each occurrence of R$^e$ is independently alkyl, halolalkyl, G$^d$, or —(CR$^{1a}$R$^{1b}$)$_q$-G$^d$;
q, at each occurrence, is independently 1, 2, or 3;
each occurrence of G$^d$ is independently aryl, heteroaryl, cycloalkyl, heterocycle, or cycloalkenyl; and is each optionally substituted with 1, 2, 3, 4, or 5 substituents independently selected from the group consisting of alkyl, alkenyl, alkynyl, halogen, haloalkyl, —CN, —OR$^j$, —OC(O)R$^j$, —OC(O)N (R$^j$)₂, —S(O)₂R$^k$, —S(O)₂N(R$^j$)₂, —C(O)R$^j$, —C(O)OR$^j$, —C(O)N(R$^j$)₂, —N(R$^j$)₂, —N(R$^j$)C(O)R$^j$, —N(R$^j$)S(O)₂R$^k$, —N($R^j$)C(O)O($R^k$), —N($R^j$)C(O)N($R^j$)$_2$, —(C$R^{1a}R^{1b}$)$_q$—O$R^j$, —(C$R^{1a}R^{1b}$)$_q$—OC(O)$R^j$, —(C$R^{1a}R^{1b}$)$_q$—OC(O)N($R^j$)$_2$, —(C$R^{1a}R^{1b}$)$_q$—S(O)$_2R^k$, —(C$R^{1a}R^{1b}$)$_q$—S(O)$_2$N($R^j$)$_2$, —(C$R^{1a}R^{1b}$)$_q$—C(O)$R^j$, —(C$R^{1a}R^{1b}$)$_q$—C(O)O$R^j$, —(C$R^{1a}R^{1b}$)$_q$—C(O)N($R^j$)$_2$, —(C$R^{1a}R^{1b}$)$^q$—N($R^j$)$_2$, —(C$R^{1a}R^{1b}$)$^q$—N($R^j$)C(O)$R^j$, —(C$R^{1a}R^{1b}$)$_q$—N(RR)S(O)$_2R^k$, —(C$R^{1a}R^{1b}$)$_q$—N($R^j$)C(O)O($R^k$), —(C$R^{1a}R^{1b}$)$_q$—N($R^j$)C(O)N($R^j$)$_2$, and —(C$R^{1a}R^{1b}$)$_q$—CN;

each occurrence of $R^j$ is independently hydrogen, alkyl, or halolalkyl; and each occurrence of $R^k$ is independently alkyl or halolalkyl.

In a further embodiment, the compound has the configuration of Formula (II-i-b):

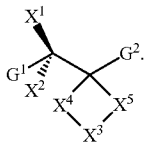

(II-i-b)

In one embodiment, the invention is directed to compounds of Formula (II-a) wherein:

$X^3$ is $CH_2$; $X^4$ is a bond, $X^5$ is $(CH_2)_n$, and n is 1; or
$X^3$ is $CH_2$; $X^4$ is $(CH_2)_m$, $X^5$ is $(CH_2)_n$, and m and n are both 2; and $X^1$ is —OH and $X^2$ is hydrogen;
$G^1$ is optionally substituted heteroaryl or optionally substituted cycloalkyl;
$G^2$ is $G^{2d}$; and
$G^{2d}$ is substituted aryl or optionally substituted heteroaryl.

In a further embodiment, the compound has the configuration of Formula (II-i-b).

In one embodiment, the invention is directed to compounds of Formula (II-a) wherein:

$X^3$ is $CH_2$; $X^4$ is a bond, $X^5$ is $(CH_2)_n$, and n is 1; or
$X^3$ is $CH_2$; $X^4$ is $(CH_2)_m$, $X^5$ is $(CH_2)_n$, and m and n are both 2; and $X^1$ is —OH and $X^2$ is hydrogen;
$G^1$ is optionally substituted pyridinyl, pyrimidinyl, thiazolyl, oxazolyl, or pyrazolyl;
$G^2$ is $G^{2d}$; and
$G^{2d}$ is substituted phenyl or optionally substituted pyridinyl.

In a further embodiment, the compound has the configuration of Formula (II-i-b).

In one embodiment, the invention is directed to compounds of Formula (II-a) wherein:

$X^3$ is $CH_2$; $X^4$ is a bond, $X^5$ is $(CH_2)_n$, and n is 1; or
$X^3$ is $CH_2$; $X^4$ is $(CH_2)_m$, $X^5$ is $(CH_2)_n$, and m and n are both 2; and $X^1$ is —OH and $X^2$ is hydrogen;
$G^1$ is pyridinyl or pyrimidinyl; each of which is optionally substituted with 1, 2, or 3 substituents independently selected from the group consisting of halogen, $C_1$-$C_6$-alkyl, $C_1$-$C_6$-haloalkyl, and N($R^{gc}$)$_2$;
$R^{gc}$ is hydrogen or $C_1$-$C_6$-alkyl;
$G^2$ is $G^{2d}$;
$G^{2d}$ is phenyl, pyridinyl, or pyrimidinyl; wherein the $G^{2d}$ phenyl is substituted with 1, 2, or 3 substituents independently selected from the group consisting of —CN, $C_1$-$C_6$-alkyl, $C_1$-$C_6$-haloalkyl, and —O$R^f$; and the $G^{2d}$ pyridinyl and pyrimidinyl are optionally substituted with 1, 2, or 3 substituents independently selected from the group consisting of halogen, —CN, $C_1$-$C_6$-alkyl, $C_1$-$C_6$-haloalkyl, and —O$R^f$; and $R^f$ is $C_1$-$C_6$-alkyl or $C_1$-$C_6$-haloalkyl.

In a further embodiment, the compound has the configuration of Formula (II-i-b).

In one embodiment, the invention is directed to compounds of Formula (II-a) wherein:

$X^3$ is $CH_2$; $X^4$ is a bond, $X^5$ is $(CH_2)_n$, and n is 1; or
$X^3$ is $CH_2$; $X^4$ is $(CH_2)_m$, $X^5$ is $(CH_2)_n$, and m and n are both 2; and $X^1$ is —OH and $X^2$ is hydrogen;
$G^1$ is pyridinyl which is optionally substituted with 1 or 2 substituents independently selected from the group consisting of halogen, $C_1$-$C_4$-alkyl, $C_1$-$C_4$-haloalkyl, and N($R^{gc}$)$_2$;
$R^{gc}$ is hydrogen or $C_1$-$C_4$-alkyl;
$G^2$ is $G^{2d}$;
$G^{2d}$ is phenyl or pyridinyl; wherein the $G^{2d}$ phenyl is substituted with 1, 2, or 3 substituents independently selected from the group consisting of $C_1$-$C_4$-alkyl, $C_1$-$C_4$-haloalkyl, and —O$R^f$; and the $G^{2d}$ pyridinyl is optionally substituted with 1, 2, or 3 substituents independently selected from the group consisting of halogen, $C_1$-$C_4$-alkyl, $C_1$-$C_4$-haloalkyl, and —O$R^f$; and $R^f$ is $C_1$-$C_4$-alkyl or $C_1$-$C_4$-haloalkyl.

In a further embodiment, the compound has the configuration of Formula (II-i-b).

In one embodiment, the invention is directed to compounds of Formula (II-a) wherein:

$X^3$ is $CH_2$; $X^4$ is a bond, $X^5$ is $(CH_2)_n$, and n is 1; or
$X^3$ is $CH_2$; $X^4$ is $(CH_2)_m$, $X^5$ is $(CH_2)_n$, and m and n are both 2; and $X^1$ is —OH and $X^2$ is hydrogen;
$G^1$ is unsubstituted pyridinyl;
$G^2$ is $G^{2d}$;
$G^{2d}$ is phenyl or pyridinyl; wherein the $G^{2d}$ phenyl is substituted with 1, 2, or 3 substituents independently selected from the group consisting of $C_1$-$C_4$-alkyl, $C_1$-$C_4$-haloalkyl, and —O$R^f$; and the $G^{2d}$ pyridinyl is optionally substituted with 1, 2, or 3 substituents independently selected from the group consisting of halogen, $C_1$-$C_4$-alkyl, $C_1$-$C_4$-haloalkyl, and —O$R^f$; and $R^f$ is $C_1$-$C_4$-alkyl or $C_1$-$C_4$-haloalkyl.

In a further embodiment, the compound has the configuration of Formula (II-i-b).

In one embodiment, the invention is directed to compounds of Formula (II-a) wherein:

$X^3$ is $CH_2$; $X^4$ is a bond, $X^5$ is $(CH_2)_n$, and n is 1; or
$X^3$ is $CH_2$; $X^4$ is $(CH_2)_m$, $X^5$ is $(CH_2)_n$, and m and n are both 2; and $X^1$ is —OH and $X^2$ is hydrogen;
$G^1$ is unsubstituted pyridin-2-yl;
$G^2$ is $G^{2d}$;
$G^{2d}$ is phenyl or pyridinyl; wherein the $G^{2d}$ phenyl is substituted with 1, 2, or 3 substituents independently selected from the group consisting of $C_1$-$C_3$-alkyl, $C_1$-$C_3$-haloalkyl, and —O$R^f$; and the $G^{2d}$ pyridinyl is optionally substituted with 1, 2, or 3 substituents independently selected from the group consisting of halogen, $C_1$-$C_3$-alkyl, $C_1$-$C_3$-haloalkyl, and —O$R^f$; and $R^f$ is $C_1$-$C_3$-alkyl or $C_1$-$C_3$-haloalkyl.

In a further embodiment, the compound has the configuration of Formula (II-i-b).

In one embodiment, the invention is directed to compounds of Formula (II-a) wherein:

$X^3$ is $CH_2$; $X^4$ is a bond, $X^5$ is $(CH_2)_n$, and n is 1; or
$X^3$ is $CH_2$; $X^4$ is $(CH_2)_m$, $X^5$ is $(CH_2)_n$, and m and n are both 2; and
  $X^1$ is —OH and $X^2$ is hydrogen;
  $G^1$ is unsubstituted pyridin-2-yl;
  $G^2$ is $G^{2d}$;
  $G^{2d}$ is phenyl which is substituted with 1, 2, or 3 substituents independently selected from the group consisting of $C_1$-$C_3$-alkyl, $C_1$-$C_3$-haloalkyl, and —$OR^f$; and
  $R^f$ is $C_1$-$C_3$-alkyl or $C_1$-$C_3$-haloalkyl.
In a further embodiment, the compound has the configuration of Formula (II-i-b).

In one embodiment, the invention is directed to compounds of Formula (II-a) wherein:
$X^3$ is $CH_2$; $X^4$ is a bond, $X^5$ is $(CH_2)_n$, and n is 1; or
$X^3$ is $CH_2$; $X^4$ is $(CH_2)_m$, $X^5$ is $(CH_2)_n$, and m and n are both 2; and
  $X^1$ is —OH and $X^2$ is hydrogen;
  $G^1$ is unsubstituted pyridin-2-yl;
  $G^2$ is $G^{2d}$;
  $G^{2d}$ is pyridinyl which is optionally substituted with 1, 2, or 3 substituents independently selected from the group consisting of halogen, $C_1$-$C_3$-alkyl, $C_1$-$C_3$-haloalkyl, and —$OR^f$; and
  $R^f$ is $C_1$-$C_3$-alkyl or $C_1$-$C_3$-haloalkyl.
In a further embodiment, the compound has the configuration of Formula (II-i-b).

In one embodiment, the invention is directed to compounds of Formula (II-a) wherein:
$X^3$ is $CH_2$; $X^4$ is a bond, $X^5$ is $(CH_2)_n$, and n is 1;
  $X^1$ is —OH and $X^2$ is hydrogen;
  $G^1$ is unsubstituted pyridin-2-yl;
  $G^2$ is $G^{2d}$;
  $G^{2d}$ is phenyl or pyridinyl; wherein the $G^{2d}$ phenyl is substituted with 1, 2, or 3 substituents independently selected from the group consisting of $C_1$-$C_3$-alkyl, $C_1$-$C_3$-haloalkyl, and —$OR^f$; and the $G^{2d}$ pyridinyl is optionally substituted with 1, 2, or 3 substituents independently selected from the group consisting of halogen, $C_1$-$C_3$-alkyl, $C_1$-$C_3$-haloalkyl, and —$OR^f$; and
  $R^f$ is $C_1$-$C_3$-alkyl or $C_1$-$C_3$-haloalkyl.
In a further embodiment, the compound has the configuration of Formula (II-i-b).

In one embodiment, the invention is directed to compounds of Formula (II-a) wherein:
$X^3$ is $CH_2$; $X^4$ is $(CH_2)_m$, $X^5$ is $(CH_2)_n$, and m and n are both 2;
  $X^1$ is —OH and $X^2$ is hydrogen;
  $G^1$ is unsubstituted pyridin-2-yl;
  $G^2$ is $G^{2d}$;
  $G^{2d}$ is phenyl or pyridinyl; wherein the $G^{2d}$ phenyl is substituted with 1, 2, or 3 substituents independently selected from the group consisting of $C_1$-$C_3$-alkyl, $C_1$-$C_3$-haloalkyl, and —$OR^f$; and the $G^{2d}$ pyridinyl is optionally substituted with 1, 2, or 3 substituents independently selected from the group consisting of halogen, $C_1$-$C_3$-alkyl, $C_1$-$C_3$-haloalkyl, and —$OR^f$; and
  $R^f$ is $C_1$-$C_3$-alkyl or $C_1$-$C_3$-haloalkyl.
In a further embodiment, the compound has the configuration of Formula (II-i-b).

(vi) Tetrahydropyranyl Ring and Substituted $G^{2d}$ Aryl

In one embodiment, the invention is directed to compounds of Formula (II-a):

$$\begin{array}{c} X^1 \\ G^1 \diagdown \diagup G^2 \\ X^2 \\ X^4 \diagdown X^5 \\ X^3 \end{array} \quad (\text{II-a})$$

wherein:
  $X^3$ is O;
  $X^4$ is $(CH_2)_m$;
  $X^5$ is $(CH_2)_n$;
  m and n are both 2;
  $X^1$ is —OH and $X^2$ is hydrogen;
  $G^1$ is aryl, heteroaryl, cycloalkyl, heterocycle, or cycloalkenyl; each of which is optionally substituted with 1, 2, 3, 4, or 5 substituents independently selected from the group consisting of alkyl, alkenyl, alkynyl, halogen, haloalkyl, $OR^{gc}$, $N(R^{gc})_2$, $N(R^{gc})C(O)$alkyl, heteroaryl, and heterocycle; wherein the heteroaryl and the heterocycle moieties are each independently unsubstituted or substituted with 1, 2, 3, 4, or 5 substituents selected from the group consisting of alkyl, O(alkyl), halogen, and haloalkyl; and wherein each $R^{gc}$ is independently hydrogen, alkyl, or haloalkyl;
  $G^2$ is $G^{2d}$ or —$(CR^{1g}R^{2g})_r$-$G^{2d}$ wherein:
    r is 1, 2, or 3;
    $R^{1g}$ and $R^{2g}$ are the same or different, and are each independently hydrogen, alkyl, halogen, $OR^{1gc}$, $N(R^{1gc})_2$, $C(O)$alkyl, or haloalkyl; wherein each $R^{1gc}$ is independently hydrogen, alkyl, or haloalkyl;
  $G^{2d}$ is aryl, heteroaryl, cycloalkyl, heterocycle, or cycloalkenyl;
    wherein the $G^{2d}$ aryl is optionally substituted with 1, 2, 3, 4, or 5 substituents independently selected from the group consisting of $G^d$, alkyl, alkenyl, alkynyl, —CN, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$, —$(CR^{1a}R^{1b})_q$-$G^d$, —$(CR^{1a}R^{1b})_q$—$OR^f$, —$(CR^{1a}R^{1b})_q$—$OC(O)R^f$, —$(CR^{1a}R^{1b})_q$—$OC(O)N(R^f)_2$, —$(CR^{1a}R^{1b})_q$—$S(O)_2R^e$, —$(CR^{1a}R^{1b})_q$—$S(O)_2N(R^f)_2$, —$(CR^{1a}R^{1b})_q$—$C(O)R^f$, —$(CR^{1a}R^{1b})_q$—$C(O)OR^f$, —$(CR^{1a}R^{1b})_q$—$C(O)N(R^f)_2$, —$(CR^{1a}R^{1b})_q$—$N(R^f)_2$, —$(CR^{1a}R^{1b})_q$—$N(R^f)C(O)R^f$, —$(CR^{1a}R^{1b})_q$—$N(R^f)S(O)_2R^e$, $(CR^{1a}R^{1b})_q$—$N(R^f)C(O)O(R^e)$, —$(CR^{1a}R^{1b})_q$—$N(R^f)C(O)N(R^f)_2$, and —$(CR^{1a}R^{1b})_q$—CN; and
    wherein the $G^{2d}$ heteroaryl, cycloalkyl, heterocycle, and cycloalkenyl are optionally substituted with 1, 2, 3, 4, or 5 substituents independently selected from the group consisting of $G^d$, alkyl, alkenyl, alkynyl, halogen, haloalkyl, —CN, —$OR^f$, —$OC(O)R^f$, —$OC(O)N(R^f)_2$, —$S(O)_2R^e$, —$S(O)_2N(R^f)_2$, —$C(O)R^f$, —$C(O)OR^f$, —$C(O)N(R^f)_2$, —$N(R^f)_2$, —$N(R^f)C(O)R^f$, —$N(R^f)S(O)_2R^e$, —$N(R^f)C(O)O(R^e)$, —$N(R^f)C(O)N(R^f)_2$, —$(CR^{1a}R^{1b})_q$-$G^d$, —$(CR^{1a}R^{1b})_q$—$OR^f$, —$(CR^{1a}R^{1b})_q$—$OC(O)R^f$, —$(CR^{1a}R^{1b})_q$—$OC(O)N(R^f)_2$, —$(CR^{1a}R^{1b})_q$—$S(O)_2R^e$, —$(CR^{1a}R^{1b})_q$—$S(O)_2N(R^f)_2$, —$(CR^{1a}R^{1b})_q$—$C(O)R^f$, —$(CR^{1a}R^{1b})_q$—$C(O)OR^f$, —$(CR^{1a}R^{1b})_q$—$C(O)N(R^f)_2$, —$(CR^{1a}R^{1b})_q$—$N(R^f)_2$, —$(CR^{1a}R^{1b})_q$—$N(R^f)C(O)R^f$, —$(CR^{1a}R^{1b})_q$—$N(R^f)S(O)_2R^e$, $(CR^{1a}R^{1b})_q$—$N(R^f)C(O)O(R^e)$, —$(CR^{1a}R^{1b})_q$—$N(R^f)C(O)N(R^f)_2$, and —$(CR^{1a}R^{1b})_q$—CN;
  $R^{1a}$ and $R^{1b}$, are the same or different, and at each occurrence are each independently hydrogen, halogen, alkyl, or haloalkyl;
  $R^{ff}$ is independently hydrogen, alkyl, $G^d$, or —$(CR^{1a}R^{1b})_q$-$G^d$;

each occurrence of $R^f$ is independently hydrogen, alkyl, halolalkyl, $G^d$, or $-(CR^{1a}R^{1b})_q-G^d$;

each occurrence of $R^e$ is independently alkyl, halolalkyl, $G^d$, or $-(CR^{1a}R^{1b})_q-G^d$;

q, at each occurrence, is independently 1, 2, or 3;

each occurrence of $G^d$ is independently aryl, heteroaryl, cycloalkyl, heterocycle, or cycloalkenyl; and is each optionally substituted with 1, 2, 3, 4, or 5 substituents independently selected from the group consisting of alkyl, alkenyl, alkynyl, halogen, haloalkyl, $-CN$, $-OR^j$, $-OC(O)R^j$, $-OC(O)N(R^j)_2$, $-S(O)_2R^k$, $-S(O)_2N(R^j)_2$, $-C(O)R^j$, $-C(O)OR^j$, $-C(O)N(R^j)_2$, $-N(R^j)_2$, $-N(R^j)C(O)R^j$, $-N(R^j)S(O)_2R^k$, $-N(R^j)C(O)O(R^k)$, $-N(R^j)C(O)N(R^j)_2$, $-(CR^{1a}R^{1b})_q-OR^j$, $-(CR^{1a}R^{1b})_q-OC(O)R^j$, $-(CR^{1a}R^{1b})_q-OC(O)N(R^j)_2$, $-(CR^{1a}R^{1b})_q-S(O)_2R^k$, $-(CR^{1a}R^{1b})_q-S(O)_2N(R^j)_2$, $-(CR^{1a}R^{1b})_q-C(O)R^j$, $-(CR^{1a}R^{1b})_q-C(O)OR^j$, $-(CR^{1a}R^{1b})_q-C(O)N(R^j)_2$, $-(CR^{1a}R^{1b})_q-N(R^j)_2$, $-(CR^{1a}R^{1b})_q-N(R^j)C(O)R^j$, $-(CR^{1a}R^{1b})_q-N(R^j)S(O)_2R^k$, $-(CR^{1a}R^{1b})_q-N(R^j)C(O)O(R^k)$, $-(CR^{1a}R^{1b})_q-N(R^j)C(O)N(R^j)_2$, and $-(CR^{1a}R^{1b})_q-CN$;

each occurrence of $R^j$ is independently hydrogen, alkyl, or halolalkyl; and each occurrence of $R^k$ is independently alkyl or halolalkyl.

In a further embodiment, the compound has the configuration of Formula (II-i-b):

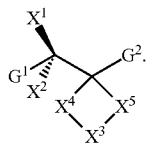

(II-i-b)

In one embodiment, the invention is directed to compounds of Formula (II-a) wherein:
$X^3$ is O;
$X^4$ is $(CH_2)_m$;
$X^5$ is $(CH_2)_n$;
m and n are both 2;
$X^1$ is $-OH$ and $X^2$ is hydrogen;
$G^1$ is optionally substituted heteroaryl or optionally substituted cycloalkyl;
$G^2$ is $G^{2d}$; and
$G^{2d}$ is substituted aryl or optionally substituted heteroaryl.

In a further embodiment, the compound has the configuration of Formula (II-i-b).

In one embodiment, the invention is directed to compounds of Formula (II-a) wherein:
$X^3$ is O;
$X^4$ is $(CH_2)_m$;
$X^5$ is $(CH_2)_n$;
m and n are both 2;
$X^1$ is $-OH$ and $X^2$ is hydrogen;
$G^1$ is optionally substituted pyridinyl, pyrimidinyl, thiazolyl, oxazolyl, or pyrazolyl;
$G^2$ is $G^{2d}$; and
$G^{2d}$ is substituted phenyl or optionally substituted pyridinyl.

In a further embodiment, the compound has the configuration of Formula (II-i-b).

In one embodiment, the invention is directed to compounds of Formula (II-a) wherein:
$X^3$ is O;
$X^4$ is $(CH_2)_m$;
$X^5$ is $(CH_2)_n$;
m and n are both 2;
$X^1$ is $-OH$ and $X^2$ is hydrogen;
$G^1$ is pyridinyl or pyrimidinyl; each of which is optionally substituted with 1, 2, or 3 substituents independently selected from the group consisting of halogen, $C_1$-$C_6$-alkyl, $C_1$-$C_6$-haloalkyl, and $N(R^{gc})_2$;
$R^{gc}$ is hydrogen or $C_1$-$C_6$-alkyl;
$G^2$ is $G^{2d}$;
$G^{2d}$ is phenyl, pyridinyl, or pyrimidinyl; wherein the $G^{2d}$ phenyl is substituted with one or more substituents selected from the group consisting of $-CN$, $C_1$-$C_6$-alkyl, and $-OR^{ff}$; and the $G^{2d}$ pyridinyl and pyrimidinyl are optionally substituted with 1, 2, or 3 substituents independently selected from the group consisting of halogen, $-CN$, $C_1$-$C_6$-alkyl, $C_1$-$C_6$-haloalkyl, and $-OR^f$;
$R^{ff}$ is $C_1$-$C_6$-alkyl; and
$R^f$ is $C_1$-$C_6$-alkyl or $C_1$-$C_6$-haloalkyl.

In a further embodiment, the compound has the configuration of Formula (II-i-b).

In one embodiment, the invention is directed to compounds of Formula (II-a) wherein:
$X^3$ is O;
$X^4$ is $(CH_2)_m$;
$X^5$ is $(CH_2)_n$;
m and n are both 2;
$X^1$ is $-OH$ and $X^2$ is hydrogen;
$G^1$ is pyridinyl which is optionally substituted with 1 or 2 substituents independently selected from the group consisting of halogen, $C_1$-$C_4$-alkyl, $C_1$-$C_4$-haloalkyl, and $N(R^{gc})_2$;
$R^{gc}$ is hydrogen or $C_1$-$C_4$-alkyl;
$G^2$ is $G^{2d}$;
$G^{2d}$ is phenyl or pyridinyl; wherein the $G^{2d}$ phenyl is substituted with one or more substituents selected from the group consisting of $-CN$, $C_1$-$C_4$-alkyl, and $-OR^{ff}$; and the $G^{2d}$ pyridinyl is optionally substituted with 1, 2, or 3 substituents independently selected from the group consisting of halogen, $C_1$-$C_4$-alkyl, $C_1$-$C_4$-haloalkyl, and $-OR^f$;
$R^{ff}$ is $C_1$-$C_4$-alkyl; and
$R^f$ is $C_1$-$C_4$-alkyl or $C_1$-$C_4$-haloalkyl.

In a further embodiment, the compound has the configuration of Formula (II-i-b).

In one embodiment, the invention is directed to compounds of Formula (II-a) wherein:
$X^3$ is O;
$X^4$ is $(CH_2)_m$;
$X^5$ is $(CH_2)_n$;
m and n are both 2;
$X^1$ is $-OH$ and $X^2$ is hydrogen;
$G^1$ is unsubstituted pyridinyl;
$G^2$ is $G^{2d}$;
$G^{2d}$ is phenyl or pyridinyl; wherein the $G^{2d}$ phenyl is substituted with one or more substituents selected from the group consisting of $-CN$, $C_1$-$C_4$-alkyl, and $-OR^{ff}$; and the $G^{2d}$ pyridinyl is optionally substituted with 1, 2, or 3 substituents independently selected from the group consisting of halogen, $C_1$-$C_4$-alkyl, $C_1$-$C_4$-haloalkyl, and $-OR^f$;
$R^{ff}$ is $C_1$-$C_4$-alkyl; and
$R^f$ is $C_1$-$C_4$-alkyl or $C_1$-$C_4$-haloalkyl.

In a further embodiment, the compound has the configuration of Formula (II-i-b).

In one embodiment, the invention is directed to compounds of Formula (II-a) wherein:
$X^3$ is O;
$X^4$ is $(CH_2)_m$;
$X^5$ is $(CH_2)_n$;
m and n are both 2;
$X^1$ is $-OH$ and $X^2$ is hydrogen;

$G^1$ is unsubstituted pyridin-2-yl;
$G^2$ is $G^{2d}$;
$G^{2d}$ is phenyl or pyridinyl; wherein the $G^{2d}$ phenyl is substituted with one or more substituents selected from the group consisting of —CN, $C_1$-$C_3$-alkyl, and —OR$^f$; and the $G^{2d}$ pyridinyl is optionally substituted with 1, 2, or 3 substituents independently selected from the group consisting of halogen, $C_1$-$C_3$-alkyl, $C_1$-$C_3$-haloalkyl, and —OR$^f$;
R$^f$ is $C_1$-$C_3$-alkyl; and
R$^f$ is $C_1$-$C_3$-alkyl or $C_1$-$C_3$-haloalkyl.
In a further embodiment, the compound has the configuration of Formula (II-i-b).

In one embodiment, the invention is directed to compounds of Formula (II-a) wherein:
$X^3$ is O;
$X^4$ is $(CH_2)_m$;
$X^5$ is $(CH_2)_n$;
m and n are both 2;
$X^1$ is —OH and $X^2$ is hydrogen;
$G^1$ is unsubstituted pyridin-2-yl;
$G^2$ is $G^{2d}$;
$G^{2d}$ is phenyl which is substituted with one or more substituents selected from the group consisting of —CN, $C_1$-$C_3$-alkyl, and —OR$^f$; and
R$^f$ is $C_1$-$C_3$-alkyl.
In a further embodiment, the compound has the configuration of Formula (II-i-b).

In one embodiment, the invention is directed to compounds of Formula (II-a) wherein:
$X^3$ is O;
$X^4$ is $(CH_2)_m$;
$X^5$ is $(CH_2)_n$;
m and n are both 2;
$X^1$ is —OH and $X^2$ is hydrogen;
$G^1$ is unsubstituted pyridin-2-yl;
$G^2$ is $G^{2d}$;
$G^{2d}$ is pyridinyl which is optionally substituted with 1, 2, or 3 substituents independently selected from the group consisting of halogen, $C_1$-$C_3$-alkyl, $C_1$-$C_3$-haloalkyl, and —OR$^f$; and
R$^f$ is $C_1$-$C_3$-alkyl or $C_1$-$C_3$-haloalkyl.
In a further embodiment, the compound has the configuration of Formula (II-i-b).

(vii) $G^1$ Substituents
In one embodiment, the invention is directed to compounds of Formula (II):

(II)

wherein:
each occurrence of $R^a$ and $R^b$, are each independently hydrogen, alkyl, haloalkyl, halogen, OH, O(alkyl), or a phenyl group which is optionally substituted with 1, 2, 3, 4, or 5 substituents independently selected from the group consisting of alkyl, haloalkyl, and halogen;
u is 0, 1, or 2;
$X^3$ is $CH_2$, O, S, $S(O)_2$, or NH;
$X^4$ is a bond or $(CH_2)_m$ and $X^5$ is $(CH_2)_n$, with the proviso that when $X^4$ is a bond and n is 1, then $X^3$ is $CH_2$;
m and n are integers that can be the same or different, and are each independently 1, 2, 3, 4, or 5;
$X^1$ is —OH and $X^2$ is hydrogen;
$G^1$ selected from the group consisting of cyclobutyl, cyclopentyl, cyclohexyl, 6,7-dihydro-5H-cyclopenta[b]pyridinyl, and 5,6,7,8-tetrahydroquinolinyl, each of which is optionally substituted with 1, 2, 3, 4, or 5 substituents independently selected from the group consisting of alkyl, alkenyl, alkynyl, halogen, haloalkyl, OR$^{gc}$, N(R$^{gc}$)$_2$, N(R$^{gc}$)C(O)alkyl, heteroaryl, and heterocycle; wherein the heteroaryl and the heterocycle moieties are each independently unsubstituted or substituted with 1, 2, 3, 4, or 5 substituents selected from the group consisting of alkyl, O(alkyl), halogen, and haloalkyl; and wherein each R$^{gc}$ is independently hydrogen, alkyl, or haloalkyl;
$G^2$ is $G^{2d}$ or —$(CR^{1g}R^{2g})_r$-$G^{2d}$ wherein:
r is 1, 2, or 3;
$R^{1g}$ and $R^{2g}$ are the same or different, and are each independently hydrogen, alkyl, halogen, OR$^{1gc}$, N(R$^{1gc}$)$_2$, C(O)alkyl, or haloalkyl; wherein each R$^{1gc}$ is independently hydrogen, alkyl, or haloalkyl;
$G^{2d}$ is aryl, heteroaryl, cycloalkyl, heterocycle, or cycloalkenyl, each of which is optionally substituted with 1, 2, 3, 4, or 5 substituents independently selected from the group consisting of G$^d$, alkyl, alkenyl, alkynyl, halogen, haloalkyl, —CN, —OR$^f$, —OC(O)R$^f$, —OC(O)N(R$^f$)$_2$, —S(O)$_2$R$^e$, —S(O)$_2$N(R$^f$)$_2$, —C(O)R$^f$, —C(O)OR$^f$, —C(O)N(R$^f$)$_2$, —N(R$^f$)$_2$, —N(R$^f$)C(O)R$^f$, —N(R$^f$)S(O)$_2$R$^e$, —N(R$^f$)C(O)O(R$^e$), —N(R$^f$)C(O)N(R$^f$)$_2$, —(CR$^{1a}$R$^{1b}$)$_q$-G$^d$, —(CR$^{1a}$R$^{1b}$)$_q$—OR$^f$, —(CR$^{1a}$R$^{1b}$)$_q$—OC(O)R$^f$, —(CR$^{1a}$R$^{1b}$)$_q$—OC(O)N(R$^f$)$_2$, —(CR$^{1a}$R$^{1b}$)$_q$—S(O)$_2$R$^e$, —(CR$^{1a}$R$^{1b}$)$_q$—S(O)$_2$N(R$^f$)$_2$, —(CR$^{1a}$R$^{1b}$)$_q$—C(O)R$^f$, —(CR$^{1a}$R$^{1b}$)$_q$—C(O)OR$^f$, —(CR$^{1a}$R$^{1b}$)$_q$—C(O)N(R$^f$)$_2$, —(CR$^{1a}$R$^{1b}$)$_q$—N(R$^f$)$_2$, —(CR$^{1a}$R$^{1b}$)$_q$—N(R$^f$)C(O)R$^f$, —(CR$^{1a}$R$^{1b}$)$_q$—N(R$^f$)S(O)$_2$R$^e$, —(CR$^{1a}$R$^{1b}$)$_q$—N(R$^f$)C(O)O (R$^e$), —(CR$^{1a}$R$^{1b}$)$_q$—N(R$^f$)C(O)N(R$^f$)$_2$, and —(CR$^{1a}$R$^{1b}$)$_q$—CN;
R$^{1a}$ and R$^{1b}$, are the same or different, and at each occurrence are each independently hydrogen, halogen, alkyl, or haloalkyl;
each occurrence of R$^f$ is independently hydrogen, alkyl, halolalkyl, G$^d$, or —(CR$^{1a}$R$^{1b}$)$_q$-G$^d$;
each occurrence of R$^e$ is independently alkyl, halolalkyl, G$^d$, or —(CR$^{1a}$R$^{1b}$)$_q$-G$^d$;
q, at each occurrence, is independently 1, 2, or 3;
each occurrence of G$^d$ is independently aryl, heteroaryl, cycloalkyl, heterocycle, or cycloalkenyl; and is each optionally substituted with 1, 2, 3, 4, or 5 substituents independently selected from the group consisting of alkyl, alkenyl, alkynyl, halogen, haloalkyl, —CN, —OR$^j$, —OC(O)R$^j$, —OC(O)N (R$^j$)$_2$, —S(O)$_2$R$^k$, —S(O)$_2$N(R$^j$)$_2$, —C(O)R$^j$, —C(O)OR$^j$, —C(O)N(R$^j$)$_2$, —N(R$^j$)$_2$, —N(R$^j$)C(O)R$^j$, —N(R$^j$)S(O)$_2$R$^k$, —N(R$^j$)C(O)O(R$^k$), —N(R$^j$)C(O)N(R$^j$)$_2$, —(CR$^{1a}$R$^{1b}$)$_q$—OR$^j$, —(CR$^{1a}$R$^{1b}$)$_q$—OC(O)R$^j$, —(CR$^{1a}$R$^{1b}$)$_q$—OC(O)N (R$^j$)$_2$, —(CR$^{1a}$R$^{1b}$)$_q$—S(O)$_2$R$^k$, —(CR$^{1a}$R$^{1b}$)$_q$—S(O)$_2$N (R$^j$)$_2$, —(CR$^{1a}$R$^{1b}$)$_q$—C(O)R$^j$, —(CR$^{1a}$R$^{1b}$)$_q$—C(O)OR$^j$, —(CR$^{1a}$R$^{1b}$)$_q$—C(O)N(R$^j$)$_2$, —(CR$^{1a}$R$^{1b}$)$_q$—N(R$^j$)$_2$, —(CR$^{1a}$R$^{1b}$)$_q$—N(R$^j$)C(O)R$^j$, —(CR$^{1a}$R$^{1b}$)$_q$—N(R$^j$)S(O)$_2$ R$^k$, —(CR$^{1a}$R$^{1b}$)$_q$—N(R$^1$)C(O)O(R$^k$), —(CR$^{1a}$R$^{1b}$)$_q$—N (R$^j$)C(O)N(R$^j$)$_2$, and —(CR$^{1a}$R$^{1b}$)$_q$—CN;
each occurrence of R$^j$ is independently hydrogen, alkyl, or halolalkyl; and
each occurrence of R$^k$ is independently alkyl or halolalkyl.
In a preferred embodiment, u is 0. In further embodiments, the compound has the configuration of Formula (II-i-a):

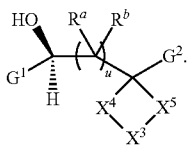

(II-i-a)

In one embodiment, the invention is directed to compounds of Formula (II) wherein:
u is 0;
$X^3$ is $CH_2$, O, S, $S(O)_2$, or NH;
$X^4$ is a bond or $(CH_2)_m$ and $X^5$ is $(CH_2)_n$, with the proviso that when $X^4$ is a bond and n is 1, then $X^3$ is $CH_2$;
m and n are integers that can be the same or different, and are each independently 1, 2, 3, 4, or 5;
$X^1$ is —OH and $X^2$ is hydrogen;
$G^1$ is selected from the group consisting of cyclobutyl, cyclopentyl, cyclohexyl, 6,7-dihydro-5H-cyclopenta[b]pyridinyl, and 5,6,7,8-tetrahydroquinolinyl;
wherein the cyclobutyl, cyclopentyl, and cyclohexyl are optionally substituted with 1 or 2 substituents that are $N(R^{gc})_2$, wherein each $R^{gc}$ is independently hydrogen or alkyl;
$G^2$ is $G^{2d}$; and
$G^{2d}$ is optionally substituted aryl or optionally substituted heteroaryl.
In a further embodiment, the compound has the configuration of Formula (II-i-a).

In one embodiment, the invention is directed to compounds of Formula (II) wherein:
u is 0;
$X^3$ is $CH_2$, O, S, $S(O)_2$, or NH;
$X^4$ is a bond or $(CH_2)_m$ and $X^5$ is $(CH_2)_n$, with the proviso that when $X^4$ is a bond and n is 1, then $X^3$ is $CH_2$;
m and n are integers that can be the same or different, and are each independently 1, 2, 3, 4, or 5;
$X^1$ is —OH and $X^2$ is hydrogen;
$G^1$ is selected from the group consisting of cyclobutyl, cyclopentyl, cyclohexyl, 6,7-dihydro-5H-cyclopenta[b]pyridinyl, and 5,6,7,8-tetrahydroquinolinyl; wherein the cyclobutyl, cyclopentyl, and cyclohexyl are optionally substituted with 1 or 2 substituents that are $N(R^{gc})_2$, wherein each $R^{gc}$ is independently hydrogen or $C_1$-$C_6$-alkyl;
$G^2$ is $G^{2d}$;
$G^{2d}$ is phenyl, pyridinyl, or pyrimidinyl; each of which is optionally substituted with 1, 2, or 3 substituents independently selected from the group consisting of halogen, —CN, $C_1$-$C_6$-alkyl, $C_1$-$C_6$-haloalkyl, and —$OR^f$; and
$R^f$ is $C_1$-$C_6$-alkyl or $C_1$-$C_6$-haloalkyl.
In a further embodiment, the compound has the configuration of Formula (II-i-a).

In one embodiment, the invention is directed to compounds of Formula (II) wherein:
u is 0;
$X^3$ is $CH_2$, O, S, $S(O)_2$, or NH;
$X^4$ is a bond or $(CH_2)_m$ and $X^5$ is $(CH_2)_n$, with the proviso that when $X^4$ is a bond and n is 1, then $X^3$ is $CH_2$;
m and n are integers that can be the same or different, and are each independently 1, 2, 3, 4, or 5;
$X^1$ is —OH and $X^2$ is hydrogen;
$G^1$ is selected from the group consisting of cyclobutyl, cyclopentyl, cyclohexyl, 6,7-dihydro-5H-cyclopenta[b]pyridinyl, and 5,6,7,8-tetrahydroquinolinyl; wherein the cyclobutyl, cyclopentyl, and cyclohexyl are optionally substituted with 1 or 2 substituents that are $N(R^{gc})_2$, wherein each $R^{gc}$ is independently hydrogen or $C_1$-$C_4$-alkyl;
$G^2$ is $G^{2d}$;
$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —$OR^f$; and
$R^f$ is $C_1$-$C_4$-alkyl or $C_1$-$C_4$-haloalkyl.
In a further embodiment, the compound has the configuration of Formula (II-i-a).

In one embodiment, the invention is directed to compounds of Formula (II) wherein:
u is 0;
$X^3$ is $CH_2$, O, S, $S(O)_2$, or NH;
$X^4$ is a bond or $(CH_2)_m$ and $X^5$ is $(CH_2)_n$, with the proviso that when $X^4$ is a bond and n is 1, then $X^3$ is $CH_2$;
m and n are integers that can be the same or different, and are each independently 1, 2, 3, 4, or 5;
$X^1$ is —OH and $X^2$ is hydrogen;
$G^1$ is selected from the group consisting of cyclobutyl, cyclopentyl, cyclohexyl, 6,7-dihydro-5H-cyclopenta[b]pyridinyl, and 5,6,7,8-tetrahydroquinolinyl; wherein the cyclobutyl, cyclopentyl, and cyclohexyl are optionally substituted with 1 or 2 substituents that are $N(R^{gc})_2$, wherein each $R^{gc}$ is independently hydrogen or $C_1$-$C_4$-alkyl;
$G^2$ is $G^{2d}$;
$G^{2d}$ is phenyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.
In a further embodiment, the compound has the configuration of Formula (II-i-a).

In one embodiment, the invention is directed to compounds of Formula (II) wherein:
u is 0;
$X^3$ is $CH_2$, O, S, $S(O)_2$, or NH;
$X^4$ is a bond or $(CH_2)_m$ and $X^5$ is $(CH_2)_n$, with the proviso that when $X^4$ is a bond and n is 1, then $X^3$ is $CH_2$;
m and n are integers that can be the same or different, and are each independently 1, 2, 3, 4, or 5;
$X^1$ is —OH and $X^2$ is hydrogen;
$G^1$ is selected from the group consisting of cyclobutyl, cyclopentyl, cyclohexyl, 6,7-dihydro-5H-cyclopenta[b]pyridinyl, and 5,6,7,8-tetrahydroquinolinyl; wherein the cyclobutyl, cyclopentyl, and cyclohexyl are optionally substituted with 1 or 2 substituents that are $N(R^{gc})_2$, wherein each $R^{gc}$ is independently hydrogen or $C_1$-$C_4$-alkyl;
$G^2$ is $G^{2d}$;
$G^{2d}$ is pyridinyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.
In a further embodiment, the compound has the configuration of Formula (II-i-a).

In one embodiment, the invention is directed to compounds of Formula (II) wherein:
u is 0;
$X^3$ is $CH_2$; $X^4$ is $(CH_2)_m$; $X^5$ is $(CH_2)_n$; and m and n are each 1; and
$X^1$ is —OH and $X^2$ is hydrogen;
$G^1$ is selected from the group consisting of cyclobutyl, cyclopentyl, cyclohexyl, 6,7-dihydro-5H-cyclopenta[b]pyridinyl, and 5,6,7,8-tetrahydroquinolinyl; wherein the cyclobutyl, cyclopentyl, and cyclohexyl are optionally substituted with 1 or 2 substituents that are $N(R^{gc})_2$, wherein each $R^{gc}$ is independently hydrogen or $C_1$-$C_4$-alkyl;
$G^2$ is $G^{2d}$;

G$^{2d}$ is phenyl or pyridinyl; each of which is optionally substituted with 1, 2, or 3 substituents independently selected from the group consisting of halogen, C$_1$-C$_4$-alkyl, C$_1$-C$_4$-haloalkyl, and —OR$^f$; and R$^f$ is C$_1$-C$_4$-alkyl or C$_1$-C$_4$-haloalkyl.

In a further embodiment, the compound has the configuration of Formula (II-i-a).

In one embodiment, the invention is directed to compounds of Formula (II) wherein:

u is 0;

X$^3$ is CH$_2$; X$^4$ is (CH$_2$)$_m$; X$^5$ is (CH$_2$)$_n$; and m and n are each 1; and X$^1$ is —OH and X$^2$ is hydrogen;

G$^1$ is selected from the group consisting of cyclobutyl, cyclopentyl, and cyclohexyl; wherein the cyclobutyl, cyclopentyl, and cyclohexyl are optionally substituted with 1 or 2 substituents that are N(R$^{gc}$)$_2$, wherein each R$^{gc}$ is independently hydrogen or C$_1$-C$_4$-alkyl;

G$^2$ is G$^{2d}$;

G$^{2d}$ is phenyl or pyridinyl; each of which is optionally substituted with 1, 2, or 3 substituents independently selected from the group consisting of halogen, C$_1$-C$_3$-alkyl, C$_1$-C$_3$-haloalkyl, and —OR$^f$; and R$^f$ is C$_1$-C$_3$-alkyl or C$_1$-C$_3$-haloalkyl.

In a further embodiment, the compound has the configuration of Formula (II-i-a).

In one embodiment, the invention is directed to compounds of Formula (II) wherein:

u is 0;

X$^3$ is CH$_2$; X$^4$ is (CH$_2$)$_m$; X$^5$ is (CH$_2$)$_n$; and m and n are each 1; and X$^1$ is —OH and X$^2$ is hydrogen;

G$^1$ is cyclopentyl; wherein the cyclopentyl is optionally substituted with 1 or 2 substituents that are N(R$^{gc}$)$_2$, wherein each R$^{gc}$ is independently hydrogen or C$_1$-C$_4$-alkyl;

G$^2$ is G$^{2d}$;

G$^{2d}$ is phenyl or pyridinyl; each of which is optionally substituted with 1, 2, or 3 substituents independently selected from the group consisting of halogen, C$_1$-C$_3$-alkyl, C$_1$-C$_3$-haloalkyl, and —OR$^f$; and R$^f$ is C$_1$-C$_3$-alkyl or C$_1$-C$_3$-haloalkyl.

In a further embodiment, the compound has the configuration of Formula (II-i-a).

In one embodiment, the invention is directed to compounds of Formula (II) wherein:

u is 0;

X$^3$ is CH$_2$; X$^4$ is (CH$_2$)$_m$; X$^5$ is (CH$_2$)$_n$; and m and n are each 1; and X$^1$ is —OH and X$^2$ is hydrogen;

G$^1$ is cyclopentyl that is substituted with 1 substituent that is N(R$^{gc}$)$_2$, wherein each R$^{gc}$ is independently hydrogen or methyl;

G$^2$ is G$^{2d}$;

G$^{2d}$ is phenyl or pyridinyl; each of which is optionally substituted with 1, 2, or 3 substituents independently selected from the group consisting of chloro, fluoro, trifluoromethyl, and —OR$^f$; and R$^f$ is trifluoromethyl.

In a further embodiment, the compound has the configuration of Formula (II-i-a).

In one embodiment, the invention is directed to compounds of Formula (II) wherein:

u is 0;

X$^3$ is O; X$^4$ is a bond, X$^5$ is (CH$_2$)$_n$, and n is 2; or
X$^3$ is O; X$^4$ is (CH$_2$)$_m$, X$^5$ is (CH$_2$)$_n$, m and n are each 1; or
X$^3$ is O; X$^4$ is (CH$_2$)$_m$, X$^5$ is (CH$_2$)$_n$, m is 1, and n is 2; or
X$^3$ is O; X$^4$ is a bond, X$^5$ is (CH$_2$)$_n$, and n is 3.

X$^1$ is —OH and X$^2$ is hydrogen;

G$^1$ is selected from the group consisting of cyclobutyl, cyclopentyl, cyclohexyl, 6,7-dihydro-5H-cyclopenta[b]pyridinyl, and 5,6,7,8-tetrahydroquinolinyl;

wherein the cyclobutyl, cyclopentyl, and cyclohexyl are optionally substituted with 1 or 2 substituents that are N(R$^{gc}$)$_2$, wherein each R$^{gc}$ is independently hydrogen or C$_1$-C$_4$-alkyl;

G$^2$ is G$^{2d}$;

G$^{2d}$ is phenyl or pyridinyl; each of which is optionally substituted with 1, 2, or 3 substituents independently selected from the group consisting of halogen, C$_1$-C$_4$-alkyl, C$_1$-C$_4$-haloalkyl, and —OR$^f$; and R$^f$ is C$_1$-C$_4$-alkyl or C$_1$-C$_4$-haloalkyl.

In a further embodiment, the compound has the configuration of Formula (II-i-a).

In one embodiment, the compound of Formula (I) is selected from the group consisting of:

(anti)-[1-(3,4-dichlorophenyl)cyclobutyl][6,7-dihydro-5H-cyclopenta[b]-pyridin-7-yl]methanol;
(syn)-[1-(3,4-dichlorophenyl)cyclobutyl][6,7-dihydro-5H-cyclopenta[b]-pyridin-7-yl]methanol;
(anti)-[1-(3,4-difluorophenyl)cyclobutyl][5,6,7,8-tetrahydroquinolin-8-yl]-methanol;
(syn)-[1-(3,4-difluorophenyl)cyclobutyl][5,6,7,8-tetrahydroquinolin-8-yl]-methanol;
(anti)-[1-(3,4-difluorophenyl)cyclobutyl][6,7-dihydro-5H-cyclopenta[b]-pyridin-7-yl]methanol;
(syn)-[1-(3,4-difluorophenyl)cyclobutyl][6,7-dihydro-5H-cyclopenta[b]-pyridin-7-yl]methanol;
(anti)-6,7-dihydro-5H-cyclopenta[b]pyridin-7-yl{1-[4-(trifluoromethyl)-phenyl]cyclobutyl}-methanol;
(syn)-6,7-dihydro-5H-cyclopenta[b]pyridin-7-yl{1-[4-(trifluoromethyl)-phenyl]cyclobutyl}-methanol;
(anti)-6,7-dihydro-5H-cyclopenta[b]pyridin-7-yl{1-[4-(trifluoromethoxy)-phenyl]cyclobutyl}methanol;
(syn)-6,7-dihydro-5H-cyclopenta[b]pyridin-7-yl{1-[4-(trifluoromethoxy)-phenyl]cyclobutyl}methanol;
(anti)-5,6,7,8-tetrahydroquinolin-8-yl{1-[4-(trifluoromethoxy)phenyl]-cyclobutyl}methanol;
(syn)-5,6,7,8-tetrahydroquinolin-8-yl{1-[4-(trifluoromethoxy)phenyl]-cyclobutyl}methanol;
(anti)-5,6,7,8-tetrahydroquinolin-8-yl{1-[3-(trifluoromethyl)phenyl]-cyclobutyl}methanol;
(syn)-5,6,7,8-tetrahydroquinolin-8-yl{1-[3-(trifluoromethyl)phenyl]-cyclobutyl}methanol;
(anti)-[1-(3,4-dichlorophenyl)cyclobutyl][5,6,7,8-tetrahydroquinolin-8-yl]-methanol;
(syn)-[1-(3,4-dichlorophenyl)cyclobutyl][5,6,7,8-tetrahydroquinolin-8-yl]-methanol;
(anti)-5,6,7,8-tetrahydroquinolin-8-yl{1-[4-(trifluoromethyl)phenyl]-cyclobutyl}methanol;
(syn)-5,6,7,8-tetrahydroquinolin-8-yl{1-[4-(trifluoromethyl)phenyl]-cyclobutyl}methanol;
(anti)-6,7-dihydro-5H-cyclopenta[b]pyridin-7-yl{1-[3-(trifluoromethyl)-phenyl]cyclobutyl}methanol;
(syn)-6,7-dihydro-5H-cyclopenta[b]pyridin-7-yl{1-[3-(trifluoromethyl)-phenyl]cyclobutyl}methanol;
(anti)-5,6,7,8-tetrahydroquinolin-8-yl{1-[3-(trifluoromethoxy)phenyl]-cyclobutyl}methanol;
(syn)-5,6,7,8-tetrahydroquinolin-8-yl{1-[3-(trifluoromethoxy)phenyl]-cyclobutyl}methanol;
(anti)-6,7-dihydro-5H-cyclopenta[b]pyridin-7-yl{1-[3-(trifluoromethoxy)-phenyl]cyclobutyl}methanol;
(syn)-6,7-dihydro-5H-cyclopenta[b]pyridin-7-yl{1-[3-(trifluoromethoxy)-phenyl]cyclobutyl}methanol;

(anti)-5,6,7,8-tetrahydroquinolin-8-yl{1-[2-(trifluoromethoxy)phenyl]-cyclobutyl}methanol;
(syn)-5,6,7,8-tetrahydroquinolin-8-yl{1-[2-(trifluoromethoxy)phenyl]-cyclobutyl}methanol;
(anti)-6,7-dihydro-5H-cyclopenta[b]pyridin-7-yl{1-[2-(trifluoromethoxy)-phenyl]cyclobutyl}methanol;
(syn)-6,7-dihydro-5H-cyclopenta[b]pyridin-7-yl{1-[2-(trifluoromethoxy)-phenyl]cyclobutyl}methanol;
(anti)-5,6,7,8-tetrahydroquinolin-8-yl{1-[2-(trifluoromethyl)phenyl]-cyclobutyl}methanol;
(syn)-5,6,7,8-tetrahydroquinolin-8-yl{1-[2-(trifluoromethyl)phenyl]-cyclobutyl}methanol;
(anti)-6,7-dihydro-5H-cyclopenta[b]pyridin-7-yl{1-[2-(trifluoromethyl)-phenyl]cyclobutyl}methanol;
(syn)-6,7-dihydro-5H-cyclopenta[b]pyridin-7-yl{1-[2-(trifluoromethyl)-phenyl]cyclobutyl}methanol;
(2-aminocyclopentyl){1-[3-(trifluoromethyl)phenyl]cyclobutyl}methanol;
(2-aminocyclopentyl){1-[4-(trifluoromethyl)phenyl]cyclobutyl}methanol;
(2-aminocyclopentyl){1-[4-(trifluoromethoxy)phenyl]cyclobutyl}methanol;
(2-aminocyclohexyl){1-[4-(trifluoromethyl)phenyl]cyclobutyl}methanol;
(2-aminocyclopentyl){1-[3-(trifluoromethoxy)phenyl]cyclobutyl}methanol;
(2-aminocyclohexyl){1-[4-(trifluoromethoxy)phenyl]cyclobutyl}methanol;
(2-aminocyclohexyl){1-[3-(trifluoromethoxy)phenyl]cyclobutyl}methanol;
(2-aminocyclohexyl)[1-(3,4-dichlorophenyl)cyclobutyl]methanol;
(2-aminocyclohexyl){1-[3-(trifluoromethyl)phenyl]cyclobutyl}methanol;
(2-aminocyclobutyl){1-[3-(trifluoromethyl)phenyl]cyclobutyl}methanol;
(2-aminocyclopentyl){1-[2-(trifluoromethoxy)phenyl]cyclobutyl}methanol;
(2-aminocyclopentyl)[1-(3,4-dichlorophenyl)cyclobutyl]methanol;
(R)-[(1S,2R)-2-aminocyclopentyl][1-(3,4-dichlorophenyl)cyclobutyl]-methanol;
(S)-[(1R,2S)-2-aminocyclopentyl][1-(3,4-dichlorophenyl)cyclobutyl]-methanol;
(R)-[(1R,2S)-2-aminocyclopentyl][1-(3,4-dichlorophenyl)cyclobutyl]-methanol;
(S)-[(1S,2S)-2-aminocyclopentyl][1-(3,4-dichlorophenyl)cyclobutyl]-methanol;
(R)-[(1R,2R)-2-aminocyclopentyl][1-(3,4-dichlorophenyl)cyclobutyl]-methanol;
(R)-[(1S,2R)-2-aminocyclopentyl]{1-[4-(trifluoromethoxy)phenyl]-cyclobutyl}methanol;
(S)-[(1S,2S)-2-aminocyclopentyl]{1-[4-(trifluoromethoxy)phenyl]-cyclobutyl}methanol;
(R)-[(1R,2R)-2-aminocyclopentyl]{1-[4-(trifluoromethoxy)phenyl]-cyclobutyl}methanol;
(R)-[(1R,2R)-2-aminocyclopentyl][1-(4-chlorophenyl)cyclobutyl]methanol;
(S)-[(1S,2S)-2-aminocyclopentyl][1-(4-chlorophenyl)cyclobutyl]methanol;
(R)-[(1R,2S)-2-aminocyclopentyl][1-(2-fluorophenyl)cyclobutyl]methanol;
(R)-[(1R,2R)-2-aminocyclopentyl]{1-[3-(trifluoromethyl)phenyl]-cyclobutyl}methanol;
(R)-[1-(3,4-dichlorophenyl)cyclobutyl][(1R,2R)-2-(methylamino)-cyclopentyl]methanol; and
(R)-[(1R,2S)-2-aminocyclopentyl]{1-[4-(trifluoromethoxy)phenyl]-cyclobutyl}methanol (viii) $G^{2d}$ Substituents In one embodiment, the invention is directed to compounds of Formula (II):

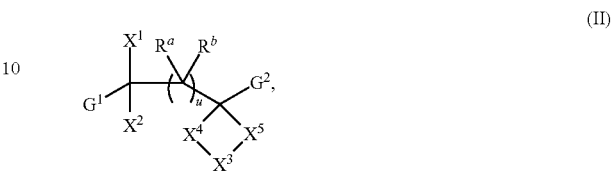

(II)

wherein:
each occurrence of $R^a$ and $R^b$, are each independently hydrogen, alkyl, haloalkyl, halogen, OH, O(alkyl), or a phenyl group which is optionally substituted with 1, 2, 3, 4, or 5 substituents independently selected from the group consisting of alkyl, haloalkyl, and halogen;
u is 0, 1, or 2;
$X^3$ is $CH_2$, O, S, $S(O)_2$, or NH;
$X^4$ is a bond or $(CH_2)_m$ and $X^5$ is $(CH_2)_n$, with the proviso that when $X^4$ is a bond and n is 1, then $X^3$ is $CH_2$;
m and n are integers that can be the same or different, and are each independently 1, 2, 3, 4, or 5;
$X^1$ is —OH and $X^2$ is hydrogen;
$G^1$ is aryl, heteroaryl, cycloalkyl, heterocycle, or cycloalkenyl; each of which is optionally substituted with 1, 2, 3, 4, or 5 substituents independently selected from the group consisting of alkyl, alkenyl, alkynyl, halogen, haloalkyl, $OR^{gc}$, $N(R^{gc})_2$, $N(R^{gc})C(O)$alkyl, heteroaryl, and heterocycle; wherein the heteroaryl and the heterocycle moieties are each independently unsubstituted or substituted with 1, 2, 3, 4, or 5 substituents selected from the group consisting of alkyl, O(alkyl), halogen, and haloalkyl; and wherein each $R^{gc}$ is independently hydrogen, alkyl, or haloalkyl;
$G^2$ is $G^{2d}$ or —$(CR^{1g}R^{2g})_r$-$G^{2d}$ wherein:
r is 1, 2, or 3;
$R^{1g}$ and $R^{2g}$ are the same or different, and are each independently hydrogen, alkyl, halogen, $OR^{1gc}$, $N(R^{1gc})_2$, C(O)alkyl, or haloalkyl; wherein each $R^{1gc}$ is independently hydrogen, alkyl, or haloalkyl; and
$G^{2d}$ is selected from the group consisting of cyclopentyl, cyclohexyl, cyclohexenyl, pyrrolidinyl, piperidinyl, tetrahydrofuranyl, dihydropyranyl, tetrahydropyranyl, benzothiazolyl, benzoxazolyl, and benzimidazolyl.

In a preferred embodiment, u is 0. In further embodiments, the compound has the configuration of Formula (II-i-a):

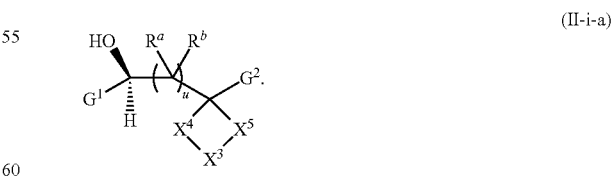

(II-i-a)

In one embodiment, the invention is directed to compounds of Formula (II) wherein:
u is 0;
$X^3$ is $CH_2$, O, S, $S(O)_2$, or NH;
$X^4$ is a bond or $(CH_2)_m$ and $X^5$ is $(CH_2)_n$, with the proviso that when $X^4$ is a bond and n is 1, then $X^3$ is $CH_2$;

m and n are integers that can be the same or different, and are each independently 1, 2, 3, 4, or 5;

$X^1$ is —OH and $X^2$ is hydrogen;

$G^1$ is optionally substituted heteroaryl or optionally substituted cycloalkyl;

$G^2$ is $G^{2d}$; and $G^{2d}$ is selected from the group consisting of cyclopentyl, cyclohexyl, cyclohexenyl, pyrrolidinyl, piperidinyl, tetrahydrofuranyl, dihydropyranyl, tetrahydropyranyl, benzothiazolyl, benzoxazolyl, and benzimidazolyl.

In a further embodiment, the compound has the configuration of Formula (II-i-a).

In one embodiment, the invention is directed to compounds of Formula (II) wherein:

u is 0;

$X^3$ is $CH_2$, O, S, $S(O)_2$, or NH;

$X^4$ is a bond or $(CH_2)_m$ and $X^5$ is $(CH_2)_n$, with the proviso that when $X^4$ is a bond and n is 1, then $X^3$ is $CH_2$;

m and n are integers that can be the same or different, and are each independently 1, 2, 3, 4, or 5;

$X^1$ is —OH and $X^2$ is hydrogen;

$G^1$ is optionally substituted pyridinyl, pyrimidinyl, thiazolyl, oxazolyl, or pyrazolyl;

$G^2$ is $G^{2d}$; and $G^{2d}$ is selected from the group consisting of cyclopentyl, cyclohexyl, cyclohexenyl, pyrrolidinyl, piperidinyl, tetrahydrofuranyl, dihydropyranyl, tetrahydropyranyl, benzothiazolyl, benzoxazolyl, and benzimidazolyl.

In a further embodiment, the compound has the configuration of Formula (II-i-a).

In one embodiment, the invention is directed to compounds of Formula (II) wherein:

u is 0;

$X^3$ is $CH_2$, O, S, $S(O)_2$, or NH;

$X^4$ is a bond or $(CH_2)_m$ and $X^5$ is $(CH_2)_n$, with the proviso that when $X^4$ is a bond and n is 1, then $X^3$ is $CH_2$;

m and n are integers that can be the same or different, and are each independently 1, 2, 3, 4, or 5;

$X^1$ is —OH and $X^2$ is hydrogen;

$G^1$ is pyridinyl or pyrimidinyl; each of which is optionally substituted with 1, 2, or 3 substituents independently selected from the group consisting of halogen, $C_1$-$C_6$-alkyl, $C_1$-$C_6$-haloalkyl, and $N(R^{gc})_2$; and $R^{gc}$ is hydrogen or $C_1$-$C_6$-alkyl;

$G^2$ is $G^{2d}$; and $G^{2d}$ is selected from the group consisting of cyclopentyl, cyclohexyl, cyclohexenyl, pyrrolidinyl, piperidinyl, tetrahydrofuranyl, dihydropyranyl, tetrahydropyranyl, benzothiazolyl, benzoxazolyl, and benzimidazolyl.

In a further embodiment, the compound has the configuration of Formula (II-i-a).

In one embodiment, the invention is directed to compounds of Formula (II) wherein:

u is 0;

$X^3$ is $CH_2$, O, S, $S(O)_2$, or NH;

$X^4$ is a bond or $(CH_2)_m$ and $X^5$ is $(CH_2)_n$, with the proviso that when $X^4$ is a bond and n is 1, then $X^3$ is $CH_2$;

m and n are integers that can be the same or different, and are each independently 1, 2, 3, 4, or 5;

$X^1$ is —OH and $X^2$ is hydrogen;

$G^1$ is pyridinyl which is optionally substituted with 1 or 2 substituents independently selected from the group consisting of halogen, $C_1$-$C_4$-alkyl, $C_1$-$C_4$-haloalkyl, and $N(R^{gc})_2$;

$R^{gc}$ is hydrogen or $C_1$-$C_4$-alkyl;

$G^2$ is $G^{2d}$; and $G^{2d}$ is selected from the group consisting of cyclopentyl, cyclohexyl, cyclohexenyl, pyrrolidinyl, piperidinyl, tetrahydrofuranyl, dihydropyranyl, tetrahydropyranyl, benzothiazolyl, benzoxazolyl, and benzimidazolyl.

In a further embodiment, the compound has the configuration of Formula (II-i-a).

In one embodiment, the invention is directed to compounds of Formula (II) wherein:

u is 0;

$X^3$ is $CH_2$, O, S, $S(O)_2$, or NH;

$X^4$ is a bond or $(CH_2)_m$ and $X^5$ is $(CH_2)_n$, with the proviso that when $X^4$ is a bond and n is 1, then $X^3$ is $CH_2$;

m and n are integers that can be the same or different, and are each independently 1, 2, 3, 4, or 5;

$X^1$ is —OH and $X^2$ is hydrogen;

$G^1$ is unsubstituted pyridinyl;

$G^2$ is $G^{2d}$; and $G^{2d}$ is selected from the group consisting of cyclopentyl, cyclohexyl, cyclohexenyl, pyrrolidinyl, piperidinyl, tetrahydrofuranyl, dihydropyranyl, tetrahydropyranyl, benzothiazolyl, benzoxazolyl, and benzimidazolyl.

In a further embodiment, the compound has the configuration of Formula (II-i-a).

In one embodiment, the invention is directed to compounds of Formula (II) wherein:

u is 0;

$X^3$ is $CH_2$, O, S, $S(O)_2$, or NH;

$X^4$ is a bond or $(CH_2)_m$ and $X^5$ is $(CH_2)_n$, with the proviso that when $X^4$ is a bond and n is 1, then $X^3$ is $CH_2$;

m and n are integers that can be the same or different, and are each independently 1, 2, 3, 4, or 5;

$X^1$ is —OH and $X^2$ is hydrogen;

$G^1$ is unsubstituted pyridin-2-yl;

$G^2$ is $G^{2d}$; and $G^{2d}$ is selected from the group consisting of cyclopentyl, cyclohexyl, cyclohexenyl, pyrrolidinyl, piperidinyl, tetrahydrofuranyl, dihydropyranyl, tetrahydropyranyl, benzothiazolyl, benzoxazolyl, and benzimidazolyl.

In a further embodiment, the compound has the configuration of Formula (II-i-a).

In one embodiment, the invention is directed to compounds of Formula (II) wherein:

u is 0;

$X^3$ is $CH_2$;

$X^4$ is $(CH_2)_m$;

$X^5$ is $(CH_2)_n$;

m and n are each 1;

$X^1$ is —OH and $X^2$ is hydrogen;

$G^1$ is unsubstituted pyridin-2-yl;

$G^2$ is $G^{2d}$; and $G^{2d}$ is selected from the group consisting of cyclopentyl, cyclohexyl, cyclohexenyl, pyrrolidinyl, piperidinyl, tetrahydrofuranyl, dihydropyranyl, tetrahydropyranyl, benzothiazolyl, benzoxazolyl, and benzimidazolyl.

In a further embodiment, the compound has the configuration of Formula (II-i-a).

In one embodiment, the invention is directed to compounds of Formula (II) wherein:

u is 0;

$X^3$ is $CH_2$;

$X^4$ is $(CH_2)_m$;

$X^5$ is $(CH_2)_n$;

m and n are each 1;

$X^1$ is —OH and $X^2$ is hydrogen;

$G^1$ is unsubstituted pyridin-2-yl;

$G^2$ is $G^{2d}$; and $G^{2d}$ is selected from the group consisting of benzothiazolyl, benzoxazolyl, and benzimidazolyl.

In a further embodiment, the compound has the configuration of Formula (II-i-a).

In one embodiment, the invention is directed to compounds of Formula (II) wherein:
u is 0;
$X^3$ is O; $X^4$ is a bond, $X^5$ is $(CH_2)_n$, and n is 2; or
$X^3$ is O; $X^4$ is $(CH_2)_m$, $X^5$ is $(CH_2)_n$, m and n are each 1; or
$X^3$ is O; $X^4$ is $(CH_2)_m$, $X^5$ is $(CH_2)_n$, m is 1, and n is 2; or
$X^3$ is O; $X^4$ is a bond, $X^5$ is $(CH_2)_n$, and n is 3;
$X^1$ is —OH and $X^2$ is hydrogen;
$G^1$ is optionally substituted heteroaryl or optionally substituted cycloalkyl;
$G^2$ is $G^{2d}$; and
$G^{2d}$ is selected from the group consisting of cyclopentyl, cyclohexyl, cyclohexenyl, pyrrolidinyl, piperidinyl, tetrahydrofuranyl, dihydropyranyl, tetrahydropyranyl, benzothiazolyl, benzoxazolyl, and benzimidazolyl.

In a further embodiment, the compound has the configuration of Formula (II-i-a).

In one embodiment, the compound of Formula (I) is selected from the group consisting of:
(1-cyclohexylcyclobutyl)(pyridin-2-yl)methanol;
(1-cyclopentylcyclobutyl)(pyridin-2-yl)methanol;
pyridin-2-yl[1-(tetrahydro-2H-pyran-4-yl)cyclobutyl]methanol;
3-{1-[hydroxy(pyridin-2-yl)methyl]cyclobutyl}tetrahydrofuran-3-ol;
[1-(3,6-dihydro-2H-pyran-4-yl)cyclobutyl](pyridin-2-yl)methanol;
[1-(4,4-difluorocyclohex-1-en-1-yl)cyclobutyl](pyridin-2-yl)methanol;
pyridin-2-yl{1-[5-(trifluoromethyl)cyclohex-1-en-1-yl]cyclobutyl}methanol;
tert-butyl 3-{1-[hydroxy(pyridin-2-yl)methyl]cyclobutyl}pyrrolidine-1-carboxylate;
[1-(1,3-benzothiazol-2-yl)cyclobutyl](pyridin-2-yl)methanol;
[1-(5,6-dihydro-2H-pyran-3-yl)cyclobutyl](pyridin-2-yl)methanol;
[1-(3,4-dihydro-2H-pyran-5-yl)cyclobutyl](pyridine-2-yl)methanol;
[1-(1,3-benzoxazol-2-yl)cyclobutyl](pyridin-2-yl)methanol;
[1-(4,4-difluorocyclohexyl)cyclobutyl](pyridin-2-yl)methanol;
[1-(1-methyl-1H-benzimidazol-2-yl)cyclobutyl](pyridin-2-yl)methanol;
tert-butyl 4-{1-[hydroxy(pyridin-2-yl)methyl]cyclobutyl}piperidine-1-carboxylate;
pyridin-2-yl{1-[4-(trifluoromethyl)cyclohexyl]cyclobutyl}methanol;
pyridin-2-yl[1-(tetrahydro-2H-pyran-3-yl)cyclobutyl]methanol;
pyridin-2-yl[1-(tetrahydrofuran-3-yl)cyclobutyl]methanol;
[1-(6-chloro-1,3-benzothiazol-2-yl)cyclobutyl](pyridin-2-yl)methanol;
[1-(6-fluoro-1,3-benzothiazol-2-yl)cyclobutyl](pyridin-2-yl)methanol; and
[1-(6-chloro-1,3-benzoxazol-2-yl)cyclobutyl](pyridin-2-yl)methanol.

Exemplary compounds include, but are not limited to:
pyridin-2-yl{3-[4-(trifluoromethyl)phenyl]tetrahydrofuran-3-yl}methanol;
4-{3-[hydroxy(pyridin-2-yl)methyl]tetrahydrofuran-3-yl}benzonitrile;
pyridin-2-yl{3-[3-(trifluoromethoxy)phenyl]tetrahydrofuran-3-yl}methanol;
3-{3-[hydroxy(pyridin-2-yl)methyl]tetrahydrofuran-3-yl}benzonitrile;
[3-(4-methoxyphenyl)tetrahydrofuran-3-yl](pyridin-2-yl)methanol;
[3-(3,4-dimethoxyphenyl)tetrahydrofuran-3-yl](pyridin-2-yl)methanol;
pyridin-2-yl{1-[6-(trifluoromethyl)pyridin-3-yl]cyclobutyl}methanol;
[3-(3-chlorophenyl)oxetan-3-yl](pyridin-2-yl)methanol;
[3-(3,4-dichlorophenyl)oxetan-3-yl](pyridin-2-yl)methanol;
(anti)-pyridin-2-yl{2-[4-(trifluoromethyl)phenyl]tetrahydrofuran-2-yl}-methanol;
(syn)-pyridin-2-yl{2-[4-(trifluoromethyl)phenyl]tetrahydrofuran-2-yl}-methanol;
[2-(2-methylphenyl)tetrahydrofuran-2-yl](pyridin-2-yl)methanol;
[2-(3-methylphenyl)tetrahydrofuran-2-yl](pyridin-2-yl)methanol;
(anti)-pyridin-2-yl{2-[3-(trifluoromethoxy)phenyl]tetrahydrofuran-2-yl}-methanol;
(syn)-pyridin-2-yl{2-[3-(trifluoromethoxy)phenyl]tetrahydrofuran-2-yl}-methanol;
(anti)-pyridin-2-yl{2-[4-(trifluoromethoxy)phenyl]tetrahydrofuran-2-yl}-methanol;
(syn)-pyridin-2-yl{2-[4-(trifluoromethoxy)phenyl]tetrahydrofuran-2-yl}-methanol;
(anti)-pyridin-2-yl{2-[2-(trifluoromethoxy)phenyl]tetrahydrofuran-2-yl}-methanol;
(syn)-pyridin-2-yl{2-[2-(trifluoromethoxy)phenyl]tetrahydrofuran-2-yl}-methanol;
(anti)-[2-(3,4-dichlorophenyl)tetrahydrofuran-2-yl](pyridin-2-yl)methanol;
(syn)-[2-(3,4-dichlorophenyl)tetrahydrofuran-2-yl](pyridin-2-yl)methanol;
(anti)-[2-(3-fluorophenyl)tetrahydrofuran-2-yl](pyridin-2-yl)methanol;
(syn)-[2-(3-fluorophenyl)tetrahydrofuran-2-yl](pyridin-2-yl)methanol;
(anti)-[2-fluorophenyl)tetrahydrofuran-2-yl](pyridin-2-yl)methanol;
(syn)-[2-(2-fluorophenyl)tetrahydrofuran-2-yl](pyridin-2-yl)methanol;
(anti)-[2-(3-chlorophenyl)tetrahydrofuran-2-yl](pyridin-2-yl)methanol;
(syn)-[2-(3-chlorophenyl)tetrahydrofuran-2-yl](pyridin-2-yl)methanol;
(anti)-pyridin-2-yl{2-[3-(trifluoromethyl)phenyl]tetrahydrofuran-2-yl}-methanol;
(syn)-pyridin-2-yl{2-[3-(trifluoromethyl)phenyl]tetrahydrofuran-2-yl}-methanol;
(anti)-[2-(3,4-difluorophenyl)tetrahydrofuran-2-yl](pyridin-2-yl)methanol;
(syn)-[2-(3,4-difluorophenyl)tetrahydrofuran-2-yl](pyridin-2-yl)methanol;
pyridin-2-yl{1-[5-(trifluoromethyl)pyridin-3-yl]cyclobutyl}methanol;
pyridin-2-yl{1-[5-(trifluoromethyl)pyridin-2-yl]cyclobutyl}methanol;
pyridin-2-yl{1-[4-(trifluoromethyl)pyridin-2-yl]cyclobutyl}methanol;
(3-aminopyridin-2-yl){1-[3-(trifluoromethyl)phenyl]cyclobutyl}methanol;
(3-aminopyridin-2-yl){1-[4-(trifluoromethoxy)phenyl]cyclobutyl}methanol;
(R)-pyridin-2-yl{1-[4-(trifluoromethyl)pyridin-2-yl]cyclobutyl}methanol;

(S)-pyridin-2-yl{1-[4-(trifluoromethyl)pyridin-2-yl]cyclobutyl}methanol;
(3-aminopyridin-2-yl){1-[3-(trifluoromethoxy)phenyl]cyclobutyl}methanol;
(3-aminopyridin-2-yl){1-[4-(trifluoromethyl)phenyl]cyclobutyl}methanol;
(3-aminopyridin-2-yl)[1-(3,4-dichlorophenyl)cyclobutyl]methanol;
(R)-[(2S)-2-(3,4-dichlorophenyl)oxetan-2-yl](pyridin-2-yl)methanol;
(R)-[(2R)-2-(3,4-dichlorophenyl)oxetan-2-yl](pyridin-2-yl)methanol;
[4-(3,4-dichlorophenyl)piperidin-4-yl](pyridin-2-yl)methanol;
pyridin-2-yl{4-[2-(trifluoromethoxy)phenyl]piperidin-4-yl}methanol;
pyridin-2-yl{4-[4-(trifluoromethoxy)phenyl]piperidin-4-yl}methanol;
pyridin-2-yl{4-[4-(trifluoromethyl)phenyl]piperidin-4-yl}methanol;
pyridin-2-yl{4-[3-(trifluoromethoxy)phenyl]piperidin-4-yl}methanol;
pyridin-2-yl{3-[4-(trifluoromethyl)phenyl]azetidin-3-yl}methanol;
(1-cyclohexylcyclobutyl)(pyridin-2-yl)methanol;
(1-cyclopentylcyclobutyl)(pyridin-2-yl)methanol;
(anti)-[1-(3,4-dichlorophenyl)cyclobutyl][6,7-dihydro-5H-cyclopenta[b]-pyridin-7-yl]methanol;
(syn)-[1-(3,4-dichlorophenyl)cyclobutyl][6,7-dihydro-5H-cyclopenta[b]-pyridin-7-yl]methanol;
(anti)-[1-(3,4-difluorophenyl)cyclobutyl][5,6,7,8-tetrahydroquinolin-8-yl]-methanol;
(syn)-[1-(3,4-difluorophenyl)cyclobutyl][5,6,7,8-tetrahydroquinolin-8-yl]-methanol;
(anti)-[1-(3,4-difluorophenyl)cyclobutyl][6,7-dihydro-5H-cyclopenta[b]-pyridin-7-yl]methanol;
(syn)-[1-(3,4-difluorophenyl)cyclobutyl][6,7-dihydro-5H-cyclopenta[b]-pyridin-7-yl]methanol;
(anti)-6,7-dihydro-5H-cyclopenta[b]pyridin-7-yl{1-[4-(trifluoromethyl)-phenyl]cyclobutyl}methanol;
(syn)-6,7-dihydro-5H-cyclopenta[b]pyridin-7-yl{1-[4-(trifluoromethyl)-phenyl]cyclobutyl}methanol;
(anti)-6,7-dihydro-5H-cyclopenta[b]pyridin-7-yl{1-[4-(trifluoromethoxy)-phenyl]cyclobutyl}methanol;
(syn)-6,7-dihydro-5H-cyclopenta[b]pyridin-7-yl{1-[4-(trifluoromethoxy)-phenyl]cyclobutyl}methanol;
(anti)-5,6,7,8-tetrahydroquinolin-8-yl{1-[4-(trifluoromethoxy)phenyl]-cyclobutyl}methanol;
(syn)-5,6,7,8-tetrahydroquinolin-8-yl{1-[4-(trifluoromethoxy)phenyl]-cyclobutyl}methanol;
(anti)-5,6,7,8-tetrahydroquinolin-8-yl{1-[3-(trifluoromethyl)phenyl]-cyclobutyl}methanol;
(syn)-5,6,7,8-tetrahydroquinolin-8-yl{1-[3-(trifluoromethyl)phenyl]-cyclobutyl}methanol;
(anti)-[1-(3,4-dichlorophenyl)cyclobutyl][5,6,7,8-tetrahydroquinolin-8-yl]-methanol;
(syn)-[1-(3,4-dichlorophenyl)cyclobutyl][5,6,7,8-tetrahydroquinolin-8-yl]-methanol;
(anti)-5,6,7,8-tetrahydroquinolin-8-yl{1-[4-(trifluoromethyl)phenyl]-cyclobutyl}methanol;
(syn)-5,6,7,8-tetrahydroquinolin-8-yl{1-[4-(trifluoromethyl)phenyl]-cyclobutyl}methanol;
(anti)-6,7-dihydro-5H-cyclopenta[b]pyridin-7-yl{1-[3-(trifluoromethyl)-phenyl]cyclobutyl}methanol;
(syn)-6,7-dihydro-5H-cyclopenta[b]pyridin-7-yl{1-[3-(trifluoromethyl)-phenyl]cyclobutyl}methanol;
(anti)-5,6,7,8-tetrahydroquinolin-8-yl{1-[3-(trifluoromethoxy)phenyl]-cyclobutyl}methanol;
(syn)-5,6,7,8-tetrahydroquinolin-8-yl{1-[3-(trifluoromethoxy)phenyl]-cyclobutyl}methanol;
(anti)-6,7-dihydro-5H-cyclopenta[b]pyridin-7-yl{1-[3-(trifluoromethoxy)-phenyl]cyclobutyl}methanol;
(syn)-6,7-dihydro-5H-cyclopenta[b]pyridin-7-yl{1-[3-(trifluoromethoxy)-phenyl]cyclobutyl}methanol;
(anti)-5,6,7,8-tetrahydroquinolin-8-yl{1-[2-(trifluoromethoxy)phenyl]-cyclobutyl}methanol;
(syn)-5,6,7,8-tetrahydroquinolin-8-yl{1-[2-(trifluoromethoxy)phenyl]-cyclobutyl}methanol;
(anti)-6,7-dihydro-5H-cyclopenta[b]pyridin-7-yl{1-[2-(trifluoromethoxy)-phenyl]cyclobutyl}methanol;
(syn)-6,7-dihydro-5H-cyclopenta[b]pyridin-7-yl{1-[2-(trifluoromethoxy)-phenyl]cyclobutyl}methanol;
(anti)-5,6,7,8-tetrahydroquinolin-8-yl{1-[2-(trifluoromethyl)phenyl]-cyclobutyl}methanol;
(syn)-5,6,7,8-tetrahydroquinolin-8-yl{1-[2-(trifluoromethyl)phenyl]-cyclobutyl}methanol;
(anti)-6,7-dihydro-5H-cyclopenta[b]pyridin-7-yl{1-[2-(trifluoromethyl)-phenyl]cyclobutyl}methanol;
(syn)-6,7-dihydro-5H-cyclopenta[b]pyridin-7-yl{1-[2-(trifluoromethyl)-phenyl]cyclobutyl}methanol;
(2-aminocyclopentyl){1-[3-(trifluoromethyl)phenyl]cyclobutyl}methanol;
(2-aminocyclopentyl){1-[4-(trifluoromethoxy)phenyl]cyclobutyl}methanol;
(2-aminocyclohexyl){1-[4-(trifluoromethyl)phenyl]cyclobutyl}methanol;
(2-aminocyclopentyl){1-[3-(trifluoromethoxy)phenyl]cyclobutyl}methanol;
(2-aminocyclohexyl){1-[4-(trifluoromethoxy)phenyl]cyclobutyl}methanol;
(2-aminocyclohexyl){1-[3-(trifluoromethoxy)phenyl]cyclobutyl}methanol;
(2-aminocyclohexyl)[1-(3,4-dichlorophenyl)cyclobutyl]methanol;
(2-aminocyclohexyl){1-[3-(trifluoromethyl)phenyl]cyclobutyl}methanol;
(2-aminocyclobutyl){1-[3-(trifluoromethyl)phenyl]cyclobutyl}methanol;
(2-aminocyclopentyl){1-[2-(trifluoromethoxy)phenyl]cyclobutyl}methanol;
(2-aminocyclopentyl)[1-(3,4-dichlorophenyl)cyclobutyl]methanol;
(R)-[(1S,2R)-2-aminocyclopentyl][1-(3,4-dichlorophenyl)cyclobutyl]-methanol;
(S)-[(1R,2S)-2-aminocyclopentyl][1-(3,4-dichlorophenyl)cyclobutyl]-methanol;
(R)-[(1R,2S)-2-aminocyclopentyl][1-(3,4-dichlorophenyl)cyclobutyl]-methanol;
(S)-[(1S,2S)-2-aminocyclopentyl][1-(3,4-dichlorophenyl)cyclobutyl]-methanol;
(R)-[(1R,2R)-2-aminocyclopentyl][1-(3,4-dichlorophenyl)cyclobutyl]-methanol;
(R)-[(1S,2R)-2-aminocyclopentyl]{1-[4-(trifluoromethoxy)phenyl]-cyclobutyl}methanol;
(S)-[(1S,2S)-2-aminocyclopentyl]{1-[4-(trifluoromethoxy)phenyl]-cyclobutyl}methanol;
(R)-[(1R,2R)-2-aminocyclopentyl]{1-[4-(trifluoromethoxy)phenyl]-cyclobutyl}methanol;
(R)-[(1R,2R)-2-aminocyclopentyl][1-(4-chlorophenyl)cyclobutyl]methanol;
(S)-[(1S,2S)-2-aminocyclopentyl][1-(4-chlorophenyl)cyclobutyl]methanol;

(R)-[(1R,2S)-2-aminocyclopentyl][1-(2-fluorophenyl)cyclobutyl]methanol;
(R)-[(1R,2R)-2-aminocyclopentyl]{1-[3-(trifluoromethyl)phenyl]-cyclobutyl}methanol;
(R)-[1-(3,4-dichlorophenyl)cyclobutyl][(1R,2R)-2-(methylamino)-cyclopentyl]methanol;
(R)-[(1R,2S)-2-aminocyclopentyl]{1-[4-(trifluoromethoxy)phenyl]-cyclobutyl}methanol;
(Z)-[1-(3,4-dichlorophenyl)cyclobutyl](pyridin-2-yl)methanone oxime;
(S)-[1-(3,4-dichlorophenyl)cyclopropyl](pyridin-2-yl)methanol;
pyridin-2-yl{1-[6-(trifluoromethyl)pyridin-2-yl]cyclobutyl}methanol;
(S)-pyridin-2-yl{1-[6-(trifluoromethyl)pyridin-2-yl]cyclobutyl}methanol;
pyridin-2-yl[1-(tetrahydro-2H-pyran-4-yl)cyclobutyl]methanol;
(S)-pyridin-2-yl{1-[2-(trifluoromethyl)pyridin-4-yl]cyclobutyl}methanol;
3-{1-[hydroxy(pyridin-2-yl)methyl]cyclobutyl}tetrahydrofuran-3-ol;
[1-(3,6-dihydro-2H-pyran-4-yl)cyclobutyl](pyridin-2-yl)methanol;
[1-(2-methylbenzyl)cyclobutyl](pyridin-2-yl)methanol;
[1-(3-fluorobenzyl)cyclobutyl](pyridin-2-yl)methanol;
[1-(4,4-difluorocyclohex-1-en-1-yl)cyclobutyl](pyridin-2-yl)methanol;
pyridin-2-yl{1-[5-(trifluoromethyl)cyclohex-1-en-1-yl]cyclobutyl}methanol;
tert-butyl 3-{1-[hydroxy(pyridin-2-yl)methyl]cyclobutyl}pyrrolidine-1-carboxylate;
[1-(1,3-benzothiazol-2-yl)cyclobutyl](pyridin-2-yl)methanol;
[1-(5,6-dihydro-2H-pyran-3-yl)cyclobutyl](pyridin-2-yl)methanol;
[1-(3,4-dihydro-2H-pyran-5-yl)cyclobutyl](pyridine-2-yl)methanol;
[1-(1,3-benzoxazol-2-yl)cyclobutyl](pyridin-2-yl)methanol;
[1-(4,4-difluorocyclohexyl)cyclobutyl](pyridin-2-yl)methanol;
[1-(1-methyl-1H-benzimidazol-2-yl)cyclobutyl](pyridin-2-yl)methanol;
tert-butyl 4-{1-[hydroxy(pyridin-2-yl)methyl]cyclobutyl}piperidine-1-carboxylate;
pyridin-2-yl{1-[4-(trifluoromethyl)cyclohexyl]cyclobutyl}methanol;
pyridin-2-yl[1-(tetrahydro-2H-pyran-3-yl)cyclobutyl]methanol;
pyridin-2-yl[1-(tetrahydrofuran-3-yl)cyclobutyl]methanol;
[1-(3,4-dichlorophenyl)cyclobutyl](5-methoxypyridin-2-yl)methanol;
(S)-pyridin-2-yl{1-[4-(trifluoromethoxy)phenyl]cyclobutyl}methyl acetate;
[1-(3,4-dichlorophenyl)cyclobutyl](4-methoxypyridin-2-yl)methanol;
[1-(6-chloro-1,3-benzothiazol-2-yl)cyclobutyl](pyridin-2-yl)methanol;
[1-(6-fluoro-1,3-benzothiazol-2-yl)cyclobutyl](pyridin-2-yl)methanol; and
[1-(6-chloro-1,3-benzoxazol-2-yl)cyclobutyl](pyridin-2-yl)methanol.

The present compounds may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

Various stereoisomers of the present compounds and mixtures thereof are included within the scope of this application. Stereoisomers include enantiomers and diastereomers, and mixtures of enantiomers or diastereomers. Individual stereoisomers may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of the mixture of optical enantical enantiomers on chiral chromatographic columns.

Geometric isomers may exist in the present compounds. Various geometric isomers and mixtures thereof resulting from the disposition of substituents around a carbon-carbon double bond, a carbon-nitrogen double bond, a cycloalkyl group, or a heterocycle group are contemplated. Substituents around a carbon-carbon double bond or a carbon-nitrogen bond are designated as being of Z or E configuration and substituents around a cycloalkyl or a heterocycle are designated as being of cis or trans configuration.

Compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to, $^{2}H$, $^{3}H$, $^{13}C$, $^{14}C$, $^{15}N$, $^{18}O$, $^{32}P$, $^{35}S$, $^{18}F$, $^{36}Cl$, and $^{125}I$. Compounds that contain other isotopes of these and/or other atoms are within the scope of this invention.

In another embodiment, the isotope-labeled compounds contain deuterium ($^{2}H$), tritium ($^{3}H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples and Schemes sections by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut,* 21(11), 1116 (1996); Brickner, S J et al., *J Med Chem,* 39(3), 673 (1996); Mallesham, B et al., *Org Lett,* 5(7), 963 (2003); PCT publications WO1997010223, WO2005099353, WO1995007271, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147;

20090093422; 20090088416; and 20090082471, the methods are hereby incorporated by reference.

The isotope-labeled compounds of the invention may be used as standards to determine the effectiveness of TRPV3 modulators in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., *J. Labelled Comp. Radiopharmaceut.*, 36(10):927-932 (1995); Kushner et al., *Can. J. Physiol. Pharmacol.*, 77, 79-88 (1999)).

In addition, non-radio active isotope containing drugs, such as deuterated drugs called "heavy drugs," can be used for the treatment of diseases and conditions related to TRPV3 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug may alter its physicochemical properties such as pKa and lipid solubility. These effects and alterations may affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmcokinetic profile or efficacy relative to the non-isotopic compound.

c. Biological Data (i) In Vitro Antagonism of Recombinant Human TRPV3 Activation.

Test compounds were evaluated for ability to antagonize the activation of recombinant human TRPV3 using FLIPR® Tetra cellular screening. Specifically, on the day prior to the experiment recombinant HEK293 cells that stably express human TRPV3 were removed from tissue culture flasks and plated in growth medium at 20,000 cells/well into Poly-d-lysine coated black/clear 384-well Plate (Corning, 3845) using a Multidrop® dispenser (ThermoScientific, Waltham, Mass.). Prior to the start of the assay, the medium was removed by aspiration, and cells were loaded with 30 µL no-wash FLIPR® Calcium-4 dye ($\lambda_{EX}$=470-495 nm, $\lambda_{EM}$=515-575 nm; Molecular Devices, Sunnyvale, Calif.). The cells were then incubated for 90-120 minutes in the dark prior to addition of the test compound.

A double-addition protocol was used. The test compound (i.e., the TRPV3 antagonist) was added at the 10 second time point, followed by the addition of a TRPV3 agonist three minutes later. Each test compound evaluated was first dissolved in DMSO to prepare a 10 mM stock solution. A solution (5×) of the test compound was then prepared in DPBS (Dulbecco's Phosphate Buffered Saline) and 10 µL of that solution was added to the cells at a delivery rate of 40 µL/sec. The TRPV3 agonist used to activate human TRPV3 expressed by the HEK3 cells was 2-aminoethoxy-diphenyl borate (2-APB; Tocris Cookson, Ellisville, Mo.) at 80 µM. Final assay volume was 50 µL. Total length of an experimental run was 10 minutes.

Changes in fluorescence were measured over time using the FLIPR® instrument. The intensity of the fluorescence was captured and digitally transferred to an interfaced computer. The maximum response minus minimum response was calculated and expressed as the percentage of the maximum 2-APB response in the absence of antagonist. The concentration of 2-APB corresponds to its $EC_{80}$.

Table 1 reports the $IC_{50}$ values measured for the test compounds as human TRPV3 antagonists. As used in Table 1, "A" refers to an $IC_{50}$ value of greater than 20 µM, "B" refers to an $IC_{50}$ value in range of 5.1 µM to 20 µM, "C" refers to an $IC_{50}$ value in range of 1.1 µM to 5 µM, "D" refers to an $IC_{50}$ value in range of 501 nM to 1,000 nM, and "E" refers to an $IC_{50}$ value in range of 50 nM to 500 nM. Actual measured values are shown parenthetically after the reported range. In most cases, the values reported are average values from at least two runs (i.e., n≥2).

TABLE 1

| EXAMPLE | IC50 (µM) |
| --- | --- |
| 1 | C (1.5) |
| 2 | E (0.32) |
| 3 | D (0.79) |
| 4 | E (0.46) |
| 5 | B (5.22) |
| 6 | E (0.35) |
| 7 | B (17.5) |
| 8 | E (0.38) |
| 9 | C (1.51) |
| 10 | C (1.1) |
| 11 | E (0.4) |
| 12 | E (0.42) |
| 13 | D (0.6) |
| 14 | A (>20) |
| 15 | E (0.31) |
| 16 | A (>20) |
| 17 | C (1.1) |
| 18 | D (0.74) |
| 19 | A (>20) |
| 20 | A (>20) |
| 21 | A (>20) |
| 22 | A (>20) |
| 23 | D (0.93) |
| 24 | C (4.7) |
| 25 | C (1.18) |
| 26 | E (0.31) |
| 27 | C (1.4) |
| 28 | E (0.44) |
| 29 | C (2.54) |
| 30 | C (1.72) |
| 31 | C (3.08) |
| 32 | A (>20) |

TABLE 1-continued

| EXAMPLE | IC50 (μM) |
|---|---|
| 33 | B (8.5) |
| 34 | A (>20) |
| 35 | B (10.2) |
| 36 | B (5.18) |
| 37 | D (0.83) |
| 38 | E (0.06*) |
| 39 | D (0.74) |
| 40 | B (13.3) |
| 41 | >10 |
| 42 | >10 |
| 43 | E (0.66) |
| 44 | B (8) |
| 45 | C (2.22) |
| 46 | B (13.7) |
| 47 | C (2.22) |
| 48 | B (5.68) |
| 49 | C (3.27) |
| 50 | C (2.42) |
| 51 | B (8.25) |
| 52 | C (5.02) |
| 53 | C (1.75) |
| 54 | A (22) |
| 55 | B (7.12) |
| 56 | C (1.07) |
| 57 | B (9.29) |
| 58 | C (3.63) |
| 59 | C (1.79) |
| 60 | B (7.55) |
| 61 | B (7.54) |
| 62 | B (11.8) |
| 63 | B (7.17) |
| 64 | C (2.34) |
| 65 | C (2.26) |
| 66 | C (1.52) |
| 67 | C (2.6) |
| 68 | C (3.68) |
| 69 | C (4.97) |
| 70 | B (12) |
| 71 | C (2.13) |
| 72 | C (2.24) |
| 73 | C (1.94) |
| 74 | E (0.41) |
| 75 | D (0.94) |
| 76 | D (0.65) |
| 77 | D (0.76) |
| 78 | C (3.56) |
| 79 | A (>20) |
| 80 | C (1.78) |
| 81 | A (>20) |
| 82 | D (0.78) |
| 83 | A (>20) |
| 84 | A (>20) |
| 85 | B (5.61) |
| 86 | C (3.56) |
| 87 | A (>20) |
| 88 | E (0.37) |
| 89 | C (2) |
| 90 | E (0.46) |
| 91 | E (0.33) |
| 92 | E (0.1) |
| 93 | D (0.59) |
| 94 | E (0.36) |
| 95 | C (1.85) |
| 96 | C (1.22) |
| 97 | E (0.3) |
| 98 | E (0.11) |
| 99 | C (1.24) |
| 100 | D (0.83) |
| 101 | A (>20) |
| 102 | A (>20) |
| 103 | C (2) |
| 104 | E (0.28) |
| 105 | B (7.57) |
| 106 | E (0.21) |
| 107 | C (2.93) |
| 108 | D (0.61) |
| 109 | B (5.81) |
| 110 | E (0.5) |
| 111 | E (0.19) |
| 112 | E (0.3) |
| 113 | E (0.26) |
| 114 | E (0.23) |
| 115 | B (19.4) |
| 116 | D (0.75) |
| 117 | C (2.42) |
| 118 | E (0.22) |
| 119 | D (0.57) |
| 120 | A (>20) |
| 121 | A (>20) |
| 122 | A (>20) |
| 123 | E (0.39) |
| 124 | A (>20) |
| 125 | B (18.6) |
| 126 | D (0.82) |
| 127 | B (11.6) |
| 128 | E (0.11) |
| 129 | E (0.33) |
| 130 | C (3.11) |
| 131 | C (0.82) |
| 132 | B (9.33) |
| 133 | E (0.12) |
| 134 | D (0.86) |
| 135 | D (1.01) |
| 136 | E (0.39) |
| 137 | C (4.87) |
| 138 | D (0.83) |
| 139 | D (0.75) |
| 140 | A (>20) |
| 141 | A (>20) |
| 142 | A (>20) |
| 143 | A (>20) |
| 144 | A (>20) |
| 145 | C (1.77) |
| 146 | B (12.8) |
| 147 | A (>20) |
| 148 | C (3.1) |
| 149 | B (6.2) |
| 150 | C (1.69) |
| 151 | C (1.24) |
| 152 | B (19.7) |
| 153 | B (8.01) |
| 154 | E (0.23) |
| 155 | B (17) |
| 156 | A (>20) |
| 157 | A (>20) |
| 158 | A (>20) |
| 159 | C (1.98) |
| 160 | B (6.11) |
| 161 | C (3.27) |
| 162 | C (3.88) |
| 163 | C (4.9) |
| 164 | C (2.61) |
| 165 | B (16.6) |
| 166 | B (5.94) |
| 167 | A (>20) |
| 168 | B (9.14) |
| 169 | B (5.82) |
| 170 | A (>20) |
| 171 | A (>20) |
| 172 | A (>20) |
| 173 | A (>20) |
| 174 | A (>20) |
| 175 | A (>20) |
| 176 | A (>20) |
| 177 | C (3.38) |
| 178 | A (>20) |
| 179 | C (2.95) |
| 180 | A (>20) |
| 181 | C (1.98) |
| 182 | A (>20) |
| 183 | C (1.4) |
| 184 | A (>20) |
| 185 | A (>20) |
| 186 | A (>20) |

TABLE 1-continued

| EXAMPLE | IC50 (µM) |
|---|---|
| 187 | A (>20) |
| 188 | A (>20) |
| 189 | A (>20) |
| 190 | A (>20) |
| 191 | >7.4 |
| 192 | A (>20) |
| 193 | A (>20) |
| 194 | A (>20) |
| 195 | A (>20) |
| 196 | A (>20) |
| 197 | A (>20) |
| 198 | A (>20) |
| 199 | A (>20) |
| 200 | B (5.25) |
| 201 | B (6.01) |
| 202 | B (5.17) |
| 203 | B (13.8) |
| 204 | C (1.6) |
| 205 | C (3.87) |
| 206 | C (2.63) |
| 207 | C (3.99) |
| 208 | C (2.06) |
| 209 | C (4.6) |
| 210 | C (3.31) |
| 211 | B (6.17) |
| 212 | C (2.87) |
| 213 | C (3.24) |
| 214 | C (1.22) |
| 215 | D (0.77) |
| 216 | C (2.26) |
| 217 | C (3.99) |
| 218 | C (1.73) |
| 219 | C (3.07) |
| 220 | D (0.65) |
| 221 | C (1.8) |
| 222 | C (2.35) |
| 223 | C (2.07) |
| 224 | C (4.84) |
| 225 | C (2.82) |
| 226 | D (0.79) |
| 227 | E (0.5) |
| 228 | C (2.52) |
| 229 | C (4.58) |
| 230 | >10 |
| 231 | D (0.54) |
| 232 | C (1.95) |
| 233 | B (10.8) |
| 234 | B (5.36) |
| 235 | C (3.32) |
| 236 | D (0.76) |
| 237 | C (3.66) |
| 238 | C (3.91) |
| 239 | ND |
| 240 | D (0.71) |
| 241 | C (1.67) |
| 242 | B (5.1) |
| 243 | B (18.5) |
| 244 | C (3.6) |
| 245 | C (3.65) |
| 246 | A (>20) |
| 247 | C (4.31) |
| 248 | C (1.17) |
| 249 | C (3.93) |
| 250 | B (9.23) |
| 251 | C (1.97) |
| 252 | A (>20) |
| 253 | C (3.4) |
| 254 | C (4.22) |
| 255 | B (5.49) |
| 256 | C (2.24) |
| 257 | B (9.51) |
| 258 | B (11) |
| 259 | E (0.47) |
| 260 | B (5.32) |
| 261 | C (1.27) |
| 262 | D (0.63) |
| 263 | C (2.8) |
| 264 | E (0.23) |
| 265 | B (5.64) |
| 266 | C (2.31) |
| 267 | C (2.41) |
| 268 | C (2.13) |
| 269 | B (11.2) |
| 270 | C (3.94) |
| 271 | C (2.19) |
| 272 | E (0.19) |
| 273 | E (0.09) |
| 274 | C (3.11) |
| 275 | B (19) |
| 276 | E (0.2) |
| 277 | C (1.97) |
| 278 | B (6.6) |
| 279 | B (7.5) |
| 280 | C (1.95) |
| 281 | B (7.69) |
| 282 | D (0.74) |
| 283 | D (0.69) |
| 284 | A (>20) |
| 285 | D (1) |
| 286 | C (1.47) |
| 287 | A (>20) |
| 288 | B (14.6) |
| 289 | A (>20) |
| 290 | A (>20) |
| 291 | B (17.3) |
| 292 | D (0.56) |
| 293 | A (>20) |
| 294 | A (>20) |
| 295 | A (>20) |
| 296 | A (>20) |
| 297 | A (>20) |
| 298 | A (>20) |
| 299 | A (>20) |
| 300 | C (4.92) |
| 301 | B (6.04) |
| 302 | D (0.95) |
| 303 | D (0.53) |
| 304 | E (0.25) |
| 305 | E (0.29) |
| 306 | E (0.14) |
| 307 | B (8.23) |
| 308 | D (1) |
| 309 | C (3.05) |
| 310 | A (>20) |
| 311 | A (>20) |
| 312 | C (1.96) |
| 313 | A (>20) |

ND = not determined.

(ii) In Vitro Metabolic Stability (Human and Rat Microsomal Stability)

Test compounds were evaluated for metabolic stability in an in vitro rat microsomal stability assay using rat (Sprague-Dawley, from BD Biosciences) liver microsomes and/or an in vitro human microsomal stability assay using human (Xenotech) liver microsomes. Incubations were conducted using a 0.5 µM substrate concentration in dimethyl sulfoxide (DMSO) and 0.25 mg/mL microsomal protein in 50 mM phosphate buffer at pH 7.4. Incubations were carried out at 37° C. with a final incubation volume of 135 µL. Time-zero samples were prepared by transferring 13.5 µL of compound-microsomal mixture to the quench plates containing 45 µL of quench solution consisting of 50 nM carbutamide as internal standard in 1:1 methanol:acetonitrile. A 1.5 µL aliquot of reduced nicotine adenine disphosphonucleotide (NADPH) (Chem-Impex Int'L Inc., Lot 12532024) was also added to the time-zero plates. The reaction was initiated by the addition of 13.5 µL NADPH to the compound-microsomal mixture and then quenched after 30 minutes by addition of 15 µL of incubation mixture to 45 µL of quench solution. The percent of parent compound remaining after the 30-minute microsomal incubation was ascertained by HPLC-MS/MS and is reported in the table.

TABLE 2

| EXAMPLE* | HUMAN MICROSOMAL STABILITY (% REMAINING AFTER 30 MINUTES) | RAT MICROSOMAL STABILITY (% REMAINING AFTER 30 MINUTES) |
|---|---|---|
| 1 | 0.38 | 0.48 |
| 2 | 17 | 0.64 |
| 3 | 28 | 3.8 |
| 4 | 19 | 4.2 |
| 5 | 0.27 | 0.06 |
| 6 | 1.2 | 2.3 |
| 7 | 0.15 | 0.32 |
| 8 | 0.13 | 0.73 |
| 9 | 0.12 | 0.18 |
| 10 | 0.42 | 0.62 |
| 11 | 0.72 | 0.80 |
| 12 | 24 | 11 |
| 13 | 7.4 | 19 |
| 15 | 5.6 | 1.2 |
| 17 | 21 | 13 |
| 18 | ND | 0.27 |
| 19 | >85 | 76 |
| 20 | 80 | 81 |
| 21 | 71 | 52 |
| 23 | 0.12 | 0.69 |
| 24 | 20 | 17 |
| 25 | 21 | 1.3 |
| 26 | 6.3 | 1.0 |
| 27 | 13 | 15 |
| 28 | 12 | 13 |
| 29 | 5.3 | 45 |
| 30 | 1.5 | 0.98 |
| 37 | ND | 7.7 |
| 38 | ND | 9.5 |
| 39 | 51 | 11 |
| 40 | 68 | 5.6 |
| 41 | 54 | 21 |
| 42 | 50 | 40 |
| 43 | 1.8 | 0.31 |
| 45 | 0.03 | 0.02 |
| 46 | 11 | 0.23 |
| 49 | 15 | 0.13 |
| 50 | 0.08 | 0.18 |
| 52 | 1.7 | 0.05 |
| 54 | ND | 0.21 |
| 55 | 1.6 | 0.29 |
| 56 | 0.42 | 1.1 |
| 57 | 16 | 10 |
| 58 | 36 | 33 |
| 59 | 45 | 12 |
| 66 | 31 | 23 |
| 67 | 58 | 47 |
| 74 | 6.8 | 0.45 |
| 75 | 44 | 0.74 |
| 76 | 39 | 0.47 |
| 77 | 11 | 0.94 |
| 82 | 35 | 16 |
| 85 | 82 | 76 |
| 87 | 47 | 8.6 |
| 88 | 38 | 7.0 |
| 89 | 70 | 4.3 |
| 90 | 35 | <0.01 |
| 91 | 46 | 1.0 |
| 92 | 2.7 | 0.23 |
| 93 | 12 | 0.33 |
| 94 | 55 | 3.8 |
| 95 | 57 | 0.61 |
| 96 | 0.68 | 0.15 |
| 97 | 6.4 | 0.16 |
| 98 | 7.6 | 0.020 |
| 99 | 30 | 0.17 |
| 100 | 26 | 2.9 |
| 101 | 40 | 0.17 |
| 102 | 45 | 0.55 |
| 103 | 73 | 0.012 |
| 104 | 15 | 0.42 |
| 105 | 42 | 0.040 |
| 106 | 3.9 | 1.6 |
| 107 | 31 | 0.23 |
| 108 | 13 | 4.9 |
| 109 | 45 | 0.74 |
| 110 | 8.0 | 2.8 |
| 111 | 52 | 23 |
| 112 | 75 | 75 |
| 113 | 24 | 18 |
| 114 | 6.9 | 11 |
| 115 | >85 | 81 |
| 116 | 37 | 25 |
| 117 | 18 | 50 |
| 118 | >85 | 74 |
| 119 | >85 | 69 |
| 120 | 1.6 | <0.01 |
| 121 | 41 | 0.18 |
| 122 | 28 | 26 |
| 123 | 21 | 11 |
| 124 | 1.6 | <0.01 |
| 125 | 53 | 8.8 |
| 126 | 21 | 7.7 |
| 127 | 51 | 1.1 |
| 128 | 59 | 67 |
| 129 | 46 | 0.01 |
| 130 | 4.0 | <0.01 |
| 131 | >85 | 50 |
| 132 | 81 | 72 |
| 133 | 73 | 61 |
| 134 | 78 | 72 |
| 135 | 33 | 3.4 |
| 136 | 24 | 9.5 |
| 137 | 77 | >85 |
| 138 | 41 | 18 |
| 139 | 41 | 26 |
| 140 | >85 | 37 |
| 141 | >85 | 59 |
| 142 | >85 | 37 |
| 143 | >85 | 80 |
| 144 | >85 | 51 |
| 145 | 68 | 42 |
| 146 | 84 | 8.9 |
| 147 | >85 | 79 |
| 148 | >85 | 53 |
| 149 | >85 | 62 |
| 150 | 42 | <0.01 |
| 151 | 32 | <0.01 |
| 152 | >85 | >85 |
| 153 | 49 | 21 |
| 154 | 56 | 78 |
| 155 | >85 | 76 |
| 156 | 26 | 0.08 |
| 157 | 28 | 0.93 |
| 158 | 3.7 | 0.04 |
| 159 | 45 | 65 |
| 160 | >85 | 60 |
| 161 | 61 | <0.01 |
| 162 | 0.02 | <0.01 |
| 163 | 0.11 | <0.01 |
| 164 | 71 | 81 |
| 165 | 83 | 77 |
| 166 | >85 | >85 |
| 167 | 9.5 | <0.01 |
| 168 | 5.6 | <0.01 |
| 169 | <0.01 | <0.01 |
| 170 | <0.01 | <0.01 |
| 171 | 2.7 | <0.01 |
| 172 | 2.4 | <0.01 |
| 173 | 45 | <0.01 |
| 174 | 26 | <0.01 |
| 175 | 29 | <0.01 |
| 176 | 20 | <0.01 |
| 177 | 0.12 | <0.01 |

TABLE 2-continued

| EXAMPLE* | HUMAN MICROSOMAL STABILITY (% REMAINING AFTER 30 MINUTES) | RAT MICROSOMAL STABILITY (% REMAINING AFTER 30 MINUTES) |
|---|---|---|
| 178 | 9.2 | <0.01 |
| 179 | <0.01 | <0.01 |
| 180 | <0.01 | <0.01 |
| 181 | <0.01 | <0.01 |
| 182 | <0.01 | <0.01 |
| 183 | <0.01 | <0.01 |
| 184 | 0.46 | <0.01 |
| 1 | >85 | 0.39 | <0.01 |
| 186 | 0.18 | <0.01 |
| 187 | <0.01 | <0.01 |
| 188 | 0.16 | <0.01 |
| 189 | 0.65 | <0.01 |
| 190 | 3.7 | <0.01 |
| 191 | <0.01 | <0.01 |
| 192 | <0.01 | <0.01 |
| 193 | 0.02 | <0.01 |
| 194 | 0.08 | <0.01 |
| 195 | <0.01 | <0.01 |
| 196 | <0.01 | <0.01 |
| 197 | 0.26 | <0.01 |
| 198 | 0.05 | <0.01 |
| 199 | >85 | >85 |
| 200 | >85 | >85 |
| 201 | 73 | >85 |
| 202 | 73 | <0.01 |
| 203 | >85 | 74 |
| 204 | >85 | >85 |
| 205 | >85 | >85 |
| 206 | 83 | 62 |
| 208 | ND | 36 |
| 212 | >85 | 3.9 |
| 213 | >85 | 72 |
| 216 | >85 | 41 |
| 217 | 73 | 68 |
| 220 | >85 | 67 |
| 221 | 83 | 56 |
| 222 | >85 | 59 |
| 223 | >85 | 65 |
| 224 | >85 | 70 |
| 225 | >85 | 34 |
| 226 | >85 | <0.01 |
| 227 | >85 | 42 |
| 228 | 70 | 25 |
| 229 | >85 | 80 |
| 230 | 33 | 30 |
| 231 | 4.0 | 17 |
| 232 | 80 | 67 |
| 233 | >85 | 67 |
| 234 | 19 | 23 |
| 235 | 20 | <0.01 |
| 236 | 54 | 41 |
| 237 | 51 | 50 |
| 238 | 7.1 | 21 |
| 239 | 57 | 0.072 |
| 240 | 50 | 38 |
| 241 | 66 | 59 |
| 242 | 45 | <0.01 |
| 243 | 64 | 55 |
| 244 | 80 | 77 |
| 245 | 57 | 72 |
| 246 | 71 | 59 |
| 247 | 62 | >85 |
| 248 | 70 | 29 |
| 249 | 61 | 3.2 |
| 250 | 70 | 70 |
| 253 | 0.21 | 0.017 |
| 254 | 1.1 | 0.57 |
| 255 | 54 | <0.01 |
| 256 | 44 | 55 |
| 257 | 42 | 57 |
| 258 | 70 | 53 |
| 259 | 76 | 73 |
| 260 | 12 | <0.01 |
| 261 | 0.01 | <0.01 |
| 262 | 48 | 57 |
| 263 | ND | >85 |
| 264 | 56 | 59 |
| 265 | 43 | 0.059 |
| 266 | 46 | 0.14 |
| 267 | 64 | 10 |
| 268 | 66 | 82 |
| 269 | 40 | 12 |
| 270 | 17 | 0.48 |
| 271 | 62 | 8.6 |
| 272 | 54 | 48 |
| 273 | 42 | 65 |
| 274 | 55 | 10 |
| 275 | 67 | 5.7 |
| 276 | 72 | 73 |
| 277 | >85 | >85 |
| 278 | 83 | >85 |
| 279 | 22 | <0.01 |
| 280 | 9.0 | <0.01 |
| 281 | >85 | 0.054 |
| 282 | >85 | >85 |
| 283 | >85 | >85 |
| 284 | >85 | 16 |
| 2 | >85 | 83 | 69 |
| 286 | >85 | 70 |
| 287 | 15 | <0.01 |
| 288 | <0.01 | <0.01 |
| 289 | 4.2 | <0.01 |
| 290 | >85 | 71 |
| 291 | >85 | 53 |
| 292 | 19 | 5.4 |
| 293 | 78 | 69 |
| 294 | >85 | >85 |
| 295 | 70 | 8.2 |
| 296 | 67 | 12 |
| 297 | >85 | 2.0 |
| 298 | 80 | 59 |
| 299 | >85 | >85 |
| 300 | 35 | 0.020 |
| 301 | 57 | 22 |
| 303 | 80 | 32 |
| 304 | >85 | 44 |
| 305 | 63 | 49 |
| 306 | >85 | >85 |
| 307 | 73 | >85 |
| 308 | 41 | 13 |
| 309 | >85 | ND |
| 310 | >85 | >85 |
| 311 | >85 | >85 |
| 312 | >85 | >85 |
| 313 | 81 | >85 |

ND = not determined.
*Microsomal stability was not determined for those Examples not listed in Table 2.

(iii) In Vivo Efficacy Against Neuropathic Pain

Test compounds were evaluated for analgesic effect in an in vivo chronic constriction injury (CCI) model of neuropathic pain. CD1 mice (Charles River) were used for these studies. Prior to testing (2-4 weeks) animals underwent a surgical procedure consisting of approximately 3 loose ligatures around the sciatic nerve. Following sterilization procedures, under isofluorane anesthetic, a 1.5 cm incision was made dorsal to the pelvis. The biceps femoris and gluteous superficialis (right side) were separated and the sciatic nerve exposed, isolated, and 2-4 loose ligatures (5-0 chromic gut) with less than 1 mm spacing were placed around it. Following hemostasis, the wound was sutured (layer of muscle closed with 5-0 nylon suture, and the wound closed with surgical staples) and coated with iodine. The mice were allowed to recover on a warming plate and were returned to their home cages (soft bedding) when able to walk on their own.

Two to four weeks after the surgery, test compound was administered orally (PO) in these mice, and mechanical allodynia was evaluated 1 hour after oral dosing where the threshold to response was assessed using calibrated von Frey monofilaments. The von Frey monofilaments were applied to the hind paw at increasing forces until the animal responded by lifting its paw. Normally, the force of the von Frey monofilament was innocuous and only in the altered state (allodynia or hyperalgesia) did the animals respond to this stimulation. Test compounds were evaluated to determine the degree to which they showed analgesic activity by prolonging the latency to respond to thermal stimulation or increasing the grams of force needed to elicit a withdrawal response. At the end of the experiment, after behavioral testing, plasma (and in some instances brain tissue) was taken for exposure analysis.

Each test compound was evaluated in eight different mice. The data reported in Table 3 represent the average value of the approximate percent effect of each compound in relieving neuropathic pain in mice receiving 100 mg/kg oral dose of the test compound. The grams of force needed to elicit a withdrawal response from the injured mouse that was challenged with vehicle was assigned a 0% effect, while the grams of force needed to elicit a withdrawal response from the control was given a 100% effect.

TABLE 3

| EXAMPLE | % EFFECT |
|---|---|
| 118 | 89 |
| 119 | 16 |
| 128 | 78 |
| 134 | 98 |
| 136 | 52 |
| 201 | 64 |
| 228 | 52 |
| 232 | 65 |
| 236 | 33 |
| 250 | 57 |
| 262 | 45 |
| 283 | 49 |
| 285 | 59 |
| 306 | 0 |

(iv) Additional In Vivo Pain ModelsThere are a number of additional animal models that can be employed for studying pain. Generally, these pain models mimic one of the mechanisms of pain (e.g., nociceptive, inflammatory, or neuropathic pain), rather than the pain associated with any one disease or injury. Such models provide evidence of whether a drug or therapy will be effective in treating any of a number of injuries, diseases, or conditions that generate pain via a particular mechanism. In addition to the Chronic Constriction Injury Model (CCI) discussed above, other animal models of pain that can be used to evaluate test compounds include, but are not limited to, the Chung model, the carageenan induced hyperalgesia model, and the Freund's complete adjuvant (CFA) induced hyperalgesia model.

(v) In Vivo Efficacy Against ItchTest compounds were evaluated for efficacy against itch in an in vivo mouse model of itch. Specifically, CD1 male mice (about 30 g) were shaved on the back of their neck about 18 hours before testing. Test compound in 10% DMSO/PEG 400 was administered orally. 60 Minutes after oral administration of the test compound, chloroquine (400 g/50 µL) was injected with a Hamilton syringe. Within a minute of injection the mice were observed for 10 minutes and the episodes of scratching were recorded.

d. Methods of Using the Compounds:

Data in Table 1 demonstrates that present compounds are modulators of TRPV3 receptors, and thus are useful in the treatment of diseases, conditions, and/or disorders modulated by TRPV3. The relationship between therapeutic effect and inhibition of TRPV3 has been shown in WO2007/056124; Wissenbach, U. et al., Biology of the cell (2004), 96, 47-54; Nilius, B. et al., Physiol Rev (2007), 87, 165-217; Okuhara, D. Y. et al., Expert Opinion on Therapeutic Targets (2007), 11, 391-401; Hu, H. Z. et al., Journal of Cellular Physiology (2006), 208, 201-212.

One embodiment is therefore directed to a method for treating a disease, condition, and/or disorder modulated by TRPV3 in a subject in need thereof, said method comprises administering to the subject a therapeutically effective amount of a compound, or pharmaceutically acceptable salt, solvate, salt of a solvate or solvate of a salt thereof, optionally with a pharmaceutically acceptable carrier.

Diseases, conditions, and/or disorders that are modulated by TRPV3 include, but are not limited to, migraine, arthralgia, cardiac pain arising from an ischemic myocardium, acute pain, chronic pain, nociceptive pain, neuropathic pain, post-operative pain, pain due to neuralgia (e.g., post-herpetic neuralgia, traumatic neuralgia, fibromyalgia, trigeminal neuralgia), pain due to diabetic neuropathy, dental pain and cancer pain, inflammatory pain conditions (e.g., arthritis and osteoarthritis).

Diseases, conditions, and/or disorders that are modulated by TRPV3 also include, but are not limited to, pain such as neuropathic pain, nociceptive pain, dental pain, HIV pain, cardiac pain arising from an ischemic myocardium, pain due to migraine, arthralgia, neuropathies, neurodegeneration, retinopathy, neurotic skin disorder, stroke, urinary bladder hypersensitiveness, urinary incontinence, vulvodynia, gastrointestinal disorders such as irritable bowel syndrome, gastro-esophageal reflux disease, enteritis, ileitis, stomach-duodenal ulcer, inflammatory bowel disease, Crohn's disease, celiac disease, an inflammatory disease such as pancreatitis, a respiratory disorder such as allergic and non-allergic rhinitis, asthma or chronic obstructive pulmonary disease, irritation of skin, eye or mucous membrane, dermatitis, itch, fervescence, muscle spasms, emesis, dyskinesias, depression, Huntington's disease, memory deficits, restricted brain function, amyotrophic lateral sclerosis (ALS), dementia, arthritis, osteoarthritis, diabetes, obesity, urticaria, actinic keratosis, keratocanthoma, alopecia, Meniere's disease, tinnitus, hyperacusis, anxiety disorders and benign prostate hyperplasia.

One embodiment provides methods for treating pain (for example, migraine, inflammatory pain, acute pain, chronic pain, neuropathic pain, nociceptive pain, arthritic pain, osteoarthritic pain, post-operative pain, cancer pain, lower back pain, diabetic neuropathy, eye pain) in a subject (including human) in need of such treatment.

Certain embodiments provides methods for treating itch in a subject (including human) in need of such treatment.

The methods comprise administering to the subject therapeutically effective amount of a compound as described herein, or a pharmaceutically acceptable salt, solvate, salt of a solvate, or solvate of a salt thereof, optionally with a pharmaceutically acceptable carrier. The method further comprises administration of the present compound as a single dose. The method also comprises repeated or chronic administration of the present compound over a period of days, weeks, months, or longer. In certain embodiments, the method comprises administering to the subject a therapeutically effective amount of a compound as described herein, or a pharmaceutically acceptable salt, solvate, salt of a solvate, or solvate of a salt thereof, in combination with one or more additional agents appropriate for the particular disease, condition, or disorder being treated.

When combinations of a TRPV3 inhibitor and one or more other compounds or agents are administered, the invention contemplates administration via the same route of administration or via differing routes of administration.

Another embodiment provides method for increasing the therapeutic effectiveness or potency of compounds described herein by repeated or chronic administration over a period of days, weeks, or months.

Actual dosage levels of active ingredients in the pharmaceutical compositions can be varied so as to obtain an amount of the active compound(s) that is effective to achieve the desired therapeutic response for a particular patient, compositions and mode of administration. The selected dosage level will depend upon the activity of the particular compound, the route of administration, the duration of treatment, other drugs, compounds and/or materials used in combination with the particular compound employed, the age, sex, weight, condition, general health and prior medical history of the patient being treated, the severity of the condition being treated, and like factors well known in the medical arts.

A physician or veterinarian having ordinary skill in the art can readily determine and prescribe the effective amount of the pharmaceutical composition required. For example, the physician or veterinarian could start doses of the compounds employed in the pharmaceutical compositions at levels lower than required to achieve the desired therapeutic effect and gradually increase the dosage until the desired effect is achieved. In the treatment of certain medical conditions, repeated or chronic administration of the compounds may be required to achieve the desired therapeutic response. "Repeated or chronic administration" refers to the administration of the compounds daily (i.e., every day) or intermittently (i.e., not every day) over a period of days, weeks, months, or longer. In particular, the treatment of chronic painful conditions is anticipated to require such repeated or chronic administration of compounds described herein. The compounds may become more effective upon repeated or chronic administration such that the therapeutically effective doses on repeated or chronic administration may be lower than the therapeutically effective dose from a single administration.

Compounds can also be administered as a pharmaceutical composition comprising the compounds of interest, or pharmaceutically acceptable salts, solvates, or salts of solvates thereof, in combination with one or more pharmaceutically acceptable carriers. The phrase "therapeutically effective amount" of a compound means a sufficient amount of the compound to treat disorders, at a reasonable benefit/risk ratio applicable to any medical treatment. It will be understood, however, that the total daily usage of the compounds and compositions will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

If desired, the effective daily dose can be divided into multiple doses for purposes of administration. Consequently, single dose compositions may contain such amounts or submultiples thereof to make up the daily dose. It is understood that the effective daily dose may vary with the duration of the treatment.

The compounds may be administered alone, or in combination with one or more other compounds described herein, or in combination (i.e. co-administered) with one or more additional pharmaceutical agents. For example, one or more compounds, or pharmaceutically acceptable salts, solvates, salts of solvates, or solvates of salts thereof, may be administered in combination with one or more analgesic such as, but not limited to, acetaminophen, salicylates, glucocorticosteroids, opioids such as, but not limited to, morphine; and nonsteroidal anti-inflammatory drugs (NSAIDs), or combinations thereof. In certain embodiments, the analgesic is opioid (e.g., morphine) or nonsteroidal anti-inflammatory drugs (NSAIDs). In one certain embodiments, a compound of the invention is co-administered with nonsteroidal anti-inflammatory drugs (NSAIDs).

Non-limiting examples of NSAIDs include aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. In certain embodiments, the nonsteroidal anti-inflammatory drug (NSAID) is ibuprofen. Combination therapy includes administration of a single pharmaceutical dosage formulation containing one or more of the compounds and one or more additional pharmaceutical agents, as well as administration of the compounds and each additional pharmaceutical agent, in its own separate pharmaceutical dosage formulation. For example, one or more compounds described herein and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, the compounds and one or more additional pharmaceutical agents may be administered at essentially the same time (e.g., concurrently) or at separately staggered times (e.g., sequentially).

e. Pharmaceutical Compositions

Further provided herein is a pharmaceutical composition that comprises a compound or a pharmaceutically acceptable salt, solvate, salt of a solvate, or solvate of a salt thereof, formulated together with a pharmaceutically acceptable carrier.

Another aspect provides pharmaceutical composition comprising a compound or a pharmaceutically acceptable salt, solvate, salt of a solvate, or solvate of a salt thereof, in combination with an analgesic (e.g., acetaminophen or opioid such as morphine or other related opioids), or in combination with a nonsteroidal anti-inflammatory drugs (NSAIDs), or a combination thereof, formulated together with a pharmaceutically acceptable carrier.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

The present ompounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of the compounds by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The compounds can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. General Synthesis

Compounds described herein when prepared by synthetic processes or by metabolic processes are encompassed within the scope of this application. Preparation of the compounds by metabolic processes includes those occurring in the human or animal body (in vivo) or processes occurring in vitro.

The compounds can be prepared by a variety of processes well known for the preparation of compounds of this class. For example, the compounds described herein wherein the groups $G^1$, $X^1$, $X^2$, $X^3$, $X^4$, $X^5$, $G^2$, $G^{2d}$, $R^{10}$, $R^{1g}$, $R^a$, $R^b$, u, p, and $Z^1$ have the meanings as set forth in the summary section unless otherwise noted, can be synthesized as shown in Schemes 1-8.

Abbreviations which have been used in the descriptions of the Schemes and the Examples that follow are: $(Boc)_2O$ for di-tert-butyl dicarbonate, DAST for (diethylamino)sulfur trifluoride; DIBAL or DIBAL-H for diisobutylaluminum hydride, DIPEA for diisopropylethyl amine, DMAP for 4-(dimethylamino)pyridine, DMF for N,N-dimethylformamide, DMSO for dimethyl sulfoxide, EtOAc for ethyl acetate, EtOH for ethanol, HATU for O-(7-azabenzotriazol-1-yl)-N, N,N',N'-tetramethyluronium hexafluorophosphate, HMDS for hexamethyl disilylazide, HMPA for hexamethylphosphoramide, IPA for isopropanol, LCMS or LC-MS for liquid chromatography-mass spectroscopy, LDA for lithium diisopropylamide; MeOH for methanol; MTBE for methyl tert-butyl ether, n-BuLi for n-butyl lithium, OTs for p-toluenesulfonate, Prep-HPLC for preparative high performance liquid chromatography, prep-TLC for preparatory thick layer chromatography, SFC for supercritical fluid chromatography, TBAF for tetrabutyl ammonium fluoride, TFA for trifluoroacetic acid, THF for tetrahydrofuran, and TsOH for p-toluenesulfonic acid.

Compounds of Formula (I) wherein u is 0 can be prepared using general procedures as illustrated in Scheme 1.

Scheme 1

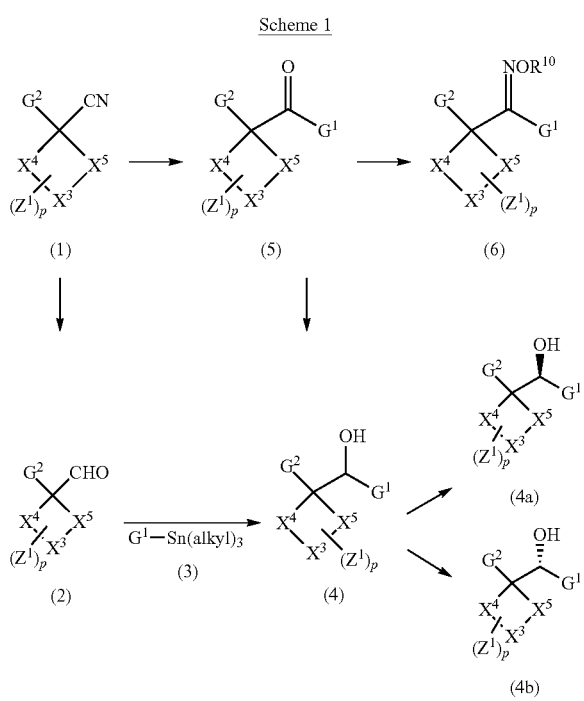

Reduction of nitriles of Formula (I) with a reducing agent such as, but not limited to, diisobutylaluminum hydride, at a temperature of about −78° C., and in a solvent such as, but not limited to, dichloromethane, produces aldehydes of Formula (2). Treatment of the aldehydes (2) with trialkylstannyl of Formula (3) in the presence of n-butyllithium and in a solvent such as, but not limited to, tetrahydrofuran, provides alcohols of Formula (4). The reaction is generally conducted at low temperature, such as at about −78° C. to about −100° C. Conversion of (2) to (4) may also be achieved by treatment of (2) with $G^1$-Li (prepared in situ from the reaction of $G^1$-H or $G^1$-Br with a base such as n-butyllithium or lithium hexamethyl disilylazide in a solvent such as THF or diethyl ether at about −78° C.) at about room temperature.

Alternatively, compounds of Formula (4) may be prepared from the nitriles of Formula (I) by (a) treatment with a bromide of formual $G^1$-Br in the presence of n-butyllithium and at about −78° C.; and (b) treating the intermediate from step (a) with sulfuric acid at about 40 to about 60° C.; to provide ketones of Formula (5); and subsequently reducing the ketones with a reducing agent such as, but not limited to, sodium borohydride at about room temperature, in a solvent such as, but not limited to, methanol.

The nitriles of Formula (I) may be prepared from reaction of nitriles of Formula (16) with halides of formula $G^2$-$R^{101}$ wherein $R^{101}$ is Br or F, in the presence of a base such as lithium, sodium, or potassium hexamethyl disilazide, or lithium diisopropylamide, and in a solvent such as, for example, toluene, at about room temperature to about 60° C.

Chiral alcohols of Formula (4a) and (4b) can be obtained by separation of the enantiomers using chiral columns or by chiral reduction of the ketones of Formula (5), for example, by reducing (5) in the presence of a chiral agent such as, but not limited to, (S,S)—N-(p-toluenesulfonyl)-1,2-diphenylethanediamine(chloro)(p-cumene)ruthenium (II), and a hydrogen source such as, but not limited to, formic acid, ammonium formate, or gaseous hydrogen.

Oximes of Formula (6) can be prepared by treatment of the ketones (5) with compounds of formula $H_2NOR^{10}$ using reaction conditions that are known to one skilled in the art.

Nitriles of Formula (I) may be purchased or prepared using general procedures known in the art such as those illustrated in Scheme 2:

Scheme 2

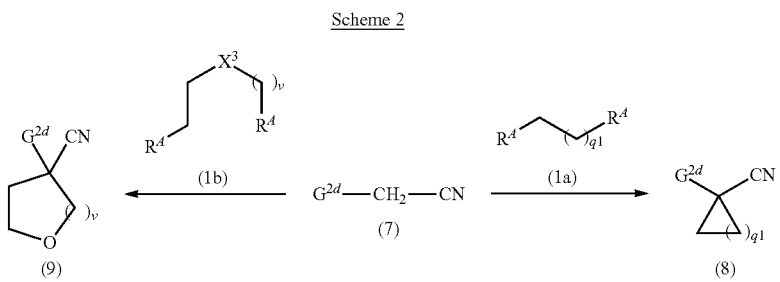

Nitriles of Formula (7) can be treated with compounds of Formula (1a) wherein q1 is 1, 2, 3, 4, 5, or 6, or Formula (1b) wherein $X^3$ is O, v is 1 or 2, and each $R^A$ in Formula (1a) and (1b) is the same or different, and is chloro, bromo, mesylate, or tosylate, to provide nitriles of Formula (8) and (9) respectively. The reaction is generally conducted in the presence of a base such as, but not limited to, sodium hydride, and in an aprotic solvent such as, but not limited to, DMSO, and at a temperature ranging from about 0° C. to about 50° C., typically at about room temperature. Alternatively, the conversion can be achieved utilizing lithium diisopropyl amide as a base, and at a temperature of about −78° C.

Scheme 3 further illustrates synthetic methods for the preparation of the intermediate nitriles used in Scheme 1.

Scheme 3

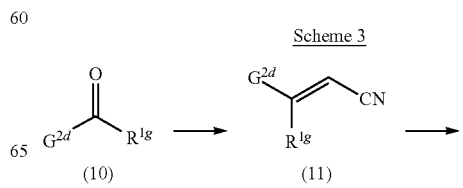

-continued

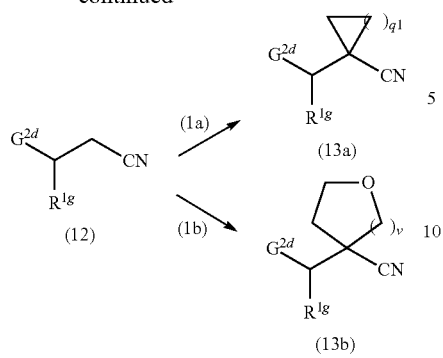

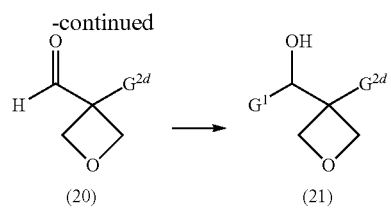

Aldehydes of Formula (18) can be treated with paraformaldehyde and calcium hydroxide to form oxenatyl alcohols of Formula (19). Swern oxidation of (19) provides aldehydes of Formula (20). Treatment of (20) with bromides of formula $G^1$-Br in the presence of n-butyllithium provides compounds of Formula (21).

Nitriles (7) may be commercially available or may be prepared using synthesis analogous to those known in the art. For example, the nitriles (7) may be prepared from the corresponding acids or ester as outlined in Scheme 6.

Scheme 6

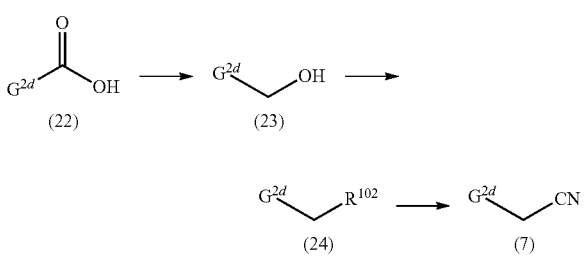

Reaction of ketones of Formula (10) with diethyl cyanomethylphosphonate in the presence of a base such as, but not limited to, sodium hydride at about room temperature provides alkenes of Formula (11). Reduction of the alkenes to compounds of Formula (12) can be accomplished by hydrogenation in the presence of Pd/C catalyst. Alternatively, the reduction reaction can be conducted in the presence of a reducing agent such as, but not limited to, sodium borohydride, in methanol, at about room temperature. Treatment of compounds of Formula (12) with (1a) or (1b) utilizing conditions as described in Scheme 2 provide the intermediate nitrile of Formula (13a) or (13b) respectively.

Scheme 4

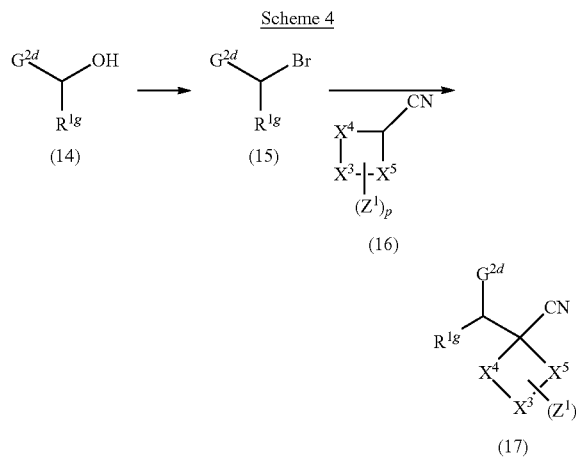

Nitriles of Formula (17) can be prepared from alcohols of Formula (14) via a two-step reactions. The alcohols are first treated with tribromophosphine at about room temperature, followed by the reaction of the resulting bromides of Formula (15) with nitriles of Formula (16) in the presence of lithium diisopropyl amide at about −78° C.

Compounds of Formula (I) wherein u is 0, $X^1$ is OH, $X^2$ is hydrogen, $X^3$ is O, $X^4$ and $X^5$ are $CH_2$, and $G^2$ is $G^{2d}$ can be prepared using general procedure as shown in Scheme 5.

Scheme 5

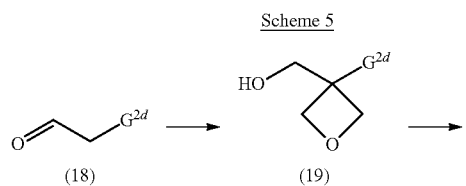

The acids (22) may be converted to the corresponding mixed anhydrides by reacting with suitable chloroformates (e.g., ethyl chloroformates) in a solvent such as, for example, THF in the presence of a base such as, for example, triethylamine or diisopropylethyl amine, at about 0° C. to about 10° C. Without isolation, the resulting mixed anhydrides obtained may be reduced to alcohols (23) in the presence of a reducing agent such as, for example, sodium borohydride, at about −78° C. Alternatively, the acids may be (a) converted to esters using methodologies known to one skilled in the art, and (b) reduced the resulting esters with a reducing agent such as, for example, sodium borohydride, in a solvent such as, methanol, at about 60° C. to provide alcohols (23).

Conversion of (23) to chlorides (24) wherein $R^{102}$ is Cl may be accomplished by treatment of (23) with phosphorous oxychloride in a solvent such as, for example, DMF, at about room temperature.

(23) may also be converted to tosylates or methanesulfonates (24) wherein $R^{102}$ is tosylate or methanesulfonate by treating alcohols (23) with p-toluenesulfonyl chloride or methanesulfonyl chloride respectively, in the presence of a base such as, for example, triethylamine, in a solvent such as, for example, dichloromethane. Displacement reaction of the tosylates, methanesulfonates, and chlorides (24) respectively with KCN in a solvent such as, for example, DMSO, or a mixture of ethanol and water, at about room temperature to about 60° C. provides nitriles (7).

Nitriles of Formula (1) wherein $G^2$ is $G^{2d}$, $X^3$ is O, $X^4$ is a bond, $X^5$ is $(CH_2)_3$, and p is 0, may be prepared as illustrated in Scheme 7.

Scheme 7

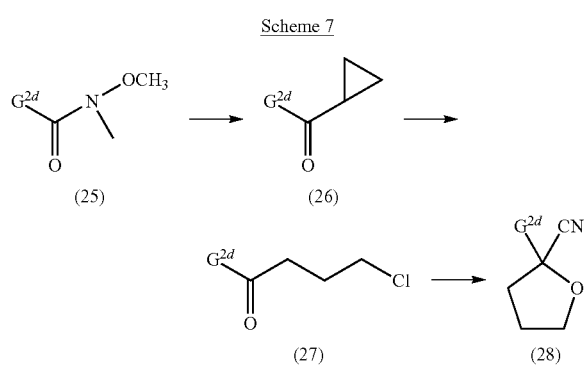

Weinreb amides (25) can be treated with cyclopropylmagnesium bromide in a solvent such as, for example, dichloromethane, at about room temperature to provide ketones (26). Ketones (26) can be reacted with p-toluenesulfonic acid and pyridine hydrochloride in a solvent such as, for example, acetonitrile, at elevated temperature (e.g., about 100° C. to about 160° C.) to provide compound (27). Treatment of (27) with potassium nitrile in methanol at a temperature from about 30 to about 50° C. provides nitriles of Formula (28).

Ketones of Formula (5) and aldehydes of Formula (2) wherein $G^2$ is $G^{2d}$, $X^3$ is O, $X^4$ is a bond, $X^5$ is $(CH_2)_2$, and p is 0, may be prepared as illustrated in Scheme 8.

Conversion of the alcohols (32) to the tosylates (33) can be accomplished by treatment with p-toluenesulfonyl chloride in the presence of a base such as, for example, 1,8-diazabicyclo[5.4.0]undec-7-ene, at about room temperature. Treatment of compounds (33) with a base such as, for example, potassium tert-butoxide, and optionally in the presence of 18-crown-6, at about room temperature, provides the esters (34).

Transformation of esters (34) to aldehydes (36) may be achieved using reaction conditions known to one skilled in the art. For example, esters of Formula (34) may be (a) reduced to primary alcohols in the presence of a reducing agent such as, for example, lithium aluminum hydride in a solvent such as, for example, THF, at about room temperature; followed by (b) Swern oxidation of the resulting alcohols to aldehydes (36).

Ketones of formual (35) may be obtained from the reaction of esters (34) with $G^1$-Li (obtained in situ from the treatment of $G^1$-Br with n-butyl lithium).

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used.

Scheme 8

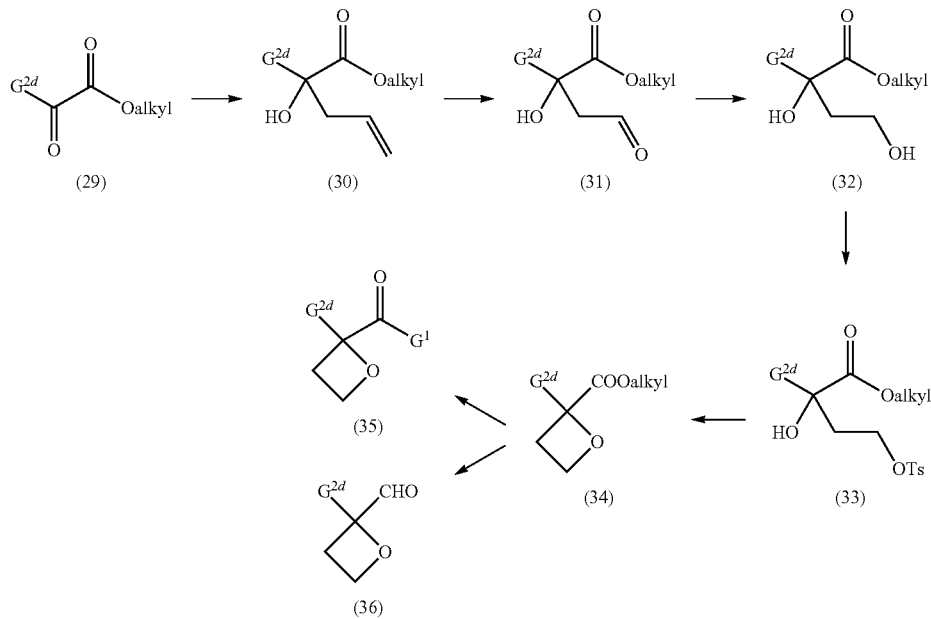

Ketoesters (29) can be reacted with allyltributyl tin in the presence of $TiCl_4$ in a solvent such as, for example, dichloromethane, at a temperature from about 0° C. to about 50° C. to provide intermediates (30). Ozonolysis of compounds (30) in a solvent such as, for example, dichloromethane, provides the aldehydes (31). Reduction of (31) to the corresponding alcohols (32) can be achieved by treatment with a reducing agent such as, for example, tetramethylammonium triacetoxyborohydride, in a solvent such as, for example, acetonitrile, at temperature ranging from about 25° C. to about 50° C.

Unless otherwise specified, solvents, temperatures and other reaction conditions may be readily selected by one of ordinary skill in the art. Specific procedures are provided in the Examples section. Reactions may be worked up in the conventional manner, e.g., by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Organic Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

EXAMPLES

Generally, LCMS measurement were run on Agilent 1200 HPLC/6100 SQ System using the follow condition: Mobile Phase: A: Water (0.05% TFA) B: Acetonitirle (0.05% TFA); Gradient Phase: 5%-95% in 1.3 min; Flow rate: 1.6 mL/min; Column: XBridge, 2.5 min; Oven temp: 50° C.

The preparation of Examples 1-77 is reported in International Application No. PCT/CN2010/001213 filed Aug. 10, 2010 (WIPO Interernational Publication No. WO12/19315 published Feb. 16, 2012).

Example 1

[1-(2-fluorophenyl)cyclobutyl](pyridin-2-yl)methanol

Example 2

[1-(3-fluorophenyl)cyclobutyl](pyridin-2-yl)methanol

Example 3

[1-(4-fluorophenyl)cyclobutyl](pyridin-2-yl)methanol

Example 4

[1-(3,4-difluorophenyl)cyclobutyl](pyridin-2-yl)methanol

Example 5 pyridin-2-yl{1-[2-(trifluoromethyl)phenyl]cyclobutyl}methanol

Example 6 pyridin-2-yl{1-[3-(trifluoromethyl)phenyl]cyclobutyl}methanol

Example 7

[1-(2-methylphenyl)cyclobutyl](pyridin-2-yl)methanol

Example 8

[1-(3-methylphenyl)cyclobutyl](pyridin-2-yl)methanol

Example 9

[1-(4-methylphenyl)cyclobutyl](pyridin-2-yl)methanol

Example 10 pyridin-2-yl{1-[2-(trifluoromethoxy)phenyl]cyclobutyl}methanol

Example 11 pyridin-2-yl{1-[3-(trifluoromethoxy)phenyl]cyclobutyl}methanol

Example 12 pyridin-2-yl{1-[4-(trifluoromethoxy)phenyl]cyclobutyl}methanol

Example 13

{1-[3,5-bis(trifluoromethyl)phenyl]cyclobutyl}(pyridin-2-yl)methanol

Example 14

{1-[3-fluoro-5-(trifluoromethyl)phenyl]cyclobutyl}(pyridin-2-yl)methanol

Example 15

{1-[4-fluoro-3-(trifluoromethyl)phenyl]cyclobutyl}(pyridin-2-yl)methanol

Example 16

{1-[4-(methylsulfonyl)phenyl]cyclobutyl}(pyridin-2-yl)methanol

Example 17

1-[3-fluoro-4-(trifluoromethyl)phenyl]cyclobutyl}(pyridin-2-yl)methanol

Example 18

{1-[4-(diethylamino)phenyl]cyclobutyl}(pyridin-2-yl)methanol

Example 19 pyridin-2-yl(1-pyridin-2-ylcyclobutyl)methanol

Example 20 pyridin-2-yl(1-pyridin-3-ylcyclobutyl)methanol

Example 21 pyridin-2-yl(1-pyridin-4-ylcyclobutyl)methanol

Example 22

[1-(1,1'-biphenyl-4-yl)cyclobutyl](pyridin-2-yl)methanol

Example 23

[1-(3-phenoxyphenyl)cyclobutyl](pyridin-2-yl)methanol

Example 24

[1-(4-phenoxyphenyl)cyclobutyl](pyridin-2-yl)methanol

Example 25

[1-(4-benzylphenyl)cyclobutyl](pyridin-2-yl)methanol

Example 26

(S)-[1-(3,4-dichlorophenyl)cyclobutyl](pyridin-2-yl)methanol

Example 27

(S)-{1-[2-fluoro-4-(trifluoromethyl)phenyl]cyclobutyl}(pyridin-2-yl)-methanol

Example 28

(S)-pyridin-2-yl{1-[4-(trifluoromethyl)phenyl]cyclobutyl}methanol

Example 29

(S)-{1-[3-fluoro-4-(trifluoromethyl)phenyl]cyclobutyl}(pyridin-2-yl)-methanol

Example 30

(S)-[1-(3,4-dichlorophenyl)cyclobutyl](3-methylpyridin-2-yl)methanol

Example 31 pyrimidin-2-yl{1-[4-(trifluoromethoxy)phenyl]cyclobutyl}methanol

Example 32

[1-(2-fluorophenyl)cyclobutyl](pyrimidin-2-yl)methanol

Example 33

[1-(3-fluorophenyl)cyclobutyl](pyrimidin-2-yl)methanol

Example 34

[1-(4-fluorophenyl)cyclobutyl](pyrimidin-2-yl)methanol

Example 35

[1-(3,4-difluorophenyl)cyclobutyl](pyrimidin-2-yl)methanol

Example 36 pyrimidin-2-yl{1-[2-(trifluoromethoxy)phenyl]cyclobutyl}methanol

Example 37 pyrimidin-2-yl{1-[3-(trifluoromethoxy)phenyl]cyclobutyl}methanol

Example 38

[1-(3,4-dichlorophenyl)cyclobutyl](pyrimidin-2-yl)methanol

Example 39

(S)-[1-(3,4-dichlorophenyl)cyclobutyl](pyrimidin-2-yl)methanol

Example 40

(R)-[1-(3,4-dichlorophenyl)cyclobutyl](pyrimidin-2-yl)methanol

Example 41

(S)-pyrimidin-2-yl{1-[4-(trifluoromethyl)phenyl]cyclobutyl}methanol

Example 42

(R)-pyrimidin-2-yl{1-[4-(trifluoromethyl)phenyl]cyclobutyl}methanol

Example 43

[1-(3,4-dichlorophenyl)cyclohexyl](pyridin-2-yl)methanol

Example 44

{1-[1-(3-chlorophenyl)ethyl]cyclobutyl}(pyridin-2-yl)methanol

Example 45

{1-[1-(2-methylphenyl)ethyl]cyclobutyl}(pyridin-2-yl)methanol

Example 46

{1-[1-(4-fluorophenyl)ethyl]cyclobutyl}(pyridin-2-yl)methanol

Example 47

{1-[1-(3-fluorophenyl)ethyl]cyclobutyl}(pyridin-2-yl)methanol

Example 48

{1-[1-(2-fluorophenyl)ethyl]cyclobutyl}(pyridin-2-yl)methanol

Example 49

{1-[1-(4-chlorophenyl)ethyl]cyclobutyl}(pyridin-2-yl)methanol

Example 50

{1-[1-(2-chlorophenyl)ethyl]cyclobutyl}(pyridin-2-yl)methanol

Example 51

[1-(1-phenylethyl)cyclobutyl](pyridin-2-yl)methanol

Example 52

[1-(4-methylbenzyl)cyclobutyl](pyridin-2-yl)methanol

Example 53 pyridin-2-yl(1-{1-[4-(trifluoromethyl)phenyl]ethyl}cyclobutyl)methanol

Example 54 pyridin-2-yl(1-{1-[3-(trifluoromethyl)phenyl]ethyl}cyclobutyl)methanol

Example 55

[1-(2,3-dihydro-1H-inden-1-yl)cyclobutyl](pyridin-2-yl)methanol

Example 56 pyridin-2-yl[1-(1,2,3,4-tetrahydronaphthalen-1-yl)cyclobutyl]methanol

Example 57

[1-(3,4-dihydro-2H-chromen-4-yl)cyclobutyl](pyridin-2-yl)methanol

Example 58 pyridin-2-yl[1-(2,2,2-trifluoro-1-phenylethyl)cyclobutyl]methanol

Example 59

[4-(3,4-dichlorophenyl)tetrahydro-2H-pyran-4-yl](pyridin-2-yl)methanol

Example 60

(4-phenyltetrahydro-2H-pyran-4-yl)(pyridin-2-yl)methanol

Example 61

[4-(3-fluorophenyl)tetrahydro-2H-pyran-4-yl](pyridin-2-yl)methanol

Example 62

[4-(4-fluorophenyl)tetrahydro-2H-pyran-4-yl](pyridin-2-yl)methanol

Example 63

[4-(3,4-difluorophenyl)tetrahydro-2H-pyran-4-yl](pyridin-2-yl)methanol

Example 64

[4-(4-chlorophenyl)tetrahydro-2H-pyran-4-yl](pyridin-2-yl)methanol

Example 65 pyridin-2-yl{4-[4-(trifluoromethyl)phenyl]tetrahydro-2H-pyran-4-yl}-methanol

Example 66 pyridin-2-yl{4-[3-(trifluoromethoxy)phenyl]tetrahydro-2H-pyran-4-yl}-methanol

Example 67 pyridin-2-yl{4-[4-(trifluoromethoxy)phenyl]tetrahydro-2H-pyran-4-yl}-methanol

Example 68

2-(1-phenylcyclobutyl)-1-(pyridin-2-yl)ethanol

Example 69

2-[1-(4-chlorophenyl)cyclobutyl]-1-(pyridin-2-yl)ethanol

Example 70

2-[1-(4-fluorophenyl)cyclobutyl]-1-(pyridin-2-yl)ethanol

Example 71

2-[1-(3-fluorophenyl)cyclobutyl]-1-(pyridin-2-yl)ethanol

Example 72

2-[1-(3-chlorophenyl)cyclobutyl]-1-(pyridin-2-yl)ethanol

Example 73

2-[1-(3,4-dichlorophenyl)cyclobutyl]-1-(pyridin-2-yl)ethanol

Example 74

1-(pyridin-2-yl)-2-{1-[3-(trifluoromethyl)phenyl]cyclobutyl}ethanol

Example 75

1-(pyridin-2-yl)-2-{1-[4-(trifluoromethyl)phenyl]cyclobutyl}ethanol

Example 76

1-(pyridin-2-yl)-2-{1-[4-(trifluoromethoxy)phenyl]cyclobutyl}ethanol

Example 77

1-(pyridin-2-yl)-2-{1-[3-(trifluoromethoxy)phenyl]cyclobutyl}ethanol

Example 78 pyridin-2-yl{3-[4-(trifluoromethyl)phenyl]tetrahydrofuran-3-yl}methanol

Example 78 was synthesized using procedures analogous to that described for the synthesis of Example 79, substituting 2-(4-(trifluoromethyl)phenyl)acetonitrile for 4-(cyanomethyl)benzonitrile. LC-MS: m/z 324 (M+H). $^1$H NMR (400 MHz, CDCl$_3$): δ ppm 8.38-8.37 8.32-8.31 (d, J=4 Hz, 1H), 7.60-7.42 (m, 3H), 7.19-6.80 (m, 4H), 4.95-4.92 (d, J=12 Hz, 1H), 4.60-4.58 4.48-4.46 (d, J=8 Hz, 1H), 4.15-3.83 (m, 3H) 2.94-2.67 (m, 1H), 2.24-2.16 (m, 1H).

Example 79

4-{3-[hydroxy(pyridin-2-yl)methyl]tetrahydrofuran-3-yl}benzonitrile

Example 79A 3-(4-cyanophenyl)tetrahydrofuran-3-carbonitrile

To a suspension of NaH (60% by weight, 1.2 g, 30 mmol) in 1-methylpyrrolidin-2-one (20 mL) was added a solution of 4-(cyanomethyl)benzonitrile (1.42 g, 10 mmol) and 1-chloro-2-(chloromethoxy)ethane (1.29 g, 10 mmol) in THF (10 mL) at −20° C. The mixture was allowed to warm to room temperature after completion of addition and stirred for 24 hours. The reaction was quenched by ice water and extracted with EtOAc (3×30 mL). The combined organic layers were washed with water (3×50 mL), brine (50 mL), dried over Na$_2$SO$_4$, filtered and concentrated to afford the crude product which was purified by Prep-TLC (EtOAc/hexane=1:5) to provide the title compound as a yellow oil (345 mg, 17.4%). LC-MS: m/z 172 (M−CN).

Example 79B 4-(3-picolinoyltetrahydrofuran-3-yl)benzonitrile

To a solution of 2-bromopyridine (0.412 g, 2.6 mmol) in dry THF was added n-BuLi (1.05 mL, 2.5 M solution in n-hexane) at −78° C. After stirring for 15 minutes, the solution of Example 79A (0.345 g, 1.74 mmol) in THF (2 mL) was added. The mixture was stirred at −78° C. for 15 minutes, then 5 mL of 1 M H$_2$SO$_4$ solution was added slowly. The mixture was heated at about 50° C.-60° C. for 30 minutes. The aqueous phase was separated and extracted with EtOAc (3×50 mL). The combined organic phases was washed with water (2×50 mL) and brine (50 mL) respectively, dried over Na$_2$SO$_4$, filtered, and concentrated in vacuo. The crude product was purified by silica gel column chromatography (petroleum ether:EtOAc=3:1) to provide the title compound (65 mg, 13.4%). LC-MS: m/z 279 (M+H).

Example 79C

4-{3-[hydroxy(pyridin-2-yl)methyl]tetrahydrofuran-3-yl}benzonitrile

To solution of compound Example 79B (0.065 g, 0.234 mmol) in methanol (25 mL) was added NaBH$_4$ (0.027 g, 0.701 mmol) in portions, and the mixture was stirred overnight at room temperature. After removal of the solvent, the pH of solution was adjusted to 7-8 by addition of 1 N HCl and then extracted with EtOAc (3×50 mL). The combined organic phases was dried over Na$_2$SO$_4$, filtered, and concentrated to afford the crude product which was purified by prep-TLC (petroleum ether:EtOAc=1:1) to provide the title compound (30 mg, 45.8%). LC-MS: m/z 281 (M+H). $^1$H NMR (400 MHz, DMSO-d$_6$): δ ppm 8.42-8.45 (m, 1H), 7.64 (t, J=8.0 Hz 2H), 7.53 (m, J=8.0 Hz 1H), 7.05-7.21 (m, 3H), 6.58 (d, J=8.0 Hz, 1H), 5.98 (s, 1H), 4.8 (s, 1H), 4.56 (d, J=8 Hz, 1H), 3.62-4.00 (m, 3H), 2.66-2.84 (m, 1H), 1.95-2.21 (m, 1H).

Example 80 pyridin-2-yl{3-[3-(trifluoromethoxy)phenyl]tetrahydrofuran-3-yl}methanol

Example 80 was synthesized using procedures analogous to that described for the synthesis of Example 79, substituting 2-(3-(trifluoromethoxy)phenyl)acetonitrile for 4-(cyanomethyl)benzonitrile. LC-MS: m/z 340 (M+H). $^1$H NMR (400 MHz, CDCl$_3$): δ ppm 8.30 (d, J=4.0 Hz, 1H), 7.49-7.42 (m, 1H), 7.21-7.15 (m, 1H), 7.09-7.00 (m, 2H), 6.92-6.67 (m, 2H), 6.58-6.52 (s, 1H), 4.83 (d, J=8.0 Hz, 1H), 4.50 (d, J=8.0 Hz, 1H), 4.08-3.80 (m, 3H), 2.83-2.57 (m, 1H), 2.16-2.06 (m, 1H).

Example 81

3-{3-[hydroxy(pyridin-2-yl)methyl]tetrahydrofuran-3-yl}benzonitrile

Example 81 was synthesized using procedures analogous to that described for the synthesis of Example 79, substituting 3-(cyanomethyl)benzonitrile for 4-(cyanomethyl)benzonitrile. LC-MS: m/z 281 (M+H). $^1$H NMR (400 MHz, CDCl$_3$): δ ppm 8.28 (d, J=4.0 Hz, 1H), 7.56-7.40 (m, 2H), 7.27-7.01 (m, 4H), 6.94 (d, J=8.0 Hz, 1H), 4.83-4.81 (m, 1H), 4.540 (d, J=8.0 Hz, 1H), 4.26 (d, J=4.0 Hz, 1H) 4.09-3.76 (m, 3H), 2.89-2.54 (m, 1H), 2.16-2.06 (m, 1H).

Example 82

[1-(3,4-dichlorophenyl)-3,3-difluorocyclobutyl](pyridin-2-yl)methanol

Example 83

[3-(4-methoxyphenyl)tetrahydrofuran-3-yl](pyridin-2-yl)methanol

Example 83 was synthesized using procedures analogous to that described for the synthesis of Example 79, substituting 2-(4-methoxyphenyl)acetonitrile for 4-(cyanomethyl)benzonitrile. LC-MS: m/z 286 (M+H). $^1$H NMR (400 MHz, CDCl$_3$): δ ppm 8.42 (d, J=4.0 Hz, 1H), 7.53-7.45 (m, 1H), 7.15-7.10 (m, 2H), 6.78-6.44 (m, 4H), 5.30 (s, 1H), 4.92-4.90 (m, 1H), 4.48 (d, J=8.0 Hz, 1H), 4.09-3.84 (m, 4H), 2.80-2.68 (m, 1H), 2.26-2.11 (m, 1H).

Example 84

[3-(3,4-dimethoxyphenyl)tetrahydrofuran-3-yl](pyridin-2-yl)methanol

Example 84 was synthesized using procedures analogous to that described for the synthesis of Example 79, substituting 2-(3,4-dimethoxyphenyl)acetonitrile for 4-(cyanomethyl)

benzonitrile. LC-MS: m/z 316 (M+H). $^1$H NMR (400 MHz, CDCl$_3$): δ ppm 8.41 (d, J=4.0 Hz, 1H), 7.54-7.46 (m, 1H), 7.15-7.12 (m, 1H), 6.81-6.67 (m, 2H), 6.55 (d, J=8.0 Hz, 1H), 6.36 (s, 1H) 4.89-4.87 (m, 1H), 4.49-4.36 (m, 2H), 4.10-3.88 (m, 3H), 3.85 (s, 3H), 3.69-3.67 (m, 2H), 2.81-2.65 (m, 1H), 2.23-2.12 (m, 1H).

Example 85 pyridin-2-yl{1-[6-(trifluoromethyl)pyridin-3-yl]cyclobutyl}methanol

Example 85A methyl 6-(trifluoromethyl)nicotinate

To a solution of 6-(trifluoromethyl)nicotinic acid (3.82 g, 20 mmol) in 120 mL of methanol was added 5 mL of concentrated H$_2$SO$_4$ and the mixture was refluxed for 5 hours. Most of the solvent was removed in vacuo and the pH of the residue was adjusted to about 7 by 1N HCl. The mixture was extracted with ethyl acetate (100 mL×3), and the combined organic layers were dried over Na$_2$SO$_4$, filtered, and concentrated in vacuo to provide the title compound (4.1 g, 100%).

Example 85B (6-(trifluoromethyl)pyridin-3-yl)methanol

To a solution of Example 85A (4.1 g, 20.0 mmol) in 100 mL of methanol was added 7.6 g of NaBH$_4$ in portions at 0° C. The resulting mixture was stirred at room temperature overnight, then quenched with water (100 mL). Most of the methanol was removed in vacuo. The residue was extracted with ethyl acetate (100 mL×3). The combined organic layers were dried over Na$_2$SO$_4$, filtered, and concentrated. The crude product was purified by silica gel column (petroleum ether:ethyl acetate=5:1) to afford the title compound (2.8 g, 79.1%). $^1$H NMR (400 MHz, CDCl$_3$): δ 8.68 (s, 1H), 7.92 (d, J=8.0 Hz, 1H), 7.70 (s, J=8.0 Hz, 1H), 4.84 (s, 2H), 2.48 (s, br, 1H).

Example 85C 5-(chloromethyl)-2-(trifluoromethyl)pyridine

To a solution of Example 85B (2.8 g, 15.8 mmol) in 20 mL of anhydrous DMF was added POCl$_3$ (5 mL) at 0° C. The resulting mixture was warmed to room temperature and stirred overnight. The solution was poured into 20 mL of icy water. The mixture was extracted with ethyl acetate (100 mL×3). The combined organic layers were dried over Na$_2$SO$_4$, filtered, and concentrated. The crude product was purified by silica gel column (petroleum ether:ethyl acetate=20:1) to afford the title compound (2.1 g, 68.2%). LC-MS: m/z 300 (M+H). $^1$H NMR (400 MHz, CDCl$_3$): δ 8.74 (s, 1H), 7.95 (d, J=8.0 Hz, 1H), 7.72 (s, J=8.0 Hz, 1H), 4.66 (s, 2H).

Example 85D 2-(6-(trifluoromethyl)pyridin-3-yl)acetonitrile

To a solution of Example 85C (2.1 g, 1.08 mmol) in 40 mL of ethanol and 15 mL of water was added KCN (0.84 g, 12.9 mmol). The mixture was refluxed for 6 hours, and then cooled to room temperature. Most of the ethanol was removed under vacuo and the residue was diluted with 25 mL of water. The resulting mixture was extracted with ethyl acetate (100 mL×3). The combined organic layers were dried over Na$_2$SO$_4$, filtered, and concentrated. The crude product was purified by silica gel column (petroleum ether:ethyl acetate=20:1) to afford the title compound (1.55 g, 64.7%). $^1$H NMR (400 MHz, CDCl$_3$): δ 8.78 (s, 1H), 7.77-7.94 (m, 2H), 3.84 (s, 2H).

Example 85E 1-(6-(trifluoromethyl)pyridin-3-yl)cyclobutanecarbonitrile

To a suspension of NaH (567 mg, 14.2 mmol, 60%) in DMSO (30 mL) was added dropwise a solution of Example 85D (1.2 g, 6.45 mmol) in THF (5 mL) at room temperature and then the mixture was stirred for 30 minutes, followed by the addition of a solution of 1,3-dibromopropane (1.4 g, 7.10 mmol) in THF (5 mL) at room temperature. The mixture was stirred for additional 2 hours. After addition of water (30 mL) carefully, the resulting mixture was extracted with EtOAc (30 mL×2). The combined organic layers were washed with water (30 mL) and brine (30 mL), dried over Na$_2$SO$_4$, filtered, and concentrated to provide the title compound (1.45 g, 6.45 mmol, yield 100%) as a oil. The crude product was used in the next step without further purification. LC-MS: m/z 227.2 (M+H)$^+$.

Example 85F 1-(6-(trifluoromethyl)pyridin-3-yl)cyclobutanecarbaldehyde

To a solution of Example 85E (1.45 g, 6.45 mmol) in DCM (50 mL) was added dropwise a solution of DIBAL (7.74 mL, 7.74 mmol, 1M in toluene) at −78° C. under nitrogen. After stirring for 3 hours at −78° C., the reaction was quenched with saturated NH$_4$Cl (10 mL) and the resulting mixture was extracted with dichloromethane (30 mL×2). The combined organic layers were washed with water (20 mL) and brine (20 mL), dried over Na$_2$SO$_4$, filtered, and concentrated. The residue was purified by column chromatography eluting with petroleum ether:EtOAc=100:1-100:3 to provide the title compound (733 mg, 3.2 mmol, 49% yield) as colorless oil. LC-MS: m/z 230 (M+H)$^+$.

Example 85G pyridin-2-yl{1-[6-(trifluoromethyl)pyridin-3-yl]cyclobutyl}methanol

To solution of 2-bromopyridine (506 mg, 3.2 mmol) in THF (10 mL) was added dropwise n-BuLi (2.4 mL, 3.84 mmol, 1.6 M) at −78° C. under nitrogen. After stirring for 30 minutes at −78° C., a solution of Example 85F (733 mg, 3.2 mmol) was added and the mixture was stirred for 30 minutes at the same temperature. The reaction mixture was allowed to warm up to room temperature, quenched with water (20 mL), extracted with dichloromethane (30 mL×2). The combined organic layers were washed with water (10 mL) and brine (10 mL), dried over Na$_2$SO$_4$, filtered, and concentrated. The residue was purified by Prep-TLC eluting with petroleum ether:EtOAc=2:1 to provide the title compound (45 mg, 4.6% yield) as a white solid. LC-MS: m/z 309.1 (M+H)$^+$; $^1$H NMR (400 MHz, CDCl$_3$): δ 8.30 (d, J=4.4 Hz, 1H), 8.07 (d, J=1.6 Hz, 1H), 7.57-7.61 (m, 1H), 7.46-7.49 (d, J=8.0 Hz, 1H), 7.34-7.39 (m, 1H), 7.14-7.17 (m, 1H), 7.04 (d, J=8.0 Hz, 1H), 5.05 (s, 1H), 4.51 (brs, 1H), 2.70-2.814 (m, 2H), 2.34-2.43 (m, 2H), 1.90-2.16 (m, 2H).

Example 86

[3-(3-chlorophenyl)oxetan-3-yl](pyridin-2-yl)methanol

Example 86A 2-(3-chlorophenyl)ethanol

To a mixture of 2-(3-chlorophenyl)acetic acid (11.4 g, 66.7 mmol) in 150 mL of THF was added LiAlH$_4$ (3.04 g, 80.0 mmol) portionwise at 0° C. The resulting mixture was warmed to room temperature and stirred for 2 hours under N$_2$ atmosphere. Then 2 N NaOH (30 mL) was added dropwise and extracted with EtOAc (2×150 mL). The organic layers were combined, dried over anhydrous Na$_2$SO$_4$, filtered, and concentrated to provide the crude product which was purified by column chromatography (silica gel, petroleum ether:ethyl acetate=50:1-10:1) to obtain 4.96 g of the title compound as a colorless oil. Yield: 55%.

Example 86B 2-(3-chlorophenyl)acetaldehyde

The mixture of Example 86A (5.73 g, 36.5 mmol) and Dess-Martin periodinane (18.6 g, 43.8 mmol) in 200 mL of dichloromethane was stirred under N$_2$ atmosphere for 4 hours at room temperature. Then saturated NaHCO$_3$ (500 mL) and Na$_2$S$_2$O$_3$ (100 mL) was added with stirring for another 30 minutes. The mixture was extracted with dichloromethane (3×300 mL). The organic layers were combined, dried over Na$_2$SO$_4$, filtered, and concentrated. The crude product was purified by distillation under reduced pressure.

Example 86C 2-(3-chlorophenyl)-2-(hydroxymethyl)propane-1,3-diol

A solution Example 86B (3.42 g, 22.09 mmol), paraformaldehyde (5.3 g, 176.7 mmol) and Ca(OH)$_2$ (16.3 g, 220.9 mmol) in THF (200 mL) was stirred at 60° C. for days. After cooling to room temperature, the mixture was filtered through a celite pad and the solvent was removed in vacuo. The residue was purified by column chromatography (silica gel, 100% ethyl acetate).

Example 86D (3-(3-chlorophenyl)oxetan-3-yl)methanol

A mixture of Example 86C (1.1 g, 5.10 mmol), diethyl carbonate (722 mg, 6.10 mmol), and KOH (15 mg) was heated at 80° C., allowing the mixture to become homogeneous. The mixture was then heated at 95° C. for 4 hours during which time EtOH distilled off from the mixture. Distillation was continued until the pot temperature was 190° C., and then the pressure was reduced to 50 mm, maintaining the pot temperature at 190° C. for 1 hour. The residue was purified by Prep-TLC (eluted with petroleum ether:ethyl acetate=1:1).

Example 86E 3-(3-chlorophenyl)oxetane-3-carbaldehyde

The mixture of Example 86D (510 mg, 2.58 mmol) and Dess-Martin periodinane (1.3 g, 3.09 mmol) in 30 mL of dichloromethane was stirred under N$_2$ atmosphere for 4 hours at room temperature. Then saturated NaHCO$_3$ (120 mL) and Na$_2$S$_2$O$_3$ (30 mL) was added with stirring for another 30 min. The mixture was extracted with dichloromethane (3×100 mL). The organic layers were combined, dried over Na$_2$SO$_4$, filtered, and concentrated to provide the crude product which was directly used in the next step without further purification.

Example 86F

[3-(3-chlorophenyl)oxetan-3-yl](pyridin-2-yl)methanol

To a mixture of 2-bromopyridine (489 mg, 3.1 mmol) in 8 mL of THF was added n-BuLi (3.35 mmol, 2.1 mL) dropwise at −78° C. under argon atmosphere. After stirring for 20 minutes at the same temperature, Example 86E (510 mg, 2.58 mmol) in 4 mL of THF was added dropwise at −78° C. The resulting mixture was stirred for another 1 hour. Then 15 mL of EtOH was added, and concentrated. The crude product was purified by Prep-TLC (eluted with ethyl acetate:petroleum ether=1.5:1) to give the title compound as a white solid. Yield: 46%. LC-MS: m/z [M+1]$^+$=276. $^1$H NMR (400 MHz, CD$_3$OD): δ 4.70-4.82 (m, 2H), 5.14-5.24 (m, 3H), 6.55 (d, J=7.2 Hz, 1H), 6.64 (s, 1H) 6.79 (d, J=8.0 Hz, 1H), 7.03-7.12 (m, 3H), 7.43-7.47 (m, 1H), 8.31 (d, J=4.8 Hz, 1H).

Example 87

[3-(3,4-dichlorophenyl)oxetan-3-yl](pyridin-2-yl)methanol

The title compound was prepared using procedures analogous to that described for the synthesis of Example 86, substituting 2-(3,4-dichlorophenyl)acetic acid for 2-(3-chlorophenyl)acetic acid LC-MS: m/z [M+1]$^+$=310. $^1$H NMR (400 MHz, CD$_3$OD): δ 4.72-4.80 (m, 2H), 5.13 (d, J=6.0 Hz, 1H), 5.23 (t, J=8.8 Hz, 2H), 6.557 (m, 1H), 6.78-6.85 (m, 2H), 7.10-7.20 (m, 2H), 7.47-7.51 (m, 1H), 8.31 (d, J=7.8 Hz, 1H).

Example 88

(anti)-pyridin-2-yl{2-[4-(trifluoromethyl)phenyl]tetrahydrofuran-2-yl}-methanol

The title compound was prepared using procedures analogous to that described for the synthesis of Example 91, substituting 4-trifluoromethyl-N-methoxy-N-methylbenzamide for N-methoxy-N,3-dimethylbenzamide followed by separation by silica gel chromatography (ethyl acetate-petroleum ether, 1:3). LC-MS: m/z (M+H): 324. $^1$H NMR (400 MHz, CDCl$_3$): δ ppm 8.19 (d, J=4.8 Hz, 1H), 7.57-7.61 (m, 1H), 7.50 (d, J=8.0 Hz, 1H), 7.26-7.30 (m, 4H), 7.06-7.08 (m, 1H), 4.83 (s, 1H), 4.10-4.15 (m, 1H), 3.88-3.94 (m, 1H), 2.69-2.76 (m, 1H), 2.31-2.38 (m, 1H), 2.02-2.05 (m, 1H), 1.76-1.81 (m, 1H).

Example 89

(syn)-pyridin-2-yl{2-[4-(trifluoromethyl)phenyl]tetrahydrofuran-2-yl}-methanol

The title compound was prepared using procedures analogous to that described for the synthesis of Example 91, substituting 4-trifluoromethyl-N-methoxy-N-methylbenzamide for N-methoxy-N,3-dimethylbenzamide followed by separation by silica gel chromatography (ethyl acetate-petroleum ether, 1:3). LC-MS: m/z (M+H): 324. $^1$H NMR (400 MHz, CDCl$_3$): δ ppm 8.55 (d, J=4.8 Hz, 1H), 7.42-7.54 (m, 5H), 7.15-7.18 (m, 1H), 6.74 (d, J=8.0 Hz, 1H), 4.83 (br, s, 2H), 3.77-3.96 (m, 2H), 2.62-2.69 (m, 1H), 2.09-2.16 (m, 1H), 1.67-1.74 (m, 2H).

Example 90

[2-(2-methylphenyl)tetrahydrofuran-2-yl](pyridin-2-yl)methanol

The title compound was prepared using procedures analogous to that described for the synthesis of Example 91, substituting N-methoxy-N,2-dimethylbenzamide for N-methoxy-N,3-dimethylbenzamide. LC-MS: m/z (M+H): 270. $^1$H NMR (400 MHz, CDCl$_3$): δ ppm 8.44 (d, J=4.8 Hz, 1H), 7.56-7.61 (m, 1H), 7.06-7.36 (m, 6H), 6.74 (d, J=8.0 Hz, 1H), 5.00 (s, 1H), 3.68-3.95 (m, 3H), 2.71-2.75 (m, 1H), 2.39 (s, 3H), 2.09-2.16 (m, 1H), 1.72-1.75 (m, 1H), 1.48-1.51 (m, 1H).

Example 91

[2-(3-methylphenyl)tetrahydrofuran-2-yl](pyridin-2-yl)methanol

Example 91A cyclopropyl(m-tolyl)methanone
To a solution of N-methoxy-N,3-dimethylbenzamide (2.86 g, 16 mmol) in THF (50 mL) was added cyclopropylmagnesium bromide (2 N in THF, 40 mmol, 20 mL) dropwise at 0° C. After addition, the reaction mixture was stirred for 4 hours at room temperature and quenched with 30 mL of aqueous NH$_4$Cl. The aqueous phase was separated and extracted with ethyl acetate (50 mL×2). The combined organic phase was washed with water (50 mL), brine (50 mL), dried over Na$_2$SO$_4$, filtered, and concentrated to give crude product as a yellow oil (2.56 g, 100%). LC-MS (M+H): m/z 161. $^1$H NMR (400 MHz, CDCl$_3$): δ ppm 7.817 (s, 2H), 7.367-7.332 (m, 2H), 2.697-2.635 (m, 1H), 2.417 (s, 3H), 1.247-1.209 (m, 2H), 1.046-1.000 (m, 2H).

Example 91B 4-chloro-1-m-tolylbutan-1-one
A solution of Example 91A (2.56 g, 16.9 mmol), TsOH.H$_2$O (3.2 g, 16.9 mmol) and pyridine hydrochloride (3.88 g, 33.8 mmol) in CH$_3$CN (60 mL) was heated at 160° C. for 3 hours under microwave and the CH$_3$CN was removed by reduced pressure to give a residue, which was re-dissolved in ethyl acetate (100 mL). The resulting organic solution was washed with aqueous NaHCO$_3$ (50 mL) and brine (50 mL), dried over MgSO$_4$, filtered, and concentrated to give a black oil. The oil was purified by chromatography on silica gel column (petroleum ether:ethyl acetate=20:1) to give the title compound (1.56 g, 50%). LC-MS (M+H): m/z 197. $^1$H NMR (400 MHz, CDCl$_3$): δ ppm 7.765-7.786 (m, 2H), 7.354-7.397 (m, 2H), 3.679 (t, J=6.2 Hz, 2H), 3.170 (t, J=6.2 Hz, 2H), 2.419 (s, 3H), 2.194-2.260 (m, 2H).

Example 91C 2-m-tolyltetrahydrofuran-2-carbonitrile
To a solution of Example 91B (1.56 g, 8 mmol) in MeOH (15 mL) was carefully added KCN (0.8 g, 12.3 mmol) and the mixture was warmed at 35° C. for 48 hours. The mixture was diluted with 50 mL ethyl acetate, washed with conccentrated aqueous NaHCO$_3$ (20 mL) and brine (10 mL). The aqueous solution was oxidized with excessive NaC100. The organic phase was dried over MgSO$_4$, filtered, and concentrated to give the title compound as an oil which was used directly for the next step (1.35 g, 90%). LC-MS: m/z (M+H): 161.

Example 91D pyridin-2-yl(2-m-tolyltetrahydrofuran-2-yl)methanone
To a solution of 2-bromopyridine (418 mg, 2.65 mmol) in THF (10 mL) was added n-BuLi (1.65 mL, 2.65 mmol, 1.6 N in hexane) at −78° C. After 15 mins, a solution of Example 91C (4.45 mg, 1.76 mmol) in THF (2 mL) was added. The mixture was stirred at −78° C. for 15 minutes and 2 mL of 1 M H$_2$SO$_4$ was added slowly. Then the mixture was heated at 50° C.-60° C. for 30 minutes. After cooling to room temperature, the aqueous phase was separated and extracted with ethyl acetate (15 mL×3). The combined organic phases was washed with water (50 mL) and brine (50 mL), dried over Na$_2$SO$_4$, filtered, and concentrated to provide the title compound. LC-MS: m/z (M+H): 268.

Example 91E

[2-(3-methylphenyl)tetrahydrofuran-2-yl](pyridin-2-yl)methanol
To a solution of Example 91D (478 mg, 1.79 mmol) in methanol (10 mL) was added NaBH$_4$ (135 mg, 3.55 mmol) portion wise, and the mixture was stirred overnight at room temperature. After evaporating most of the solvent, the residue was diluted with 10 mL of water, and extracted with ethyl acetate (15 mL×3). The combined organic phases was dried over Na$_2$SO$_4$, filtered, and concentrated. The residue was purified by prep-TLC (petroleum ether:ethyl acetate=3:1) to give the title compound (182.7 mg, 38%). LC-MS: m/z (M+H): 270. $^1$H NMR (400 MHz, CDCl$_3$): δ ppm 8.27 (d, J=4.4 Hz, 1H), 6.93-7.59 (m, 7H), 4.83 (d, J=6.0 Hz, 1H), 4.63 (d, J=6.0 Hz, 1H), 3.87-4.07 (m, 2H), 2.60-2.65 (m, 1H), 2.28-2.31 (m, 1H), 2.21 (s, 3H), 1.79-1.92 (m, 2H).

Example 92

(anti)-pyridin-2-yl{2-[3-(trifluoromethoxy)phenyl]tetrahydrofuran-2-yl}-methanol
The title compound was prepared using procedures analogous to that described for the synthesis of Example 91, substituting 3-trifluoromethoxy-N-methoxy-N-methylbenzamide for N-methoxy-N,3-dimethylbenzamide followed by separation by silica gel chromatography (ethyl acetate-petroleum ether, 1:3). LC-MS: m/z (M+H): 340. $^1$H NMR (400 MHz, CDCl$_3$): δ ppm 8.19 (d, J=4.8 Hz, 1H), 7.56-7.60 (m, 1H), 7.47 (d, J=7.6 Hz, 1H), 6.92-7.17 (m, 5H), 5.21 (br, s, 1H), 4.81 (s, 1H), 4.10-4.14 (m, 1H), 3.88-3.94 (m, 1H), 2.66-2.72 (m, 1H), 2.31-2.38 (m, 1H), 2.02-2.06 (m, 1H), 1.80-1.85 (m, 1H).

Example 93

(syn)-pyridin-2-yl{2-[3-(trifluoromethoxy)phenyl]tetrahydrofuran-2-yl}-methanol
The title compound was prepared using procedures analogous to that described for the synthesis of Example 91, substituting 3-trifluoromethoxy-N-methoxy-N-methylbenzamide for N-methoxy-N,3-dimethylbenzamide followed by separation by silica gel chromatography (ethyl acetate-petroleum ether, 1:3). LC-MS: m/z (M+H): 340. $^1$H NMR (400 MHz, CDCl$_3$): δ ppm 8.54 (d, J=4.8 Hz, 1H), 7.07-7.43 (m, 6H), 6.61 (d, J=8.0 Hz, 1H), 4.81 (br, s, 2H), 3.78-3.98 (m, 2H), 2.65-2.72 (m, 1H), 2.10-2.16 (m, 1H), 1.71-1.80 (m, 2H).

Example 94

(anti)-pyridin-2-yl{2-[4-(trifluoromethoxy)phenyl]tetrahydrofuran-2-yl}-methanol
The title compound was prepared using procedures analogous to that described for the synthesis of Example 91, substituting 4-trifluoromethoxy-N-methoxy-N-methylbenzamide for N-methoxy-N,3-dimethylbenzamide followed by separation by silica gel chromatography (ethyl acetate-petroleum ether, 1:3). LC-MS: m/z (M+H): 340. $^1$H NMR (400 MHz, CDCl$_3$): δ ppm 8.54 (d, J=4.8 Hz, 1H), 7.41-7.45 (m, 1H), 7.10-7.33 (m, 5H), 6.70 (d, J=8.0 Hz, 1H), 4.80 (br, s, 2H), 3.78-3.94 (m, 2H), 2.60-2.767 (m, 1H), 2.09-2.15 (m, 1H), 1.25-1.76 (m, 2H).

Example 95

(syn)-pyridin-2-yl{2-[4-(trifluoromethoxy)phenyl]tetrahydrofuran-2-yl}-methanol

The title compound was prepared using procedures analogous to that described for the synthesis of Example 91, substituting 4-trifluoromethoxy-N-methoxy-N-methylbenzamide for N-methoxy-N,3-dimethylbenzamide followed by separation by silica gel chromatography (ethyl acetate-petroleum ether, 1:3). LC-MS: m/z (M+H): 340. $^1$H NMR (400 MHz, CDCl$_3$): δ ppm 8.20 (d, J=4.4 Hz, 1H), 7.56-7.60 (m, 1H), 7.46 (d, J=8.0 Hz, 1H), 6.92-7.16 (m, 5H), 4.96 (br, 1H), 4.80 (br, 1H), 3.88-4.14 (m, 2H), 2.65-2.70 (m, 1H), 2.29-2.36 (m, 1H), 1.78-1.84 (m, 2H).

Example 96

(anti)-pyridin-2-yl{2-[2-(trifluoromethoxy)phenyl]tetrahydrofuran-2-yl}-methanol The title compound was prepared using procedures analogous to that described for the synthesis of Example 91, substituting 2-trifluoromethoxy-N-methoxy-N-methylbenzamide for N-methoxy-N,3-dimethylbenzamide followed by separation by silica gel chromatography (ethyl acetate-petroleum ether, 1:3). LC-MS: m/z (M+H): 340. $^1$H NMR (400 MHz, CDCl$_3$): δ ppm 8.53 (d, J=4.8 Hz, 1H), 7.22-7.29 (m, 4H), 7.01-7.07 (m, 2H), 6.20 (d, J=8.0 Hz, 1H), 5.13 (d, J=6.8 Hz, 1H), 4.84 (br, d, J=48.0 Hz, 1H), 4.13-4.17 (m, 1H), 3.72-3.76 (m, 1H), 2.96-2.30 (m, 1H), 2.04-2.21 (m, 2H), 1.82-1.84 (m, 1H).

Example 97

(syn)-pyridin-2-yl{2-[2-(trifluoromethoxy)phenyl]tetrahydrofuran-2-yl}-methanol

The title compound was prepared using procedures analogous to that described for the synthesis of Example 91, substituting 2-trifluoromethoxy-N-methoxy-N-methylbenzamide for N-methoxy-N,3-dimethylbenzamide followed by separation by silica gel chromatography (ethyl acetate-petroleum ether, 1:3). LC-MS: m/z (M+H): 340. $^1$H NMR (400 MHz, CDCl$_3$): δ ppm 8.51 (d, J=4.8 Hz, 1H), 7.61-7.66 (m, 2H), 7.15-7.35 (m, 5H), 5.02 (d, J=4.0 Hz, 1H), 3.97 (br, s, 1H), 3.66-3.83 (m, 2H), 2.67-2.73 (m, 1H), 2.09-2.16 (m, 1H), 1.66-1.68 (m, 1H), 1.19-1.22 (m, 1H).

Example 98

(anti)-2-(3,4-dichlorophenyl)tetrahydrofuran-2-yl](pyridin-2-yl)methanol

The title compound was prepared using procedures analogous to that described for the synthesis of Example 91, substituting 3,4-dichloro-N-methoxy-N-methylbenzamide for N-methoxy-N,3-dimethylbenzamide followed by separation by silica gel chromatography (ethyl acetate-petroleum ether, 1:3). LC-MS: m/z (M+H): 324. $^1$H NMR (400 MHz, CDCl$_3$): δ ppm 8.23 (d, J=4.4 Hz, 1H), 6.98-7.62 (m, 6H), 5.13 (br, 1H), 4.79 (s, 1H), 3.87-4.13 (m, 2H), 2.62-2.70 (m, 2H), 2.25-2.32 (m, 1H), 1.98-2.04 (m, 1H), 1.24-1.27 (m, 1H).

Example 99

(syn)-[2-(3,4-dichlorophenyl)tetrahydrofuran-2-yl](pyridin-2-yl)methanol

The title compound was prepared using procedures analogous to that described for the synthesis of Example 91, substituting 3,4-dichloro-N-methoxy-N-methylbenzamide for N-methoxy-N,3-dimethylbenzamide followed by separation by silica gel chromatography (ethyl acetate-petroleum ether, 1:3). LC-MS: m/z (M+H): 324. $^1$H NMR (400 MHz, CDCl$_3$): δ ppm 8.55 (t, J=2.4 Hz, 1H), 6.83-7.53 (m, 6H), 4.78 (s, 1H), 3.87-4.13 (m, 2H), 3.73-3.91 (m, 2H), 2.52-2.59 (m, 1H), 2.02-2.09 (m, 1H), 1.63-1.72 (m, 2H).

Example 100

(anti)-[2-(3-fluorophenyl)tetrahydrofuran-2-yl](pyridin-2-yl)methanol

The title compound was prepared using procedures analogous to that described for the synthesis of Example 91, substituting 3-fluoro-N-methoxy-N-methylbenzamide for N-methoxy-N,3-dimethylbenzamide followed by separation by silica gel chromatography (ethyl acetate-petroleum ether, 1:3). LC-MS: m/z (M+H): 274. $^1$H NMR (400 MHz, CDCl$_3$): δ ppm 8.22 (d, J=4.8 Hz, 1H), 7.44-7.59 (m, 2H), 6.77-7.08 (m, 5H), 4.98 (br, 1H), 4.84 (s, 1H), 3.90-4.10 (m, 2H), 2.62-2.68 (m, 1H), 2.30-2.33 (m, 1H), 1.97-2.04 (m, 1H), 1.78-1.80 (m, 1H).

Example 101

(syn)-[2-(3-fluorophenyl)tetrahydrofuran-2-yl](pyridin-2-yl)methanol

The title compound was prepared using procedures analogous to that described for the synthesis of Example 91, substituting 3-fluoro-N-methoxy-N-methylbenzamide for N-methoxy-N,3-dimethylbenzamide followed by separation by silica gel chromatography (ethyl acetate-petroleum ether, 1:3). LC-MS: m/z (M+H): 274, retention time: 1.992 min/3.3 min; $^1$H NMR (400 MHz, CDCl$_3$): δ ppm 8.54 (d, J=5.2 Hz, 1H), 6.91-7.41 (m, 6H), 6.64 (d, J=8.0 Hz, 1H), 4.83 (s, 2H), 3.80-3.95 (m, 2H), 2.63-2.68 (m, 1H), 2.10-2.14 (m, 1H), 1.71-1.75 (m, 2H).

Example 102

(anti)-[2-fluorophenyl)tetrahydrofuran-2-yl](pyridin-2-yl)methanol

The title compound was prepared using procedures analogous to that described for the synthesis of Example 91, substituting 2-fluoro-N-methoxy-N-methylbenzamide for N-methoxy-N,3-dimethylbenzamide followed by separation by silica gel chromatography (ethyl acetate-petroleum ether, 1:3). LC-MS: m/z (M+H): 274. $^1$H NMR (400 MHz, CDCl$_3$): δ ppm 8.47 (d, t, J=4.4 Hz, 1H), 6.85-7.24 (m, 6H), 6.27 (d, J=7.6 Hz, 1H), 5.04 (s, 1H), 4.03-4.78 (m, 1H), 3.74-3.79 (m, 1H), 2.83-2.90 (m, 1H), 2.16-2.23 (m, 1H), 1.92-2.02 (m, 1H), 1.67-1.77 (m, 1H).

Example 103

(syn)-[2-(2-fluorophenyl)tetrahydrofuran-2-yl](pyridin-2-yl)methanol

The title compound was prepared using procedures analogous to that described for the synthesis of Example 91, substituting 2-fluoro-N-methoxy-N-methylbenzamide for N-methoxy-N,3-dimethylbenzamide followed by separation by silica gel chromatography (ethyl acetate-petroleum ether, 1:3). LC-MS: m/z (M+H): 274. $^1$H NMR (400 MHz, CDCl$_3$): δ ppm 8.37 (d, t, J=4.4 Hz, 1H), 7.56 (t, J=4.0 Hz, 1H), 6.86-7.54 (m, 6H), 4.92 (d, J=6.0 Hz, 1H), 4.00 (br, s, 1H), 3.67-3.79 (m, 2H), 2.56-2.60 (m, 1H), 2.15-2.19 (m, 1H), 1.62-1.65 (m, 1H), 1.40-1.43 (m, 1H).

Example 104

(anti)-[2-(3-chlorophenyl)tetrahydrofuran-2-yl](pyridin-2-yl)methanol

The title compound was prepared using procedures analogous to that described for the synthesis of Example 91, substituting 3-chloro-N-methoxy-N-methylbenzamide for N-methoxy-N,3-dimethylbenzamide followed by separation by silica gel chromatography (ethyl acetate-petroleum ether, 1:3). LC-MS: m/z (M+H): 290. $^1$H NMR (400 MHz, CDCl$_3$): δ ppm 8.16 (d, J=4.8 Hz, 1H), 7.50-7.54 (m, 1H), 7.34 (d, J=8.0 Hz, 1H), 6.96-7.05 (m, 5H), 4.88 (br, s, 1H), 4.73 (s, 1H), 3.80-4.05 (m, 2H), 2.55-2.62 (m, 1H), 2.20-2.27 (m, 1H), 1.70-1.93 (m, 2H).

Example 105

(syn)-[2-(3-chlorophenyl)tetrahydrofuran-2-yl](pyridin-2-yl)methanol

The title compound was prepared using procedures analogous to that described for the synthesis of Example 91, substituting 3-chloro-N-methoxy-N-methylbenzamide for N-methoxy-N,3-dimethylbenzamide followed by separation by silica gel chromatography (ethyl acetate-petroleum ether, 1:3). LC-MS: m/z (M+H): 290. $^1$H NMR (400 MHz, CDCl$_3$): δ ppm 8.47 (d, J=4.8 Hz, 1H), 7.06-7.34 (m, 6H), 6.60 (d, J=8.0 Hz, 1H), 4.74 (br, s, 2H), 3.71-3.88 (m, 2H), 2.53-2.60 (m, 1H), 2.00-2.07 (m, 1H), 1.62-1.69 (m, 2H).

Example 106

(anti)-pyridin-2-yl{2-[3-(trifluoromethyl)phenyl]tetrahydrofuran-2-yl}-methanol

The title compound was prepared using procedures analogous to that described for the synthesis of Example 91, substituting 3-trifluoromethyl-N-methoxy-N-methylbenzamide for N-methoxy-N,3-dimethylbenzamide followed by separation by silica gel chromatography (ethyl acetate-petroleum ether, 1:3). LC-MS: m/z (M+H): 324. $^1$H NMR (400 MHz, CDCl$_3$): δ ppm 8.17 (t, J=4.8 Hz, 1H), 7.22-7.61 (m, 6H), 7.05-7.08 (m, 1H), 5.14 (br, s, 1H), 4.99 (s, 1H), 3.88-4.12 (m, 2H), 2.70-2.77 (m, 1H), 2.32-2.39 (m, 1H), 2.02-2.09 (m, 1H), 1.79-1.84 (m, 1H).

Example 107

(syn)-pyridin-2-yl{2-[3-(trifluoromethyl)phenyl]tetrahydrofuran-2-yl}-methanol

The title compound was prepared using procedures analogous to that described for the synthesis of Example 91, substituting 3-trifluoromethyl-N-methoxy-N-methylbenzamide for N-methoxy-N,3-dimethylbenzamide followed by separation by silica gel chromatography (ethyl acetate-petroleum ether, 1:3). LC-MS: m/z (M+H): 324. $^1$H NMR (400 MHz, CDCl$_3$): δ ppm 8.47 (t, J=2.4 Hz, 1H), 7.30-7.45 (m, 5H), 7.07-7.09 (m, 1H), 6.34 (d, J=4.4 Hz, 1H), 4.74 (br, s, 2H), 3.71-3.89 (m, 2H), 2.55-2.62 (m, 1H), 2.02-2.09 (m, 1H), 1.60-1.68 (m, 2H).

Example 108

(anti)-[2-(3,4-difluorophenyl)tetrahydrofuran-2-yl](pyridin-2-yl)methanol

The title compound was prepared using procedures analogous to that described for the synthesis of Example 91, substituting 3,4-difluoro-N-methoxy-N-methylbenzamide for N-methoxy-N,3-dimethylbenzamide followed by separation by silica gel chromatography (ethyl acetate-petroleum ether, 1:3). LC-MS: m/z (M+H): 292. $^1$H NMR (400 MHz, CDCl$_3$): δ ppm 8.23 (d, J=4.8 Hz, 1H), 7.47-7.61 (m, 2H), 6.86-7.10 (m, 4H), 5.19 (br, s, 1H), 4.78 (s, 1H), 3.88-4.13 (m, 2H), 2.62-2.69 (m, 1H), 2.26-2.33 (m, 1H), 1.99-2.06 (m, 1H), 1.76-1.82 (m, 1H).

Example 109

(syn)-[2-(3,4-difluorophenyl)tetrahydrofuran-2-yl](pyridin-2-yl)methanol

The title compound was prepared using procedures analogous to that described for the synthesis of Example 91, substituting 3,4-difluoro-N-methoxy-N-methylbenzamide for N-methoxy-N,3-dimethylbenzamide followed by separation by silica gel chromatography (ethyl acetate-petroleum ether, 1:3). LC-MS: m/z (M+H): 292. $^1$H NMR (400 MHz, CDCl$_3$): δ ppm 8.55 (d, J=4.8 Hz, 1H), 7.01-7.50 (m, 5H), 6.80 (d, J=3.6 Hz, 4H), 4.78 (br, 2H), 3.79-3.91 (m, 2H), 2.55-2.60 (m, 1H), 2.04-2.08 (m, 1H), 1.68-1.73 (m, 2H).

Example 110 pyridin-2-yl{1-[5-(trifluoromethyl)pyridin-3-yl] cyclobutyl}methanol

The title compound was prepared using procedures analogous to that described for the synthesis of Example 85, substituting 5-(trifluoromethyl)nicotinic acid for 6-(trifluoromethyl)nicotinic acid. LC-MS: m/z 241 (M+H). $^1$H NMR (400 MHz, CDCl$_3$): δ 8.63 (s, 1H), 8.23-8.29 (m, 1H), 7.56-7.62 (m, 1H), 7.06-7.62 (m, 3H), 5.06 (d, J=6.4 Hz, 1H), 4.42 (d, J=6.4 Hz, 1H), 1.94-2.82 (m, 6H).

Example 111

(S)-[1-(3,4-dichlorophenyl)-3,3-difluorocyclobutyl](pyridin-2-yl)methanol hydrochloride Example 112

{3,3-difluoro-1-[4-(trifluoromethoxy)phenyl]cyclobutyl} (pyridin-2-yl)-methanol

Example 113

{3,3-difluoro-1-[3-(trifluoromethyl)phenyl]cyclobutyl} (pyridin-2-yl)-methanol

Example 114

{3,3-difluoro-1-[3-(trifluoromethoxy)phenyl]cyclobutyl} (pyridin-2-yl)-methanol

Example 115 pyridin-2-yl{1-[5-(trifluoromethyl)pyridin-2-yl]cyclobutyl}methanol

Example 115A

1-[5-(trifluoromethyl)pyridin-2-yl]cyclobutanecarbonitrile

2-Fluoro-5-(trifluoromethyl)pyridine (0.603 mL, 5 mmol) and cyclobutanecarbonitrile (0.514 mL, 5.50 mmol) were dissolved in toluene (20 mL). 1M NaHMDS (5.50 mL, 5.50 mmol) in THF was added, and the reaction stirred at ambient temperature for 3 days. The reaction mixture was quenched with water and extracted three times with diethyl ether. The combined organic layers were washed with brine, dried with $MgSO_4$, filtered, and concentrated. The residue was chromatographed on an AnaLogix SF25-60 g column and eluted with 5% EtOAc in hexanes to give Example 115A (0.36 g, 1.592 mmol, 31.8% yield). MS ($DCI^+$): m/z 244.0 ($M+NH_4$). $^1H$ NMR (300 MHz, DMSO-$d_6$) δ 9.09-9.02 (m, 1H), 8.33 (dd, J=8.3, 2.2 Hz, 1H), 7.85 (d, J=8.3 Hz, 1H), 2.89-2.69 (m, 4H), 2.39-2.21 (m, 1H), 2.16-2.00 (m, 1H).

Example 115B pyridin-2-yl{1-[5-(trifluoromethyl)pyridin-2-yl]cyclobutyl}methanone 2.5M n-Butyllithium (0.778 mL, 1.945 mmol) in hexanes was added to diethyl ether (3 mL) and cooled to −78° C. in a dry ice/acetone bath. 2-Bromopyridine (0.190 mL, 1.945 mmol) was added, and the reaction mixture was stirred for 30 minutes. Example 115A (0.40 g, 1.768 mmol) in diethyl ether (5 mL) was added, and the reaction warmed to ambient temperature over 2 hours. The reaction was quenched with water, and 3N hydrochloric acid (5 mL) was added. The reaction mixture was stirred for 2.5 hours, then diluted with water, neutralized with 10 N sodium hydroxide (1.5 mL), and extracted with diethyl ether and ethyl acetate. The combined organic layers were washed with brine, dried with $MgSO_4$, filtered, and concentrated. The residue was chromatographed on an AnaLogix SF25-40 g column, eluted with 20% EtOAc in hexanes to give Example 115B (0.13 g, 0.424 mmol, 24% yield). MS ($DCI^+$): m/z 307.1 (M+H). $^1H$ NMR (300 MHz, DMSO-$d_6$) δ 8.71 (dd, J=1.5, 0.8 Hz, 1H), 8.35 (ddd, J=4.7, 1.7, 1.0 Hz, 1H), 8.21-8.15 (m, 1H), 8.07-8.03 (m, 1H), 7.98-7.87 (m, 2H), 7.47-7.41 (m, 1H), 2.90-2.76 (m, 2H), 2.67-2.54 (m, 2H), 2.19-2.01 (m, 1H), 1.98-1.82 (m, 1H).

Example 115C pyridin-2-yl{1-[5-(trifluoromethyl)pyridin-2-yl]cyclobutyl}methanol Example 115B (0.13 g, 0.424 mmol) was dissolved in ethanol (5 mL) and sodium borohydride (0.016 g, 0.424 mmol) was added. The reaction was stirred at ambient temperature for 2 hours, and then quenched with 1N hydrochloric acid (5 mL). The reaction mixture was then neutralized with saturated $NaHCO_3$ solution and extracted twice with diethyl ether. The organic layers were washed with brine, dried with $MgSO_4$, filtered, and concentrated. The residue was chromatographed on an AnaLogix $SF10^{-4}$-g column with 25% EtOAc in hexanes. The isolated product was dissolved in 2N hydrogen chloride in methanol, followed by removal of solvent to give Example 115C as HCl salt (0.043 g, 0.113 mmol, 26.6% yield). MS ($DCI^+$): m/z 309.1 (M+H). $^1H$ NMR (300 MHz, DMSO-$d_6$) δ 8.69-8.61 (m, 1H), 8.56 (d, J=5.1 Hz, 1H), 8.34 (t, J=7.6 Hz, 1H), 8.15 (dd, J=8.3, 2.3 Hz, 1H), 7.82 (t, J=6.6 Hz, 1H), 7.57 (t, J=9.2 Hz, 2H), 5.41 (s, 1H), 2.75-2.59 (m, 2H), 2.47-2.31 (m, 2H), 2.01-1.82 (m, 1H), 1.81-1.62 (m, 1H). Calculated for $C_{16}H_{15}F_3N_2O.2HCl.2.5H_2O$: C, 45.08%; H, 5.20%; N, 6.57%. Found: C, 45.08%; H, 5.21%; N, 6.32%.

Example 116 pyridin-2-yl{1-[4-(trifluoromethyl)pyridin-2-yl]cyclobutyl}methanol

Example 116A

1-[4-(trifluoromethyl)pyridin-2-yl]cyclobutanecarbonitrile

2-Fluoro-4-(trifluoromethyl)pyridine (0.731 mL, 6 mmol) and cyclobutanecarbonitrile (0.841 mL, 9.00 mmol) were dissolved in toluene (10 mL). 0.5M KHMDS (18.00 mL, 9.00 mmol) in toluene was added, and the reaction stirred at ambient temperature for 3 days. The reaction mixture was quenched with water and extracted three times with diethyl ether. The combined organic layers were washed with brine, dried with $MgSO_4$, filtered, and concentrated. The residue was chromatographed on an AnaLogix SF25-60 g column and eluted with 10% EtOAc in hexanes to give Example 116A (0.88 g, 3.89 mmol, 64.8% yield). MS ($DCI^+$): m/z 227.2 (M+H), 244.1 ($M+NH_4$). $^1H$ NMR (300 MHz, DMSO-$d_6$) δ 8.93 (d, J=5.0 Hz, 1H), 7.96-7.90 (m, 1H), 7.82 (ddd, J=5.1, 1.5, 0.7 Hz, 1H), 2.90-2.68 (m, 4H), 2.35-2.21 (m, 1H), 2.13-2.00 (m, 1H).

Example 116B pyridin-2-yl{1-[4-(trifluoromethyl)pyridin-2-yl]cyclobutyl}methanone 2.5M n-Butyllithium (2.334 mL, 5.84 mmol) in hexanes was added to diethyl ether (10 mL), and cooled to −78° C. in a dry ice/acetone bath. 2-Bromopyridine (0.569 mL, 5.84 mmol) was added, and the reaction was stirred for 40 minutes. Example 116A (0.88 g, 3.89 mmol) in diethyl ether (10 mL) was added, and the reaction allowed to warm to ambient temperature over 3 hours. The reaction was quenched with 3N hydrochloric acid (5 mL) and allowed to stir overnight. The reaction mixture was then neutralized with saturated $NaHCO_3$ solution and extracted twice with diethyl ether. The organic layers were washed with brine, dried with $MgSO_4$, filtered, and concentrated. The residue was chromatographed on an AnaLogix SF25-40 g column and eluted with 15% EtOAc in hexanes to give Example 116B (0.56 g, 1.828 mmol, 47% yield). MS ($DCI^+$): m/z 307.1 (M+H). $^1H$ NMR (300 MHz, DMSO-$d_6$) δ 8.56 (d, J=5.1 Hz, 1H), 8.34 (d, J=4.7 Hz, 1H), 8.03 (d, J=7.8 Hz, 1H), 7.99 (s, 1H), 7.93 (td, J=7.7, 1.7 Hz, 1H), 7.52 (d, J=5.8 Hz, 1H), 7.49-7.39 (m, 1H), 2.93-2.77 (m, 2H), 2.71-2.58 (m, 2H), 2.16-2.00 (m, 1H), 1.96-1.82 (m, 1H).

Example 116C pyridin-2-yl{1-[4-(trifluoromethyl)pyridin-2-yl]cyclobutyl}methanol Example 116B (0.56 g, 1.828 mmol) was dissolved in ethanol (10 mL), and sodium borohydride (0.069 g, 1.828 mmol) added. The reaction was stirred at ambient temperature for 2.5 hours, and then quenched with 1N hydrochloric acid (5 mL). The reaction mixture was then neutralized with saturated $NaHCO_3$ solution and extracted twice with diethyl ether. The combined organic layers were washed with brine, dried with MgSO$_4$, filtered, and concentrated. The residue was chromatographed on an AnaLogix SF25-40 g column and eluted with 40% EtOAc in hexanes. The isolated product was dissolved in 2N hydrogen chloride in methanol, followed by removal of solvent to give Example 116C as HCl salt (0.36 g, 0.944 mmol, 51.6%). MS (DCI$^+$): m/z 309.2 (M+H). $^1$H NMR (300 MHz, DMSO-d$_6$) δ 8.60-8.49 (m, 2H), 8.37 (td, J=7.9, 0.9 Hz, 1H), 7.85 (t, J=6.5 Hz, 1H), 7.63-7.51 (m, 3H), 5.45 (s, 1H), 2.75-2.59 (m, 2H), 2.47-2.33 (m, 2H), 2.03-1.85 (m, 1H), 1.82-1.63 (m, 1H).

Example 117

3-(3,4-dichlorophenyl)-3-[(S)-hydroxy(pyridin-2-yl)methyl]cyclobutanone

Example 118

(trans)-3-(3,4-dichlorophenyl)-3-[(S)-hydroxy(pyridin-2-yl)methyl]-cyclobutanol

Example 119

(cis)-3-(3,4-dichlorophenyl)-3-[(S)-hydroxy(pyridin-2-yl)methyl]-cyclobutanol

Example 120

(3-aminopyridin-2-yl){1-[3-(trifluoromethyl)phenyl]cyclobutyl}methanol

Example 120A tert-butyl 2-bromopyridin-3-ylcarbamate

To a solution of 2-bromopyridin-3-amine (5.0 g, 28.9 mmol) in THF (50 mL) was added Boc$_2$O (18.92 g, 87 mmol) and DMAP (0.353 g, 2.89 mmol). The resulting mixture was refluxed for about 3 hours, cooled to room temperature and K$_2$CO$_3$ (11.98 g, 87 mmol) and 50 mL of MeOH were added respectively. The resulting mixture was stirred at reflux for about 3 hours, then cooled to room temperature, filtrated, and concentrated to give the crude product. The residue was chromatographed on silica gel column (50:1 Hexanes/EtOAc) to afford the product as a white solid (4.0 g, yield: 50.7%). $^1$H NMR (400 MHz, CDCl$_3$): δ 8.45-8.47 (d, 1H, J=8 Hz), 7.02-8.03 (d, 1H, J=4.4 Hz), 7.23-7.26 (m, 1H), 7.05 (s, 1H), 1.55 (s, 9H).

Example 120B 1-(3-(trifluoromethyl)phenyl)cyclobutanecarbonitrile

The mixture of sodium hydride (1.312 g, 54.7 mmol) and DMSO was stirred for about 10 minutes at room temperature. Then a solution of 2-(3-(trifluoromethyl)phenyl)acetonitrile (5 g, 24.86 mmol) and 1,3-dibromopropane (5.02 g, 24.86 mmol) in MTBE (80 mL) was added dropwise via dropping funnel. After addition, the mixture was stirred for about 12 hours, and quenched with 60 mL of water. The aqueous phase was extracted with MTBE (3×30 mL). The combined organic layers were washed with water (3×30 mL) and brine (3×30 mL), dried over sodium sulfate, filtered, and concentrated. The residue was chromatographed on silica gel column (20:1 Hexanes/ethyl acetate) to obtain the title compound as a transparent liquid (3.8 g, 63.4%). LC-MS: m/z (M+H) 226.

Example 120C 1-(3-(trifluoromethyl)phenyl)cyclobutanecarbaldehyde

To a solution of Example 120B (1.0 g, 4.15 mmol) in dichloromethane (20 mL) was added DIBAL-H (5 mL, 4.97 mmol) dropwise at −78° C. The resulting mixture was stirred at about −78° C. for about 3 hours; then quenched with 10 mL of saturated ammonium chloride solution. The resulting mixture was stirred for another 1 hour. The temperature was allowed to warm to ambient temperature gradually. The mixture was filtered through a pad of celite. The organic layer was separated and washed with water, and brine sequentially. The organic layer was dried over sodium sulfate, filtered, and concentrated. The residue was chromatographed on silica gel column (50:1 Hexanes/EtOAc) to afford title compound as a liquid (0.5 g, 49.4%). $^1$H NMR (400 MHz, CDCl$_3$): δ 9.596 (s, 1H), 7.50-7.60 (m, 2H), 7.425 (s, 1H), 7.28-7.36 (d, 1H, J=8 Hz), 2.77-2.84 (m, 2H), 2.4-2.5 (m, 2H), 1.94-2.13 (m, 2H).

Example 120D tert-butyl 2-(hydroxy(1-(3-(trifluoromethyl)phenyl)cyclobutyl)methyl)-pyridin-3-ylcarbamate To a solution of Example 120A (400 mg, 1.465 mmol) in THF (5 mL) was added n-BuLi (3.08 mmol) at −78° C. The resulting solution was stirred at about −78° C. for about 1 hour and then a solution of Example 120C (365 mg, 1.611 mmol) in 10 mL of THF was added. The temperature was warmed to room temperature, stirred for another 1 hour, quenched with 10 mL of water, and extracted with ethyl acetate. The organic layer was washed with brine, and the combined organic phases were dried over sodium sulfate, filtered, and concentrated to give the desired crude product, which was used for next step without further purification. LC-MS: m/z (M+H) 439.

Example 120E (3-aminopyridin-2-yl){1-[3-(trifluoromethyl)phenyl]cyclobutyl}methanol To a solution of Example 120D (96 mg, 0.229 mmol) in dichloromethane (2 mL) was added trifluoroacetic acid (2 mL). The resulting solution was stirred at room temperature for about 2 hours, and concentrated in vacuum. The residue was treated with saturated NaHCO$_3$ and extracted with ethyl acetate three times. Combined organic phases were washed with water and brine sequentially, dried over Na$_2$SO$_4$, filtered, and concentrated. The residue was purified by prep-HPLC (Column: BOSTON-C18 20×250 mm 10 μm, eluent: water (0.05% NH$_4$HCO$_3$): acetonitrile, 1:1 to 5:95) (60 mg, 30%) to provide the title compound. LC-LC-MS: m/z (M+H) 323. $^1$H NMR (400 MHz, CDCl$_3$): δ 7.78-7.80 (m, 1H), 7.35-6.99 (m, 4H), 6.82-6.86 (m, 1H), 6.58-6.61 (m, 1H), 4.77 (s, 1H), 3.00 (b, 3H), 2.69-2.82 (m, 2H), 2.14-2.27 (m, 2H), 1.65-1.95 (m, 2H).

Example 121

(3-aminopyridin-2-yl){1-[4-(trifluoromethoxy)phenyl]cyclobutyl}methanol

The title compound was prepared using procedures analogous to that described for the synthesis of Example 120, substituting 2-(4-(trifluoromethoxy)phenyl)-acetonitrile for 2-(3-(trifluoromethyl)phenyl)acetonitrile in Example 120B. LC-MS: m/z (M+H) 339. $^1$H NMR (400 MHz, CDCl$_3$): δ

7.80-7.82 (m, 1H), 6.83-6.99 (m, 5H), 6.59-6.62 (m, 1H), 4.70 (b, 2H), 2.68-3.00 (b, 4H), 2.06-2.27 (m, 2H), 1.66-1.94 (m, 2H).

Example 122

(R)-pyridin-2-yl{1-[4-(trifluoromethyl)pyridin-2-yl] cyclobutyl}methanol

The HCl salt of Example 116C (120 mg) in MTBE (100 mL) was treated with 2N NaOH (20 mL), dried over $Na_2SO_4$, filtered and concentrated in vacuo. The residue was separated by chiral SFC using Chiralpak OD-H 21×250 mm and eluted with 20-40% methanol/$CO_2$ to give Example 122 (53 mg) and Example 123 (39 mg). MS m/z (M+H) 309. $^1$H NMR (400 MHz, DMSO-$d_6$) δ 8.64 (d, J=5.1 Hz, 1H), 8.33 (ddd, J=4.8, 1.8, 0.9 Hz, 1H), 7.57 (td, J=7.7, 1.8 Hz, 1H), 7.49 (dd, J=5.2, 1.6 Hz, 1H), 7.24 (d, J=1.6 Hz, 1H), 7.16 (ddd, J=7.5, 4.8, 1.2 Hz, 1H), 6.93 (d, J=7.9 Hz, 1H), 5.70 (bs, 1H), 4.93 (s, 1H), 2.74-2.64 (m, 2H), 2.46-2.24 (m, 2H), 1.81-1.60 (m, 2H). $[α]_D$=+41.7° (c 0.17, MeOH).

Example 123

(S)-pyridin-2-yl{1-[4-(trifluoromethyl)pyridin-2-yl] cyclobutyl}methanol

The HCl salt of Example 116C (120 mg) in MTBE (100 mL) was treated with 2N NaOH (20 mL), dried over $Na_2SO_4$, filtered and concentrated in vacuo. The residue was separated by chiral SFC using Chiralpak OD-H 21×250 mm eluted with 20-40% methanol/$CO_2$ to give Example 122 (53 mg) and desired Example 123 (39 mg). MS m/z (M+H) 309. $^1$H NMR (400 MHz, DMSO-$d_6$) δ 8.64 (d, J=5.1 Hz, 1H), 8.33 (ddd, J=4.8, 1.8, 0.9 Hz, 1H), 7.57 (td, J=7.7, 1.8 Hz, 1H), 7.49 (dd, J=5.2, 1.6 Hz, 1H), 7.24 (d, J=1.6 Hz, 1H), 7.16 (ddd, J=7.5, 4.8, 1.2 Hz, 1H), 6.93 (d, J=7.9 Hz, 1H), 5.70 (bs, 1H), 4.93 (s, 1H), 2.74-2.64 (m, 2H), 2.46-2.24 (m, 2H), 1.81-1.60 (m, 2H). $[α]_D$=−27.0° (c 0.10, MeOH).

Example 124

(3-aminopyridin-2-yl){1-[3-(trifluoromethoxy)phenyl] cyclobutyl}methanol

The title compound was prepared using procedures analogous to that described for the synthesis of Example 120, substituting 2-(3-(trifluoromethoxy)phenyl)-acetonitrile for 2-(3-(trifluoromethyl)phenyl)acetonitrile in Example 120B. LC-MS: m/z (M+H) 339. $^1$H NMR (400 MHz, CDCl$_3$): δ 7.86-7.88 (m, 1H), 7.17-7.22 (m, 1H), 6.85-6.98 (m, 3H), 6.60-6.64 (m, 2H), 4.70 (b, 2H), 2.73-2.87 (b, 4H), 2.22-2.30 (m, 1H), 1.94-2.13 (m, 2H), 1.69-1.77 (m, 1H).

Example 125

(R)-{3,3-difluoro-1-[4-(trifluoromethyl)pyridin-2-yl]cyclobutyl}(pyridin-2-yl)methanol Example 126

(S)-{3,3-difluoro-1-[4-(trifluoromethyl)pyridin-2-yl]cyclobutyl}(pyridin-2-yl)methanol Example 127

(3-aminopyridin-2-yl){1-[4-(trifluoromethyl)phenyl] cyclobutyl}methanol

The title compound was prepared using procedures analogous to that described for the synthesis of Example 120, substituting 2-(4-(trifluoromethyl)phenyl)-acetonitrile for 2-(3-(trifluoromethyl)phenyl)acetonitrile in Example 120B. LC-MS: m/z (M+H) 323. $^1$H NMR (400 MHz, CDCl$_3$): δ 7.80-7.82 (m, 1H), 7.37-7.39 (m, 2H), 7.00-7.03 (m, 2H), 6.84-6.88 (m, 1H), 6.63-6.65 (m, 1H), 4.75 (b, 2H), 2.74 (b, 4H), 2.10-2.26 (m, 2H), 1.68-1.91 (m, 2H).

Example 128

(S)-{3,3-difluoro-1-[4-(trifluoromethoxy)phenyl]cyclobutyl}(pyridin-2-yl)-methanol Example 129

{3,3-dimethoxy-1-[4-(trifluoromethoxy)phenyl]cyclobutyl}(pyridin-2-yl)-methanol

Example 130

(3-aminopyridin-2-yl) [1-(3,4-dichlorophenyl)cyclobutyl] methanol

The title compound was prepared using procedures analogous to that described for the synthesis of Example 120, substituting 2-(3,4-(dichloro)phenyl)-acetonitrile for 2-(3-(trifluoromethyl)phenyl)acetonitrile in Example 120B. LC-MS: m/z (M+H) 323. $^1$H NMR (400 MHz, CDCl$_3$): δ 7.76-7.78 (m, 1H), 7.08-7.19 (m, 1H), 6.81-6.93 (m, 2H), 6.65-6.73 (m, 2H), 4.74-4.92 (m, 2H), 3.22 (b, 2H), 2.56-2.75 (m, 2H), 2.00-2.18 (m, 2H), 1.50-1.89 (m, 2H).

Example 131 cis-3-[(S)-hydroxy(pyridin-2-yl)methyl]-3-[4-(trifluoromethoxy)phenyl]-cyclobutanol Example 132

(trans)-3-[(S)-hydroxy(pyridin-2-yl)methyl]-3-[4-(trifluoromethoxy)phenyl]-cyclobutanol Example 133

{3,3-difluoro-1-[4-(trifluoromethyl)phenyl]cyclobutyl} (pyridin-2-yl)-methanol

Example 134 cis-3-[(S)-hydroxy(pyridin-2-yl)methyl]-1-methyl-3-[4-(trifluoromethoxy)-phenyl]cyclobutanol Example 135

(R)-[(2S)-2-(3,4-dichlorophenyl)oxetan-2-yl](pyridin-2-yl)methanol

Example 135A ethyl 2-(3,4-dichlorophenyl)-2-hydroxypent-4-enoate

To the solution of ethyl 2-(3,4-dichlorophenyl)-2-oxoacetate (100 g, 3.8 mol) in $CH_2Cl_2$ was added allyltributyltin (1.2 equivalents) and TiCl$_4$ (1.2 equivalents) at 0° C. and mixture was stirred for 40 hours at 0° C. to room temperature. Purification by chromatography on silica gel provided title compound (90 g, 77%).

Example 135B ethyl 2-(3,4-dichlorophenyl)-2-hydroxy-4-oxobutanoate
Ozonolysis of Example 135A (25 g, 86.5 mmol) in $CH_2Cl_2$ at −78° C. for 4 hours followed by treatment with DMSO and $CH_2Cl_2$ (−78° C. to room temperature, 9 hours) provided the title compound (33 g) that was used in the next step without further purification.

Example 135C ethyl 2-(3,4-dichlorophenyl)-2,4-dihydroxybutanoate
Reduction of Example 135B (33 g, 113 mmol) in acetonitrile and acetic acid with tetramethylammonium triacetoxyborohydride at 40° C. for 40 hours provided the title compound (24 g) that was used in the next step without further purification.

Example 135D ethyl 2-(3,4-dichlorophenyl)-2-hydroxy-4-(tosyloxy)butanoate
To the solution of Example 135C (8.8 g, 30 mmol) in $CH_2Cl_2$ was added tosyl chloride (2 equivalents) and 1,8-diazabicyclo[5.4.0]undec-7-ene (2.5 equivalents) and the mixture stirred overnight at room temperature. Purification by column chromatography on silica gel provided title compound (3.3 g, 25%).

Example 135E ethyl 2-(3,4-dichlorophenyl)oxetane-2-carboxylate
Treatment of Example 135E (5.4 g, 12 mmol) in THF with potassium tert-butoxide and 18-crown-6 at room temperature for 2 hours provided the title compound (2.1 g) that was used in the next step without further purification.

Example 135F

[2-(3,4-dichlorophenyl)oxetan-2-yl](pyridin-2-yl)methanone
2.5M n-Butyllithium (8.72 mL, 21.81 mmol) in hexanes was added to diethyl ether (30 mL) and cooled to −78° C. in a dry ice/acetone bath. 2-Bromopyridine (2.216 mL, 22.72 mmol) was added and the reaction stirred at −78° C. for 30 minutes. Example 135E (5 g, 18.17 mmol) in diethyl ether (25 mL) was added dropwise. The reaction was warmed to 0° C. over a period of 2.5 hours, and then quenched with saturated $NH_4Cl$ solution. The mixture was extracted twice with diethyl ether, and the combined organic layers washed with brine, dried with $MgSO_4$, filtered, and concentrated. The residue was chromatographed on an AnaLogix SF40-120 g column and eluted with 20% EtOAc in hexanes to give title compound (3.66 g, 11.88 mmol, 65.4% yield). MS (DCI$^+$): m/z 308.1 (M+H). $^1$H NMR (300 MHz, DMSO-d$_6$) δ 8.66-8.60 (m, 1H), 8.01-7.96 (m, 2H), 7.79 (d, J=2.1 Hz, 1H), 7.66-7.55 (m, 2H), 7.47 (dd, J=8.4, 2.1 Hz, 1H), 4.57-4.39 (m, 2H), 3.55-3.42 (m, 1H), 3.26-3.14 (m, 1H).

Example 135G (R)-[(2S)-2-(3,4-dichlorophenyl)oxetan-2-yl](pyridin-2-yl)methanol
Example 135F (3.66 g, 11.88 mmol) was dissolved in triethylamine (4.14 mL, 29.7 mmol) and formic acid (1.96 mL, 51.1 mmol). (S,S)—N-(p-toluenesulfonyl)-1,2-diphenylethanediamine(chloro)(p-cymene)ruthenium(II) (0.076 g, 0.119 mmol) was added and the reaction stirred overnight at 35° C. The reaction was cooled to ambient temperature, diluted with dichloromethane and washed with saturated $NaHCO_3$ solution. The organic layer was dried with $MgSO_4$, filtered, and concentrated. The residue was chromatographed on an AnaLogix SF40-150 g column and eluted with 35% EtOAc in hexanes to give Example 135G (1.19 g, 3.84 mmol, 32.3% yield). Example 135G (1.19 g, 3.84 mmol) was dissolved in 2N hydrogen chloride in methanol and concentrated to provide the HCl salt (1.14 g, 3.29 mmol, 85.7% yield). MS (DCI$^+$): m/z 310.0 (M+H). $^1$H NMR (300 MHz, DMSO-d$_6$) δ 8.67 (d, J=5.1 Hz, 1H), 8.27 (t, J=7.3 Hz, 1H), 7.78 (t, J=6.1 Hz, 1H), 7.57 (s, 1H), 7.54 (s, 1H), 7.35 (d, J=2.0 Hz, 1H), 7.05 (dd, J=8.3, 2.0 Hz, 1H), 5.21 (s, 1H), 4.42-4.27 (m, 2H), 3.40-3.27 (m, 1H), 2.69-2.57 (m, 1H). [α]$_D$=+43.7° (c 0.600, MeOH). Calculated for $C_{15}H_{13}Cl_2NO_2$·HCl: C, 51.97%; H, 4.07%; N, 4.04%. Found: C, 51.98%; H, 3.82%; N, 3.94%.

Example 136

(R)-[(2R)-2-(3,4-dichlorophenyl)oxetan-2-yl](pyridin-2-yl)methanol
Example 135F (3.66 g, 11.88 mmol) was dissolved in triethylamine (4.14 mL, 29.7 mmol) and formic acid (1.96 mL, 51.1 mmol). (S,S)—N-(p-toluenesulfonyl)-1,2-diphenylethanediamine(chloro)(p-cymene)ruthenium(II) (0.076 g, 0.119 mmol) was added and the reaction heated overnight at 35° C. The reaction was cooled to ambient temperature, diluted with dichloromethane and washed with saturated $NaHCO_3$ solution. The organic layer was dried with $MgSO_4$, filtered, and concentrated. The residue was chromatographed on an AnaLogix SF40-150 g column and eluted with 35% EtOAc in hexanes to give Example 135G (1.19 g, 3.84 mmol, 32.3% yield) and mixed fractions. The mixed fractions were concentrated and chromatographed on an AnaLogix SF40-120 g column with 45% EtOAc in hexanes to give Example 136 (1.46 g, 4.71 mmol, 39.6% yield). Example 136 (1.46 g, 4.71 mmol) was dissolved in 2N hydrogen chloride in methanol, concentrated and triturated with dichloromethane/hexanes. The solid collected by filtration was the HCl salt of Example 136 (0.76 g, 2.19 mmol, 46.6% yield). MS (DCI$^+$): m/z 310.0 (M+H). $^1$H NMR (300 MHz, DMSO-d$_6$) δ 8.63 (d, J=5.4 Hz, 1H), 8.37 (t, J=7.5 Hz, 1H), 7.82 (t, J=6.4 Hz, 1H), 7.75 (d, J=8.0 Hz, 1H), 7.51 (d, J=8.3 Hz, 1H), 7.24 (d, J=2.0 Hz, 1H), 6.95 (dd, J=8.4, 2.0 Hz, 1H), 5.51 (s, 1H), 4.55-4.33 (m, 2H), 3.22-3.10 (m, 1H), 2.78-2.66 (m, 1H). [α]$_D$=−22.3° (c 0.705, MeOH). Calculated for $C_{15}H_{13}Cl_2NO_2$·HCl: C, 51.97%; H, 4.07%; N, 4.04%. Found: C, 52.02%; H, 3.87%; N, 4.11%.

Example 137

{3,3-difluoro-1-[5-(trifluoromethyl)pyridin-2-yl]cyclobutyl}(pyridin-2-yl)-methanol

Example 138

{1-[4-chloro-3-(trifluoromethyl)phenyl]-3,3-difluorocyclobutyl}(pyridin-2-yl)methanol

Example 139

{3,3-difluoro-1-[4-fluoro-3-(trifluoromethyl)phenyl]cyclobutyl}(pyridin-2-yl)methanol

Example 140

[4-(3,4-dichlorophenyl)piperidin-4-yl](pyridin-2-yl)methanol

Example 140A tert-butyl 4-cyano-4-(3,4-dichlorophenyl)piperidine-1-carboxylate To a solution of 1,2-dichloro-4-fluorobenzene (1.64 g, 10 mmol) in toluene (25 mL) was added tert-butyl 4-cyanopiperidine-1-carboxylate (2.10 g, 10 mmol) and KHMDS (0.5 M in toluene) (2.99 g, 15.00 mmol). The reaction mixture was stirred at 60° C. for 16 hours and cooled to room temperature. After the addition of 1N HCl (25 mL), the reaction mixture was extracted with EtOAc (3×20 mL). The combined organic extracts were washed with brine (100 mL), dried over $MgSO_4$, filtered, and concentrated. The residue was purified by Prep-TLC (eluted with ethyl acetate:petroleum ether=1:5) to provide Example 140A. LCMS: 255 [M−100]$^+$.

Example 140B tert-butyl 4-(3,4-dichlorophenyl)-4-picolinoylpiperidine-1-carboxylate To a solution of 2-bromopyridine (0.768 g, 4.86 mmol) in dry THF (20 mL) was added n-butyllithium (2.5 M in hexane, 0.6 mL, 4.86 mmol) at −78° C. After stirring for 30 minutes, the solution of Example 140A (1.2 g, 3.24 mmol) in THF (5 mL) was added. The mixture was stirred at −78° C. for 30 minutes, diluted with saturated $NH_4Cl$ (2×20 mL) and extracted with EtOAc (2×20 mL). The combined organic layers were dried over $Na_2SO_4$, filtered, and concentrated. The resulting residue was purified by column chromatography on silica gel (petroleum ether/EtOAc=10/1) to give Example 140B.

Example 140C tert-butyl 4-(3,4-dichlorophenyl)-4-(hydroxy(pyridin-2-yl)methyl)piperidine-1-carboxylate To a solution of Example 140B (500 mg, 1.11 mmol) in dry MeOH (5 mL) was added $NaBH_4$ (84 mg, 2.22 mmol) at 0° C. The mixture was stirred at 25° C. for 1 hour and water (10 mL) was added slowly. The aqueous phase was separated and extracted with dichloromethane (2×20 mL). The combined organic phases were washed with water, brine, dried over $Na_2SO_4$, filtered, and concentrated in vacuo. The resulting residue was purified by column chromatography on silica gel (petroleum ether/EtOAc=1/1) to give Example 140C.

Example 140D

[4-(3,4-dichlorophenyl)piperidin-4-yl](pyridin-2-yl)methanol

To a solution of Example 140C (390 mg, 0.866 mmol) in MeOH (2 mL) was added HCl/MeOH (2 M, 2 mL, 4 mmol) at room temperature. The reaction mixture was stirred at ambient temperature overnight. The solvent was removed in vacuo. The resulting residue was partitioned between EtOAc (20 mL) and saturated $NaHCO_3$ (20 mL). The organic layer was separated, dried over $Na_2SO_4$, filtered, and concentrated. Crude product was purified by Prep-HPLC (Column: Waters X-bridge ODS C18 21.2×250 mm, water (0.05% TFA): acetonitrile 45-85%) to give Example 140D. LCMS: 450[M+1]. $^1$H NMR (400 MHz, DMSO-$d_6$): δ 12.81 (s, 1H), 7.76 (s, 1H), 7.63 (d, J=7.6 Hz, 1H), 7.37-7.46 (m, 3H), 7.20 (d, J=16.0 Hz, 1H), 2.61 (s, 3H), 2.37 (s, 3H).

Example 141

[4-(3,4-dichlorophenyl)-1-methylpiperidin-4-yl](pyridin-2-yl)methanol

Example 142 pyridin-2-yl{4-[2-(trifluoromethoxy)phenyl]piperidin-4-yl}methanol

The title compound was prepared using procedures analogous to that described for the synthesis of Example 140, substituting 1-fluoro-2-(trifluoromethoxy)benzene for 1,2-dichloro-4-fluorobenzene in Example 140A. LCMS: 353 [M+1]; $^1$H NMR (400 MHz, DMSO-$d_6$): δ 8.38 (d, J=4.8 Hz, 1H), 7.53-7.57 (m, 1H), 7.32-7.36 (m, 1H), 7.16-7.25 (m, 4H), 6.80 (s, 1H), 4.68 (s, 1H), 2.95-2.99 (m, 2H), 2.50-2.66 (m, 4H), 1.99-2.15 (m, 2H).

Example 143

{1-methyl-4-[4-(trifluoromethyl)phenyl]piperidin-4-yl}(pyridin-2-yl)-methanol

Example 144 pyridin-2-yl{4-[4-(trifluoromethoxy)phenyl]piperidin-4-yl}methanol

The title compound was prepared using procedures analogous to that described for the synthesis of Example 140, substituting 1-fluoro-4-(trifluoromethoxy)-benzene for 1,2-dichloro-4-fluorobenzene in Example 140A. LCMS: 353 [M+1]. $^1$H NMR (400 MHz, DMSO-$d_6$): δ 8.37 (d, J=5.2 Hz, 1H), 7.51-7.55 (m, 1H), 7.13-7.24 (m, 5H), 6.67 (d, J=8.4 Hz, 1H), 4.68 (s, 1H), 2.94-2.97 (m, 2H), 2.50-2.61 (m, 3H), 2.17-2.21 (m, 1H), 1.99-2.10 (m, 2H).

Example 145

{1-methyl-4-[4-(trifluoromethoxy)phenyl]piperidin-4-yl}(pyridin-2-yl)-methanol

Example 146

{1-methyl-4-[3-(trifluoromethoxy)phenyl]piperidin-4-yl}(pyridin-2-yl)-methanol

Example 147 pyridin-2-yl{4-[4-(trifluoromethyl)phenyl]piperidin-4-yl}methanol

The title compound was prepared using procedures analogous to that described for the synthesis of Example 140, substituting 1-fluoro-4-(trifluoromethyl)-benzene for 1,2-dichloro-4-fluorobenzene in Example 140A. $^1$H NMR (400 MHz, DMSO-$d_6$): δ 12.81 (s, 1H), 7.76 (s, 1H), 7.63 (d, J=7.6 Hz, 1H), 7.37-7.46 (m, 3H), 7.20 (d, J=16.0 Hz, 1H), 2.61 (s, 3H), 2.37 (s, 3H).

Example 148 pyridin-2-yl{4-[3-(trifluoromethoxy)phenyl]piperidin-4-yl}methanol

The title compound was prepared using procedures analogous to that described for the synthesis of Example 140, substituting 1-fluoro-3-(trifluoromethoxy)-benzene for 1,2-dichloro-4-fluorobenzene in Example 140A. LCMS: 353 [M+1]. $^1$H NMR (400 MHz, DMSO-$d_6$): δ 12.81 (s, 1H), 7.76 (s, 1H), 7.63 (d, J=7.6 Hz, 1H), 7.37-7.46 (m, 3H), 7.20 (d, J=16.0 Hz, 1H), 2.61 (s, 3H), 2.37 (s, 3H).

Example 149

{1-methyl-4-[2-(trifluoromethoxy)phenyl]piperidin-4-yl}(pyridin-2-yl)-methanol

Example 150

(S)-[cis-1-(3,4-dichlorophenyl)-3-methoxycyclobutyl](pyridin-2-yl)methanol

Example 151

(S)-[1-(3,4-dichlorophenyl)-3-methoxycyclobutyl](pyridin-2-yl)methanol

Example 152 pyridin-2-yl{3-[4-(trifluoromethyl)phenyl]azetidin-3-yl}methanol

The title compound was prepared using procedures analogous to that described for the synthesis of Example 140, substituting 1-fluoro-4-(trifluoromethyl)-benzene for 1,2-dichloro-4-fluorobenzene and substituting tert-butyl 3-cyanoazetidine-1-carboxylate for tert-butyl 4-cyanopiperidine-1-carboxylate, in Example 140A. LCMS: 309 [M+1]. $^1$H NMR (400 MHz, DMSO-$d_6$): δ 12.81 (s, 1H), 7.76 (s, 1H), 7.63 (d, J=7.6 Hz, 1H), 7.37-7.46 (m, 3H), 7.20 (d, J=16.0 Hz, 1H), 2.61 (s, 3H), 2.37 (s, 3H).

Example 153 tert-butyl 3-[hydroxy(pyridin-2-yl)methyl]-3-[4-(trifluoromethyl)phenyl]-azetidine-1-carboxylate Example 154

(S)-{3,3-difluoro-1-[4-(trifluoromethyl)phenyl]cyclobutyl}(pyridin-2-yl)-methanol Example 155

{1-methyl-3-[4-(trifluoromethyl)phenyl]azetidin-3-yl}(pyridin-2-yl)methanol

Example 156 tert-butyl 4-[hydroxy(pyridin-2-yl)methyl]-4-[4-(trifluoromethyl)phenyl]-piperidine-1-carboxylate Example 157 tert-butyl 4-[hydroxy(pyridin-2-yl)methyl]-4-[4-(trifluoromethoxy)phenyl]-piperidine-1-carboxylate Example 158 tert-butyl 4-[hydroxy(pyridin-2-yl)methyl]-4-[3-(trifluoromethoxy)phenyl]-piperidine-1-carboxylate Example 159

(R)-{3,3-difluoro-1-[4-(trifluoromethoxy)phenyl]cyclobutyl}(pyridin-2-yl)methanol Example 160

3-[hydroxy(pyridin-2-yl)methyl]-3-[4-(trifluoromethyl)phenyl]cyclobutanone

Example 161 pyridin-2-yl{2-[4-(trifluoromethyl)phenyl]-5,8-dioxaspiro[3.4]oct-2-yl}-methanol Example 162

(1-cyclohexylcyclobutyl)(pyridin-2-yl)methanol

The title compound was prepared using procedures analogous to that described for the synthesis of Example 163, substituting bromocyclohexane for bromocyclopentane in Example 163A. LC-MS: 246 [M+H)]. $^1$H NMR (400 MHz, CDCl$_3$): δ 9.58 (brs, 1H), 8.82 (d, J=5.2 Hz, 1H), 8.32 (t, J=7.8 Hz 1H), 7.84 (d, J=8.0 Hz, 1H), 7.79 (t, J=6.6 Hz, 1H), 5.13 (s, 1H), 2.21-2.14 (m, 1H), 2.02-1.63 (m, 9H), 1.38-1.22 (m, 2H), 1.12-1.00 (m, 5H).

Example 163

(1-cyclopentylcyclobutyl)(pyridin-2-yl)methanol

Example 163A 1-cyclopentylcyclobutanecarbonitrile

To a solution of cyclobutanecarbonitrile (405 mg, 5 mmol) in THF (7 mL) was added dropwise LDA (2.0 M, 2.5 mL, 5 mmol) at −78° C. over 10 minutes. After stirring for 30 minutes, a solution of bromocyclopentane (888 mg, 6.0 mmol) in HMPA (268 mg, 1.5 mmol) was added and the mixture was stirred at room temperature for 3 hours. The reaction mixture was quenched with the addition of 1N aqueous HCl (10 mL) and extracted with EtOAc (20 mL×3). The combined organic phases were washed with brine, dried over Na$_2$SO$_4$, filtered and concentrated. The residue was purified by column chromatography (petroleum ether/EtOAc=20/1) to give Example 163A (0.46 g, yield 62.3%) as a colorless oil. $^1$H NMR (400 MHz, CDCl$_3$): δ 2.53-2.44 (m, 2H), 2.25-2.07 (m, 4H), 2.03-1.95 (m, 1H), 1.86-1.69 (m, 4H), 1.62-1.54 (m, 2H).

Example 163B (1-cyclopentylcyclobutyl)(pyridin-2-yl)methanone

To a solution of 2-bromopyridine (533 mg, 3.4 mmol) in THF (7 mL) was added dropwise n-BuLi (2.5 M, 1.5 mL, 3.7 mmol) at −78° C. After stirring for 30 minutes, a solution of Example 163A (460 mg, 3.1 mmol) in THF (2 mL) was added and the mixture was warmed to room temperature for 1 hour. After addition of 2N H$_2$SO$_4$ (2 mL), the reaction was refluxed for 0.5 hours. The reaction mixture was adjusted to pH=8 with NaHCO$_3$ and extracted with EtOAc (20 mL×3). The combined organic phases were washed with brine, dried over Na$_2$SO$_4$, filtered, and concentrated to give Example 163B (0.38 g, yield 53.5%) as a reddish oil. LC-MS: 230 [M+H].

Example 163C (1-cyclopentylcyclobutyl)(pyridin-2-yl)methanol

To a solution of Example 163B (0.38 g, 1.66 mmol) in CH$_3$OH (10 mL) was added NaBH$_4$ (189 mg, 5 mmol) at room temperature. After stirring for 2 hours at room temperature, the reaction mixture was quenched by the addition of aqueous NH$_4$Cl (10 mL) and extracted with EtOAc (20 mL×2). The combined organic phases were washed with brine, dried over Na$_2$SO$_4$, filtered, and concentrated. The residue was purified by Prep-HPLC (Column: Hanbon Benetnach C18 10 μm, 20×250 mm, eluent: water (0.05% TFA): acetonitrile, 55-85%) to give Example 163C (322 mg, yield 84.1%) as a white solid. LC-MS: 232 [M+H)]. $^1$H NMR (400 MHz, CDCl$_3$): δ 8.55 (d, J=4.8 Hz, 1H), 7.66-7.62 (m, 1H), 7.28-7.19 (m, 2H), 4.65 (d, J=5.6 Hz, 1H), 4.36 (d, J=6.0 Hz, 1H), 2.26-2.19 (m, 1H), 2.16-2.09 (m, 1H), 1.89-1.23 (m, 13H).

Example 164

3-[(S)-hydroxy(pyridin-2-yl)methyl]-3-[4-(trifluoromethyl)phenyl]-cyclobutanone

Example 165

3-[(R)-hydroxy(pyridin-2-yl)methyl]-3-[4-(trifluoromethyl)phenyl]cyclobutanone

Example 166

3-[(S)-hydroxy(pyridin-2-yl)methyl]-3-[4-(trifluoromethyl)phenyl]-cyclobutanol

Example 167

(anti)-[1-(3,4-dichlorophenyl)cyclobutyl][6,7-dihydro-5H-cyclopenta[b]-pyridin-7-yl]methanol

Example 167A 1-(3,4-(dichloro)phenyl)cyclobutanecarbaldehyde

The title compound was prepared using procedures analogous to that described for the synthesis of Example 179D, substituting 2-(3,4-(dichloro)phenyl)acetic acid for 2-(3-(trifluoromethyl)phenyl)acetic acid in Example 179A. LC-MS: 229 (M+H).

Example 167B (anti)-[1-(3,4-dichlorophenyl)cyclobutyl][6,7-dihydro-5H-cyclopenta[b]-pyridin-7-yl]methanol The title compound was prepared using procedures analogous to that described for the synthesis of Example 185, substituting Example 167A for Example 179D. LC-MS: 348 (M+H). $^1$H NMR (400 MHz, CD$_3$OD): δ 8.28 (d, J=4.8 Hz, 1H), 7.54 (d, J=7.6 Hz, 1H), 7.43-7.47 (m, 2H), 7.25-7.28 (dd, J=8.4 Hz, J=2.0 Hz, 1H), 7.12 (m, 1H), 4.59 (s, 1H), 3.09-3.13 (m, 1H), 2.52-2.79 (m 4H), 2.09-2.40 (m, 3H), 1.86-1.88 (m, 1H), 1.43-1.53 (m, 2H).

Example 168

(syn)-[1-(3,4-dichlorophenyl)cyclobutyl][6,7-dihydro-5H-cyclopenta[b]-pyridin-7-yl]methanol The title compound was prepared using procedures analogous to that described for the synthesis of Example 185, substituting Example 167A for Example 179D. LC-MS: 348 (M+H). $^1$H NMR (400 MHz, CD$_3$OD): δ 8.20 (d, J=5.2 Hz, 1H), 7.61 (d, J=2.0 Hz, 1H), 7.57 (d, J=7.6 Hz, 1H), 7.39-7.47 (m, 1H), 7.10 (m, 1H), 4.15 (d, J=9.6 Hz, 1H), 2.67-2.86 (m, 4H), 2.41-2.51 (m, 3H), 2.26-2.29 (m, 1H), 1.95-2.08 (m, 2H), 1.70-1.90 (m, 2H).

Example 169

(anti)-[1-(3,4-difluorophenyl)cyclobutyl][5,6,7,8-tetrahydroquinolin-8-yl]-methanol The title compound was prepared using procedures analogous to that described for the synthesis of Example 179, substituting 2-(3,4-(difluoro)phenyl)acetic acid for 2-(3-(trifluoromethyl)phenyl)acetic acid in Example 179A. LC-MS: 330 (M+H). $^1$H NMR (400 MHz, CDCl$_3$): δ 8.08 (d, J=4.0 Hz, 1H), 6.87-7.26 (m, 5H), 4.60 (d, J=7.6 Hz, 1H), 2.59-2.90 (m, 5H), 2.22-2.31 (m, 2H), 1.45-1.95 (m, 7H).

Example 170

(syn)-[1-(3,4-difluorophenyl)cyclobutyl][5,6,7,8-tetrahydroquinolin-8-yl]-methanol The title compound was prepared using procedures analogous to that described for the synthesis of Example 179, substituting 2-(3,4-(difluoro)phenyl)acetic acid for 2-(3-(trifluoromethyl)phenyl)acetic acid in Example 179A. LC-MS: 330 (M+H). $^1$H NMR (400 MHz, CDCl$_3$): δ 8.24 (d, J=4.0 Hz, 1H), 7.75 (s, 1H). 7.53-7.58 (m, 1H), 7.38 (d, J=7.6 Hz, 2H), 7.03-7.14 (m, 2H), 4.1 (d, J=9.2 Hz, 1H), 2.15-2.77 (m, 7H), 1.58-1.93 (m, 4H), 1.43-1.52 (m, 7H).

Example 171

(anti)-[1-(3,4-difluorophenyl)cyclobutyl][6,7-dihydro-5H-cyclopenta[b]-pyridin-7-yl]methanol

Example 171A 1-(3,4-(difluoro)phenyl)cyclobutanecarbaldehyde

The title compound was prepared using procedures analogous to that described for the synthesis of Example 179D, substituting 2-(3,4-(difluoro)phenyl)acetic acid for 2-(3-(trifluoromethyl)phenyl)acetic acid in Example 179A. LC-MS: 197 (M+H).

Example 171B (anti)-[1-(3,4-difluorophenyl)cyclobutyl][6,7-dihydro-5H-cyclopenta[b]-pyridin-7-yl]methanol The title compound was prepared using procedures analogous to that described for the synthesis of Example 185, substituting Example 171A for Example 179D. LC-MS: 316 (M+H). $^1$H NMR (400 MHz, CDCl$_3$): δ 8.24 (d, J=4.8 Hz, 1H), 7.35 (d, J=7.6 Hz, 1H), 6.99-7.13 (m, 3H), 6.91-6.94 (dd, J=7.2 Hz, J=4.8 Hz, 1H), 4.64 (s, 1H), 2.93-2.97 (t, J=8.4 Hz, 1H), 2.48-2.70 (m, 4H), 2.15-2.27 (m, 2H), 1.95-2.04 (m, 2H), 1.48-1.83 (m, 3H).

Example 172

(syn)-[1-(3,4-difluorophenyl)cyclobutyl][6,7-dihydro-5H-cyclopenta[b]-pyridin-7-yl]methanol The title compound was prepared using procedures analogous to that described for the synthesis of Example 185, substituting Example 171A for Example 179D. LC-MS: 316 (M+H). $^1$H NMR (400 MHz, CDCl$_3$): δ 8.20 (d, J=4.8 Hz, 1H), 7.47 (d, J=7.2 Hz, 1H), 7.30-7.35 (m, 1H), 7.18-7.21 (m, 1H), 6.93-7.13 (m, 2H), 4.15 (d, J=9.6 Hz, 1H), 2.68-2.86 (m, 3H), 2.48-2.53 (m, 1H), 2.24-2.39 (m, 4H), 1.90-2.06 (m, 2H), 1.65-1.85 (m, 2H).

Example 173

(anti)-6,7-dihydro-5H-cyclopenta[b]pyridin-7-yl{1-[4-(trifluoromethyl)-phenyl]cyclobutyl}methanol Example 173A 1-(4-(trifluoromethyl)phenyl)cyclobutanecarbaldehyde
The title compound was prepared using procedures analogous to that described for the synthesis of Example 179D, substituting 2-(4-(trifluoromethyl)phenyl)-acetic acid for 2-(3-(trifluoromethyl)phenyl)acetic acid in Example 179A. LC-MS: 229 (M+H).

Example 173B (anti)-6,7-dihydro-5H-cyclopenta[b]pyridin-7-yl{1-[4-(trifluoromethyl)-phenyl]cyclobutyl}methanol
The title compound was prepared using procedures analogous to that described for the synthesis of Example 185, substituting Example 173A for Example 179D. LC-MS: 348 (M+H). $^1$H NMR (400 MHz, CDCl$_3$): δ 8.33 (d, J=4.4 Hz, 1H), 7.58 (d, J=8.4 Hz 2H), 7.50 (d, J=8.0 Hz, 2H), 7.43 (d, J=7.6 Hz 1H), 7.26 (s, 1H), 7.00 (dd, J=7.2 Hz, J=5.2 Hz, 1H), 4.77 (s, 1H), 3.02 (t, J=8.4 Hz, 1H), 2.63-2.76 (m, 4H), 2.34-2.41 (m, 2H), 2.00-2.10 (m, 2H), 1.85-1.89 (m, 1H), 1.57-1.74 (m, 1H).

Example 174

(syn)-6,7-dihydro-5H-cyclopenta[b]pyridin-7-yl{1-[4-(trifluoromethyl)-phenyl]cyclobutyl}methanol
The title compound was prepared using procedures analogous to that described for the synthesis of Example 185, substituting Example 173A for Example 179D. LC-MS: 348 (M+H). $^1$H NMR (400 MHz, CDCl$_3$): δ 8.15 (d, J=5.2 Hz, 1H), 7.50-7.55 (m, 4H), 7.41 (d, J=7.6 Hz, 1H), 6.94-6.97 (m, 2H), 4.16 (d, J=9.6 Hz 1H), 2.64-2.79 (m, 3H), 2.26-2.43 (m, 4H), 1.92-2.00 (m, 2H), 1.66-1.80 (m, 2H).

Example 175

(anti)-6,7-dihydro-5H-cyclopenta[b]pyridin-7-yl{1-[4-(trifluoromethoxy)-phenyl]cyclobutyl}methanol Example 175A 1-(4-(trifluoromethoxy)phenyl)cyclobutanecarbaldehyde
The title compound was prepared using procedures analogous to that described for the synthesis of Example 179D, substituting 2-(4-(trifluoromethoxy)-phenyl)acetic acid for 2-(3-(trifluoromethyl)phenyl)acetic acid in Example 179A. LC-MS: 245 (M+H).

Example 175B (anti)-6,7-dihydro-5H-cyclopenta[b]pyridin-7-yl{1-[4-(trifluoromethoxy)-phenyl]cyclobutyl}methanol
The title compound was prepared using procedures analogous to that described for the synthesis of Example 185, substituting Example 175A for Example 179D. LC-MS: 364 (M+H). $^1$H NMR (400 MHz, CDCl$_3$): δ 8.32 (d, J=4.8 Hz, 1H), 7.42 (d, J=6.8 Hz 1H), 7.36-7.39 (m, 2H), 7.26 (s, 1H), 7.17 (d, J=8.0 Hz, 2H), 6.98-7.02 (dd, J=8.0 Hz, J=5.2 Hz 1H), 4.72 (d, J=3.2 Hz, 1H), 3.029 (t, J=8.8 Hz, 1H), 2.61-2.76 (m, 4H), 2.30-2.38 (m, 2H), 2.00-2.08 (m, 2H), 1.85-1.90 (m, 1H), 169-1.74 (m, 1H).

Example 176

(syn)-6,7-dihydro-5H-cyclopenta[b]pyridin-7-yl{1-[4-(trifluoromethoxy)-phenyl]cyclobutyl}methanol
The title compound was prepared using procedures analogous to that described for the synthesis of Example 185, substituting Example 175A for Example 179D. LC-MS: 364 (M+H). $^1$H NMR (400 MHz, CDCl$_3$): δ 8.12 (d, J=4.8 Hz, 1H), 7.42-7.44 (m, 2H), 7.39 (d, J=7.6 Hz, 1H), 7.10 (d, J=8.0 Hz, 2H), 6.96 (dd, J=7.2 Hz, J=6.4 Hz 2H), 4.20 (d, J=9.6 Hz, 1H), 2.61-2.79 (m, 3H), 2.22-2.48 (m, 4H), 1.88-2.02 (m, 2H), 1.62-1.81 (m, 2H).

Example 177

(anti)-5,6,7,8-tetrahydroquinolin-8-yl{1-[4-(trifluoromethoxy)phenyl]-cyclobutyl}methanol
The title compound was prepared using procedures analogous to that described for the synthesis of Example 179, substituting 2-(4-(trifluoromethoxy)-phenyl)acetic acid for 2-(3-(trifluoromethyl)phenyl)acetic acid in Example 179A. LC-MS: 378 (M+H). $^1$H NMR (400 MHz, CDCl$_3$): δ 8.05-8.04 (d, J=4.4 Hz 1H), 7.35-7.33 (d, J=8.8 Hz 2H), 7.18-7.16 (d, J=8.4 Hz, 1H), 6.97-6.95 (d, J=8 Hz, 2H), 6.87-6.84 (dd, J=7.2 Hz, 1H), 4.65-4.64 (d, J=3.2 Hz, 1H), 2.91-2.57 (m, 5H), 2.37-2.27 (m, 2H), 1.96-1.67 (m, 6H), 1.48-1.44 (m, 1H).

Example 178

(syn)-5,6,7,8-tetrahydroquinolin-8-yl{1-[4-(trifluoromethoxy)phenyl]-cyclobutyl}methanol
The title compound was prepared using procedures analogous to that described for the synthesis of Example 179, substituting 2-(4-(trifluoromethoxy)phenyl)acetic acid for 2-(3-(trifluoromethyl)phenyl)acetic acid in Example 179A. LC-MS: 378 (M+H). $^1$H NMR (400 MHz, CDCl$_3$): δ 8.22-8.21 (d, J=4 Hz 1H), 7.71-7.69 (d, J=8.4 Hz 2H), 7.36-7.34 (d, J=7.6 Hz, 1H), 7.19-7.17 (d, J=8 Hz, 2H), 7.04-7.02 (m, 1H), 4.16-4.13 (d, J=9.2 Hz, 1H), 2.78-2.57 (m, 4H), 2.39-2.19 (m, 3H), 1.92-1.84 (m, 4H), 1.51-1.46 (m, 1H).

Example 179

(anti)-5,6,7,8-tetrahydroquinolin-8-yl{1-[3-(trifluoromethyl)phenyl]-cyclobutyl}methanol Example 179A ethyl 2-(3-(trifluoromethyl)phenyl)acetate
To a solution of 2-(3-(trifluoromethyl)phenyl)acetic acid (4.3 g, 21.06 mmol) in ethanol (100 mL) was added concentrated H$_2$SO$_4$ (1.123 μL, 0.021 mmol). The mixture was refluxed overnight. After cooling to room temperature, the reaction mixture was concentrated under reduced pressure. The mixture was diluted with ethyl acetate (150 mL), washed with water (60 mL), saturated NaHCO$_3$ (150 mL) and brine (80 mL). The organic layer was dried over Na$_2$SO$_4$, filtered and concentrated to afford the Example 179A (4.26 g, yield: 93%) as a yellow oil. LC-MS: 233 (M+H).

Example 179B ethyl 1-(3-(trifluoromethyl)phenyl)cyclobutanecarboxylate

To a suspension of NaH (1.600 g, 40.0 mmol) in DMSO (10 mL) at 0° was added dropwise a solution of Example 179A (4.64 g, 20 mmol) and 1,3-dibromopropane (4.44 g, 22.00 mmol) in THF (5 mL) under nitrogen atmosphere. The mixture was stirred at 0° to room temperature for 3 hours. LC-MS showed the completion of the reaction. Water (60 mL) was added, the aqueous layer was extracted with ethyl acetate (2×50 mL). The organic layers were washed with brine (75 mL), dried over $Na_2SO_4$, filtered, and concentrated to afford Example 179B (3.6 g, yield: 40%) as a yellow oil. LC-MS: 273 (M+H).

Example 179C (1-(3-(trifluoromethyl)phenyl)cyclobutyl)methanol

To a solution of Example 179B (3.48 g, 12.78 mmol) in THF (20 mL) was added $LiAlH_4$ (1.455 g, 38.3 mmol) carefully. Then the mixture was filled with $N_2$ and stirred at room temperature overnight. Water (20 mL) was added carefully, the aqueous layer was extracted with ethyl acetate (50 mL). The organic layer was washed with brine (75 mL), dried over $MgSO_4$, filtered and concentrated. The residue was purified by column chromatography on silica gel, (petroleum ether: ethyl acetate=6:1) to afford the title compound (2.0 g, yield: 42%) as a colorless oil. LC-MS: 213 (M+H).

Example 179D 1-(3-(trifluoromethyl)phenyl)cyclobutanecarbaldehyde

To a solution of Example 179C (920 mg, 4.00 mmol) in dichloromethane (40 mL) was added Dess-Martin Periodinane (3390 mg, 7.99 mmol) and sodium bicarbonate (3357 mg, 40.0 mmol). The resulting mixture was stirred at 25° C. for 16 h, after which sat. $Na_2SO_3$ (60 mL) was added. The mixture was stirred at r.t. for 30 min and extracted with ethyl acetate (75 mL). The organic layer was washed with sat $NaHCO_3$ (75 mL), brine (60 mL), dried over $MgSO_4$, filtered and concentrated to afford Example 179D (760 mg, yield: 40%) as a yellow solid. The product was used directly for next step without further purification. LC-MS: 229 (M+H).

Example 179E (anti)-5,6,7,8-tetrahydroquinolin-8-yl{1-[3-(trifluoromethyl)phenyl]-cyclobutyl}methanol To a solution of 5,6,7,8-tetrahydroquinoline (233 mg, 1.753 mmol) in THF (10 mL) at −78° C. was added BuLi (1.315 mL, 2.103 mmol) under $N_2$. The mixture was stirred at −20° C. for 30 minutes. A solution of Example 179D (400 mg, 1.753 mmol) in THF (5 mL) was added slowly and the mixture was warmed up to −20° C. for 60 minutes and then to room temperature. Saturated $NH_4Cl$ solution (60 mL) was added, then the mixture was extracted with ethyl acetate (50 mL). The organic layer was washed with brine (50 mL), dried over $Na_2SO_4$, filtered and concentrated. The residue was purified by prep-HPLC (Column: Hanbon Benetnach C18 10 μm, 20×250 mm, eluent: water (10 mM $NH_4HCO_3$): acetonitrile, 55-85%) to afford Example 179E (80 mg, yield: 13%) and Example 180 (90 mg, yield: 15%). LC-MS: 362 (M+H). $^1$H NMR (400 MHz, $CDCl_3$): δ 7.95 (s, 1H), 7.52 (s, 2H), 7.21-7.26 (m, 2H), 7.14 (d, J=7.6 Hz, 1H), 6.78 (t, J=6.2 Hz, 1H), 4.61 (d, J=7.6 Hz, 1H), 2.97-2.99 (m, 1H), 2.76-2.81 (m, 1H), 2.57-2.66 (m, 3H), 2.34-2.40 (m, 2H), 171-1.98 (m, 6H).

Example 180

(syn)-5,6,7,8-tetrahydroquinolin-8-yl{1-[3-(trifluoromethyl)phenyl]-cyclobutyl}methanol The title compound was the second isomer isolated along with Example 179E. LC-MS: 362 (M+H). $^1$H NMR (400 MHz, $CDCl_3$): δ 8.22 (s, 1H), 7.88-7.91 (m, 2H), 7.43-7.49 (m, 2H), 7.35 (d, J=7.6 Hz, 1H), 7.02-7.05 (m, 1H), 4.17 (d, J=9.6 Hz, 1H), 2.56-2.84 (m, 4H), 2.37-2.44 (m, 1H), 2.13-2.29 (m, 2H), 1.79-1.95 (m, 4H), 1.42-1.51 (m, 2H).

Example 181

(anti)-[1-(3,4-dichlorophenyl)cyclobutyl][5,6,7,8-tetrahydroquinolin-8-yl]-methanol The title compound was prepared using procedures analogous to that described for the synthesis of Example 179, substituting 2-(3,4-dichlorophenyl)acetic acid for 2-(3-(trifluoromethyl)phenyl)acetic acid in Example 179A. LC-MS: 362 (M+H). $^1$H NMR (400 MHz, $CDCl_3$): δ 7.95 (d, J=4.0 Hz, 1H), 7.32 (d, J=6 Hz, 1H), 7.09-7.20 (m, 3H), 6.83-6.86 (m, 1H), 4.52 (d, J=7.6 Hz, 1H), 3.05-3.08 (m, 1H), 2.53-2.75 (m, 4H), 2.27-2.33 (m, 2H), 1.45-2.05 (m, 7H).

Example 182

(syn)-[1-(3,4-dichlorophenyl)cyclobutyl][5,6,7,8-tetrahydroquinolin-8-yl]-methanol The title compound was prepared using procedures analogous to that described for the synthesis of Example 179, substituting 2-(3,4-dichlorophenyl)acetic acid for 2-(3-(trifluoromethyl)phenyl)acetic acid in Example 179A. LC-MS: 362 (M+H). $^1$H NMR (400 MHz, $CDCl_3$): δ 8.23 (d, J=4.8 Hz, 1H), 7.85 (s, 2H), 7.55 (d, J=8.4 Hz, 1H), 7.36-7.41 (m, 2H), 7.04-7.07 (m, 1H), 4.13 (d, J=9.6 Hz, 1H), 2.68-2.77 (m, 3H), 2.15-2.53 (m, 4H), 1.79-1.92 (m, 4H), 1.44-1.49 (m, 2H).

Example 183

(anti)-5,6,7,8-tetrahydroquinolin-8-yl{1-[4-(trifluoromethyl)phenyl]-cyclobutyl}methanol The title compound was prepared using procedures analogous to that described for the synthesis of Example 179, substituting 2-(4-(trifluoromethyl)phenyl)-acetic acid for 2-(3-(trifluoromethyl)phenyl)acetic acid in Example 179A. LC-MS: 362 (M+H). $^1$H NMR (400 MHz, $CDCl_3$): δ 8.01-7.96 (m, 1H), 7.43-7.32 (m, 4H), 7.15-6.82 (m, 1H), 6.81-6.78 (m, 1H), 4.67-4.62 (m, 1H), 2.81-2.58 (m, 5H), 2.33 (s, 2H), 1.87-1.43 (m, 5H), 1.43 (s, 1H).

Example 184

(syn)-5,6,7,8-tetrahydroquinolin-8-yl{1-[4-(trifluoromethyl)phenyl]-cyclobutyl}methanol The title compound was prepared using procedures analogous to that described for the synthesis of Example 179, substituting 2-(4-(trifluoromethyl)phenyl)-acetic acid for 2-(3-(trifluoromethyl)phenyl)acetic acid in Example 179A. LC-MS: 362 (M+H). $^1$H NMR (400 MHz, $CDCl_3$): δ 8.21-8.16 (m, 1H), 7.79-7.72 (m, 2H), 7.60-7.59 (m, 2H), 7.35-7.29 (m, 1H), 7.04-6.98 (m, 1H), 4.17-4.10 (m, 1H), 2.81-2.67 (m, 4H), 2.39-2.18 (s, 3H), 1.84-1.80 (m, 4H), 1.46-1.43 (m, 2H).

Example 185

(anti)-6,7-dihydro-5H-cyclopenta[b]pyridin-7-yl{1-[3-(trifluoromethyl)-phenyl]cyclobutyl}methanol To a solution of 6,7-dihydro-5H-cyclopenta[b]pyridine (157 mg, 1.315 mmol) in THF (10 mL) at −78° C. was added n-BuLi (0.986 mL, 1.577 mmol) carefully under $N_2$. The mixture was stirred at −20° C. for 30 minutes. A solution of Example 179D (300 mg, 1.315 mmol) in THF (5 mL) was added slowly and the mixture was warmed up to −20° C. and stirred for 60 minutes. Saturated $NH_4Cl$ solution (60 mL) was added, then the mixture was extracted with ethyl acetate (75 mL). The organic layer was washed with brine (1×75 mL), dried over $Na_2SO_4$, filtered and concentrated. The residue was purified by Prep-HPLC (Column: Hanbon Benetnach C18 10 μm, 20×250 mm, eluent: water (10 mM $NH_4HCO_3$):acetonitrile, 55-85%) to afford Example 185 (32 mg, yield: 7%) and Example 186 (22 mg, yield: 5%). LC-MS: 348 (M+H). $^1$H NMR (400 MHz, $CDCl_3$): δ 8.33 (d, J=4.8 Hz, 1H), 7.60 (s, 1H), 7.54 (d, J=7.6 Hz, 1H), 7.41-7.48 (m, 3H), 7.00 (t, J=6.2 Hz, 1H), 4.77 (s, 1H), 3.06 (t, J=8.6 Hz, 1H), 2.60-2.75 (m, 4H), 2.34-2.43 (m, 2H), 1.87-2.12 (m, 2H), 1.52-1.67 (m, 2H).

Example 186

(syn)-6,7-dihydro-5H-cyclopenta[b]pyridin-7-yl{1-[3-(trifluoromethyl)-phenyl]cyclobutyl}methanol The title compound was the second isomer isolated along with Example 185. LC-MS: 348 (M+H). $^1$H NMR (400 MHz, $CDCl_3$): δ 8.20 (s, 1H), 7.69-7.73 (m, 2H), 7.43-7.47 (m, 3H), 6.99-7.05 (m, 2H), 4.21 (d, J=9.2 Hz, 1H), 2.71-2.86 (m, 3H), 2.32-2.50 (m, 4H), 2.01-2.06 (m, 2H), 1.73-1.98 (m, 2H).

Example 187

(anti)-5,6,7,8-tetrahydroquinolin-8-yl{1-[3-(trifluoromethoxy)phenyl]-cyclobutyl}methanol The title compound was prepared using procedures analogous to that described for the synthesis of Example 179, substituting 2-(3-(trifluoromethoxy)-phenyl)acetic acid for 2-(3-(trifluoromethyl)phenyl)acetic acid in Example 179A. LC-MS: 378 (M+H). $^1$H NMR (400 MHz, $CDCl_3$): δ 8.11 (d, J=4.4 Hz, 1H), 7.16-7.28 (m, 4H), 6.84-6.90 (m, 2H), 4.69 (d, J=4.4 Hz, 1H), 2.54-2.83 (m, 5H), 2.26-2.37 (m, 2H), 1.67-1.98 (m, 4H), 1.48-1.67 (m, 2H).

Example 188

(syn)-5,6,7,8-tetrahydroquinolin-8-yl{1-[3-(trifluoromethoxy)phenyl]-cyclobutyl}methanol The title compound was prepared using procedures analogous to that described for the synthesis of Example 179, substituting 2-(3-(trifluoromethoxy)-phenyl)acetic acid for 2-(3-(trifluoromethyl)phenyl)acetic acid in Example 179A. LC-MS: 378 (M+H). $^1$H NMR (400 MHz, $CDCl_3$): δ 8.23 (d, J=4.4 Hz, 1H), 7.62 (d, J=7.6 Hz, 1H), 7.52 (s, 1H), 7.34-7.37 (m, 2H), 7.03-7.09 (m, 2H), 4.14 (d, J=9.2 Hz, 1H), 2.53-2.82 (m, 4H), 2.35-2.42 (m, 1H), 2.17-2.26 (m, 2H), 1.78-2.05 (m, 4H), 1.43-1.49 (m, 2H), 1.21-1.28 (m, 1H).

Example 189

(anti)-6,7-dihydro-5H-cyclopenta[b]pyridin-7-yl{1-[3-(trifluoromethoxy)-phenyl]cyclobutyl}methanol

Example 189A 1-(3-(trifluoromethoxy)phenyl)cyclobutanecarbaldehyde

The title compound was prepared using procedures analogous to that described for the synthesis of Example 179D, substituting 2-(3-(trifluoromethoxy)-phenyl)acetic acid for 2-(3-(trifluoromethyl)phenyl)acetic acid in Example 179A. LC-MS: 245 (M+H).

Example 189B (anti)-6,7-dihydro-5H-cyclopenta[b]pyridin-7-yl{1-[3-(trifluoromethoxy)-phenyl]cyclobutyl}methanol The title compound was prepared using procedures analogous to that described for the synthesis of Example 185, substituting Example 189A for Example 179D. LC-MS: 364 (M+H). $^1$H NMR (400 MHz, $CDCl_3$): δ 8.35 (d, J=4.8 Hz, 1H), 7.42 (d, J=7.6 Hz, 1H), 7.27-7.37 (m, 3H), 7.21 (s, 1H), 6.99-7.08 (m, 2H), 4.74 (s, 1H), 3.03 (t, J=8.4 Hz, 1H), 2.59-2.74 (m, 4H), 2.29-2.42 (m, 2H), 2.08-2.10 (m, 1H), 1.87-1.92 (m, 2H), 1.61-1.69 (m, 2H).

Example 190

(syn)-6,7-dihydro-5H-cyclopenta[b]pyridin-7-yl{1-[3-(trifluoromethoxy)-phenyl]cyclobutyl}methanol The title compound was prepared using procedures analogous to that described for the synthesis of Example 185, substituting Example 189A for Example 179D. LC-MS: 364 (M+H). $^1$H NMR (400 MHz, $CDCl_3$): δ 8.20 (d, J=5.2 Hz, 1H), 7.45 (t, J=9.0 Hz, 1H), 7.33-7.37 (m, 2H), 6.90-7.08 (m, 3H), 4.19 (d, J=9.6 Hz, 1H), 2.70-2.85 (m, 3H), 2.49-2.53 (m, 1H), 2.31-2.40 (m, 3H), 1.99-2.06 (m, 2H), 1.84-1.89 (m, 1H), 1.69-1.74 (m, 1H).

Example 191

(anti)-5,6,7,8-tetrahydroquinolin-8-yl{1-[2-(trifluoromethoxy)phenyl]-cyclobutyl}methanol The title compound was prepared using procedures analogous to that described for the synthesis of Example 179, substituting 2-(2-(trifluoromethoxy)-phenyl)acetic acid for 2-(3-(trifluoromethyl)phenyl)acetic acid in Example 179A. LC-MS: 378 (M+H). $^1$H NMR (400 MHz, $CDCl_3$): δ 8.13 (d, J=4.0 Hz, 1H), 7.74-7.79 (m, 2H). 7.11-7.23 (m, 3H), 6.85-6.88 (m, 1H), 5.03 (s, 1H), 2.45-2.92 (m, 7H), 2.17-2.14 (m, 1H), 1.54-1.93 (m, 4H), 1.38-1.42 (m, 1H).

Example 192

(syn)-5,6,7,8-tetrahydroquinolin-8-yl{1-[2-(trifluoromethoxy)phenyl]-cyclobutyl}methanol The title compound was prepared using procedures analogous to that described for the synthesis of Example 179, substituting 2-(2-(trifluoromethoxy)-phenyl)acetic acid for 2-(3-(trifluoromethyl)phenyl)acetic acid in Example 179A. LC-MS: 378 (M+H). $^1$H NMR (400 MHz, $CDCl_3$): δ 8.23 (d, J=4.0 Hz, 1H), 7.73-7.78 (m, 2H). 7.15-7.21 (m, 3H), 6.99-7.02 (m, 1H), 5.98 (s, 1H), 4.13 (d, J=6.8 Hz, 1H), 2.41-2.89 (m, 7H), 2.07-2.14 (m, 1H), 1.51-1.89 (m, 4H), 1.28-1.30 (m, 1H).

Example 193

(anti)-6,7-dihydro-5H-cyclopenta[b]pyridin-7-yl{1-[2-(trifluoromethoxy)-phenyl]cyclobutyl}methanol

Example 193A 1-(2-(trifluoromethoxy)phenyl)cyclobutanecarbaldehyde

The title compound was prepared using procedures analogous to that described for the synthesis of Example 179D, substituting 2-(2-(trifluoromethoxy)-phenyl)acetic acid for 2-(3-(trifluoromethyl)phenyl)acetic acid in Example 179A. LC-MS: 245 (M+H).

Example 193B (anti)-6,7-dihydro-5H-cyclopenta[b]pyridin-7-yl{1-[2-(trifluoromethoxy)-phenyl]cyclobutyl}methanol The title compound was prepared using procedures analogous to that described for the synthesis of Example 185, substituting Example 193A for Example 179D. LC-MS: 364 (M+H). $^1$H NMR (400 MHz, CDCl$_3$): δ 8.40 (d, J=4.8 Hz, 1H), 7.42 (d, J=7.2 Hz, 1H), 7.20-7.30 (m, 4H), 7.02 (dd, J=7.6 Hz, J=5.2 Hz, 1H), 4.96 (d, J=4.4 Hz, 1H), 3.20 (t, J=8.4 Hz, 1H), 2.53-2.80 (m, 5H), 2.40-2.46 (m, 1H), 2.16-2.31 (m, 1H), 1.82-1.90 (m, 2H), 1.58-1.74 (m, 2H).

Example 194

(syn)-6,7-dihydro-5H-cyclopenta[b]pyridin-7-yl{1-[2-(trifluoromethoxy)-phenyl]cyclobutyl}methanol The title compound was prepared using procedures analogous to that described for the synthesis of Example 185, substituting Example 193A for Example 179D. LC-MS: 364 (M+H). $^1$H NMR (400 MHz, CDCl$_3$): δ 8.21 (d, J=4.8 Hz, 1H), 7.39-7.48 (m, 3H), 7.20-7.25 (m, 3H), 7.03 (dd, J=7.6 Hz, J=5.2 Hz, 1H), 4.31 (d, J=8.8 Hz, 1H), 2.92-2.99 (m, 1H), 2.64-2.86 (m, 4H), 2.38-2.53 (m, 2H), 2.11-2.19 (m, 1H), 1.77-1.93 (m, 2H), 1.41-1.46 (m, 1H).

Example 195

(anti)-5,6,7,8-tetrahydroquinolin-8-yl{1-[2-(trifluoromethyl)phenyl]-cyclobutyl}methanol The title compound was prepared using procedures analogous to that described for the synthesis of Example 179, substituting 2-(2-(trifluoromethyl)phenyl)-acetic acid for 2-(3-(trifluoromethyl)phenyl)acetic acid in Example 179A. LC-MS: 362 (M+H). $^1$H NMR (400 MHz, CDCl$_3$): δ 8.32 (d, J=7.6 Hz, 1H), 7.61 (d, J=8.0 Hz, 1H), 7.26-7.44 (m, 4H), 6.96-6.99 (m, 1H), 5.16 (s, 1H), 3.29 (s, 1H), 2.98 (s, 1H), 2.50-2.72 (m, 6H), 2.09-2.17 (m, 1H), 1.73 (s, 2H), 1.42 (s, 2H).

Example 196

(syn)-5,6,7,8-tetrahydroquinolin-8-yl{1-[2-(trifluoromethyl)phenyl]-cyclobutyl}methanol The title compound was prepared using procedures analogous to that described for the synthesis of Example 179, substituting 2-(2-(trifluoromethyl)phenyl)-acetic acid for 2-(3-(trifluoromethyl)phenyl)acetic acid in Example 179A. LC-MS: 362 (M+H). $^1$H NMR (400 MHz, CDCl$_3$): δ 8.35 (d, J=4.8 Hz, 1H), 7.65 (d, J=8.0 Hz, 1H), 7.29-7.48 (m, 4H), 7.04-7.07 (m, 1H), 5.43 (s, 1H), 4.06 (d, J=5.2 Hz, 1H), 2.86-2.94 (m, 3H), 2.47-2.68 (m, 5H), 2.05-2.12 (m, 1H), 1.45-1.83 (m, 4H).

Example 197

(anti)-6,7-dihydro-5H-cyclopenta[b]pyridin-7-yl{1-[2-(trifluoromethyl)-phenyl]cyclobutyl}methanol

Example 197A 1-(2-(trifluoromethyl)phenyl)cyclobutanecarbaldehyde

The title compound was prepared using procedures analogous to that described for the synthesis of Example 179D, substituting 2-(2-(trifluoromethyl)-phenyl)acetic acid for 2-(3-(trifluoromethyl)phenyl)acetic acid in Example 179A. MS: 229 (M+H).

Example 197B (anti)-6,7-dihydro-5H-cyclopenta[b]pyridin-7-yl{1-[2-(trifluoromethyl)-phenyl]cyclobutyl}methanol The title compound was prepared using procedures analogous to that described for the synthesis of Example 185, substituting Example 197A for Example 179D. LC-MS: 348 (M+H). $^1$H NMR (400 MHz, CDCl$_3$): δ 8.39 (d, J=4.8 Hz, 1H), 7.65 (d, J=8.0 Hz, 1H), 7.30-7.50 (m, 4H), 7.04-7.07 (m, 1H), 5.04 (s, 1H), 2.47-2.96 (m, 6H), 2.14-2.21 (m, 1H), 1.72-1.80 (m, 4H).

Example 198

(syn)-6,7-dihydro-5H-cyclopenta[b]pyridin-7-yl{1-[2-(trifluoromethyl)-phenyl]cyclobutyl}methanol The title compound was prepared using procedures analogous to that described for the synthesis of Example 185, substituting Example 197A for Example 179D. LC-MS: 348 (M+H). $^1$H NMR (400 MHz, CDCl$_3$): δ 8.25 (d, J=4.8 Hz, 1H), 7.63 (d, J=8.0 Hz, 1H), 7.49 (s, 3H), 7.31-7.33 (m, 1H), 7.06-7.09 (m, 1H), 4.20 (s, 1H), 2.49-2.96 (m, 8H), 1.79-2.14 (m, 3H).

Example 199

3-[(R)-hydroxy(pyridin-2-yl)methyl]-3-[4-(trifluoromethyl)phenyl]-cyclobutanol

Example 200 cis-3-[(S)-hydroxy(pyridin-2-yl)methyl]-3-[4-(trifluoromethyl)phenyl]-cyclobutanol

Example 201 trans-3-[(S)-hydroxy(pyridin-2-yl)methyl]-3-[4-(trifluoromethyl)phenyl]-cyclobutanol

Example 202 pyridin-2-yl{2-[4-(trifluoromethoxy)phenyl]-5,8-dioxaspiro[3.4]oct-2-yl}-methanol

Example 203 trans-3-[(S)-hydroxy(pyridin-2-yl)methyl]-1-methyl-3-[4-(trifluoromethoxy)-phenyl]cyclobutanol

Example 204

(2-aminocyclopentyl){1-[3-(trifluoromethyl)phenyl]cyclobutyl}methanol

The title compound was prepared using procedures analogous to that described for the synthesis of Example 205, substituting 3-(trifluoromethyl)phenyl acetonitrile for 4-(trifluoromethyl)phenyl acetonitrile in Example 205A. LC/MS:

314 [M+1]. ¹H NMR (400 MHz, CD₃OD): δ 1.690-2.529 (m, 12H), 3.20-3.29 (m, 2H), 3.79-3.82 (d, 2H), 7.41-7.56 (m, 4H).

Example 205

(2-aminocyclopentyl){1-[4-(trifluoromethyl)phenyl]cyclobutyl}methanol

Example 205A 1-(4-(trifluoromethyl)phenyl)cyclobutanecarbonitrile

To a suspension of NaH (0.95 g, 23.7 mmol) in DMSO (15 mL) was added dropwise a solution of 4-(trifluoromethyl)phenyl acetonitrile (2.0 g, 10.8 mmol) and 1,3-dibromopropane (2.37 g, 11.9 mmol) in ether (40 mL) at 0° C. The mixture was stirred for 4 hours at room temperature. After addition of water (15 mL), the mixture was extracted with diethyl ether (100 mL×2). The combined organic layers were washed with water (50 mL), brine (50 mL), dried over Na₂SO₄, filtered, and concentrated. The residue was purified by column chromatography on silica gel (petroleum ether/EtOAc=10/1) to obtain Example 205A (1.5 g, yield 61%) as a solid. LC-MS: 226 [M+H].

Example 205B 1-(4-(trifluoromethyl)phenyl)cyclobutanecarbaldehyde

To a solution of Example 205A (1.5 g, 6.66 mmol) in DCM (20 mL) was added dropwise DIBAL-H (1.0 M, 7 mL, 7 mmol) at −78° C. The resulting mixture was stirred for 2.5 hours. After addition of saturated NH₄Cl (10 mL), the mixture was extracted with dichloromethane (100 mL×3). The combined organic layers were dried over Na₂SO₄, filtered and concentrated to give Example 205B which was used directly for the next step without further purification. LC-MS: 229 [M+H]

Example 205C 2-(hydroxy(1-(4-(trifluoromethyl)phenyl)cyclobutyl)methyl)cyclopentanone To the mixture of cyclopentanone (0.67 g, 8.0 mmol) in dry THF (20 mL) was added dropwise LiHMDS (1.0 M, 9.0 mL, 9.0 mmol) at −78° C. After stirring for 1 hour, a solution of Example 205B (1.5 g, 6.66 mmol) in THF (10 mL) was added dropwise at −78° C. Then the reaction mixture was stirred for overnight at room temperature. After addition of aqueous NH₄Cl (15 mL), the mixture was extracted with EtOAc (100 mL×2). The combined organic layers were washed with brine (50 mL×1), dried over Na₂SO₄, filtered, and concentrated. The crude product was purified by Prep-TLC (eluted with EtOAc/petroleum ether=1/4) to obtain Example 205C (0.99 g, yield 48%). LC-MS: 295 [M−OH].

Example 205D (2-aminocyclopentyl){1-[4-(trifluoromethyl)phenyl]cyclobutyl}methanol The mixture of Example 205C (200 mg, 0.64 mmol) and ammonium acetate (197 mg, 2.56 mmol) in EtOH (20 mL) was stirred for 2 hours, after which NaBH₃CN (81 mg, 1.28 mmol) was added, the mixture was stirred overnight at room temperature and concentrated. The reaction mixture was partitioned between EtOAc (20 mL) and water (20 mL). The organic phase was separated, washed with brine, dried over Na₂SO₄, filtered, and concentrated. The resulting residue was purified by Prep-HPLC (Column: Hanbon Benetnach C18 10 μm, 20×250 mm, eluent: water (0.05% TFA): acetonitrile, 55-85%) to give Example 205D (102 mg, yield 50%) as white solid. LC/MS: 314 [M+1]. ¹H NMR (400 MHz, CD₃OD): δ 1.2-2.64 (m, 14H), 3.32-3.40 (m, 1H), 3.92-3.948 (d, 1H), 7.58-7.65 (m, 4H).

Example 206

(2-aminocyclopentyl){1-[4-(trifluoromethoxy)phenyl]cyclobutyl}methanol

The title compound was prepared using procedures analogous to that described for the synthesis of Example 205, substituting 4-(trifluoromethoxy)phenyl acetonitrile for 4-(trifluoromethyl)phenyl acetonitrile in Example 205A. LC/MS: 330 [M+1]. ¹H NMR (400 MHz, CD₃OD): δ 1.2-2.08 (m, 9H), 2.29-2.60 (m, 4H), 3.32-3.40 (m, 1H), 3.89 (d, 1H), 7.24 (d, 2H), 7.50 (d, 2H).

Example 207

(2-aminocyclohexyl){1-[4-(trifluoromethyl)phenyl]cyclobutyl}methanol

The title compound was prepared using procedures analogous to that described for the synthesis of Example 205, substituting cyclohexanone for cyclopentanone in Example 205C. LC/MS: 328 [M+1]. ¹H NMR (400 MHz, CD₃OD): δ 0.81-2.77 (m, 15H), 3.88-3.94 (m, 1H), 7.51-7.68 (m, 4H).

Example 208

(2-aminocyclopentyl){1-[3-(trifluoromethoxy)phenyl]cyclobutyl}methanol

The title compound was prepared using procedures analogous to that described for the synthesis of Example 205, substituting 3-(trifluoromethoxy)phenyl acetonitrile for 4-(trifluoromethyl)phenyl acetonitrile in Example 205A. LC/MS: 330 [M+1]. ¹H NMR (400 MHz, CD₃OD): δ 1.20-2.62 (m, 14H), 3.32-3.40 (m, 1H), 3.90 (d, 1H), 7.13-7.46 (m, 4H).

Example 209

(2-aminocyclohexyl){1-[4-(trifluoromethoxy)phenyl]cyclobutyl}methanol

The title compound was prepared using procedures analogous to that described for the synthesis of Example 205, substituting 4-(trifluoromethoxy)phenyl acetonitrile for 4-(trifluoromethyl)phenyl acetonitrile in Example 205A and substituting cyclohexanone for cyclopentanone in Example 205C. LC/MS: 344 [M+1]. ¹H NMR (400 MHz, CD₃OD): δ 0.81-2.72 (m, 15H), 3.32-3.36 (m, 1H), 3.83-3.89 (m, 1H), 7.25-7.59 (m, 4H).

Example 210

(2-aminocyclohexyl){1-[3-(trifluoromethoxy)phenyl]cyclobutyl}methanol

The title compound was prepared using procedures analogous to that described for the synthesis of Example 205, substituting 3-(trifluoromethoxy)phenyl acetonitrile for 4-(trifluoromethyl)phenyl acetonitrile in Example 205A and substituting cyclohexanone for cyclopentanone in Example 205C. LC/MS: 344 [M+1]. ¹H NMR (400 MHz, CD₃OD): δ 0.5-2.88 (m, 15H), 3.13-3.71 (m, 1H), 6.96-7.28 (m, 4H).

Example 211

(2-aminocyclohexyl) [1-(3,4-dichlorophenyl)cyclobutyl] methanol

The title compound was prepared using procedures analogous to that described for the synthesis of Example 205, substituting 3,4-dichlorophenyl acetonitrile for 4-(trifluoromethyl)phenyl acetonitrile in Example 205A and substituting cyclohexanone for cyclopentanone in Example 205C. LC/MS: 328.1 [M+1]. $^1$H NMR (400 MHz, CD$_3$OD): δ 0.82-1.99 (m, 12H), 2.21-2.32 (m, 1H), 2.38-2.70 (m, 2H), 3.05 (m, 1H), 3.95 (m, 1H), 7.25-7.65 (m, 3H).

Example 212

(2-aminocyclohexyl){1-[3-(trifluoromethyl)phenyl] cyclobutyl}methanol

The title compound was prepared using procedures analogous to that described for the synthesis of Example 205, substituting 3-(trifluoromethyl)phenyl acetonitrile for 4-(trifluoromethyl)phenyl acetonitrile in Example 205A and substituting cyclohexanone for cyclopentanone in Example 205C. LC/MS: 328.2 [M+1]. $^1$H NMR (400 MHz, CD$_3$OD): δ 0.77-2.01 (m, 12H), 2.28-2.91 (m, 4H), 3.95 (m, 1H), 7.52-7.57 (m, 3H), 7.74-7.75 (d, J=5.2 Hz, 1H).

Example 213

(2-aminocyclobutyl){1-[3-(trifluoromethyl)phenyl] cyclobutyl}methanol

The title compound was prepared using procedures analogous to that described for the synthesis of Example 205, substituting 3-(trifluoromethyl)phenyl acetonitrile for 4-(trifluoromethyl)phenyl acetonitrile in Example 205A and substituting cyclobutanone for cyclopentanone in Example 205C. LC/MS: 300 [M+1]. $^1$H NMR (400 MHz, CD$_3$OD): δ 0.97-2.82 (m, 11H), 3.32-4.2 (m, 2H), 7.48-7.53 (m, 4H).

Example 214

(2-aminocyclopentyl){1-[2-(trifluoromethoxy)phenyl] cyclobutyl}methanol

The title compound was prepared using procedures analogous to that described for the synthesis of Example 205, substituting 2-(trifluoromethoxy)phenyl acetonitrile for 4-(trifluoromethyl)phenyl acetonitrile in Example 205A. LC/MS: 330 [M+1] $^1$H NMR (400 MHz, CD$_3$OD): δ 1.05-2.64 (m, 13H), 3.36-3.53 (m, 1H), 3.99 (m, 1H), 7.24-7.36 (m, 4H).

Example 215

(2-aminocyclopentyl) [1-(3,4-dichlorophenyl)cyclobutyl] methanol

Example 215A 1-(3,4-dichlorophenyl)cyclobutanecarbaldehyde

The title compound was prepared using procedures analogous to that described for the synthesis of Example 205B, substituting 1-(3,4-dichlorophenyl)-cyclobutanecarbonitrile for Example 205A

Example 215B 2-((1-(3,4-dichlorophenyl)cyclobutyl)(hydroxy)methyl) cyclopentanone (2-aminocyclopentyl)[1-(3,4-dichlorophenyl)cyclobutyl] methanol The title compound was prepared using procedures analogous to that described for the synthesis of Example 205C, substituting Example 215A for Example 205B

Example 215C (2-aminocyclopentyl)[1-(3,4-dichlorophenyl)cyclobutyl] methanol The title compound was prepared using procedures analogous to that described for the synthesis of Example 205D, substituting Example 215B for Example 205C.
MS: 314 [M+1]$^+$; $^1$H NMR (400 MHz, CD$_3$OD): δ 1.24-2.6 (m, 13H), 3.32-3.42 (m, 1H), 3.87-3.90 (d, 1H), 7.23-7.55 (m, 3H).

Example 216

(R)-[(1S,2R)-2-aminocyclopentyl][1-(3,4-dichlorophenyl)cyclobutyl]-methanol

Example 216A (R)-2-{(R)-[1-(3,4-dichlorophenyl)cyclobutyl](hydroxy) methyl}-cyclopentanone A suspension of Example 215A (310 mg, 1.353 mmol) and L-proline (55 mg, 0.478 mmol) in cyclopentanone (10 mL, 113 mmol) was stirred for 3 days at ambient temperature. The reaction mixture was injected directly onto a Grace Reveleris 40 g column, eluted with 0-40% EtOAc in hexanes (30 mL/min), and crude product came off with the excess cyclopentanone. Chromatography was repeated on a Grace Reveleris 12 g column, eluted with 0-40% EtOAc in hexanes (20 mL/min) to yield Example 216A (134 mg, 0.428 mmol, 31.6% yield) as a white solid. MS (DCI$^+$): m/z 330.1 (M+NH$_4$). $^1$H NMR (300 MHz, DMSO-d$_6$) δ 7.54 (d, J=8.3, 1H), 7.41 (d, J=2.1, 1H), 7.21 (dd, J=8.4, 2.1, 1H), 5.24 (d, J=5.4, 1H), 4.14 (dd, J=5.3, 1.2, 1H), 2.32-2.00 (m, 4H), 1.95-1.62 (m, 5H), 1.59-1.37 (m, 2H), 1.30-1.10 (m, 1H).

Example 216B (R)-[(1S,2R)-2-aminocyclopentyl][1-(3,4-dichlorophenyl)cyclobutyl]-methanol Example 216A (134 mg, 0.428 mmol) and ammonium acetate (989 mg, 12.83 mmol) were dissolved in methanol (10 mL) and stirred for 1 hour at ambient temperature. Sodium cyanoborohydride (94 mg, 1.497 mmol) was added and stirred overnight. The reaction mixture was concentrated to a colorless oil, added 25 mL 1N sodium hydroxide, and extracted with 50 mL EtOAc. The organic phase was washed with 25 mL brine, dried over Na$_2$SO$_4$, filtered, and concentrated. The crude product was purified by reverse phase chromatography (Column: Zorbax SB-Phenyl 4.6 mm×150 mm ID, Mobile Phase: MeOH/H$_2$O (Phos Buffer, pH=8)=80/20) and the collected fractions were dissolved in 15 mL EtOAc, washed with 10 mL 1N sodium hydroxide and 10 mL brine, dried over Na$_2$SO$_4$, filtered, and concentrated to provide Example 216B (39.6 mg, 0.126 mg, 29.5% yield) as a colorless oil. MS (ESI$^+$): m/z 314.0 (M+H). $^1$H NMR (500 MHz, DMSO-d$_6$) δ 7.54 (d, J=8.3 Hz, 1H), 7.48 (d, J=2.1 Hz, 1H), 7.30 (dd, J=8.4, 2.1 Hz, 1H), 3.76 (d, J=9.3 Hz, 1H), 2.81 (dd, J=17.0, 9.2 Hz, 1H), 2.31-2.19 (m, 2H), 2.10-2.02 (m, 1H), 1.91-1.81 (m, 1H), 1.76-1.62 (m, 2H), 1.51-1.37 (m, 3H), 1.17-1.00 (m, 2H), 0.73-0.64 (m, 1H).

Example 217

(S)-[(1R,2S)-2-aminocyclopentyl][1-(3,4-dichlorophenyl)cyclobutyl]-methanol

Example 217A (S)-2-((S)-(1-(3,4-dichlorophenyl)cyclobutyl)(hydroxy)methyl)-cyclopentanone A suspension of Example 215A (4.50 g, 19.64 mmol) and D-proline (0.798 g, 6.93 mmol) in cyclopentanone (23.700 mL, 268 mmol) was stirred over night at ambient temperature. The reaction mixture was poured into ethyl acetate (300 mL) and washed with water (2×100 mL) and brine (100 mL), dried ($Na_2SO_4$), filtered, concentrated. The residue was purified on silica gel (hexane/ethyl acetate 0-20%) to give Example 217A (1.06 g, 17.23% yield). MS (ESI⁻) M/Z 311 (M−H). ¹H NMR (300 MHz, DMSO-$d_6$) δ ppm 7.54 (d, J=8.4 Hz, 1H), 7.52 (d, J=2.1 Hz, 1H), 7.33 (dd, J=8.4, 2.2 Hz, 1H), 5.22 (d, J=4.1 Hz, 1H), 3.81 (dd, J=5.4, 4.0 Hz, 1H), 2.51-2.64 (m, 1H), 2.34-2.48 (m, 1H), 2.09-2.25 (m, 2H), 1.96-2.09 (m, 2H), 1.75-1.91 (m, 3H), 1.44-1.74 (m, 4H).

Example 217B (S)-[(1R,2S)-2-aminocyclopentyl][1-(3,4-dichlorophenyl)cyclobutyl]-methanol A mixture of Example 217A (50 mg, 0.160 mmol), MeOH (1 mL), sodium acetate (20.95 mg, 0.255 mmol) and hydroxylamine hydrochloride (18.86 mg, 0.271 mmol) was stirred at room temperature for 14 hours, followed by addition of nickel (II) chloride hexahydrate (68.3 mg, 0.287 mmol) and sodium borohydride (54.4 mg, 1.437 mmol). After 10 minutes, LC-MS showed complete reduction to 1:1 diastereomer mixture. The reaction mixture was treated with 2N NaOH, stirred for 30 minutes at room temperature, then diluted with EtOAc. The aqueous phase was extracted with EtOAc. The combined organic phase was dried ($Na_2SO_4$), filtered, and concentrated. HPLC separation (Column: Zorbax SB-Phenyl 4.6 mm×150 mm ID, Mobile Phase: MeOH/$H_2O$ (Phos Buffer, pH=8)=80/20) provided Example 217B as 2,2,2-trifluoroacetate salt (11 mg, 0.026 mmol, 16.09% yield). MS (ESI⁺) M/Z 314 (M+H)⁺. ¹H NMR (300 MHz, $CD_3OD$) δ ppm 7.45 (d, J=11.1 Hz, 1H), 7.44 (d, J=2.5 Hz, 1H), 7.23 (dd, J=8.3, 2.2 Hz, 1H), 4.19 (d, J=1.1 Hz, 1H), 3.49-3.58 (m, 1H), 2.55-2.65 (m, 1H), 2.18-2.43 (m, 3H), 1.76-2.07 (m, 4H), 1.36-1.76 (m, 4H), 0.90-1.08 (m, 1H).

Example 218

(R)-[(1R,2S)-2-aminocyclopentyl][1-(3,4-dichlorophenyl)cyclobutyl]-methanol

Example 220B (200 mg, 0.609 mmol) and MeOH (25 mL) were added to Ra—Ni 2800 (water slurry, 500 mg, 9.93 mmol) in a 50 mL pressure bottle and stirred for 16 hours at 30 psi at room temperature, and filtered through a nylon membrane. The filtrate was concentrated and purified using a Waters C8 OBD SunFire 30 mm×75 mm column and eluted with acetonitrile/0.1% TFA to provide the trifluoroacetate salt of Example 218 (3.8% yield). MS (ESI⁺) M/Z 314 (M+H). ¹H NMR (300 MHz, DMSO-$d_6$) δ 7.59 (d, J=8.3 Hz, 1H), 7.52 (d, J=2.1 Hz, 1H), 7.33 (dd, J=8.4, 2.1 Hz, 1H), 5.85 (d, J=4.3 Hz, 2H), 3.74 (dd, J=9.7, 3.5 Hz, 2H), 3.31-3.19 (m, 3H), 2.40-2.04 (m, 3H), 1.89-1.08 (m, 8H).

Example 219

(S)-[(1S,2S)-2-aminocyclopentyl][1-(3,4-dichlorophenyl)cyclobutyl]-methanol

Example 219A (R)-2-((S)-(1-(3,4-dichlorophenyl)cyclobutyl)(hydroxy)methyl)cyclopentanone The title compound was one of the diastereomers collected from the column chromatography of the mixture described in Example 217A (1.32 g, 4.21 mmol, 21.46% yield). MS (ESI⁻) M/Z 311 (M−H). ¹H NMR (300 MHz, DMSO-$d_6$) δ ppm 7.54 (d, J=8.4 Hz, 1H), 7.52 (d, J=2.1 Hz, 1H), 7.33 (dd, J=8.4, 2.2 Hz, 1H), 5.22 (d, J=4.1 Hz, 1H), 3.81 (dd, J=5.4, 4.0 Hz, 1H), 2.51-2.64 (m, 1H), 2.34-2.48 (m, 1H), 2.09-2.25 (m, 2H), 1.96-2.09 (m, 2H), 1.75-1.91 (m, 3H), 1.44-1.74 (m, 4H).

Example 219B (S)-2-((S)-(1-(3,4-dichlorophenyl)cyclobutyl)(hydroxy)methyl)-cyclopentanone oxime Example 219A, MeOH (5 mL), sodium acetate (147 mg, 1.788 mmol) and hydroxylamine hydrochloride (132 mg, 1.900 mmol) were heated at 50° C. for 1 hour, cooled, and extracted with ethyl acetate (100 mL). The organic phase was washed with water (50 mL), dried ($Na_2SO_4$), filtered, and concentrated. The residue was purified on silica gel (hexane/0-25% ethyl acetate) to give Example 219B (247 mg, 67.3% yield). MS (ESI⁻) M/Z 326 (M−H)⁻, 372 (M+COOH)—. ¹H NMR (300 MHz, DMSO-$d_6$) δ ppm 7.57 (d, J=2.0 Hz, 1H), 7.56 (d, J=8.3 Hz, 1H), 7.39 (dd, J=8.4, 2.1 Hz, 1H), 5.04 (d, J=1.6 Hz, 1H), 3.88 (dd, J=8.5, 1.5 Hz, 1H), 2.52-2.63 (m, 1H), 2.03-2.43 (m, 5H), 1.80-1.93 (m, 1H), 1.61-1.79 (m, 4H), 1.23-1.48 (m, 2H), 1.18 (t, J=7.1 Hz, 1H).

Example 219C (S)-[(1S,2S)-2-aminocyclopentyl][1-(3,4-dichlorophenyl)cyclobutyl]-methanol Example 219B (350 mg, 1.066 mmol) and MeOH (25 mL) were added to Ra—Ni 2800 (water slurry, 700 mg, 11.93 mmol) in a 50 mL pressure bottle, stirred for 16 hours at 30 psi and at room temperature, and filtered through a nylon membrane. The filtrate was concentrated in vacuo and the resulting residue was purified on reverse phase column using a Waters C8 OBD SunFire 30 mm×75 mm and eluted with acetonitrile/0.1% TFA to afford trifluoroacetate salt of Example 219C (9.4% yield). MS (ESI) M/Z 314 (M+H). ¹H NMR (300 MHz, $CD_3OD$) δ ppm 7.45 (d, J=8.3 Hz, 1H), 7.42 (d, J=2.1 Hz, 1H), 7.22 (dd, J=8.3, 2.2 Hz, 1H), 3.98 (s, 1H), 3.40 (q, J=6.2 Hz, 1H), 2.57-2.66 (m, 1H), 2.41-2.51 (m, 1H), 2.12-2.36 (m, 2H), 1.75-2.08 (m, 3H), 1.68 (q, J=8.3 Hz, 1H), 1.09-1.61 (m, 5H).

Example 220

(R)-[(1R,2R)-2-aminocyclopentyl][1-(3,4-dichlorophenyl)cyclobutyl]-methanol

Example 220A (S)-2-((R)-(1-(3,4-dichlorophenyl)cyclobutyl)(hydroxy)methyl)-cyclopentanone A suspension of Example 215A (4.95 g, 21.61 mmol) and L-proline (0.878 g, 7.63 mmol) in cyclopentanone (7 mL) was stirred overnight at ambient temperature. The reaction mixture was poured into ethyl acetate (300 mL) and washed with water (2×100 mL), brine (100 mL), dried (Na₂SO₄), filtered and concentrated. The residue was purified on SiO₂ (hexane/ethyl acetate 0-20%) to provide Example 220A (27%). MS (ESI⁻) M/Z 311 (M−H)⁻. ¹H NMR (300 MHz, DMSO-d₆) δ ppm 7.54 (d, J=8.4 Hz, 1H), 7.52 (d, J=2.1 Hz, 1H), 7.33 (dd, J=8.4, 2.2 Hz, 1H), 5.21 (d, J=4.0 Hz, 1H), 3.81 (dd, J=5.4, 4.0 Hz, 1H), 2.52-2.65 (m, 1H), 2.34-2.47 (m, 1H), 1.97-2.21 (m, 5H), 1.58-1.89 (m, 6H).

Example 220B (R)-2-((R)-(1-(3,4-dichlorophenyl)cyclobutyl)(hydroxy)methyl)-cyclopentanone oxime A mixture of Example 220A (189 mg, 0.603 mmol), MeOH (5 mL), sodium acetate (79 mg, 0.965 mmol) and hydroxylamine hydrochloride (71.3 mg, 1.026 mmol) was heated at 50° C. for 2 hours, extracted with ethyl acetate (100 mL), washed with water (50 mL), dried (Na₂SO₄), filtered, concentrated. The residue was purified on SiO₂ (hexane/0-25% ethyl acetate) to obtain Example 220B (171 mg, 0.521 mmol, 86% yield. MS (ESI⁻) M/Z 326 (M−H). ¹H NMR (300 MHz, DMSO-d₆) δ ppm 7.55 (d, J=2.0 Hz, 1H), 7.52 (d, J=8.3 Hz, 1H), 7.36 (dd, J=8.4, 2.1 Hz, 1H), 5.01 (d, J=1.6 Hz, 1H), 3.83 (dd, J=8.5, 1.5 Hz, 1H), 2.50-2.60 (m, 1H), 2.01-2.13 (m, 5H), 1.80-1.91 (m, 1H), 1.61-1.76 (m, 4H), 1.21-1.46 (m, 2H), 1.17 (t, J=7.1 Hz, 1H)

Example 220C (R)-[(1R,2R)-2-aminocyclopentyl][1-(3,4-dichlorophenyl)cyclobutyl]-methanol A mixture of Example 220B (200 mg, 0.609 mmol) in MeOH (25 mL) was added to Ra—Ni 2800, (water slurry, 500 mg, 9.93 mmol) in a 50 mL pressure bottle and stirred for 16 hours at 30 psi at room temperature, and filtered through a nylon membrane. The filtrate was concentrated and purified using a Waters C8 OBD SunFire 30 mm×75 mm column eluted with acetonitrile/0.1% TFA to afford Example 220C in 4.71% yield. MS (ESI⁺) M/Z 314 (M+H)⁺. ¹H NMR (300 MHz, DMSO-d₆) δ ppm 7.58 (d, J=8.3 Hz, 1H), 7.52 (d, J=2.1 Hz, 1H), 7.34 (dd, J=8.4, 2.1 Hz, 1H), 5.85 (d, J=4.3 Hz, 1H), 3.74 (dd, J=9.7, 3.5 Hz, 1H), 3.21-3.29 (m, 1H), 2.06-2.38 (m, 5H), 1.10-1.88 (m, 10H);

Example 221

(R)-[(1S,2R)-2-aminocyclopentyl]{1-[4-(trifluoromethoxy)phenyl]-cyclobutyl}methanol Example 221A 1-(4-(trifluoromethoxy)phenyl)cyclobutanecarbaldehyde
The title compound was prepared using procedures analogous to that described for the synthesis of Example 205B, substituting Example 288A for Example 205A.

Example 221B (R)-2-((R)-hydroxy(1-(4-(trifluoromethoxy)phenyl)cyclobutyl)methyl)-cyclopentanone A suspension of Example 221A (1.80 g, 7.37 mmol) and L-proline (0.300 g, 2.60 mmol) and cyclopentanone (7 mL) was stirred overnight at room temperature for 96 hours. The reaction mixture was poured into ethyl acetate (300 mL), washed with water (2×100 mL), brine (100 mL), dried (Na₂SO₄), filtered, and concentrated. The residue was purified on SiO₂ (hexane/ethyl acetate 0-20%) to provide Example 221B (448 mg, 18.51% yield). MS (ESIf) M/Z 329 (M+H). ¹H NMR (300 MHz, DMSO-d₆) δ 7.38-7.24 (m, 5H), 5.21 (d, J=5.3 Hz, 1H), 4.14-4.05 (m, 2H), 4.06-3.97 (m, 2H), 2.19-1.64 (m, 14H), 1.18 (t, J=7.1 Hz, 3H).

Example 221C (S)-2-((R)-hydroxy(1-(4-(trifluoromethoxy)phenyl)cyclobutyl)methyl)-cyclopentanone oxime The title compound was prepared according to the procedure described for Example 220B, substituting Example 221B for Example 220A. MS (ESIf) M/Z 344 (M+H). ¹H NMR (300 MHz, DMSO-d₆) δ 10.21 (s, 1H), 7.38-7.32 (m, 2H), 7.29-7.23 (m, 2H), 5.06 (d, J=5.3 Hz, 1H), 4.17 (dd, J=5.3, 1.6 Hz, 1H), 2.39-1.99 (m, 6H), 2.01-1.90 (m, 1H), 1.91-1.53 (m, 3H), 1.39-1.13 (m, 2H), 1.01-0.87 (m, 1H).

Example 221D (R)-[(1S,2R)-2-aminocyclopentyl]{1-[4-(trifluoromethoxy)phenyl]-cyclobutyl}methanol Example 221C (305 mg, 0.888 mmol), MeOH (5 mL) and nickel (II) chloride hexahydrate (380 mg, 1.599 mmol) were mixed and allowed to go into solution. Sodium borohydride (1.0 equivalent) was added in portions. The mixture stirred was stirred for 10 minutes, treated with 2N NaOH (5 mL), and extracted with ethyl acetate (50 mL). The organic phase was dried (Na₂SO₄), filtered and concentrated. The residue was purified using a Waters C8 OBD SunFire 30 mm×75 mm and eluted with acetonitrile/0.1% TFA to provide the trifluoroacetate salt of Example 221D (57.3 mg, 14.55% yield). MS (ESI⁺) M/Z 330 (M+H). ¹H NMR (400 MHz, DMSO-d₆) δ ppm 7.37-7.57 (bs, 2H), 7.31-7.37 (m, 2H), 7.25-7.31 (m, 2H), 4.18 (s, 1H), 3.41-3.48 (m, 1H), 3.17 (d, J=5.2 Hz, 2H), 2.52-2.63 (m, 1H), 2.29-2.42 (m, 1H), 2.16-2.28 (m, 1H), 2.05-2.16 (m, 1H), 1.81-1.95 (m, 1H), 1.63-1.81 (m, 3H), 1.41-1.61 (m, 2H), 1.18-1.39 (m, 2H), 0.63-0.78 (m, 1H)

Example 222

(S)-[(1S,2S)-2-aminocyclopentyl]{1-[4-(trifluoromethoxy)phenyl]-cyclobutyl}methanol Example 222A (R)-2-((S)-hydroxy(1-(4-(trifluoromethoxy)phenyl)cyclobutyl)methyl)-cyclopentanone The title compound was prepared according to the procedure described for Example 221B, substituting D-proline for L-proline. MS (ESI⁺) M/Z 329 (M+H). ¹H NMR (300 MHz, DMSO-d₆) δ 7.56-7.41 (m, 4H), 7.39-7.29 (m, 2H), 7.31-7.08 (m, 3H), 2.44-2.28 (m, 4H), 2.09-1.81 (m, 11H).

Example 222B (S)-[(1S,2S)-2-aminocyclopentyl]{1-[4-(trifluoromethoxy)phenyl]-cyclobutyl}methanol The mixture of Example 222A (285 mg, 0.868 mmol), methanol (5 mL), sodium acetate (85 mg, 1.042 mmol) and hydroxylamine hydrochloride (72.4 mg, 1.042 mmol) was heated in a 50° C. oil bath. After 15 minutes, the reaction mixture was cooled to room temperature and added ammonium acetate (736 mg, 9.55 mmol), sodium cyanoborohydride (164 mg, 2.60 mmol), and titanium(III)chloride (2.414 mL, 1.910 mmol) (dropwise to keep the internal temperature at about 35° C.). After 10 minutes, 2N NaOH was added and the mixture was extracted with EtOAc. The organic phase was dried (Na$_2$SO$_4$), filtered, and concentrated. Purification of the residue using a Waters C8 OBD SunFire 30 mm×75 mm eluted with acetonitrile/0.1% TFA afforded Example 222B as a trifluoroacetate salt in 34% yield. MS (ESI$^+$) M/Z 330 (M+H). $^1$H NMR (500 MHz, CD$_3$OD) δ ppm 7.47-7.49 (m, 2H), 7.21-7.23 (m, 2H), 3.87 (d, J=9.5 Hz, 1H), 3.35 (q, J=8.4 Hz, 1H), 2.51-2.58 (m, 1H), 2.39-2.47 (m, 1H), 2.32-2.39 (m, 1H), 2.24-2.32 (m, 1H), 1.90-2.05 (m, 2H), 1.76-1.85 (m, 1H), 1.57-1.76 (m, 3H), 1.25-1.45 (m, 3H).

Example 223

(R)-[(1R,2R)-2-aminocyclopentyl]{1-[4-(trifluoromethoxy)phenyl]-cyclobutyl}methanol Example 223A (S)-2-((R)-hydroxy(1-(4-(trifluoromethoxy)phenyl)cyclobutyl)methyl)-cyclopentanone The title compound was one of the diastereomers collected from the column chromatography of the mixture described in Example 22 1B.

Example 223B (R)-2-((R)-hydroxy(1-(4-(trifluoromethoxy)phenyl)cyclobutyl)methyl)-cyclopentanone oxime The title compound was prepared according to the procedure described for Example 220B, substituting Example 223A for Example 220A. MS (ESI$^+$) M/Z 344 (M+H). $^1$H NMR (300 MHz, DMSO-d$_6$) δ ppm 10.62 (s, 1H), 7.48-7.51 (m, 2H), 7.26-7.30 (m, 2H), 5.00 (d, J=1.5 Hz, 1H), 3.89 (dd, J=8.2, 1.2 Hz, 1H), 2.52-2.65 (m, 1H), 2.34 (t, J=7.7 Hz, 3H), 2.08-2.21 (m, 2H), 1.79-1.96 (m, 1H), 1.63-1.79 (m, 4H), 1.23-1.45 (m, 2H); MS (ESI) M/Z 344 (M+H)$^+$.

Example 223C (R)-[(1R,2R)-2-aminocyclopentyl]{1-[4-(trifluoromethoxy)phenyl]-cyclobutyl}methanol In a 100 mL round-bottomed flask was added TiCl$_4$ (1.895 mL, 17.24 mmol) and NaBH$_4$ (1.215 mL, 34.5 mmol) in 1,2-dimethoxyethane (30 mL). The reaction was cooled to 0° C. with a ice-bath. To the mixture was added Example 223B (2.96 g, 8.62 mmol) in 1,2-dimethoxyethane (5 mL) and the reaction was warmed to room temperature and stirred overnight. The mixture was quenched with cold water, basified with 2N NaOH, and extracted with ethyl acetate (50 mL). The organic phase was dried (Na$_2$SO$_4$), filtered and concentrated to give Example 223C (2.46 g, 7.47 mmol, 87% yield). MS (ESI$^-$) M/Z 311 (M–H). $^1$H NMR (300 MHz, DMSO-d$_6$) δ ppm 7.60-7.67 (m, 2H), 7.51-7.58 (m, 2H), 5.22 (d, J=4.0 Hz, 1H), 3.86 (dd, J=5.7, 3.9 Hz, 1H), 2.60-2.68 (m, 1H), 2.40-2.48 (m, 1H), 2.13-2.27 (m, 2H), 1.79-2.10 (m, 5H), 1.44-1.74 (m, 4H).

Example 224

(R)-[(1R,2R)-2-aminocyclopentyl][1-(4-chlorophenyl) cyclobutyl]methanol

Example 224A (2-aminocyclopentyl)(1-(4-chlorophenyl)cyclobutyl) methanol

The title compound was prepared using procedures analogous to that described for the synthesis of Example 205, substituting 4-chlorophenyl acetonitrile for 4-(trifluoromethyl)phenyl acetonitrile in Example 205A.

Example 224B (R)-[(1R,2R)-2-aminocyclopentyl][1-(4-chlorophenyl) cyclobutyl]methanol Example 224A (410 mg, 1.465 mmol) was separated on a ob Zorbax SB-Phenyl column (MeOH/water, phosphate buffer pH=8; 80:20) followed by purification using a Waters C8 OBD SunFire 30 mm×75 mm (acetonitrile/0.1% TFA) to obtain the trifluoroacetate salt of Example 224B (53 mg, 0.135 mmol, 9.18% yield) and the trifluoroacetate salt of Example 225 (46 mg, 0.117 mmol, 7.97% yield). MS (DCI$^+$) M/Z 280 (M+H). $^1$H NMR (300 MHz, CD$_3$OD) δ ppm 7.34-7.39 (m, 2H), 7.29-7.34 (m, 2H), 3.85 (d, J=9.2 Hz, 1H), 3.34 (q, J=8.0 Hz, 1H), 2.22-2.55 (m, 5H), 1.86-2.08 (m, 2H), 1.76-1.85 (m, 1H), 1.53-1.76 (m, 2H), 1.20-1.46 (m, 3H).

Example 225

(S)-[(1S,2S)-2-aminocyclopentyl][1-(4-chlorophenyl)cyclobutyl]methanol

Example 224A (410 mg, 1.465 mmol) was separated ob Zorbax SB-Phenyl column (MeOH/water, phosphate buffer pH=8; 80:20) followed by purification using a Waters C8 OBD SunFire 30 mm×75 mm (acetonitrile/0.1% TFA) to obtain the trifluoroacetate salt of Example 224B (53 mg, 0.135 mmol, 9.18% yield) and the trifluoroacetate salt of Example 225 (46 mg, 0.117 mmol, 7.97% yield). MS (DCI$^+$) M/Z 280 (M+H). $^1$H NMR (300 MHz, CD$_3$OD) δ ppm 7.34-7.40 (m, 2H), 7.28-7.34 (m, 2H), 3.85 (d, J=9.2 Hz, 1H), 3.34 (q, J=7.9 Hz, 1H), 2.25-2.55 (m, 5H), 1.85-2.09 (m, 2H), 1.76-1.86 (m, 1H), 1.54-1.76 (m, 2H), 1.23-1.46 (m, 3H).

Example 226

(R)-[(1R,2S)-2-aminocyclopentyl][1-(2-fluorophenyl)cyclobutyl]methanol

Example 226A 2-((1-(2-fluorophenyl)cyclobutyl)(hydroxy)methyl)cyclopentanone

The title compound was prepared using procedures analogous to that described for the synthesis of Example 205C, substituting 2-fluorophenyl acetonitrile for 4-(trifluoromethyl)phenyl acetonitrile in Example 205A.

Example 226B (R)-2-((R)-(1-(2-fluorophenyl)cyclobutyl)(hydroxy)methyl)cyclopentanone oxime The title compound was prepared according to the procedure described for Example 220B, substituting Example 226A for Example 220A. MS (ESI$^+$) M/Z 278 (M+H). $^1$H NMR (300 MHz, DMSO-d$_6$) δ 10.56 (s, 1H), 7.36 (td, J=7.9, 1.9 Hz, 1H), 7.30-7.02 (m, 3H), 5.21 (d, J=2.8 Hz, 1H), 3.96-3.88 (m, 1H), 2.69-2.57 (m, 2H), 2.41-2.27 (m, 2H), 2.21-2.02 (m, 3H), 2.01-1.84 (m, 1H), 1.78-1.53 (m, 3H), 1.41-1.10 (m, 2H).

Example 226C (R)-[(1R,2S)-2-aminocyclopentyl][1-(2-fluorophenyl)cyclobutyl]methanol In a 100 mL round-bottomed flask was added titanium tetrachloride (0.428 mL, 3.90 mmol) and sodium borohydride (0.274 mL, 7.79 mmol) in 1,2-dimethoxyethane (10 mL) and the reaction was cooled to 0° C. with a ice-bath. To the mixture was added Example 226B (540 mg, 1.947 mmol) in 1,2-dimethoxyethane (5 mL) and the reaction was warmed to room temperature and stirred overnight. The mixture was quenched with cold water, basified with 2N NaOH, and extracted with ethyl acetate (3×50 mL). The organic phase was dried ($Na_2SO_4$), filtered, and concentrated. The residue was purified by reverse phase chromatography using a Waters C8 OBD SunFire 30 mm×75 mm (acetonitrile/0.1% TFA) to obtain the trifluoroacetate salt of Example 226C (57 mg, 7.7%). MS ($DCI^+$) M/Z 264 (M+H). $^1$H NMR (500 MHz, Pyridine-$d_5$) δ ppm 7.95-10.37 (bs, 3H), 7.41 (td, J=7.9, 1.4 Hz, 1H), 7.20-7.28 (m, 1H), 7.15 (td, J=7.6, 1.1 Hz, 1H), 7.09 (ddd, J=11.5, 8.2, 1.1 Hz, 1H), 4.63 (d, J=7.8 Hz, 1H), 4.00 (t, J=5.3 Hz, 1H), 2.89-3.04 (m, 1H), 2.70-2.84 (m, 1H), 2.53 (q, J=9.5 Hz, 1H), 2.45 (q, J=9.4 Hz, 1H), 2.00-2.17 (m, 3H), 1.89-1.99 (m, 1H), 1.71-1.86 (m, 3H), 1.56-1.66 (m, 1H), 1.45-1.56 (m, 1H).

Example 227

(R)-[(1R,2R)-2-aminocyclopentyl]{1-[3-(trifluoromethyl)phenyl]-cyclobutyl}methanol The HCl salt of the title compound was prepared using procedures analogous to that described for the synthesis of Example 220, substituting Example 179D for Example 215A used in Example 220A. MS ($ESI^+$) M/Z 314 (M+H). $^1$H NMR (300 MHz, $CD_3OD$) δ ppm 7.61-7.64 (m, 2H), 7.53-7.59 (m, 2H), 4.01 (d, J=5.6 Hz, 1H), 3.11-3.22 (m, 1H), 2.55-2.66 (m, 1H), 2.28-2.54 (m, 3H), 1.95-2.10 (m, 1H), 1.74-1.95 (m, 3H), 1.47-1.74 (m, 5H).

Example 228

(R)-[1-(3,4-dichlorophenyl)cyclobutyl][(1R,2R)-2-(methylamino)-cyclopentyl]methanol Example 220A (460 mg, 1.469 mmol), MeOH (6 mL), potassium acetate (288 mg, 2.94 mmol), methylamine hydrochloride (198 mg, 2.94 mmol), and sodium cyanoborohydride (185 mg, 2.94 mmol) were stirred at 50° C. for 1 hour. The reaction mixture was cooled to room temperature, diluted with MTBE and 2N NaOH, and partitioned. The organic phase was washed with brine, dried ($Na_2SO_4$), filtered, and concentrated to give Example 228 (302 mg, 0.920 mmol, 62.6% yield) as a crude product. MS ($DCI^+$) M/Z 329 (M+H). $^1$H NMR (300 MHz, $CD_3OD$) δ ppm 7.53 (d, J=2.1 Hz, 1H), 7.47 (d, J=8.3 Hz, 1H), 7.33 (dd, J=8.4, 2.2 Hz, 1H), 3.88 (d, J=9.7 Hz, 1H), 3.26-3.36 (m, 1H), 2.56 (s, 3H), 2.49-2.61 (m, 1H), 2.17-2.48 (m, 3H), 1.88-2.12 (m, 2H), 1.60-1.87 (m, 4H), 1.18-1.52 (m, 3H); MS (ESI) M/Z, 328 (M+$NH_4$—$H_2O$)$^+$.

This crude product was treated with $Boc_2O$ (0.429 mL, 1.850 mmol) in THF (10 mL) for 1 hour at room temperature. The mixture was concentrated and chromatographed on silica gel (0-25% EtOAc/hexanes) to give tert-butyl (1R,2R)-2-((R)-(1-(3,4-dichlorophenyl)cyclobutyl)(hydroxy)methyl)cyclopentyl)(methyl)carbamate (45.7% yield) and tert-butyl (1S,2R)-2-((R)-(1-(3,4-dichlorophenyl)cyclobutyl)(hydroxy)-methyl)cyclopentyl)(methyl)carbamate (43.3% yield). $^1$H NMR (300 MHz, DMSO-$d_6$) δ ppm 7.54 (d, J=8.4 Hz, 1H), 7.45 (d, J=2.1 Hz, 1H), 7.27 (dd, J=8.4, 2.1 Hz, 1H), 4.98 (d, J=5.0 Hz, 1H), 3.52-3.61 (m, 1H), 2.50-2.63 (m, 1H), 2.31-2.48 (m, 3H), 2.10-2.25 (m, 1H), 1.92-2.04 (m, 1H), 1.23-1.76 (m, 20H); MS ($DCI^+$) M/Z 428 (M+H)$^+$.

Removal of Boc group from tert-butyl (1R,2R)-2-((R)-(1-(3,4-dichlorophenyl)cyclobutyl)(hydroxy)methyl)cyclopentyl)(methyl)carbamate (302 mg, 0.705 mmol) was achieved by reacting it with 4N HCl (0.441 mL, 1.762 mmol) in MTBE (3 mL) at 50° C. overnight. The yellow oil was cooled to room temperature and 4N HCl was added. The mixture was washed with MTBE (30 mL) and partitioned. The aqueous layer was made basic with 2N NaOH and extracted with MTBE (2×30 mL). The combined organic phase was dried over $Na_2SO_4$, filtered, and concentrated. 2 mL of methanol was added to the residue and followed by slow addition of water (4 mL). The white solid formed was collected by filtration and washed with water (2 mL) and dried in a vacuum oven at 50° C. to give Example 228 (52.2 mg, 0.143 mmol, 20.30% yield). $^1$H NMR (300 MHz, $CD_3OD$) δ ppm 7.53 (d, J=2.1 Hz, 1H), 7.47 (d, J=8.3 Hz, 1H), 7.33 (dd, J=8.4, 2.2 Hz, 1H), 3.88 (d, J=9.7 Hz, 1H), 3.26-3.36 (m, 1H), 2.56 (s, 3H), 2.49-2.61 (m, 1H), 2.17-2.48 (m, 3H), 1.88-2.12 (m, 2H), 1.60-1.87 (m, 4H), 1.18-1.52 (m, 3H); MS ($ESI^+$) M/Z, 328 (M+$NH_4$—$H_2O$).

Example 229

(R)-[(1R,2S)-2-aminocyclopentyl]{1-[4-(trifluoromethoxy)phenyl]-cyclobutyl}methanol

Example 229A (S)-2-((R)-hydroxy(1-(4-(trifluoromethoxy)phenyl)cyclobutyl)methyl)-cyclopentanone A suspension of Example 221A (5.2 g, 21.29 mmol), L-proline (1.839 g, 15.97 mmol), cyclopentanone (60.3 mL, 681 mmol) and DMSO (7.56 mL, 106 mmol) was stirred at room temperature for 3 days. The reaction mixture was poured into ethyl acetate (300 mL) and washed with water (2×100 mL), brine (100 mL), dried ($Na_2SO_4$), filtered, and concentrated. The residue was purified on silica gel (hexane/ethyl acetate 0-20%) to provide two major products: Example 221B (3.35 g, 10.20 mmol, 47.9% yield) and Example 229A (3.29 g, 47.1% yield). MS (ESI) M/Z 327 (M–H). $^1$H NMR (300 MHz, DMSO-$d_6$) δ ppm 7.42-7.46 (m, 2H), 7.25-7.29 (m, 2H), 5.17 (d, J=3.9 Hz, 1H), 3.82 (dd, J=5.5, 3.9 Hz, 1H), 2.52-2.66 (m, 1H), 2.39-2.48 (m, 1H), 2.13-2.30 (m, 2H), 1.40-2.12 (m, 9H); MS ($ESI^-$) M/Z 327 (M–H)$^-$.

Example 229B (R)-2-((R)-hydroxy(1-(4-(trifluoromethoxy)phenyl)cyclobutyl)methyl)-cyclopentanone oxime The title compound was prepared according to the procedure described for Example 220B, substituting Example 229A for Example 220A. MS ($ESI^+$) M/Z 344 (M+H). $^1$H NMR (300 MHz, DMSO-$d_6$) δ ppm 10.62 (s, 1H), 7.48-7.51 (m, 2H), 7.26-7.30 (m, 2H), 5.00 (d, J=1.5 Hz, 1H), 3.89 (dd, J=8.2, 1.2 Hz, 1H), 2.52-2.65 (m, 1H), 2.34 (t, J=7.7 Hz, 3H), 2.08-2.21 (m, 2H), 1.79-1.96 (m, 1H), 1.63-1.79 (m, 4H), 1.23-1.45 (m, 2H).

Example 229C (1R)-((1R)-2-aminocyclopentyl)(1-(4-(trifluoromethoxy)phenyl)cyclobutyl)-methanol In a 100 mL round-bottomed flask was added titanium tetrachloride (1.895 mL, 17.24 mmol) and sodium borohydride (1.215 mL, 34.5 mmol) in 1,2-dimethoxyethane (30 mL) and the reaction was cooled to 0° C. To the mixture was added Example 229B (2.96 g, 8.62 mmol) in 1,2-dimethoxyethane (5 mL) and the reaction was warmed to room temperature and stirred overnight. The reaction was quenched with cold water, basified with 2N NaOH, and extracted with ethyl acetate (3×50 mL). The organic phase was dried ($Na_2SO_4$), filtered, and concentrated to give Example 229C (2.46 g, 7.47 mmol, 87% yield). MS (ESI$^+$) M/Z 330 (M+H). $^1$H NMR (300 MHz, DMSO-$d_6$) δ 7.45-7.37 (m, 2H), 7.32-7.22 (m, 2H), 3.75 (d, J=9.2 Hz, 1H), 2.31-1.02 (m, 14H).

Example 229D tert-butyl (1S,2R)-2-((R)-hydroxy(1-(4-(trifluoromethoxy)phenyl)-cyclobutyl)methyl)cyclopentylcarbamate To a 500 mL round bottom flask containing Example 229C (2.46 g, 7.47 mmol) was added THF (50 mL) and di-tert-butyl dicarbonate (1.887 mL, 8.22 mmol). The reaction was stirred at 45° C. for 4 hours, and concentrated. The residue was purified on silica gel (hexane/ethyl acetate 0-10%) to afford Example 229D (583 mg, 1.357 mmol, 18.17% yield). MS (ESI$^+$) M/Z 430 (M+H). $^1$H NMR (300 MHz, DMSO-$d_6$) δ ppm 7.42-7.45 (m, 2H), 7.23-7.27 (m, 2H), 6.87-6.92 (m, 1H), 4.92 (d, J=4.0 Hz, 1H), 3.64-3.76 (m, 2H), 2.06-2.37 (m, 3H), 1.76-1.91 (m, 1H), 1.57-1.76 (m, 2H), 1.23-1.56 (m, 15H), 0.91-1.05 (m, 1H).

Example 229E (R)-[(1R,2S)-2-aminocyclopentyl]{1-[4-(trifluoromethoxy)phenyl]-cyclobutyl}methanol To a solution of Example 229D (583 mg, 1.357 mmol) in MTBE (20 mL) was added 4N HCl in dioxane and 2 mL of MeOH and the mixture was heated at 50° C. for 3 hours. The reaction was concentrated to dryness, treated with 2N NaOH (50 mL) and MTBE (200 mL), and partitioned. The organic layer was washed with brine (50 mL), dried ($Na_2SO_4$), filtered, and concentrated. The residue was purified on silica gel (dichloromethane to 10% MeOH with 2% $NH_4OH$) to afford Example 229E (360 mg, 1.093 mmol, 81% yield) as a colorless oil which solidified to a white solid. MS (ESI$^+$) M/Z 330 (M+H). $^1$H NMR (300 MHz, $CD_3OD$) δ ppm 7.41-7.45 (m, 2H), 7.17-7.23 (m, 2H), 3.90 (d, J=8.9 Hz, 1H), 3.21 (td, J=5.4, 1.6 Hz, 1H), 2.52-2.62 (m, 1H), 2.37 (t, J=7.8 Hz, 2H), 2.24-2.34 (m, 1H), 1.87-2.03 (m, 1H), 1.70-1.87 (m, 2H), 1.31-1.70 (m, 5H), 1.18-1.31 (m, 1H).

Example 230

(Z)-[1-(3,4-dichlorophenyl)cyclobutyl](pyridin-2-yl) methanone oxime

Example 230A

[1-(3,4-dichlorophenyl)cyclobutyl](pyridin-2-yl)methanone

To a solution of 2-bromopyridine (0.697 mL, 7.16 mmol) in THF (20 mL) at −75° C. was added 2.5M n-butyllithium (2.87 mL, 7.16 mmol) in hexanes. After 5 minutes, a solution of 1-(3,4-dichlorophenyl)cyclobutanecarbonitrile (1.08 g, 4.78 mmol) in THF (5 mL) was added. The brown-red mixture was stirred for 15 minutes at −75° C. The cooling bath was removed, sulfuric acid (20 mL) was added, and the mixture was heated at 50-60° C. for 30 minutes, diluted with MTBE, and washed twice with water. The organic layer was concentrated and the residue chromatographed on silica gel, eluted with 2-10% EtOAc in hexanes to give Example 230A (1.33 g, 4.34 mmol, 91% yield) as a clear viscous oil. MS (DCI$^+$): m/z 306.1 (M+H). $^1$H NMR (300 MHz, DMSO-$d_6$) δ 8.58-8.52 (m, 1H), 7.97-7.92 (m, 2H), 7.65 (d, J=2.2 Hz, 1H), 7.56-7.48 (m, 2H), 7.36 (dd, J=8.4, 2.1 Hz, 1H), 3.00-2.84 (m, 2H), 2.67-2.54 (m, 2H), 2.01-1.72 (m, 2H).

Example 230B (Z)-[1-(3,4-dichlorophenyl)cyclobutyl](pyridin-2-yl) methanone oxime To a solution of Example 230A (0.3 g, 0.980 mmol) in pyridine (4 mL) was added hydroxylamine hydrochloride (0.202 g, 2.91 mmol). The solution was stirred for 48 hours at ambient temperature, concentrated, diluted with diethyl ether, and washed twice with water. The organic layer was concentrated and the residue chromatographed on silica gel (5-20% EtOAc in hexanes) to give (E)-[1-(3,4-dichlorophenyl)cyclobutyl](pyridin-2-yl)methanone oxime (0.06 g, 0.187 mmol, 19.1% yield) as an oil and Example 230B (0.18 g, 0.560 mmol, 57.2% yield) as an oil that crystallized. MS (DCI$^+$): m/z 321.1 (M+H). $^1$H NMR (300 MHz, DMSO-$d_6$) δ 11.17 (s, 1H), 8.50 (ddd, J=4.8, 1.7, 1.0 Hz, 1H), 7.67 (td, J=7.8, 1.8 Hz, 1H), 7.49 (d, J=8.4 Hz, 1H), 7.32 (d, J=2.1 Hz, 1H), 7.25 (ddd, J=7.5, 4.8, 1.1 Hz, 1H), 7.18-7.08 (m, 2H), 2.94-2.80 (m, 2H), 2.45-2.31 (m, 2H), 2.00-1.78 (m, 2H).

Example 231

(S)-[1-(3,4-dichlorophenyl)cyclopropyl](pyridin-2-yl) methanol

Example 231A

[1-(3,4-dichlorophenyl)cyclopropyl](pyridin-2-yl)methanone

A solution of 2-bromopyridine (0.688 mL, 7.07 mmol) in THF (10 mL) was cooled to −75° C. 2.3M n-Hexyllithium (3.08 mL, 7.07 mmol) in hexane was added dropwise at −75° C. After 10 minutes, 1-(3,4-dichlorophenyl)cyclopropanecarbonitrile (1.00 g, 4.72 mmol) was added. After 15 minutes, 2N sulfuric acid (10 mL) was added and the mixture was heated at 50° C. for 15 minutes. The mixture was cooled to ambient temperature, diluted with MTBE and water, and partitioned. The organic layer was washed with brine, dried over $Na_2SO_4$, filtered, and concentrated. The residue was chromatographed on silica gel and eluted with 0-20% EtOAc in hexanes to give Example 231A (1.27 g, 92% yield). MS (DCIf): m/z 290.2 (M+H). $^1$H NMR (300 MHz, DMSO-$d_6$) δ 8.46 (ddd, J=4.7, 1.7, 1.0 Hz, 1H), 7.91 (td, J=7.7, 1.7 Hz, 1H), 7.82-7.76 (m, 1H), 7.52 (d, J=2.1 Hz, 1H), 7.50-7.42 (m, 2H), 7.22 (dd, J=8.4, 2.1 Hz, 1H), 1.75 (q, J=4.2 Hz, 2H), 1.45 (q, J=4.3 Hz, 2H).

Example 231B (S)-[1-(3,4-dichlorophenyl)cyclopropyl](pyridin-2-yl) methanol

A solution of Example 231A (1.08 g, 3.70 mmol) in THF (1.1 mL) was cooled to below 5° C., and (+)-B-chlorodiisopinocampheylborane (3.47 mL, 5.54 mmol) was added. The reaction was complete after 2 hours. After 2N hydrochloric acid was added, the mixture was washed with MTBE. The aqueous layer was basified with 2N sodium hydroxide and extracted with dichloromethane. The organic layer was dried over $Na_2SO_4$, filtered, and concentrated. The residue was chromatographed on silica gel and eluted with 0-75% EtOAc in hexanes to give Example 231B (437 mg, 40.2% yield) as a light yellow oil. MS (DCI+): m/z 294.0 (M+H). $^1$H NMR (500 MHz, DMSO-d$_6$) δ 8.45 (d, J=4.7 Hz, 1H), 7.64 (td, J=7.7, 1.7 Hz, 1H), 7.36 (d, J=8.3 Hz, 1H), 7.23-7.17 (m, 2H), 7.09 (d, J=7.9 Hz, 1H), 6.94 (dd, J=8.3, 2.0 Hz, 1H), 5.65 (d, J=4.2 Hz, 1H), 4.37 (d, J=4.2 Hz, 1H), 1.25-1.18 (m, 1H), 1.06-0.99 (m, 1H), 0.82-0.71 (m, 2H). [α]$_D$=−38° (c 0.610, MeOH).

Example 232 cis-3-[(S)-hydroxy(pyridin-2-yl)methyl]-1-methyl-3-[4-(trifluoromethyl)-phenyl]cyclobutanol

Example 233 trans-3-[(S)-hydroxy(pyridin-2-yl)methyl]-1-methyl-3-[4-(trifluoromethyl)-phenyl]cyclobutanol

Example 234 pyridin-2-yl{1-[6-(trifluoromethyl)pyridin-2-yl]cyclobutyl}methanol

Example 234A 1-(6-(trifluoromethyl)pyridin-2-yl)cyclobutanecarbonitrile

Cyclobutanecarbonitrile (1.474 g, 18.17 mmol) and 2-fluoro-6-(trifluoromethyl)pyridine (2.0 g, 12.11 mmol) were dissolved in toluene (30 mL). 0.5M potassium hexamethyl disilazide (36.3 mL, 18.17 mmol) in toluene was added, the solution turned dark, and the reaction was exothermic. The brown solution was stirred overnight at ambient temperature. The reaction was quenched with saturated NH$_4$Cl solution and diluted with EtOAc. The organic layer was washed with saturated NH$_4$Cl solution, dried over Na$_2$SO$_4$, filtered, and concentrated. The residue was chromatographed on silica (5-50% EtOAc in heptane) to give Example 234A (1.188 g, 5.25 mmol, 43.4% yield) as a yellow liquid. MS (DCI+): m/z 244 (M+NH$_4$). $^1$H NMR (300 MHz, DMSO-d$_6$) δ 8.21 (t, J=8.0 Hz, 1H), 7.95 (d, J=4.7 Hz, 1H), 7.92 (d, J=4.5 Hz, 1H), 2.86-2.69 (m, 4H), 2.38-2.19 (m, 1H), 2.15-1.96 (m, 1H).

Example 234B pyridin-2-yl{1-[6-(trifluoromethyl)pyridin-2-yl]cyclobutyl}methanone A solution of 2.5M n-butyl lithium (3.15 mL, 7.88 mmol) in hexanes and anhydrous diethyl ether (10 mL) was chilled to −75° C., followed by dropwise addition of 2-bromopyridine (0.794 mL, 8.14 mmol). The solution turned orange-red and was stirred for 50 minutes. Example 234A (1.188 g, 5.25 mmol) in diethyl ether (7.5 mL) was added dropwise, and the mixture was slowly warmed to 0° C. while stirring for 1 hour. The reaction was quenched with 3N hydrochloric acid (20 mL), followed by the addition of diethyl ether (20 mL). The biphasic mixture was stirred overnight at ambient temperature, followed by the addition of 3N sodium hydroxide (30 mL), and extraction with EtOAc (2×200 mL). The organic phase was washed with brine, dried over Na$_2$SO$_4$, filtered, and concentrated. The residue was chromatographed on silica (0-30% EtOAc in hexanes) to give Example 234B (1.424 g, 4.65 mmol, 89% yield) as a yellow oil. MS (ESI+): m/z 307 (M+H). $^1$H NMR (300 MHz, DMSO-d$_6$) δ 8.32 (ddd, J=4.8, 1.5, 0.8 Hz, 1H), 8.11-7.88 (m, 4H), 7.66-7.60 (m, 1H), 7.42 (ddd, J=7.5, 4.7, 1.4 Hz, 1H), 2.93-2.77 (m, 2H), 2.69-2.55 (m, 2H), 2.19-2.01 (m, 1H), 2.00-1.82 (m, 1H).

Example 234C pyridin-2-yl{1-[6-(trifluoromethyl)pyridin-2-yl]cyclobutyl}methanol Example 234B (201 mg, 0.656 mmol) was dissolved in dichloromethane (10 mL) and MeOH (2 mL), then sodium borohydride (27 mg, 0.714 mmol) was added to the colorless solution. The reaction was stirred overnight at ambient temperature, followed by the addition of 3N sodium hydroxide (50 mL), and extraction with EtOAc (2×100 mL). The organic phase was washed with brine, dried over Na$_2$SO$_4$, filtered, and concentrated. The residue was chromatographed on silica (0-100% EtOAc in hexanes) to give Example 234C (170 mg, 0.551 mmol, 84% yield) as a white solid. MS (ESI+): m/z 309 (M+H). $^1$H NMR (300 MHz, DMSO-d$_6$) δ 8.31 (ddd, J=4.9, 1.8, 0.9 Hz, 1H), 7.91 (td, J=7.8, 0.8 Hz, 1H), 7.61 (dd, J=7.6, 0.6 Hz, 1H), 7.55 (td, J=7.7, 1.8 Hz, 1H), 7.45 (d, J=8.0 Hz, 1H), 7.14 (ddd, J=7.5, 4.8, 1.2 Hz, 1H), 6.89 (d, J=7.9 Hz, 1H), 5.66 (d, J=3.5 Hz, 1H), 4.92 (d, J=2.3 Hz, 1H), 2.75-2.60 (m, 2H), 2.42-2.21 (m, 2H), 1.80-1.56 (m, 2H).

Example 235 pyridin-2-yl{2-[3-(trifluoromethoxy)phenyl]-5,8-dioxaspiro[3.4]oct-2-yl}-methanol

Example 236 cis-3-[(S)-hydroxy(pyridin-2-yl)methyl]-1-methyl-3-[3-(trifluoromethyl)-phenyl]cyclobutanol

Example 237

3-[hydroxy(pyridin-2-yl)methyl]-3-[3-(trifluoromethoxy)phenyl]-cyclobutanone

Example 238

(S)-pyridin-2-yl{1-[6-(trifluoromethyl)pyridin-2-yl]cyclobutyl}methanol

Example 234B (1.225 g, 4.00 mmol) was dissolved in a mixture of formic acid (1.319 mL, 34.4 mmol) and triethylamine (2.77 mL, 20.00 mmol), followed by the addition of (S,S)—N-(p-toluenesulfonyl)-1,2-diphenylethanediamine (chloro)(p-cumene)-ruthenium(II) (0.064 g, 0.100 mmol) was added. The reaction was heated overnight at 35° C., followed by the addition of dichloromethane (200 mL), and washed twice with saturated NaHCO$_3$ solution (200 mL). The organic phase was dried over Na$_2$SO$_4$, filtered, and concentrated. The residue was chromatographed on silica (0-100% EtOAc in hexanes) to give Example 238 (0.723 g, 2.345 mmol, 58.6% yield) as a beige solid. MS (ESI+): m/z 309 (M+H). $^1$H NMR (300 MHz, DMSO-d$_6$) δ 8.32 (ddd, J=4.8, 1.7, 0.9 Hz, 1H), 7.96-7.87 (m, 1H), 7.61 (dd, J=7.8, 0.6 Hz, 1H), 7.55 (td, J=7.7, 1.8 Hz, 1H), 7.45 (d, J=8.0 Hz, 1H), 7.14 (ddd, J=7.5, 4.9, 1.2 Hz, 1H), 6.89 (d, J=7.9 Hz, 1H), 5.67 (d, J=4.6 Hz, 1H), 4.92 (d, J=4.3 Hz, 1H), 2.75-2.58 (m, 2H), 2.42-2.22 (m, 2H), 1.80-1.56 (m, 2H). [α]$_D$=−57.3° (c 1.0, MeOH).

Example 239 pyridin-2-yl[1-(tetrahydro-2H-pyran-4-yl)cyclobutyl]methanol

Example 239A 1-(4-hydroxytetrahydro-2H-pyran-4-yl)cyclobutanecarbonitrile

To a solution of cyclobutanecarbonitrile (405 mg, 5 mmol) in THF (7 mL) was added 2.0M lithium diisopropylamide (2.5 ml, 5 mmol) dropwise at −78° C. and the reaction solution was stirred at −78° C. for 40 minutes. A solution of dihydro-2H-pyran-4(3H)-one (550 mg, 5.5 mmol) in hexamethylphosphoramide (268 mg, 1.5 mmol) was added and the mixture was warmed up to room temperature, and stirred for 3 hours. The reaction mixture was quenched with 1N aqueous HCl solution and extracted with EtOAc (3×20 mL). The combined organic phases were washed with brine (10 mL), dried over $Na_2SO_4$, filtered, and concentrated. The residue was purified by column chromatography (eluted with petroleum ether: EtOAc=20:1) to obtain the title compound as a corloless oil (0.40 g, yield 44%). $^1$H NMR (400 MHz, $CDCl_3$): δ 3.97 (dd, J=11.4, 4.2 Hz, 1H), 3.60-3.50 (m, 2H), 3.40-3.33 (m, 1H), 2.66-2.57 (m, 2H), 2.30-2.16 (m, 3H), 1.99-1.87 (m, 2H), 1.72 (dd, J=8.8, 3.6 Hz, 2H), 1.63-1.58 (m, 1H).

Example 239B 1-(tetrahydro-2H-pyran-4-yl)cyclobutanecarbonitrile

To a solution of Example 239A (0.4 g, 2.2 mmol) in pyridine (5 mL) was added $POCl_3$ (2 mL, 22 mmol) at room temperature. and the mixture was refluxed overnight. The reaction mixture was cooled to room temperature and carefully quenched with cold water. The resulting mixture was extracted with EtOAc (2×30 mL). The combined organic phases were washed with brine (10 mL), dried over $Na_2SO_4$, filtered and concentrated to obtain a dehydration product 1-(3,6-dihydro-2H-pyran-4-yl)cyclobutanecarbonitrile (0.28 g). This crude material was dissolved in EtOH, followed by the addition of Pd/C. The solution was hydrogenated at room temperature overnight, filtered, and concentrated to obtain the title compound (0.24 g), which was used in the next step without further purification.

Example 239C pyridin-2-yl[1-(tetrahydro-2H-pyran-4-yl)cyclobutyl]methanol

To a solution of Example 239B (0.24 g, 1.46 mmol) in dichloromethane (5 mL) was added DIBAL-H (2.1 mL, 2.1 mmol) dropwise at −78° C. and the reaction solution was stirred at −78° C. for 1 hour. The reaction mixture was quenched by aqueous 1N HCl solution and extracted with dichloromethane (20 mL). The organic phase was washed with brine (10 mL), dried over $Na_2SO_4$, filtered, and concentrated to obtain 1-(tetrahydro-2H-pyran-4-yl)cyclobutanecarbaldehyde as a yellow oil (0.20 g). A solution of the yellow oil in THF (2 mL) was added to 2-pyridyl lithium (prepared by dropwise addition of 2.5N n-BuLi solution (0.6 mL, 1.54 mmol) to 2-bromopyridine ((203 mg, 1.28 mmol) in THF (5 mL) at −78° C.). After stirring at room temperature for 1 hour, the reaction mixture was quenched by aqueous $NH_4Cl$ solution and extracted with EtOAc (2×20 mL). The combined organic phase was washed with brine (10 mL), dried over $Na_2SO_4$, filtered and concentrated. The residue was purified by Prep-HPLC (C18 column, water (0.05% TFA):$CH_3CN$, 55:45 to 85:15) to obtain the title compound (65 mg, 12%). LC-MS: (M+H)$^+$: 248.2. $^1$HNMR (400 MHz, $CDCl_3$): δ 8.57 (d, J=4.8 Hz, 1H), 7.69-7.65 (m, 1H), 7.28-7.22 (m, 2H), 4.76 (d, J=6.0 Hz, 1H), 4.26 (d, J=6.8 Hz, 1H), 4.03-3.98 (m, 2H), 3.38-3.29 (m, 2H), 2.20-2.12 (m, 1H), 2.03-1.96 (m, 1H), 1.93-1.81 (m, 1H), 1.74-1.68 (m, 1H), 1.60-1.44 (m, 5H), 1.32-1.21 (m, 2H).

Example 240

(S)-pyridin-2-yl{1-[2-(trifluoromethyl)pyridin-4-yl]cyclobutyl}methanol

Example 240A

1-[2-(trifluoromethyl)pyridin-4-yl]cyclobutanecarbonitrile

A solution of cyclobutanecarbonitrile (1.36 g, 16.77 mmol) and 4-chloro-2-(trifluoromethyl)pyridine (2.89 g, 15.92 mmol) in anhydrous THF (55 mL) was chilled to −75° C. 1.0M lithium hexamethyl disilazide (24 mL, 24.00 mmol) in THF was added dropwise, and the reaction was permitted to warm to ambient temperature overnight. The reaction was quenched with saturated $NH_4Cl$ solution (200 mL) and extracted with EtOAc (300 mL). The organic layer was washed with saturated $NH_4Cl$ solution (200 mL), dried over $Na_2SO_4$, filtered, and concentrated. The residue was chromatographed on silica (5-50% EtOAc in heptane) to give Example 240A (2.162 g, 7.65 mmol, 48% yield) as an orange oil. LC/MS (APCI+): m/z 227 (M+H). $^1$H NMR (300 MHz, DMSO-$d_6$) δ 8.84 (d, J=5.1 Hz, 1H), 8.00 (d, J=1.3 Hz, 1H), 7.90-7.82 (m, 1H), 2.89-2.66 (m, 4H), 2.42-2.22 (m, 1H), 2.13-1.90 (m, 1H).

Example 240B pyridin-2-yl{1-[2-(trifluoromethyl)pyridin-4-yl]cyclobutyl}methanone A solution of 2.5M n-butyl lithium (5.73 mL, 14.34 mmol) in hexanes plus anhydrous diethyl ether (20 mL) was chilled to −75° C., followed by the dropwise addition of 2-bromopyridine (1.445 mL, 14.81 mmol) in diethyl ether (6 mL). The orange-red solution was stirred for 1 hour, follwed by the dropwise addition of Example 240A (2.162 g, 9.56 mmol) in diethyl ether (9 mL). The mixture was slowly warmed to 0° C. while stirring for 1 hour. The reaction was quenched with 3N hydrochloric acid (40 mL), added diethyl ether (40 mL), and the biphasic mixture was stirred overnight at ambient temperature. 3N sodium hydroxide (60 mL) was added to the mixture and extracted twice with EtOAc (250 mL). The organic phase was washed with brine, dried over $Na_2SO_4$, filtered, and concentrated. The residue was chromatographed on silica (0-50% EtOAc in hexanes) to give Example 240B (1.965 g, 5.13 mmol, 53.7% yield) as a yellow oil. MS (ESI+): m/z 307 (M+H). $^1$H NMR (300 MHz, DMSO-$d_6$) δ 8.65 (d, J=5.1 Hz, 1H), 8.50 (ddd, J=4.7, 1.7, 1.0 Hz, 1H), 8.03-7.90 (m, 2H), 7.85 (d, J=1.0 Hz, 1H), 7.68 (dd, J=5.3, 1.1 Hz, 1H), 7.52 (ddd, J=6.9, 4.7, 1.9 Hz, 1H), 3.01-2.87 (m, 2H), 2.75-2.60 (m, 2H), 2.05-1.78 (m, 2H).

Example 240C (S)-pyridin-2-yl{1-[2-(trifluoromethyl)pyridin-4-yl]cyclobutyl}methanol Example 240B (1.665 g, 5.44 mmol) was dissolved in a mixture of formic acid (2.9 mL, 76 mmol) and triethylamine (6.1 mL, 44.0 mmol), follwed by the addition of (S,S)—N-(p-toluenesulfonyl)-1,2-diphenylethanediamine(chloro)(p-cumene)ruthenium(II) (0.087 g, 0.136 mmol), and stirred overnight at 35° C. To the mixture was added dichloromethane (300 mL). The solution was washed twice with saturated NaHCO₃ solution (200 mL), dried over Na₂SO₄, filtered, and concentrated. The residue was chromatographed on silica (0-100% EtOAc in heptane) to give Example 240C (1.470 g, 4.77 mmol, 88% yield) as a dark yellow oil. MS (ESI+): m/z 309 (M+H). $^1$H NMR (300 MHz, DMSO-$d_6$) δ 8.52 (d, J=5.0 Hz, 1H), 8.42 (ddd, J=4.8, 1.7, 0.8 Hz, 1H), 7.54 (td, J=7.7, 1.8 Hz, 1H), 7.19 (ddd, J=7.5, 4.8, 1.1 Hz, 1H), 7.11 (dd, J=5.0, 1.1 Hz, 1H), 7.06-7.02 (m, 1H), 6.76 (d, J=7.9 Hz, 1H), 5.81 (s, 1H), 4.99 (s, 1H), 2.91-2.79 (m, 1H), 2.79-2.68 (m, 1H), 2.35-2.13 (m, 2H), 2.02-1.85 (m, 1H), 1.82-1.66 (m, 1H). $[α]_D$=−99.1° (c 1.0, MeOH).

Example 241

3-[(S)-hydroxy(pyridin-2-yl)methyl]-3-[3-(trifluoromethyl)phenyl]-cyclobutanone

Example 242 pyridin-2-yl{2-[3-(trifluoromethyl)phenyl]-5,8-dioxaspiro[3.4]oct-2-yl}-methanol Example 243

3-[(R)-hydroxy(pyridin-2-yl)methyl]-3-[3-(trifluoromethyl)phenyl]-cyclobutanone

Example 244 trans-3-[(S)-hydroxy(pyridin-2-yl)methyl]-1-methyl-3-[3-(trifluoromethyl)-phenyl]cyclobutanol Example 245

3-[hydroxy(pyridin-2-yl)methyl]-3-[3-(trifluoromethyl)phenyl]cyclobutanone

Example 246

3-{1-[hydroxy(pyridin-2-yl)methyl]cyclobutyl}tetrahydrofuran-3-ol

Example 246A 1-(3-hydroxytetrahydrofuran-3-yl)cyclobutanecarbonitrile

To a solution of cyclobutanecarbonitrile (405 mg, 5 mmol) in THF (7 ml) was added 2.0M lithium diisopropylamide (2.5 ml, 5 mmol) dropwise at −78° C. The reaction solution was stirred at −78° C. for 40 minutes, followed by the addition of a solution of dihydrofuran-3(2H)-one (473 mg, 5.5 mmol) in hexamethylphosphoramide (268 mg, 1.5 mmol). The mixture was warmed to room temperature and stirred for 3 hours. The reaction mixture was quenched with 1N aqueous HCl solution and extracted with EtOAc (3×20 mL). The combined organic phases were washed with brine (10 mL), dried over Na₂SO₄, filtered and concentrated. The residue was purified by column chromatography (eluted with petroleum ether: EtOAc=20:1) to provide the title compound as a corloless oil (0.37 g, yield 44%). $^1$H NMR (400 MHz, CDCl₃): δ 4.15-4.05 (m, 2H), 3.86 (d, J=10.0 Hz, 1H), 3.74 (d, J=9.6 Hz, 1H), 2.47-2.42 (m, 4H), 2.39-2.31 (m, 3H), 2.01-1.94 (m, 2H).

Example 246B (1-(3-hydroxytetrahydrofuran-3-yl)cyclobutyl)(pyridin-2-yl)methanone The title compound was prepared using procedures analogous to that described for the synthesis of Example 163B, substituting Example 246A for Example 163A and using 2.2 equivalents of n-BuLi. LC-MS: MS (M+H)⁺ 247.9.

Example 246C

3-{1-[hydroxy(pyridin-2-yl)methyl]cyclobutyl}tetrahydrofuran-3-ol

To a solution of Example 246B (15 mg, 0.06 mmol) in MeOH (5 mL) was added NaBH₄ (13 mg, 0.34 mmol) in one portion. The mixture was stirred at room temperature for 2 hours. The reaction mixture was quenched with aqueous NH₄Cl solution and extracted with EtOAc (20 mL×2). The combined organic phase was washed with brine (10 mL), dried over Na₂SO₄, filtered, and concentrated. The residue was purified by Prep-HPLC to obtain the title compounds as corloless oils (5.0 mg, yield 30%). MS (M+1) δ 250.2; $^1$H NMR: (400 MHz, CDCl₃): δ 8.60 (d, J=3.6 Hz, 1H), 7.76-7.72 (m, 1H), 7.49-7.46 (m, 1H), 7.31-7.28 (m, 1H), 4.96 (s, 1H), 4.84 (brs, 1H), 4.09-3.83 (m, 3H), 3.76 (d, J=9.6 Hz, 0.66H), 3.56 (d, J=10.0 Hz, 0.44H), 2.27-2.14 (m, 1H), 2.08-1.80 (m, 5H), 1.68-1.50 (m, 1H), 1.16-1.04 (m, 0.67H), 0.95-0.83 (m, 0.48H).

Example 247 cis-3-(3,4-dichlorophenyl)-3-[(R)-hydroxy(pyridin-2-yl)methyl]cyclobutanol

Example 248

(S)-{3-(hydroxyimino)-1-[4-(trifluoromethoxy)phenyl]cyclobutyl}(pyridin-2-yl)methanol Example 249

(S)-{3-(methoxyimino)-1-[4-(trifluoromethoxy)phenyl]cyclobutyl}(pyridin-2-yl)methanol Example 250 cis-3-[(R)-hydroxy(pyridin-2-yl)methyl]-1-methyl-3-[4-(trifluoromethoxy)-phenyl]cyclobutanol Example 251

3-[(S)-hydroxy(pyridin-2-yl)methyl]-3-[4-(trifluoromethoxy)phenyl]-cyclobutanone Example 252

[1-(3,6-dihydro-2H-pyran-4-yl)cyclobutyl](pyridin-2-yl)methanol

Example 252A 1-(4-hydroxytetrahydro-2H-pyran-4-yl)cyclobutanecarbonitrile

The title compound was prepared using procedures analogous to that described for the synthesis of Example 246A, substituting dihydro-2H-pyran-4(3H)-one for dihydrofuran-3(2H)-one. $^1$H NMR (400 MHz, CDCl₃): δ 3.97 (dd, J=11.4, 4.2 Hz, 1H), 3.60-3.50 (m, 2H), 3.40-3.33 (m, 1H), 2.66-2.57 (m, 2H), 2.30-2.16 (m, 3H), 1.99-1.87 (m, 2H), 1.72 (dd, J=8.8, 3.6 Hz, 2H), 1.63-1.58 (m, 1H).

Example 252B 1-(3,6-dihydro-2H-pyran-4-yl)cyclobutanecarbonitrile

The title compound was prepared using procedures analogous to that described for the synthesis of Example 284A, substituting Example 252A for Example 246A.

Example 252C 1-(3,6-dihydro-2H-pyran-4-yl)cyclobutanecarbaldehyde

The title compound was prepared using procedures analogous to that described for the synthesis of Example 284C, substituting Example 252B for Example 284B.

Example 252D

[1-(3,6-dihydro-2H-pyran-4-yl)cyclobutyl](pyridin-2-yl)methanol

The title compound was prepared using procedures analogous to that described for the synthesis of Example 284D, substituting Example 252C for Example 284C. LC-MS: MS (M+H)$^+$: 246.2; $^1$H NMR (400 MHz, CDCl$_3$): δ 8.52 (d, J=4.8 Hz, 1H), 7.63-7.59 (m, 1H), 7.21-7.17 (m, 2H), 5.25-5.23 (m, 1H), 4.76 (s, 1H), 4.32 (br, 1H), 4.13-4.10 (m, 2H), 3.66 (t, J=5.4 Hz, 2H), 2.42-2.29 (m, 2H), 2.07-1.90 (m, 3H), 1.79-1.64 (m, 3H).

Example 253

[1-(2-methylbenzyl)cyclobutyl](pyridin-2-yl)methanol

Example 253A 1-(2-methylbenzyl)cyclobutanecarbonitrile n-BuLi (0.018 mol, 7.2 ml, 2.5M) was added to a solution of diisopropylamine (1.7 g, 0.017 mol) in THF (15 mL) at −78° C. After 5 minutes neat cyclobutancarbonitrile (1.2 g, 0.015 mol) was added and the mixture was stirred at −78° C. for 1 hour. Then a solution of 1-(bromomethyl)-2-methylbenzene (3.3 g, 0.018 mol) in THF (3 mL) was added and the mixture was stirred at −78° C. for 1 hour. The mixture was quenched with water and extracted with EtOAc. The organic phase was concentrated and the residue was directly used to the next step without further purification. MS: m/z 186 (M+H)

Example 253B (1-(2-methylbenzyl)cyclobutyl)(pyridin-2-yl)methanone

To a solution of 2-bromopyridine (0.237 g, 0.0015 mol) in THF (5 mL) was added n-BuLi (0.6 mL, 2.5 M) at −78° C. After 15 minutes Example 253A (0.18 g, 0.001 mol) in THF (20 mL) was added. The mixture was stirred at −78° C. for 15 minutes and 1M H$_2$SO$_4$ (2 mL) was added slowly. The resulting mixture was heated at about 50° C.-60° C. for 30 minutes and partitioned. The aqueous phase was extracted with EtOAc. The combined organic phases were washed with water, brine, dried over Na$_2$SO$_4$, and filtered. After concentration, the residue was used for the next step without further purification. MS: m/z 265 (M+H).

Example 253C

[1-(2-methylbenzyl)cyclobutyl](pyridin-2-yl)methanol

To a solution of Example 253B (0.19 g, 0.0007 mol) was added NaBH$_4$ (0.03 g, 0.84 mmol) in small portions at 0° C. The minxture was stirred at 0° C. for 1 hour, and concentrated. The residure was purified by Prep. TLC on silica gel and eluted with petroleum ether/EtOAc (5:1) to give the title compound (total yiled for 3 steps 15%). MS: m/z 268 (M+H); $^1$H NMR (400 MHz, CDCl$_3$) δ 8.58 (d, J=4.8 Hz, 1H), 7.66 (m, 1H), 7.23 (m, 5H), 4.94 (s, 1H), 4.63 (b, 1H), 2.79 (d, J=14.0 Hz, 1H), 2.27 (d, J=14.0 Hz, 1H), 2.17 (m, 2H), 2.12 (s, 3H), 1.90 (m, 2H), 1.56 (m, 2H).

Example 254

[1-(3-fluorobenzyl)cyclobutyl](pyridin-2-yl)methanol

Example 254A 1-(3-fluorobenzyl)cyclobutanecarbonitrile

The title compound was prepared using procedures analogous to that described for the synthesis of Example 253A, substituting 1-(bromomethyl)-3-fluorobenzene for 1-(bromomethyl)-2-methylbenzene. MS: m/z 190 (M+H).

Example 254B (1-(3-fluorobenzyl)cyclobutyl)(pyridin-2-yl)methanone

The title compound was prepared using procedures analogous to that described for the synthesis of Example 253B, substituting Example 254A for Example 253A. MS: m/z 270 (M+H).

Example 254C

[1-(3-fluorobenzyl)cyclobutyl](pyridin-2-yl)methanol

The title compound was prepared using procedures analogous to that described for the synthesis of Example 253C, substituting Example 254B for Example 253B. MS: m/z 272 (M+H); $^1$H NMR (400 MHz, CDCl$_3$) δ 8.57 (d, J=4.8 Hz, 1H), 7.68 (m, 1H), 7.23 (m, 3H), 7.05 (m, 2H), 4.79 (s, 1H), 4.59 (b, 1H), 2.84 (d, J=14.8 Hz, 1H), 2.54 (d, J=14.8 Hz, 1H), 2.26 (m, 1H), 2.11 (m, 1H), 1.98 (m, 1H), 1.87 (m, 1H), 1.38 (m, 2H).

Example 255

[2-(3-chloro-4-fluorophenyl)-5,8-dioxaspiro[3.4]oct-2-yl](pyridin-2-yl)-methanol Example 256

3-[(S)-hydroxy(pyridin-2-yl)methyl]-3-[3-(trifluoromethoxy)phenyl]-cyclobutanone Example 257

3-[(R)-hydroxy(pyridin-2-yl)methyl]-3-[3-(trifluoromethoxy)phenyl]-cyclobutanone Example 258

3-(3-chloro-4-fluorophenyl)-3-[hydroxy(pyridin-2-yl)methyl]cyclobutanone

Example 259 cis-3-[(S)-hydroxy(pyridin-2-yl)methyl]-3-[3-(trifluoromethyl)phenyl]-cyclobutanol

Example 260

[1-(4,4-difluorocyclohex-1-en-1-yl)cyclobutyl](pyridin-2-yl)methanol

Example 260A 1-(4,4-difluoro-1-hydroxycyclohexyl)cyclobutanecarbonitrile

The title compound was prepared using procedures analogous to that described for the synthesis of Example 246A, substituting 4,4-difluorocyclohexanone for dihydrofuran-3(2H)-one. $^1$H NMR (400 MHz, CDCl$_3$): δ 2.46-2.41 (m, 2H), 2.39-2.23 (m, 3H), 2.16-2.02 (m, 4H), 1.94-1.85 (m, 3H), 1.75-1.69 (m, 2H).

Example 260B 1-(4,4-difluorocyclohex-1-enyl)cyclobutanecarbonitrile

The title compound was prepared using procedures analogous to that described for the synthesis of Example 284A, substituting Example 260A for Example 246A. $^1$H NMR (400 MHz, CDCl$_3$): δ 5.59 (t, J=2.4 Hz, 1H), 2.63-2.40 (m, 4H), 2.38-2.28 (m, 5H), 2.14-2.03 (m, 2H), 1.96-1.88 (m, 1H).

Example 260C 1-(4,4-difluorocyclohex-1-enyl)cyclobutanecarbaldehyde

The title compound was prepared using procedures analogous to that described for the synthesis of Example 284C, substituting Example 260B for Example 284B. $^1$H NMR (400 MHz, CDCl$_3$): δ 9.68 (s, 1H), 5.45 (t, J=2.1 Hz, 1H), 2.30-2.23 (m, 2H), 1.98-1.95 (m, 4H), 1.88-1.82 (m, 2H), 1.74-1.71 (m, 4H).

Example 260D

[1-(4,4-difluorocyclohex-1-en-1-yl)cyclobutyl](pyridin-2-yl)methanol

The title compound was prepared using procedures analogous to that described for the synthesis of Example 284D, substituting Example 260C for Example 284C. LC-MS: MS (M+H)$^+$: 280.1; $^1$H NMR (400 MHz, CDCl$_3$): δ 8.53 (d, J=4.8 Hz, 1H), 7.63-7.60 (m, 1H), 7.21-7.14 (m, 2H), 5.04 (t, J=2.8 Hz, 1H), 4.78 (s, 1H), 4.42 (brs, 1H), 2.49-2.32 (m, 4H), 2.15-2.07 (m, 2H), 2.06-1.77 (m, 4H), 1.75-1.58 (m, 2H).

Example 261 pyridin-2-yl{1-[5-(trifluoromethyl)cyclohex-1-en-1-yl]cyclobutyl}methanol

Example 261A 1-(1-hydroxy-3-(trifluoromethyl)cyclohexyl)cyclobutanecarbonitrile The title compound was prepared using procedures analogous to that described for the synthesis of Example 246A, substituting 3-(trifluoromethyl)-cyclohexanone for dihydrofuran-3(2H)-one. $^1$H NMR (400 MHz, CDCl$_3$): δ 2.51-2.41 (m, 3H), 2.37-2.26 (m, 2H), 2.03-1.78 (m, 4H), 1.69-1.43 (m, 4H), 1.39-1.23 (m, 2H).

Example 261B 1-(3-(trifluoromethyl)cyclohex-1-enyl)cyclobutanecarbonitrile and 1-(5-(trifluoromethyl)cyclohex-1-enyl)cyclobutanecarbonitrile The title compounds were prepared using procedures analogous to that described for the synthesis of Example 284A, substituting Example 261A for Example 246A. $^1$H NMR (400 MHz, CDCl$_3$): δ 5.76 (t, J=2.6 Hz, 1H), 2.53-2.48 (m, 2H), 2.35-2.33 (m, 2H), 2.19-2.10 (m, 3H), 2.04-1.87 (m, 3H), 1.65-1.42 (m, 3H).

Example 261C 1-(5-(trifluoromethyl)cyclohex-1-enyl)cyclobutanecarbaldehyde and 1-(3-(trifluoromethyl)cyclohex-1-enyl)cyclobutanecarbaldehyde The title compounds were prepared using procedures analogous to that described for the synthesis of Example 284C, substituting Example 261B for Example 284B. $^1$H NMR (400 MHz, CDCl$_3$): δ 9.38 (s, 1H), 5.60 (t, J=2.2 Hz, 1H), 2.42-2.36 (m, 3H), 2.18-2.09 (m, 5H), 1.84-1.77 (m, 3H), 1.52-1.45 (m, 2H).

Example 261D pyridin-2-yl{1-[5-(trifluoromethyl)cyclohex-1-en-1-yl]cyclobutyl}methanol The title compound was prepared using procedures analogous to that described for the synthesis of Example 284D, substituting Example 261C for Example 284C. LC-MS: MS (M+H)$^+$: 312; $^1$H NMR (400 MHz, CDCl$_3$): δ 8.55 (t, J=4.8 Hz, 1H), 7.63-7.59 (m, 1H), 7.22-7.16 (m, 2H), 5.34 (t, J=40.0 Hz, 1H), 4.79 (d, J=24.8 Hz, 1H), 4.38 (brd, 1H), 2.45-2.39 (m, 1H), 2.37-2.20 (m, 2H), 2.19-2.00 (m, 4H), 1.96-1.76 (m, 4H), 1.68-1.42 (m, 2H).

Example 262 cis-3-[(S)-hydroxy(pyridin-2-yl)methyl]-1-methyl-3-[3-(trifluoromethoxy)-phenyl]cyclobutanol

Example 263 trans-3-[(S)-hydroxy(pyridin-2-yl)methyl]-1-methyl-3-[3-(trifluoromethoxy)-phenyl]cyclobutanol

Example 264 trans-3-[(S)-hydroxy(pyridin-2-yl)methyl]-3-[3-(trifluoromethyl)phenyl]-cyclobutanol

Example 265 tert-butyl 3-{1-[hydroxy(pyridin-2-yl)methyl]cyclobutyl}pyrrolidine-1-carboxylate

Example 265A tert-butyl 3-(1-cyanocyclobutyl)-3-hydroxypyrrolidine-1-carboxylate To a solution of cyclobutanecarbonitrile (1.75 g, 21.5 mmol) in THF (15 mL) was added 2.0M lithium diisopropylamide (11 mL, 22.5 mmol) dropwise and the solution was stirred at −78° C. for 45 minutes. Then a solution of tert-butyl 3-oxopyrrolidine-1-carboxylate (4.0 g, 21.5 mmol) in THF (2 mL) was added to the solution and the mixture was stirred at −78° C. for 2 hours. The reaction mixture was quenched with saturated NH$_4$Cl solution and extracted with EtOAc (25 mL×3). The organic phase was washed with brine (20 mL), dried over Na$_2$SO$_4$, filtered, and concentrated. The residue was purified by column chromatography eluted with petroleum ether:EtOAc=2:1 to obtain the title compound (0.9 g, 38.2% yield) as a white solid. $^1$H NMR: (400 MHz, CDCl$_3$): δ 3.64-3.40 (m, 4H), 2.44 (t, J=7.8 Hz, 2H), 2.33-2.23 (m, 2H), 2.13-1.88 (m, 4H), 1.47 (s, 9H)

Example 265B tert-butyl 3-(1-cyanocyclobutyl)-2,5-dihydro-1H-pyrrole-1-carboxylate To a solution of Example 265A (2.4 g, 9 mmol) in pyridine (50 mL) was added POCl$_3$ (8.4 mL, 90 mmol) dropwise and the solution was stirred at 60° C. for 12 hours. Pyridine was removed under reduced pressure and the solution was basified with 1 N NaOH. The aqueous layer was extracted with EtOAc (25 mL×3). The combined organic phases were washed with brine (50 mL), dried over Na$_2$SO$_4$, filtered, and concentrated. The residue was purified by column chromatography eluted with petroleum ether:ethyl acetate=20:1 to obtain the title compound (2.6 g, 44.3% yield) as a colorless oil. $^1$H NMR: (400 MHz, CDCl$_3$): δ 5.80 (d, J=9.6 Hz, 1H), 4.26-4.17 (m, 4H), 2.66-2.59 (m, 2H), 2.45-2.38 (m, 2H), 2.34-2.24 (m, 1H), 2.10-2.00 (m, 1H), 1.49 (s, 9H).

Example 265C tert-butyl 3-(1-cyanocyclobutyl)pyrrolidine-1-carboxylate

The solution of Example 265B (0.8 g, 3.2 mmol) in EtOH (15 mL) was hydrogenated in the presence of Pd/C (320 mg). The resulting mixture was stirred at room temperature for 12 hours. After the filtration to remove Pd/C, the filtrate was concentrated under reduced pressure to give title compound (780 mg, 92% yield) as a colorless oil, which was used in the next step without further purification. $^1$H NMR: (400 MHz, CDCl$_3$): δ 3.68-3.38 (m, 2H), 3.33-3.03 (m, 2H), 2.77-2.33 (m, 3H), 2.26-2.12 (m, 2H), 1.90-1.62 (m, 4H), 1.49 (s, 9H).

Example 265D tert-butyl 3-(1-picolinoylcyclobutyl)pyrrolidine-1-carboxylate

To a solution of 2-bromopyridine (410 mg, 2.6 mmol) in ether (10 mL) was added 2.5M n-BuLi (1.04 mL, 2.6 mmol) dropwise and the solution was stirred at −78° C. for 45 minutes. Then a solution of Example 265C (500 mg, 2.0 mmol) in ether (2 mL) was added to the solution at −78° C. and the mixture was stirred for 2 hours. 1N HCl aqueous solution was added to the mixture till pH<7 and the resulting solution was stirred at room temperature for 1 hour. The reaction mixture was basified with aqueous solution of NaHCO$_3$ and the solution was extracted with EtOAc (20 mL×3). The combined organic phases were washed with brine (30 mL), dried over Na$_2$SO$_4$, filtered, and concentrated to obtain the title compound (140 mg, 21% yield) as a yellow oil. MS: m/z 275 (M−55).

Example 265E tert-butyl 3-{1-[hydroxy(pyridin-2-yl)methyl]cyclobutyl}pyrrolidine-1-carboxylate To a solution of Example 265D (140 mg, 0.43 mmol) in THF (4 mL) and MeOH (4 mL) was added NaBH$_4$ (60 mg, 2.5 mmol) and the solution was stirred at room temperature for 2 hours. The reaction mixture was quenched with saturated NH$_4$Cl solution and the resulting mixture extracted with EtOAc (10 mL×3). The combined organic phases were washed with brine (10 mL), dried over Na$_2$SO$_4$, filtered, and concentrated. The residue was purified by Prep-HPLC to obtain the title compound (0.11 g, 76% yield) as a white solid. MS: m/z 333 (M+H); $^1$H NMR: (400 MHz, CDCl$_3$): δ 8.57 (d, J=4.3 Hz, 1H), 7.67 (t, J=6.8 Hz, 1H), 7.31-7.23 (m, 2H), 4.73 (s, 1H), 4.55-4.43 (m, 1H), 3.56-3.26 (m, 2H), 3.13-2.79 (m, 2H), 2.28-2.07 (m, 3H), 2.05-1.85 (m, 2H), 1.75-1.70 (m, 4H), 1.46 (s, 9H).

Example 266

[1-(1,3-benzothiazol-2-yl)cyclobutyl](pyridin-2-yl)methanol

Example 266A 1-(benzo[d]thiazol-2-yl)cyclobutanecarbonitrile

The title compound was prepared using procedures analogous to that described for the synthesis of Example 275B, substituting 2-chlorobenzo[d]thiazole for Example 275A. MS (M+H)$^+$: 215.

Example 266B (1-(benzo[d]thiazol-2-yl)cyclobutyl)(pyridin-2-yl)methanone

The title compound was prepared using procedures analogous to that described for the synthesis of Example 275C, substituting Example 266A for Example 275B. MS (M+H)$^+$: 295

Example 266C

[1-(1,3-benzothiazol-2-yl)cyclobutyl](pyridin-2-yl)methanol

The title compound was prepared using procedures analogous to that described for the synthesis of Example 275D, substituting Example 266B for Example 275C. MS (M+H)$^+$: 297; $^1$H NMR (400 MHz, CDCl$_3$): δ 8.43 (d, J=4.4 Hz, 1H), 7.96 (d, J=8.0 Hz, 1H), 7.82 (d, J=8.0 Hz, 1H), 7.47-7.43 (m, 2H), 7.37-7.33 (m, 1H), 7.12-7.08 (m, 1H), 6.92 (d, J=7.6 Hz, 1H), 5.30 (s, 1H), 5.22 (s, 1H), 2.95-2.89 (m, 1H), 2.80-2.75 (m, 1H), 2.62-2.55 (m, 1H), 2.47-2.39 (m, 1H), 2.04-1.94 (m, 2H).

Example 267

(S)-{3-(dimethylhydrazinylidene)-1-[4-(trifluoromethoxy)phenyl]-cyclobutyl}(pyridin-2-yl)methanol

Example 268

3-(3-chloro-4-fluorophenyl)-3-[(S)-hydroxy(pyridin-2-yl)methyl]-cyclobutanone

Example 269

[1-(5,6-dihydro-2H-pyran-3-yl)cyclobutyl](pyridin-2-yl)methanol

Example 269A 1-(3-hydroxytetrahydro-2H-pyran-3-yl)cyclobutanecarbonitrile

The title compound was prepared using procedures analogous to that described for the synthesis of Example 246A, substituting dihydro-2H-pyran-3(4H)-one for dihydrofuran-3(2H)-one. $^1$H NMR (400 MHz, CDCl$_3$): δ 3.97 (dd, J=11.4, 4.2 Hz, 1H), 3.60-3.50 (m, 2H), 3.40-3.33 (m, 1H), 2.66-2.57 (m, 2H), 2.30-2.16 (m, 3H), 1.99-1.87 (m, 2H), 1.72 (dd, J=8.8, 3.6 Hz, 2H), 1.63-1.58 (m, 1H).

Example 269B 1-(5,6-dihydro-2H-pyran-3-yl)cyclobutanecarbonitrile and 1-(3,4-dihydro-2H-pyran-5-yl)cyclobutanecarbonitrile The title compounds were prepared using procedures analogous to that described for the synthesis of Example 284A, substituting Example 269A for Example 246A. $^1$H NMR (400 MHz, CDCl$_3$): δ 6.47 (s, 0.25H), 5.89-5.87 (m, 0.72H), 4.17-4.15 (m, 2H), 3.95-3.91 (m, 1H), 3.76 (t, J=5.6 Hz, 2H), 2.53-2.47 (m, 2H), 2.43-2.27 (m, 4H), 2.23-2.19 (m, 2H), 2.05 (t, J=6.8 Hz, 1H), 1.99-1.86 (m, 2H).

Example 269C 1-(5,6-dihydro-2H-pyran-3-yl)cyclobutanecarbaldehyde and 1-(3,4-dihydro-2H-pyran-5-yl)cyclobutanecarbaldehyde The title compounds were prepared using procedures analogous to that described for the synthesis of Example 284C, substituting Example 269B for Example 284B. $^1$H NMR (400 MHz, CDCl$_3$): δ 9.40 (s, 1H), 5.60 (t, J=2.6 Hz, 1H), 4.23-4.20 (m, 2H), 3.77 (t, J=5.4 Hz, 3H), 2.42-2.36 (m, 2H), 2.18-2.10 (m, 2H), 1.93-1.90 (m, 2H), 1.88-1.82 (m, 2H).

Example 269D

[1-(5,6-dihydro-2H-pyran-3-yl)cyclobutyl](pyridin-2-yl)methanol

To a solution of compound 2-bromopyridine (383 mg, 2.42 mmol) in THF (8 mL) was added 2.5M n-BuLi solution (1.2 mL, 2.9 mmol) dropwise and the reaction mixture was stirred at −78° C. for 1.5 hours. Then a solution of Example 269C (368 mg, 2.2 mmol) in THF (3 mL) was added in one portion and the mixture was warmed up to room temperature and stirred for 1 hour. The reaction mixture was quenched with aqueous NH$_4$Cl solution and extracted with EtOAc (2×20 mL). The combinced organic phases was washed with brine (10 mL), dried over Na$_2$SO$_4$, filtered, and concentrated. The residue was purified by Prep-HPLC(C18 column, water (0.05% TFA):CH$_3$CN, 55:45 to 85:15). The first eluting peak was collected and concentrated to provide the title compound as corloless oil (105 mg, yield 42.8%). LC-MS; MS (M+H)$^+$: 246.1; $^1$H NMR (400 MHz, CDCl$_3$): δ 8.52 (d, J=4.8 Hz, 1H), 7.64-7.60 (m, 1H), 7.23-7.17 (m, 2H), 5.32-5.30 (m, 1H), 4.76 (d, J=5.6 Hz, 1H), 4.45 (d, J=6.4 Hz, 1H), 3.98-3.93 (m, 1H), 3.77-3.58 (m, 3H), 2.41-2.31 (m, 2H), 2.15-1.94 (m, 4H), 1.84-1.74 (m, 2H).

Example 270

[1-(3,4-dihydro-2H-pyran-5-yl)cyclobutyl](pyridine-2-yl)methanol

The second eluting peak from the Prep-HPLC purification of Example 269D was collected and concentrated to provide the title compound (33.6 mg, yield 13.6%). LC-MS; MS (M+H)$^+$: 246.1. $^1$H NMR (400 MHz, CDCl$_3$): δ 8.51 (d, J=4.8 Hz, 1H), 7.64-7.59 (m, 1H), 7.23 (d, J=8.0 Hz, 1H), 7.20-7.17 (m, 1H), 6.05 (s, 1H), 4.73 (d, J=4.8 Hz, 1H), 4.28 (d, J=6.0 Hz, 1H), 3.90-3.79 (m, 2H), 2.36-2.27 (m, 2H), 2.03-1.96 (m, 1H), 1.91-1.69 (m, 6H), 1.49-1.42 (m, 1H).

Example 270

[1-(1,3-benzoxazol-2-yl)cyclobutyl](pyridin-2-yl)methanol

Example 271A 1-(benzo[d]oxazol-2-yl)cyclobutanecarbonitrile

The title compound was prepared using procedures analogous to that described for the synthesis of Example 275B, substituting 2-chlorobenzo[d]oxazole for Example 275A. MS (M+H)$^+$: 199.

Example 271B (1-(benzo[d]oxazol-2-yl)cyclobutyl)(pyridin-2-yl)methanone

The title compound was prepared using procedures analogous to that described for the synthesis of Example 275C, substituting Example 271A for Example 275B. MS (M+H)$^+$: 279

Example 271C

[1-(1,3-benzoxazol-2-yl)cyclobutyl](pyridin-2-yl)methanol

The title compound was prepared using procedures analogous to that described for the synthesis of Example 275D, substituting Example 271B for Example 275C. MS (M+H)$^+$: 281; $^1$H NMR (400 MHz, CDCl$_3$): δ 8.42 (d, J=4.4 Hz, 1H), 7.68-7.66 (m, 1H), 7.50-7.46 (m, 2H), 7.33-7.27 (m, 2H), 7.15-7.12 (m, 1H), 6.85 (d, J=7.6 Hz, 1H), 5.23 (d, J=6.4 Hz, 1H), 5.01 (s, d, J=7.2 Hz, 1H), 2.83-2.80 (m, 1H), 2.63-2.49 (m, 3H), 2.02-1.88 (m, 2H).

Example 272 cis-3-[(S)-hydroxy(pyridin-2-yl)methyl]-3-[3-(trifluoromethoxy)phenyl]-cyclobutanol

Example 273 trans-3-[(S)-hydroxy(pyridin-2-yl)methyl]-3-[3-(trifluoromethoxy)phenyl]-cyclobutanol

Example 274

[1-(4,4-difluorocyclohexyl)cyclobutyl](pyridin-2-yl)methanol

Example 274A 1-(4,4-difluoro-1-hydroxycyclohexyl)cyclobutanecarbonitrile

The title compound was prepared using procedures analogous to that described for the synthesis of Example 246A, substituting 4,4-difluorocyclohexanone for dihydrofuran-3 (2H)-one. $^1$H NMR (400 MHz, CDCl$_3$): δ 2.46-2.41 (m, 2H), 2.39-2.23 (m, 3H), 2.16-2.02 (m, 4H), 1.94-1.85 (m, 3H), 1.75-1.69 (m, 2H).

Example 274B 1-(4,4-difluorocyclohex-1-enyl)cyclobutanecarbonitrile

The title compounds were prepared using procedures analogous to that described for the synthesis of Example 284A, substituting Example 274A for Example 246A. $^1$H NMR (400 MHz, CDCl$_3$): δ 5.59 (t, J=2.4 Hz, 1H), 2.63-2.40 (m, 4H), 2.38-2.28 (m, 5H), 2.14-2.03 (m, 2H), 1.96-1.88 (m, 1H).

Example 274C 1-(4,4-difluorocyclohexyl)cyclobutanecarbonitrile

The title compound was prepared using procedures analogous to that described for the synthesis of Example 284B, substituting Example 274B for Example 284A. $^1$H NMR (400 MHz, CDCl$_3$): δ 2.78-2.62 (m, 1H), 2.50-2.43 (m, 1H), 2.29-2.11 (m, 4H), 1.99-1.91 (m, 2H), 1.82-1.69 (m, 4H), 1.66-1.41 (m, 3H).

Example 274D 1-(4,4-difluorocyclohexyl)cyclobutanecarbaldehyde

The title compound was prepared using procedures analogous to that described for the synthesis of Example 284C, substituting Example 274C for Example 284B. $^1$H NMR (400 MHz, CDCl$_3$): δ 9.68 (s, 1H), 2.30-2.23 (m, 3H), 1.98-1.95 (m, 4H), 1.88-1.82 (m, 4H), 1.74-1.71 (m, 4H)

Example 274E

[1-(4,4-difluorocyclohexyl)cyclobutyl](pyridin-2-yl)methanol

The title compound was prepared using procedures analogous to that described for the synthesis of Example 284D, substituting Example 274D for Example 284C. LC-MS: MS (M+H)$^+$: 282.2; $^1$H NMR (400 MHz, CDCl$_3$): δ 8.48 (d, J=4.8 Hz, 1H), 7.86-7.82 (m, 1H), 7.65-7.63 (m, 1H), 7.35-7.32 (m, 1H), 4.75 (s, 1H), 2.37-2.23 (m, 1H), 2.21-2.16 (m, 2H), 2.07-2.05 (m, 2H), 1.95-1.77 (m, 4H), 1.70-1.54 (m, 4H), 1.57-1.53 (m, 2H).

Example 275

[1-(1-methyl-1H-benzimidazol-2-yl)cyclobutyl](pyridin-2-yl)methanol

Example 275A 2-chloro-1-methyl-1H-benzo[d]imidazole

To a solution of 2-chloro-1H-benzo[d]imidazole (2.0 g, 13.1 mmol) in DMF (10 mL) was added NaH (0.63 g, 15.7 mmol) at 0° C. under N$_2$. After stirring for 30 min at 0° C., iodomethane (5.58 g, 39.3 mmol) was added and the mixture was stirred at room temperature for additional 1 hour. The reaction mixture was quenched with water (100 mL). The aqueous layer was extracted with EtOAc (3×20 mL). The combined organic layers were dried over Na$_2$SO$_4$, filtered, and concentrated to give the title compound (1.9 mg, 8.9 mmol, 67.9% yield) as a white solid. MS: MS (M+H)$^+$; $^1$H NMR (400 MHz, CDCl$_3$): δ 7.71-7.68 (m, 1H), 7.31-7.27 (m, 3H), 3.79 (s, 3H).

Example 275B 1-(1-methyl-1H-benzo[d]imidazol-2-yl)cyclobutanecarbonitrile

To a solution of Example 275A (1.90 g, 11.4 mmol) in toluene (30 mL) was added cyclobutanecarbonitrile (1.01 g, 12.5 mmol) and potassium hexamethyldisilazide (34.2 mL, 17.1 mmol). The reaction mixture was stirred at room temperature overnight. The mixture was poured into 1N HCl solution (50 mL) and the aqueous layer was extracted with EtOAc (3×20 mL). The combined layers were washed with brine (100 mL), dried over MgSO$_4$, filtered, and concentrated. The residue was purified by prep. TLC on silicagel (eluted with EtOAc:petroleum ether=1:10) to give the title compound (1.0 g, 4.69 mmol, 41.1% yield) as a white solid. MS: MS (M+H)$^+$; $^1$H NMR (400 MHz, CDCl$_3$): δ 7.80-7.78 (m, 1H), 7.36-7.30 (m, 3H), 3.83 (s, 3H), 3.13-3.05 (m, 2H), 2.99-2.92 (m, 2H), 2.48-2.41 (m, 1H), 2.24-2.18 (m, 1H).

Example 275C (1-(1-methyl-1H-benzo[d]imidazol-2-yl)cyclobutyl)(pyridin-2-yl)methanone To a solution of 2-bromopyridine (449 mg, 2.84 mmol) in THF (10 mL) was added dropwise n-butyl lithium (1.6 N, 1.77 mL, 2.84 mmol) at −78° C. After stirring at the same temperature for 30 minutes, a solution of Example 275B (400 mg, 1.89 mmol) in THF (2 mL) was added. The mixture was stirred at −78° C. for additional 30 minutes and then quenched with aqueous H$_2$SO$_4$ solution (1 N, 5 mL) slowly. The reaction mixture was warmed up to room temperature and partitioned. The aqueous phase was separated and extracted with EtOAc (3×10 mL). The combined organic phases were washed with water (30 mL) and brine (30 mL), dried over Na$_2$SO$_4$, filtered, and concentrated to give the title compound (430 mg, 0.50 mmol, 26.4% yield) as a yellow solid. MS: MS (M+H)$^+$.

Example 275D

[1-(1-methyl-1H-benzimidazol-2-yl)cyclobutyl](pyridin-2-yl)methanol

To a solution of Example 275E (430 mg, 1.47 mmol) in MeOH (5 mL) was added NaBH$_4$ (168 mg, 4.43 mmol) in portions. The reaction mixture was stirred at room temperature for 1 hour. After the removal of the solvent, the aqueous layer was extracted with EtOAc (3×10 mL). The combined organic phases were dried over Na$_2$SO$_4$, filtered, and concentrated. The residue was purified by Prep-HPLC (Column XBridge Prep C18 OBD, 19×250 mm; mobile Phase: water (10 mM NH$_4$HCO$_3$)—CH$_3$CN; Gradient 30-70%) to give title compound (150 mg, 0.51 mmol, 34.6% yield) as a white solid. MS: MS (M+H)$^+$; $^1$H NMR (400 MHz, CDCl$_3$): δ 8.44 (d, J=4.4 Hz, 1H), 7.69-7.67 (m, 1H), 7.44 (t, J=7.6 Hz, 1H), 7.25-7.22 (m, 3H), 7.16-7.13 (m, 1H), 6.64 (d, J=8.0 Hz, 1H), 5.18 (d, J=5.6 Hz, 1H), 4.84 (d, J=6.8 Hz, 1H), 3.38 (s, 3H), 2.95-2.88 (m, 1H), 2.82-2.64 (m, 3H), 2.12-2.07 (m, 1H), 1.97-1.88 (m, 1H).

Example 276

3-(3-chloro-4-fluorophenyl)-3-[(S)-hydroxy(pyridin-2-yl)methyl]-cyclobutanol

Example 277

3-[(S)-hydroxy(pyridin-2-yl)methyl]-3-[4-(trifluoromethyl)pyridin-2-yl]-cyclobutanone

Example 278

3-[(R)-hydroxy(pyridin-2-yl)methyl]-3-[4-(trifluoromethyl)pyridin-2-yl]-cyclobutanone

Example 279 tert-butyl 4-{1-[hydroxy(pyridin-2-yl)methyl]cyclobutyl}piperidine-1-carboxylate

Example 279A tert-butyl 4-(1-cyanocyclobutyl)-4-hydroxypiperidine-1-carboxylate The title compound was prepared using procedures analogous to that described for the synthesis of Example 265A, substituting tert-butyl 4-oxopiperidine-1-carboxylate for tert-butyl 3-oxopyrrolidine-1-carboxylate. $^1$H NMR (400 MHz, CDCl$_3$): δ 4.13-4.01 (m, 2H), 3.25 (s, 1H), 3.06 (s, 1H), 2.54-2.46 (m, 2H), 2.30-2.22 (m, 3H), 1.90-1.87 (m, 1H), 1.73-1.65 (m, 2H), 1.49 (m, 2H), 1.46 (s, 9H).

Example 279B tert-butyl 4-(1-cyanocyclobutyl)-5,6-dihydropyridine-1(2H)-carboxylate The title compound was prepared using procedures analogous to that described for the synthesis of Example 265B, substituting 279A for Example 265A. $^1$H NMR (400 MHz, CDCl$_3$): δ 5.69 (s, 1H), 3.96 (d, J=1.2 Hz, 2H), 3.54 (s, J=5.6 Hz, 2H), 2.54-2.48 (m, 2H), 2.40-2.30 (m, 3H), 2.28 (s, 2H), 2.18-1.92 (m, 1H), 1.49 (s, 9H).

Example 279C tert-butyl 4-(1-cyanocyclobutyl)piperidine-1-carboxylate

The title compound was prepared using procedures analogous to that described for the synthesis of Example 265C, substituting 279B for Example 265B. $^1$H NMR (400 MHz, CDCl$_3$): δ 2.73-2.59 (m, 2H), 2.48-211 (m, 4H), 2.00-1.83 (m, 2H), 1.70-1.58 (m, 4H), 1.49 (s, 9H), 1.37-1.16 (m, 3H).

Example 279D tert-butyl 4-(1-picolinoylcyclobutyl)piperidine-1-carboxylate

The title compound was prepared using procedures analogous to that described for the synthesis of Example 265D, substituting 279C for Example 265C.
MS: m/z 288 (M−55)$^+$

Example 279E tert-butyl 4-{1-[hydroxy(pyridin-2-yl)methyl]cyclobutyl}piperidine-1-carboxylate The title compound was prepared using procedures analogous to that described for the synthesis of Example 265E, substituting 279D for Example 265D. MS: m/z 347 (M+H); $^1$H NMR (400 MHz, CDCl$_3$): δ 8.57 (d, J=4.8 Hz, 1H), 7.69-7.64 (m, 1H), 7.27-7.22 (m, 2H), 4.75 (d, J=6.0 Hz, 1H), 4.25 (d, J=6.4 Hz, 1H), 4.15 (m, 3H), 2.58 (t, J=8.7 Hz, 2H), 2.20-2.13 (m, 1H), 2.02-1.95 (m, 1H), 1.90-1.77 (m, 2H), 1.74-1.71 (m, 1H), 1.66-1.55 (m, 2H), 1.46 (s, 9H), 1.39-1.19 (m, 4H).

Example 280 pyridin-2-yl{1-[4-(trifluoromethyl)cyclohexyl]cyclobutyl}methanol

Example 280A 1-(1-hydroxy-4-(trifluoromethyl)cyclohexyl)cyclobutanecarbonitrile The title compound was prepared using procedures analogous to that described for the synthesis of Example 246A, substituting 4-trifluorocyclohexanone for dihydrofuran-3(2H)-one. $^1$H NMR (400 MHz, CDCl$_3$): δ 2.74-2.71 (m, 1H), 2.61-2.58 (m, 2H), 2.38-2.27 (m, 4H), 1.88-1.83 (m, 2H), 1.73-1.64 (m, 2H), 1.28-1.24 (m, 4H).

Example 280B 1-(4-(trifluoromethyl)cyclohex-1-enyl)cyclobutanecarbonitrile

The title compounds were prepared using procedures analogous to that described for the synthesis of Example 284A, substituting Example 280A for Example 246A. $^1$H NMR (400 MHz, CDCl$_3$): δ 5.73 (t, J=2.6 Hz, 1H), 2.64-2.60 (m, 1H), 2.58-2.46 (m, 2H), 2.45-2.26 (m, 4H), 2.20-2.08 (m, 2H), 1.99-1.92 (m, 2H), 1.64-1.52 (m, 2H).

Example 280C 1-(4-(trifluoromethyl)cyclohexyl)cyclobutanecarbonitrile

The title compound was prepared using procedures analogous to that described for the synthesis of Example 284B, substituting Example 280B for Example 284A. $^1$H NMR (400 MHz, CDCl$_3$): δ 2.48-2.40 (m, 2H), 2.33-2.28 (m, 2H), 2.25-2.00 (m, 3H), 1.98-1.86 (m, 3H), 1.65-1.42 (m, 4H), 1.35-1.24 (m, 2H).

Example 280D 1-(4-(trifluoromethyl)cyclohexyl)cyclobutanecarbaldehyde

The title compound was prepared using procedures analogous to that described for the synthesis of Example 284C, substituting Example 280C for Example 284B. $^1$H NMR (400 MHz, CDCl$_3$): δ 9.38 (s, 1H), 2.26-2.20 (m, 2H), 2.19-2.05 (m, 2H), 1.98-1.91 (m, 2H), 1.85-1.74 (m, 2H), 1.72-1.49 (m, 5H), 1.43-1.30 (m, 4H)

Example 280E pyridin-2-yl{1-[4-(trifluoromethyl)cyclohexyl]cyclobutyl}methanol The title compound was prepared using procedures analogous to that described for the synthesis of Example 284D, substituting Example 280D for Example 284C. LC-MS: MS (M+H)$^+$: 314.2. $^1$H NMR (400 MHz, CDCl$_3$): δ 8.48 (d, J=4.8 Hz, 1H), 7.85-7.81 (m, 1H), 7.62-7.60 (m, 1H), 7.35-7.31 (m, 1H) 4.74 (s, 1H), 2.37-2.22 (m, 2H), 2.20-2.16 (m, 1H), 2.09-2.03 (m, 2H), 1.94-1.84 (m, 1H), 1.83-1.74 (m, 2H), 1.67-1.42 (m, 6H), 1.39-1.24 (m, 2H).

Example 281 pyridin-2-yl[1-(tetrahydro-2H-pyran-3-yl)cyclobutyl]methanol

Example 281A 1-(tetrahydro-2H-pyran-3-yl)cyclobutanecarbonitrile

The title compound was prepared using procedures analogous to that described for the synthesis of Example 284B, substituting Example 269B for Example 284A.

Example 281B 1-(tetrahydro-2H-pyran-3-yl)cyclobutanecarbaldehyde

The title compound was prepared using procedures analogous to that described for the synthesis of Example 284C, substituting Example 281A for Example 284B.

Example 281C pyridin-2-yl[1-(tetrahydro-2H-pyran-3-yl)cyclobutyl]methanol

The title compound was prepared using procedures analogous to that described for the synthesis of Example 284D, substituting Example 281B for Example 284C. LC-MS: MS (M+H)$^+$: 248.0. $^1$H NMR (400 MHz, CD$_3$OD): δ 8.77 (d, J=5.2 Hz, 1H), 8.58-8.52 (m, 1H), 8.10 (dd, J1=8.0, J$_2$=3.6 Hz, 1H), 8.02-7.96 (m, 1H), 5.13 (d, J=12.0 Hz, 1H), 4.08-3.87 (m, 2H), 3.43-3.34 (m, 2H), 2.84-2.63 (m, 1H), 2.30-2.22 (m, 2H), 2.17-2.00 (m, 3H), 1.93-1.84 (m, 2H), 1.78-1.45 (m, 5H).

Example 282 cis-3-[(S)-hydroxy(pyridin-2-yl)methyl]-3-[4-(trifluoromethyl)pyridin-2-yl]-cyclobutanol

Example 283 trans-3-[(S)-hydroxy(pyridin-2-yl)methyl]-3-[4-(trifluoromethyl)pyridin-2-yl]cyclobutanol

Example 284 pyridin-2-yl[1-(tetrahydrofuran-3-yl)cyclobutyl]methanol

Example 284A 1-(2,5-dihydrofuran-3-yl)cyclobutanecarbonitrile and 1-(4,5-dihydrofuran-3-yl)cyclobutanecarbonitrile To a solution of Example 246A (0.37 g, 2.2 mmol) in pyridine (5 mL) was added POCl$_3$ (2 mL, 22 mmol) at room temperature and the mixture was refluxed overnight. The reaction mixture was cooled to room temperature, quenched carefully with cold water, and the mixture extracted with EtOAc (2×30 mL). The combined organic phases were washed with brine (10 mL), dried over Na$_2$SO$_4$, filtered, and concentrated to obtain the title compound (0.27 g) as a yellow oil, which was used in the next step without further purification. $^1$H NMR (400 MHz, CDCl$_3$): δ 5.88 (s, 1H), 5.35 (s, 0.4H), 4.72 (s, 4H), 2.69-2.55 (m, 5H), 2.44-2.22 (m, 8H), 2.07-1.84 (m, 3H).

Example 284B 1-(tetrahydrofuran-3-yl)cyclobutanecarbonitrile

To a solution of Example 284A (0.27 g, 1.81 mmol) in EtOH (7 ml) was added Pd/C and the solution was hydrogenated at room temperature overnight. The reaction mixture was filtered and the filtrate concentrated to obtain the title compound as a yellow oil (0.22 g), which was used in the next step without further purification. $^1$H NMR (400 MHz, CDCl$_3$): δ 3.99-3.93 (m, 2H), 3.84-3.78 (m, 1H), 3.61-3.57 (m, 1H), 2.75-1.70 (m, 9H).

Example 284C 1-(tetrahydrofuran-3-yl)cyclobutanecarbaldehyde

To a solution of Example 284B (0.22 g, 1.46 mmol) in dichloromethane (5 mL) was added DIBAL-H (2.1 mL, 2.1 mmol) dropwise at −78° C. and the solution was stirred at −78° C. for 1 hour. The reaction mixture was quenched with aqueous 1N HCl solution and extracted with dichloromethane (20 mL). The organic phase was washed with brine (10 mL), dried over Na$_2$SO$_4$, filtered, and concentrated to obtain the title compound as a yellow oil (0.18 g), which was used in the next step without further purification. $^1$H NMR (400 MHz, CDCl$_3$): δ 9.67 (s, 1H), 3.91-3.82 (m, 2H), 3.75-3.69 (m, 1H), 3.65-3.61 (m, 1H), 2.64-2.57 (m, 2H), 2.30-2.22 (m, 2H), 2.02-1.96 (m, 1H), 1.72-1.65 (m, 1H).

Example 284D pyridin-2-yl[1-(tetrahydrofuran-3-yl)cyclobutyl]methanol

To a solution of 2-bromopyridine (203 mg, 1.28 mmol) in THF (5 mL) was added 2.5N n-BuLi solution (0.6 mL, 1.54 mmol) dropwise and stirred at −78° C. for 1.5 hours. Then a solution of Example 284C (0.18 g, 1.17 mmol) in THF (2 mL) was added and stirred at room temperature for 1 hour. The reaction mixture was quenched with aqueous NH$_4$Cl solution and extracted with EtOAc (2×20 mL). The combined organic phase was washed with brine (10 mL), dried over Na$_2$SO$_4$, filtered, and concentrated. The residue was purified by Prep-HPLC(C18 column, water (0.05% TFA):CH$_3$CN, 55:45 to 85:15) to obtain the title compound as a colorless oil (31.2 mg, yield 11.5%). LC-MS: MS (M+H)$^+$ 234.1; $^1$H NMR (400 MHz, CDCl$_3$): δ 8.55 (d, J=4.8 Hz, 1H), 7.69-7.64 (m, 1H), 7.30 (d, J=7.6 Hz 1H), 7.26-7.22 (m, 1H), 4.71 (d, J=28.8 Hz, 1H), 4.53 (brs, 1H), 3.89-3.79 (m, 1.5H), 3.65-3.54 (m, 2H), 3.38 (t, J=8.6 Hz, 0.5H), 2.35-2.04 (m, 3H), 1.99-1.55 (m, 6H).

Example 285 cis-3-[(S)-hydroxy(pyridin-2-yl)methyl]-1-methyl-3-[4-(trifluoromethyl)-pyridin-2-yl]cyclobutanol

Example 286 trans-3-[(S)-hydroxy(pyridin-2-yl)methyl]-3-[4-(trifluoromethyl)pyridin-2-yl]cyclobutanol

Example 287

[1-(3,4-dichlorophenyl)cyclobutyl](5-methoxypyridin-2-yl)methanol

Example 287A

[1-(3,4-dichlorophenyl)cyclobutyl](5-methoxypyridin-2-yl)methanone

A solution of 2.5M n-Butyl lithium (6.5 mL, 16.25 mmol) in hexanes plus anhydrous diethyl ether (50 mL) was chilled to −75° C., followed by the dropwise addition of 2-bromo-5-methoxypyridine (3.12 g, 16.59 mmol) in diethyl ether (5 mL). The brown solution was stirred for 1 hour, followed by the addition of 1-(3,4-dichlorophenyl)-cyclobutanecarbonitrile (3.0 g, 13.27 mmol) in diethyl ether (5 mL). The reaction was warmed to 0° C. while stirring for 2 hours. The reaction was quenched with 1N hydrochloric acid (100 mL) and the biphasic mixture was stirred for 1 hour at ambient temperature. Added 3N sodium hydroxide (100 mL) and extracted twice with EtOAc (200 mL). The combined organic phases was washed with brine, dried over $Na_2SO_4$, filtered, and concentrated. The residue was chromatographed on silica (0-100% EtOAc in heptane) to give Example 287A (4.046 g, 12.03 mmol, 91% yield) as a light yellow oil. MS (ESI+): m/z 336 (M+H). $^1$H NMR (500 MHz, $CD_3CN$) δ 8.14 (d, J=2.9 Hz, 1H), 7.96 (d, J=8.8 Hz, 1H), 7.64 (d, J=2.1 Hz, 1H), 7.40 (d, J=8.3 Hz, 1H), 7.35 (dd, J=8.4, 2.1 Hz, 1H), 7.31 (dd, J=8.8, 2.9 Hz, 1H), 3.86 (s, 3H), 3.00-2.89 (m, 2H), 2.66-2.54 (m, 2H), 2.02-1.91 (m, 1H), 1.89-1.77 (m, 1H).

Example 287B

[1-(3,4-dichlorophenyl)cyclobutyl](5-methoxypyridin-2-yl)methanol

Example 287A (4.046 g, 12.03 mmol) was dissolved in dichloromethane (50 mL) and MeOH (5 mL), then sodium borohydride (0.55 g, 14.54 mmol) was added to the yellow solution. The reaction was stirred for 7 hours at ambient temperature, followed by the addition of 1N sodium hydroxide (200 mL) and extraction with EtOAc (2×200 mL). The combined organic phases was washed with brine, dried over $Na_2SO_4$, filtered, and concentrated. The residue was chromatographed on silica (0-100% EtOAc in heptane) to give Example 287B (4.060 g, 12.00 mmol, 100% yield) as a colorless oil. MS (ESI+): m/z 338 (M+H). $^1$H NMR (400 MHz, $CD_3CN$) δ 8.06 (d, J=2.8 Hz, 1H), 7.27 (d, J=8.3 Hz, 1H), 7.13 (dd, J=8.6, 3.0 Hz, 1H), 6.93 (d, J=2.1 Hz, 1H), 6.83 (d, J=8.7 Hz, 1H), 6.72 (dd, J=8.3, 2.1 Hz, 1H), 4.91 (d, J=6.2 Hz, 1H), 3.96 (d, J=6.3 Hz, 1H), 3.80 (s, 3H), 2.74-2.58 (m, 2H), 2.31-2.15 (m, 2H), 2.03-1.88 (m, 1H), 1.83-1.70 (m, 1H).

Example 288

(S)-pyridin-2-yl{1-[4-(trifluoromethoxy)phenyl]cyclobutyl}methyl acetate

Example 288A 1-(4-(trifluoromethoxy)phenyl)cyclobutanecarbonitrile

The title compound was prepared using procedures analogous to that described for the synthesis of Example 85E, substituting 2-(4-(trifluoromethoxy)phenyl)-acetonitrile for Example 85D. MS (DCI$^+$) m/z 259 (M+NH$_4$)$^+$.

Example 288B pyridin-2-yl(1-(4-(trifluoromethoxy)phenyl)cyclobutyl)methanone

The title compound was prepared using procedures analogous to that described for the synthesis of Example 116B, substituting Example 288A for Example 116A. MS (DCI$^+$) m/z 322 (M+H)$^+$.

Example 288C (S)-pyridin-2-yl(1-(4-(trifluoromethoxy)phenyl)cyclobutyl)methanol

A mixture of Example 288B (6.63 g, 20.64 mmol), triethylamine (7.19 ml, 51.6 mmol), formic acid (3.40 ml, 89 mmol), and (S,S)—N-(p-touenesulfonyl)-1,2-diphenylethanediamine(chloro)(p-cumene)ruthenium (II) (0.131 g, 0.206 mmol) was heated at 35° C. for 16 hours. The reaction mixture was cooled, diluted with saturated NaHCO$_3$ solution, and extracted twice with CH$_2$Cl$_2$. The combined organic layers were dried with MgSO$_4$, filtered, and concentrated. The residue was chromatographed on an analogix SF40-150 g column and eluted with 20% to 50% EtOAc/hexanes to obtain the title compound (5.2 g). $[\alpha]_D$=−91.1° (c=0.805, MeOH). MS (DCI$^+$) m/z 324 (M+H)$^+$.

Example 288D (S)-pyridin-2-yl{1-[4-(trifluoromethoxy)phenyl]cyclobutyl}methyl acetate Example 288C (15 mg, 47 mol) and triethylamine (15 µL, 108 mol) were dissolved in anhydrous 2-methyltetrahydrofuran (200 µL), treated with acetyl chloride (3.7 µL, 52 mol), and stirred overnight. More acetyl chloride (7 µL, 0.1 mmol) was added and the mixture was stirred overnight. Again, more acetyl chloride (1.3 µL, 18 mol) was added and the mixture was stirred overnight. The resulting suspension was placed on a silica column for chromatography (20 to 100% diethyl ether/hexanes then 0.5% triethylamine in diethyl ether) to give the title compound (8 mg). MS (ESI) m/z=366 (M+H)$^+$. $^1$H NMR (400 MHz, CD$_2$Cl$_2$) d 8.48 (ddd, J=4.8, 1.8, 0.9 Hz, 1H), 7.38 (ddd, J=7.7, 1.8 Hz, 1H), 7.12 (ddd, J=7.5, 4.8, 1.1 Hz, 1H), 7.04-7.00 (m, 2H), 6.86 (d, J=8.8 Hz, 2H), 6.50-6.47 (m, 1H), 6.06 (s, 1H), 2.88-2.79 (m, 1H), 2.64-2.55 (m, 1H), 2.44-2.36 (m, 1H), 2.33-2.24 (m, 1H), 2.13-2.00 (m, 1H), 2.09 (s, 3H), 1.84 (dtt, J=11.4, 9.4, 4.6 Hz, 1H).

Example 289

[1-(3,4-dichlorophenyl)cyclobutyl](4-methoxypyridin-2-yl)methanol

Example 289A

[1-(3,4-dichlorophenyl)cyclobutyl](4-methoxypyridin-2-yl)methanone

A solution of 2.5M n-butyl lithium (6.5 mL, 16.25 mmol) in hexanes plus anhydrous diethyl ether (50 mL) was chilled to −75° C., then 2-bromo-4-methoxypyridine (3.12 g, 16.59 mmol) in diethyl ether (5 mL) was added dropwise. The red solution was warmed to −40° C. while stirring for 75 minutes, and then chilled to −75° C. Next, 1-(3,4-dichlorophenyl)cyclobutanecarbonitrile (3.0 g, 13.27 mmol) in diethyl ether (5 mL) was added. The reaction was warmed to −10° C. while stirring for 2 hours. The reaction was quenched with 1N hydrochloric acid (100 mL) and the biphasic mixture was stirred for 1 hour at ambient temperature. Added 3N sodium hydroxide (100 mL) and extracted twice with EtOAc (200 mL). The combined organic phases was washed with brine, dried over Na$_2$SO$_4$, filtered, and concentrated. The residue was chromatographed on silica (0-100% EtOAc in heptane) to give Example 289A (4.433 g, 13.19 mmol, 99% yield) as a colorless oil. MS (ESI+): m/z 336 (M+H). $^1$H NMR (400 MHz, CD$_3$CN) δ 8.29 (d, J=5.9 Hz, 1H), 7.64 (d, J=2.1 Hz, 1H), 7.47 (d, J=2.5 Hz, 1H), 7.40 (d, J=8.4 Hz, 1H), 7.34 (dd, J=8.4, 2.2 Hz, 1H), 6.93 (dd, J=5.6, 2.7 Hz, 1H), 3.84 (s, 3H), 3.02-2.91 (m, 2H), 2.66-2.56 (m, 2H), 2.02-1.91 (m, 1H), 1.91-1.78 (m, 1H).

Example 289B

[1-(3,4-dichlorophenyl)cyclobutyl](4-methoxypyridin-2-yl)methanol

Example 289A (4.433 g, 13.19 mmol) was dissolved in dichloromethane (50 mL) and MeOH (5 mL), then sodium borohydride (0.60 g, 15.86 mmol) was added to the yellow solution. The reaction was stirred for 5 hours at ambient temperature. Added 1N sodium hydroxide (200 mL) and extracted twice with EtOAc (200 mL). The combined organic phases was washed with brine, dried over $Na_2SO_4$, filtered, and concentrated. The residue was chromatographed on silica (0-100% EtOAc in heptane) to give Example 289B (4.400 g, 13.01 mmol, 99% yield) as a colorless oil. MS (ESI+): m/z 338 (M+H). $^1$H NMR (400 MHz, $CD_3CN$) δ 8.16 (d, J=5.7 Hz, 1H), 7.28 (d, J=8.3 Hz, 1H), 6.96 (d, J=2.1 Hz, 1H), 6.77 (dd, J=8.3, 2.1 Hz, 1H), 6.73 (dd, J=5.7, 2.6 Hz, 1H), 6.38 (d, J=2.5 Hz, 1H), 4.89 (d, J=6.3 Hz, 1H), 4.16 (d, J=6.3 Hz, 1H), 3.69 (s, 3H), 2.80-2.69 (m, 1H), 2.69-2.59 (m, 1H), 2.32-2.17 (m, 2H), 2.06-1.90 (m, 1H), 1.84-1.71 (m, 1H).

Example 290 cis-3-[(R)-hydroxy(pyridin-2-yl)methyl]-3-[4-(trifluoromethyl)pyridin-2-yl]-cyclobutanol Example 291

3-[(R)-hydroxy(pyridin-2-yl)methyl]-3-[6-methyl-4-(trifluoromethyl)pyridin-2-yl]cyclobutanone Example 292

[1-(6-chloro-1,3-benzothiazol-2-yl)cyclobutyl](pyridin-2-yl)methanol

Example 292A 1-(6-chlorobenzo[d]thiazol-2-yl)cyclobutanecarbonitrile

The title compound was prepared using procedures analogous to that described for the synthesis of Example 275B, substituting 2,6-dichlorobenzo[d]thiazole for Example 275A.

Example 292B (1-(6-chlorobenzo[d]thiazol-2-yl)cyclobutyl)(pyridin-2-yl)methanone The title compound was prepared using procedures analogous to that described for the synthesis of Example 275C, substituting Example 292A for Example 275B.

Example 292C

[1-(6-chloro-1,3-benzothiazol-2-yl)cyclobutyl](pyridin-2-yl)methanol

The title compound was prepared using procedures analogous to that described for the synthesis of Example 275D, substituting Example 292B for Example 275C. MS (M+H)$^+$: 331; $^1$H NMR (400 MHz, $CDCl_3$): δ 8.41-8.40 (d, J=4.4 Hz, 1H), 7.86-7.84 (d, J=8.8 Hz, 1H), 7.78 (d, J=2.0 Hz, 1H), 7.49-7.38 (m, 2H), 7.12-7.09 (m, 2H), 5.19 (s, 1H), 2.92-2.89 (m, 1H), 2.87-2.79 (m, 1H), 2.64-2.57 (m, 1H), 2.44-2.38 (m, 1H), 2.06-1.94 (m, 2H).

Example 293

3-[hydroxy(pyridin-2-yl)methyl]-3-[4-(trifluoromethyl)pyridin-2-yl]cyclobutanone Example 294

3-[(S)-hydroxy(pyridin-2-yl)methyl]-3-[4-(trifluoromethyl)pyridin-2-yl]cyclobutanol Example 295

3-[hydroxy(pyridin-2-yl)methyl]-3-[5-(trifluoromethyl)pyridin-3-yl]cyclobutanone Example 296

3-[(S)-hydroxy(pyridin-2-yl)methyl]-3-[5-(trifluoromethyl)pyridin-3-yl]cyclobutanone Example 297 pyridin-2-yl{2-[2-(trifluoromethyl)pyridin-4-yl]-5,8-dioxaspiro[3.4]oct-2-yl}methanol Example 298

3-[hydroxy(pyridin-2-yl)methyl]-3-[2-(trifluoromethyl)pyridin-4-yl]cyclobutanone Example 299

3-[(S)-hydroxy(pyridin-2-yl)methyl]-3-[2-(trifluoromethyl)pyridin-4-yl]cyclobutanone Example 300

[1-(6-fluoro-1,3-benzothiazol-2-yl)cyclobutyl](pyridin-2-yl)methanol

Example 300A 1-(6-fluorobenzo[d]thiazol-2-yl)cyclobutanecarbonitrile

The title compound was prepared using procedures analogous to that described for the synthesis of Example 275B, substituting 2-chloro-6-fluorobenzo[d]thiazole for Example 275A.

Example 300B (1-(6-fluorobenzo[d]thiazol-2-yl)cyclobutyl)(pyridin-2-yl)methanone The title compound was prepared using procedures analogous to that described for the synthesis of Example 275C, substituting Example 300A for Example 275B.

Example 300C

[1-(6-fluoro-1,3-benzothiazol-2-yl)cyclobutyl](pyridin-2-yl)methanol

The title compound was prepared using procedures analogous to that described for the synthesis of Example 275D, substituting Example 300B for Example 275C. MS: 315 (M+H)$^+$; $^1$H NMR (400 MHz, $CDCl_3$): δ 8.42 (d, J=4.4 Hz, 1H), 7.59 (d, J=0.4 Hz, 2H), 7.31-7.26 (m, 1H), 7.16-7.09 (m, 2H), 7.00 (d, J=8.0 Hz, 1H), 5.23 (brs, 2H), 2.92-2.90 (m, 1H), 2.89-2.80 (m, 1H), 2.78-2.66 (m, 1H), 2.44-2.41 (m, 1H), 2.04-1.93 (m, 2H).

Example 301

[1-(6-chloro-1,3-benzoxazol-2-yl)cyclobutyl](pyridin-2-yl)methanol

Example 301A 1-(6-chlorobenzo[d]oxazol-2-yl)cyclobutanecarbonitrile

The title compound was prepared using procedures analogous to that described for the synthesis of Example 275B, substituting 2,6-dichlorobenzo[d]oxazole for Example 275A.

MS: 233 (M+H)$^+$.

Example 301B (1-(6-chlorobenzo[d]oxazol-2-yl)cyclobutyl)(pyridin-2-yl)methanone The title compound was prepared using procedures analogous to that described for the synthesis of Example 275C, substituting Example 301A for Example 275B. MS: 313 (M+H)$^+$.

Example 301C

[1-(6-chloro-1,3-benzoxazol-2-yl)cyclobutyl](pyridin-2-yl)methanol

The title compound was prepared using procedures analogous to that described for the synthesis of Example 275D, substituting Example 301B for Example 275C. MS: 315 (M+H)$^+$; $^1$H NMR (400 MHz, CDCl$_3$): δ 8.42-8.41 (d, J=4.0 Hz, 1H), 7.57-7.49 (m, 3H), 7.30-7.28 (m, J=8.4 Hz, 1H), 7.16-7.13 (m, 1H), 6.88-6.86 (m, J=8.4 Hz, 1H), 5.20 (s, 1H), 4.89 (brs, 1H), 2.79-2.77 (m, 1H), 2.75-2.48 (m, 3H), 2.00-1.61 (m, 2H).

Example 302 cis-3-[(S)-hydroxy(pyridin-2-yl)methyl]-1-methyl-3-[2-(trifluoromethyl)-pyridin-4-yl]cyclobutanol

Example 303 cis-3-[(S)-hydroxy(pyridin-2-yl)methyl]-3-[5-(trifluoromethyl)pyridin-3-yl]-cyclobutanol

Example 304 trans-3-[(S)-hydroxy(pyridin-2-yl)methyl]-3-[5-(trifluoromethyl)pyridin-3-yl]cyclobutanol

Example 305 cis-3-[(S)-hydroxy(pyridin-2-yl)methyl]-3-[2-(trifluoromethyl)pyridin-4-yl]-cyclobutanol

Example 306 trans-3-[(S)-hydroxy(pyridin-2-yl)methyl]-3-[2-(trifluoromethyl)pyridin-4-yl]cyclobutanol

Example 307 trans-3-[(S)-hydroxy(pyridin-2-yl)methyl]-1-methyl-3-[2-(trifluoromethyl)-pyridin-4-yl]cyclobutanol

Example 308 cis-3-[(S)-hydroxy(pyridin-2-yl)methyl]-1-methyl-3-[5-(trifluoromethyl)-pyridin-3-yl]cyclobutanol

Example 309 trans-3-[(S)-hydroxy(pyridin-2-yl)methyl]-1-methyl-3-[5-(trifluoromethyl)-pyridin-3-yl]cyclobutanol

Example 310

(trans)-3-((S)-hydroxy(pyrimidin-2-yl)methyl)-1-methyl-3-(4-(trifluoromethoxy)phenyl)cyclobutanol

Example 311

(trans)-3-((R)-hydroxy(pyrimidin-2-yl)methyl)-1-methyl-3-(4-(trifluoromethoxy)phenyl)cyclobutanol

Example 312

(trans)-3-(3,4-dichlorophenyl)-3-((S)-hydroxy(pyrimidin-2-yl)methyl)-cyclobutanol

Example 313

(trans)-3-(3,4-dichlorophenyl)-3-((R)-hydroxy(pyrimidin-2-yl)methyl)-cyclobutanol It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

The invention claimed is:

1. A compound according to Formula (II):

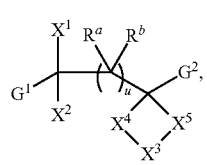

(II)

or a salt thereof, wherein:

$R^a$ and $R^b$ are absent;

u is 0;

$X^3$ is O; $X^4$ is a bond, $X^5$ is $(CH_2)_n$, and n is 2; or $X^3$ is O; $X^4$ is $(CH_2)_m$, $X^5$ is $(CH_2)_n$, m and n are each 1; or $X^3$ is O; $X^4$ is $(CH_2)_m$, $X^5$ is $(CH_2)_n$, m is 1, and n is 2; or $X^3$ is O; $X^4$ is a bond, $X^5$ is $(CH_2)_n$, and n is 3; and $X^1$ is —OH and $X^2$ is hydrogen;

$G^1$ is pyridinyl or pyrimidinyl; each of which is optionally substituted with 1, 2, or 3 substituents independently selected from the groups consisting of halogen $C_1$-$C_6$-alkyl $C_1$-$C_6$-haloalkyl, and $N(R^{gc})_2$;

$R^{gc}$ is hydrogen or $C_1$-$C_6$-alkyl;
$G^2$ is $G^{2d}$;
$G^{2d}$ is phenyl, pyridinyl, or pyrimidinyl; each of which is optionally substituted with 1, 2, or 3 substituents independently selected from the groups consisting of halogen —CN, $C_1$-$C_6$-alkyl $C_1$-$C_6$-haloalkyl, and —OR$^f$; and
$R^f$ is $C_1$-$C_6$-alkyl or $C_1$-$C_6$-haloalkyl.

2. The compound according to claim 1, or a salt thereof, wherein the compound has the configuration of Formula (II-i-a):

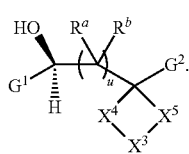

(II-i-a)

3. The compound according to claim 1, or a salt thereof, wherein:
$G^1$ is pyridinyl which is optionally substituted with 1 or 2 substituents independently selected from the group consisting of halogen, $C_1$-$C_4$-alkyl, $C_1$-$C_4$-haloalkyl, and $N(R^{gc})_2$;
$R^{gc}$ is hydrogen or $C_1$-$C_4$-alkyl;
$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —OR$^f$; and
$R^f$ is $C_1$-$C_4$-alkyl or $C_1$-$C_4$-haloalkyl.

4. The compound according to claim 1, or a salt thereof, wherein:
$G^1$ is unsubstituted pyridinyl;
$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —OR$^f$; and
$R^f$ is $C_1$-$C_4$-alkyl or $C_1$-$C_4$-haloalkyl.

5. The compound according to claim 1, or a salt thereof, wherein:
$G^1$ is unsubstituted pyridin-2-yl;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —OR$^f$; and
$R^f$ is $C_1$-$C_3$-alkyl or $C_1$-$C_3$-haloalkyl.

6. The compound according to claim 5, or a salt thereof, wherein:
$G^{2d}$ is phenyl which is optionally substituted with 1, 2, or 3 substituents independently selected from the group consisting of halogen, $C_1$-$C_3$-alkyl, $C_1$-$C_3$-haloalkyl, and —OR$^f$; and
$R^f$ is $C_1$-$C_3$-alkyl or $C_1$-$C_3$-haloalkyl.

7. The compound according to claim 5, or a salt thereof, wherein:
$G^{2d}$ is phenyl which is substituted with 1, 2, or 3 substituents independently selected from the group consisting of halogen, $C_1$-$C_3$-alkyl or $C_1$-$C_3$-haloalkyl.

8. The compound according to claim 5, or a salt thereof, wherein:
$G^{2d}$ is phenyl which is substituted with 1, 2, or 3 substituents independently selected from halogen.

9. The compound according to claim 5, or a salt thereof, wherein:
$G^{2d}$ is pyridinyl which is optionally substituted with 1, 2, or 3 substituents independently selected from the group consisting of halogen, $C_1$-$C_3$-alkyl, $C_1$-$C_3$-haloalkyl, and —OR$^f$; and
$R^f$ is $C_1$-$C_3$-alkyl or $C_1$-$C_3$-haloalkyl.

10. The compound according to claim 1, or a salt thereof, wherein $X^3$ is O; $X^4$ is a bond, $X^5$ is $(CH_2)_n$, and n is 2.

11. The compound according to claim 1, or a salt thereof, wherein $X^3$ is O; $X^4$ is $(CH_2)_m$, $X^5$ is $(CH_2)_n$, m and n are each 1.

12. The compound according to claim 1, or a salt thereof, wherein $X^3$ is O; $X^4$ is $(CH_2)_m$, $X^5$ is $(CH_2)_n$, m is 1, and n is 2.

13. The compound according to claim 1, or a salt thereof, wherein $X^3$ is O; $X^4$ is a bond, $X^5$ is $(CH_2)_n$, and n is 3.

14. The compound according to claim 1, or a salt thereof, selected from the group consisting of:
pyridin-2-yl{3-[4-(trifluoromethyl)phenyl]tetrahydrofuran-3-yl}methanol;
4-{3-[hydroxy(pyridin-2-yl)methyl]tetrahydrofuran-3-yl}benzonitrile;
pyridin-2-yl {3-[3-(trifluoromethoxy)phenyl]tetrahydrofuran-3-yl}methanol;
3-{3-[hydroxy(pyridin-2-yl)methyl]tetrahydrofuran-3-yl}benzonitrile;
[3-(4-methoxyphenyl)tetrahydrofuran-3-yl](pyridin-2-yl)methanol;
[3-(3,4-dimethoxyphenyl)tetrahydrofuran-3-yl](pyridin-2-yl)methanol;
[3-(3-chlorophenyl)oxetan-3-yl](pyridin-2-yl)methanol;
[3-(3,4-dichlorophenyl)oxetan-3-yl](pyridin-2-yl)methanol;
(anti)-pyridin-2-yl{2-[4-(trifluoromethyl)phenyl]tetrahydrofuran-2-yl}methanol;
(syn)-pyridin-2-yl{2-[4-(trifluoromethyl)phenyl]tetrahydrofuran-2-yl}methanol;
[2-(2-methylphenyl)tetrahydrofuran-2-yl](pyridin-2-yl)methanol;
[2-(3-methylphenyl)tetrahydrofuran-2-yl](pyridin-2-yl)methanol;
(anti)-pyridin-2-yl{2-[3-(trifluoromethoxy)phenyl]tetrahydrofuran-2-yl}methanol;
(syn)-pyridin-2-yl{2-[3-(trifluoromethoxy)phenyl]tetrahydrofuran-2-yl}methanol;
(anti)-pyridin-2-yl{2-[4-(trifluoromethoxy)phenyl]tetrahydrofuran-2-yl}methanol;
(syn)-pyridin-2-yl{2-[4-(trifluoromethoxy)phenyl]tetrahydrofuran-2-yl}methanol;
(anti)-pyridin-2-yl{2-[2-(trifluoromethoxy)phenyl]tetrahydrofuran-2-yl}methanol;
(syn)-pyridin-2-yl{2-[2-(trifluoromethoxy)phenyl]tetrahydrofuran-2-yl}methanol;
(anti)-2-(3,4-dichlorophenyl)tetrahydrofuran-2-yl](pyridin-2-yl)methanol;
(syn)-[2-(3,4-dichlorophenyl)tetrahydrofuran-2-yl](pyridin-2-yl)methanol;
(anti)-[2-(3-fluorophenyl)tetrahydrofuran-2-yl](pyridin-2-yl)methanol;
(syn)-[2-(3-fluorophenyl)tetrahydrofuran-2-yl](pyridin-2-yl)methanol;
(anti)-[2-fluorophenyl)tetrahydrofuran-2-yl](pyridin-2-yl)methanol;
(syn)-[2-(2-fluorophenyl)tetrahydrofuran-2-yl](pyridin-2-yl)methanol;
(anti)-[2-(3-chlorophenyl)tetrahydrofuran-2-yl](pyridin-2-yl)methanol;

(syn)-[2-(3-chlorophenyl)tetrahydrofuran-2-yl](pyridin-2-yl)methanol;
(anti)-pyridin-2-yl{2-[3-(trifluoromethyl)phenyl]tetrahydrofuran-2-yl}methanol;
(syn)-pyridin-2-yl{2-[3-(trifluoromethyl)phenyl]tetrahydrofuran-2-yl}methanol;
(anti)-[2-(3,4-difluorophenyl)tetrahydrofuran-2-yl](pyridin-2-yl)methanol;
(syn)-[2-(3,4-difluorophenyl)tetrahydrofuran-2-yl](pyridin-2-yl)methanol;
(R)-[(2S)-2-(3,4-dichlorophenyl)oxetan-2-yl](pyridin-2-yl)methanol;
(R)-[(2R)-2-(3,4-dichlorophenyl)oxetan-2-yl](pyridin-2-yl)methanol; and
salts thereof.

15. The compound, or a salt thereof, of claim 1, wherein the salt is a pharmaceutically acceptable salt.

16. A pharmaceutical composition comprising a therapeutically effective amount of a compound of formula (I) according to claim 1, or a pharmaceutically acceptable salt thereof, in combination with a pharmaceutically acceptable carrier.

17. The compound according to claim 2, or a salt thereof, wherein:
$G^1$ is pyridinyl which is optionally substituted with 1 or 2 substituents independently selected from the group consisting of halogen, $C_1$-$C_4$-alkyl, $C_1$-$C_4$-haloalkyl, and $N(R^{gc})_2$;
$R^{gc}$ is hydrogen or $C_1$-$C_4$-alkyl;
$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —$OR^f$; and
$R^f$ is $C_1$-$C_4$-alkyl or $C_1$-$C_4$-haloalkyl.

18. The compound according to claim 2, or a salt thereof, wherein:
$G^1$ is unsubstituted pyridinyl;
$G^{2d}$ is phenyl or pyridinyl; each of which is optionally substituted with 1, 2, or 3 substituents independently selected from the group consisting of halogen, $C_1$-$C_4$-alkyl, $C_1$-$C_4$-haloalkyl, and —$OR^f$; and
$R^f$ is $C_1$-$C_4$-alkyl or $C_1$-$C_4$-haloalkyl.

19. The compound according to claim 2, or a salt thereof, wherein:
$G^1$ is unsubstituted pyridin-2-yl;
$G^{2d}$ is phenyl or pyridinyl; each of which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

20. The compound according to claim 19, or a salt thereof, wherein:
$G^{2d}$ is phenyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

21. The compound according to claim 19, or a salt thereof, wherein:
$G^{2d}$ is pyridinyl which is optionally substituted with 1, 2, or 3 substituents independently selected from the group consisting of halogen, $C_1$-$C_3$-alkyl, $C_1$-$C_3$-haloalkyl, and —$OR^f$; and
$R^f$ is $C_1$-$C_3$-alkyl or $C_1$-$C_3$-haloalkyl.

22. The compound according to claim 17, or a salt thereof, wherein $X^3$ is O; $X^4$ is a bond, $X^5$ is $(CH_2)_n$, and n is 2.

23. The compound according to claim 17, or a salt thereof, wherein $X^3$ is O; $X^4$ is $(CH_2)_m$, $X^5$ is $(CH_2)_n$, m and n are each 1.

24. The compound according to claim 17, or a salt thereof, wherein $X^3$ is O; $X^4$ is $(CH_2)_m$, $X^5$ is $(CH_2)_n$, m is 1, and n is 2.

25. The compound according to claim 17, or a salt thereof, wherein $X^3$ is O; $X^4$ is a bond, $X^5$ is $(CH_2)_n$, and n is 3.

26. The compound or salt of claim 1 that is (syn)-pyridin-2-yl{2-[3-(trifluoromethoxy)phenyl]tetrahydrofuran-2-yl}-methanol, or a pharmaceutically acceptable salt thereof.

27. The pharmaceutical composition of claim 16, wherein the compound or salt is (syn)-pyridin-2-yl{2-[3-(trifluoromethoxy)phenyl]tetrahydrofuran-2-yl}-methanol, or a pharmaceutically acceptable salt thereof.

28. The compound or salt of claim 1 that is (anti)-2-(3,4-dichlorophenyl)tetrahydrofuran-2-yl](pyridin-2-yl)methanol, or a pharmaceutically acceptable salt thereof.

29. The pharmaceutical composition of claim 16, wherein the compound or salt is (anti)-2-(3,4-dichlorophenyl)tetrahydrofuran-2-yl](pyridin-2-yl)methanol, or a pharmaceutically acceptable salt thereof.

30. The compound or salt of claim 1 that is (R)-[(2S)-2-(3,4-dichlorophenyl)oxetan-2-yl](pyridin-2-yl)methanol, or a pharmaceutically acceptable salt thereof.

31. The pharmaceutical composition of claim 16, wherein the compound or salt is (R)-[(2S)-2-(3,4-dichlorophenyl)oxetan-2-yl](pyridin-2-yl)methanol, or a pharmaceutically acceptable salt thereof.

32. The compound or salt of claim 1 that is (R)-[(2R)-2-(3,4-dichlorophenyl)oxetan-2-yl](pyridin-2-yl)methanol, or a pharmaceutically acceptable salt thereof.

33. The pharmaceutical composition of claim 16, wherein the compound or salt is (R)-[(2R)-2-(3,4-dichlorophenyl)oxetan-2-yl](pyridin-2-yl)methanol, or a pharmaceutically acceptable salt thereof.

* * * * *